US010988752B2

(12) United States Patent
Stricher et al.

(10) Patent No.: US 10,988,752 B2
(45) Date of Patent: *Apr. 27, 2021

(54) 3-METHYLCROTONIC ACID DECARBOXYLASE (MDC) VARIANTS

(71) Applicant: Global Bioenergies, Evry (FR)

(72) Inventors: François Stricher, Wolfisheim (FR); Benoît Villiers, Alfortville (FR)

(73) Assignee: Global Bioenergies, Evry (FR)

( * ) Notice: Subject to any disclaimer, the term of this patent is extended or adjusted under 35 U.S.C. 154(b) by 60 days.

This patent is subject to a terminal disclaimer.

(21) Appl. No.: 16/502,472

(22) Filed: Jul. 3, 2019

(65) Prior Publication Data

US 2019/0322996 A1 Oct. 24, 2019

Related U.S. Application Data

(63) Continuation-in-part of application No. 16/153,681, filed on Oct. 5, 2018, now Pat. No. 10,808,237, which is a continuation-in-part of application No. 16/026,333, filed on Jul. 3, 2018, now abandoned, which is a continuation of application No. PCT/EP2017/060621, filed on May 4, 2017, and application No. 16/153,681, Oct. 5, 2018, which is a continuation-in-part of application No. 16/026,332, filed on Jul. 3, 2018, now abandoned, which is a continuation-in-part of application No. PCT/EP2017/060621, filed on May 4, 2017.

(30) Foreign Application Priority Data

May 4, 2016 (EP) ..................... 16168448
Nov. 18, 2016 (EP) ..................... 16199502
Jul. 3, 2018 (EP) ..................... 18181522

(51) Int. Cl.
*C12N 9/88* (2006.01)
*C12P 5/02* (2006.01)
*C12N 9/00* (2006.01)

(52) U.S. Cl.
CPC ............... *C12N 9/88* (2013.01); *C12P 5/026* (2013.01); *C12Y 401/01028* (2013.01)

(58) Field of Classification Search
None
See application file for complete search history.

(56) References Cited

FOREIGN PATENT DOCUMENTS

WO 2016042011 A1 3/2016
WO 2017085167 A2 5/2017
WO 2017191239 A1 11/2017

OTHER PUBLICATIONS

Anonymous, "Hypothetical Protein TGAM01 10611 [Trichoderma Gamsii]—Protein—NCBI Reference Sequence", Retrieved from the Internet: URL:https://www.ncbi.nlm.nih.gov/protein/1087785219, (2016).
Anonymous, "Hypothetical Protein TRIATDRAFT 53567 [Trichoderma Atroviride IMI 206040] Protein—NCBI Reference Sequence", Retrieved from the Internet: URL:https://www.ncbi.nlm.nih.gov/protein/X P 013946967.1 (2015).
Baroncelli et. al., "Draft Whole-Genome Sequence of Trichoderma Gamsii T6085, a Promising Biocontrol Agent of Fusarium Head Blight on Wheat", Genome Announcements, vol. 4, No. 1, pp. pp. e01747-15, (2016).
Bhuiya et al., "Structure and Mechanism of Ferulic Acid Decarboxylase (FDC1) from *Saccharomyces cerevisiae*", Applied and Environmental Microbiology, vol. 81, No. 12, pp. 4216-4223 (2015).
Database UniProt [Online] Apr. 12, 2017 (Apr. 12, 2017), RecName: Full=UbiD-like decarboxylase {EC0:0000256: HAMAP-Rule:MF-01983}; EC=4.1.1.-{EC0:0000256:HAMAP-Rule:MF 01983}; AltName: Full=Ferulic acid-decarboxylase-like protein {EC0:0000256:HAMAP-Rule:MF-01983}; 11 , XP002787742, retrieved from EBI accession No. UNIPROT:A0AIS2PMH4 Database accession No. A0AIS2PMH4 * the whole document*.
Database UniProt [Online] Mar. 4, 2015 (Mar. 4, 2015), "RecName: Full=UbiD-like decarboxylase {EC0:0000256: HAMAP-Rule:MF-01983}; EC=4.1.1.-{EC0:0000256:HAMAP-Rule:MF 01983}; AltName: Full=Ferulic acid-decarboxylase-like protein {EC0:0000256:HAMAP-Rule:MF-01983};", XP002787741, retrieved from EBI accession No. UNIPROT:A0A0A8EV26 Database accession No. A0A0A8EV26 *sequence*.
Extended European Search Report dated Jan. 28, 2019 and received in Application No. 18 18 1522.6.
Gogerty et al., "Formation of Isobutene from 3-Hydroxy-3-Methylbutyrate by Diphosphomevalonate Decarboxylase", Applied and Environmental Microbiology, vol. 76, No. 24, pp. 8004-8010, (2010).
Kubicek et. al., "Comparative Genome Sequence Analysis Underscores Mycoparasitism as the Ancestral Life Style of Trichoderma", Genome Biology, vol. 12:R40, pp. 1-15, (2011).
Ladygina, N. et al.,"A Review on Microbial Synthesis of Hydrocarbons, Process Biochemistry", vol. 41, No. 5, pp. 1001-1014, (2006).
Lin et al., "Isofunctional Enzymes PAD1 and UbiX Catalyze Formation of a Novel Cofactor Required by Ferulic Acid Decarboxylase and 4-Hydroxy-3-Polyprenylbenzoic Acid Decarboxylase", ACS Chemical Biology, vol. 10. No. 4, pp. 1137-1144 (2015).

(Continued)

*Primary Examiner* — Suzanne M Noakes
*Assistant Examiner* — Jae W Lee
(74) *Attorney, Agent, or Firm* — Michele M. Wales; Inhouse Patent Counsel, LLC

(57) ABSTRACT

Described are 3-methylcrotonic acid decarboxylase (MDC) variants showing an improved activity in converting 3-methylcrotonic acid into isobutene as well as methods for the production of isobutene using such enzyme variants.

16 Claims, 4 Drawing Sheets

Figure 1A:
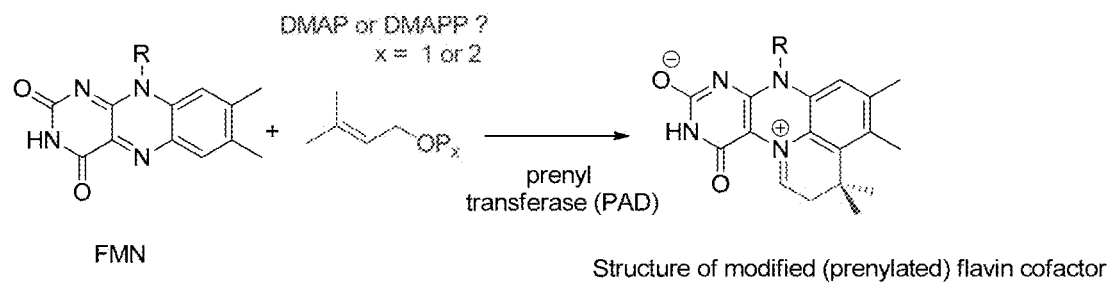

Specification includes a Sequence Listing.

(56) References Cited

OTHER PUBLICATIONS

Payne et. al., "New Cofactor Supports α,β-unsaturated Acid Decarboxylation via 1,3-Dipolar Cycloaddition", Nature, vol. 522, No. 7557, pp. 497-501, (2015).
Van Leeuwen et al., "Fermentative Production of Isobutene", Applied Microbiology and Biotechnology, vol. 93, pp. 1377-1387, (2012).
Wang et al., "Biosynthesis and Activity of Prenylated FMN Cofactors", Cell Chemical Biology, vol. 25, pp. 560-570, (2018).
Written Opinion and International Search Report dated Aug. 16, 2017 in PCT/EP2017/060621.
Database REfseq [Online] Jul. 23, 2017 (Jul. 23, 2017), "UBID family decarboxylase [*Streptomyces* sp.NRRL S-1448].", XP002794755,accession No. ebi Database accession No. WP030411030 sequences.
Database UniProt [Online] Apr. 13, 2016 (Apr. 13, 2016), "RecName: Full=UbiD-like decarboxylase {ECO:0000256: HAMAP-Rule:MF-01983}; EC=4.1.1.-{ECO:0000256:HAMAP-Rule:MF 01983}; AltName: Full=Ferulic acid-decarboxylase-like protein {ECO:0000256:HAMAP-Rule:MF-01983};", XP002794753, retrieved from EBI accession No. UNIPROT:A0AI01TBL5 Database accession No. A0AI01TBL5 sequence.
Database UniProt [Online] Nov. 2, 2016 (Nov. 2, 2016), "RecName: Full=UbiD-like decarboxylase {ECO:0000256:HAMAP-Rule:MF-01983}; EC=4.1.1.-{ECO:0000256:HAMAP-Rule:MF 01983}; AltName: Full=Ferulic acid-decarboxylase-like protein {ECO:0000256:HAMAP-Rule:MF-01983};", XP002794754, retrieved from EBI accession No. UNIPROT:A0AIB2GL43 Database accession No. A0A1B2GL43 sequence.
International Search Report and Written Opinion dated Oct. 18, 2019 and received in PCT/EP2019/067788.

3-methyl-crotonic acid
*aka* prenate isobutene

3-METHYLCROTONIC ACID DECARBOXYLASE (MDC) VARIANTS

This application claims priority and is a Continuation-in-Part of U.S. Ser. No. 16/153,681 filed on Oct. 5, 2018, which is a Continuation-in-Part of U.S. Ser. No. 16/026,332 filed on Jul. 3, 2018, now abandoned, which is a Continuation-in-Part of PCT/EP2017/060621 filed on May 4, 2017, which claims priority to EP 16168448.5 filed on May 4, 2016 and EP 16199502.2 filed on Nov. 18, 2016; this application also claims priority and is a Continuation-in-Part of U.S. Ser. No. 16/153,681 filed on Oct. 5, 2018, which is a Continuation-in-Part of U.S. Ser. No. 16/026,333 filed on Jul. 3, 2018, which is a Continuation of PCT/EP2017/060621 filed on May 4, 2017, which claims priority to EP 16168448.5 filed on May 4, 2016 and EP 16199502.2 filed on Nov. 18, 2016; this application also claims priority to EP 18181522.6 filed Jul. 3, 2018. All of these documents are hereby incorporated by reference in their entirety.

Described are 3-methylcrotonic acid decarboxylase (MDC) variants showing an improved activity in converting 3-methylcrotonic acid into isobutene as well as methods for the production of isobutene using such enzyme variants.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Butylene exists in four forms, one of which, isobutene (also referred to as isobutylene), enters into the composition of methyl-tert-butyl-ether (MTBE), an anti-knock additive for automobile fuel. Isobutene can also be used to produce isooctene, which in turn can be reduced to isooctane (2,2,4-trimethylpentane); the very high octane rating of isooctane makes it the best fuel for so-called "gasoline" engines. Alkenes such as isobutene are currently produced by catalytic cracking of petroleum products (or by a derivative of the Fischer-Tropsch process in the case of hexene, from coal or gas). The production costs are therefore tightly linked to the price of oil. Moreover, catalytic cracking is sometimes associated with considerable technical difficulties which increase process complexity and production costs.

The production by a biological pathway of alkenes such as isobutene is called for in the context of a sustainable industrial operation in harmony with geochemical cycles. The first generation of biofuels consisted in the fermentative production of ethanol, as fermentation and distillation processes already existed in the food processing industry. The production of second generation biofuels is in an exploratory phase, encompassing in particular the production of long chain alcohols (butanol and pentanol), terpenes, linear alkanes and fatty acids. Two recent reviews provide a general overview of research in this field: Ladygina et al. (Process Biochemistry 41 (2006), 1001) and Wackett (Current Opinions in Chemical Biology 21 (2008), 187).

Different routes for the enzymatic generation of isobutene have previously been described; see, e.g., Fujii et al. (Appl. Environ. Microbiol. 54 (1988), 583); Gogerty et al. (Appl. Environm. Microbiol. 76 (2010), 8004-8010) and van Leeuwen et al. (Appl. Microbiol. Biotechnol. 93 (2012), 1377-1387) and WO2010/001078.

In addition to these routes, there are also alternative routes for the provision of isobutene utilizing the enzymatic conversion of 3-methylcrotonic acid into isobutene by a decarboxylation reaction. A decarboxylation is a chemical reaction that removes a carboxyl group and releases ($CO_2$).

The decarboxylation of 3-methylcrotonic acid has already been suggested in US-A1-2009/0092975 while there is no experimental evidence for this conversion. In US-A1-2009/0092975, a nucleic acid sequence called PAD1 derived from *Saccharomyces cerevisiae* is described and is disclosed to encode a decarboxylation enzyme. This enzyme is suggested to be useful as a selectable marker in a recombinant organism while it is described that a "weak acid" may be used as the selecting agent. 3-methylcrotonic acid is mentioned, among many others, as a potential "weak acid".

However, it was only later found that the above PAD1, in reality, does not provide for the decarboxylase activity.

In fact, the bacterial ubiD and ubiX or the homologous eukaryotic fdc1 and pad1 genes have been implicated in the non-oxidative reversible decarboxylation. The combined action of phenylacrylic acid decarboxylase (PAD) and ferulic acid decarboxylase (FDC) is considered to be essential for the decarboxylation of phenylacrylic acid in *Saccharomyces cerevisiae* (J. Biosci. Bioeng. 109, (2010), 564-569; AMB Express, 5:12 (2015) 1-5; ACS Chem. Biol. 10 (2015), 1137-1144).

Recently, the above enzyme family described as phenylacrylic acid decarboxylase (PAD) was characterized as an FMN prenyl-transferase and no longer as a decarboxylase. It has been shown that Fdc1 (but not PAD) is solely responsible for the reversible decarboxylase activity and that it requires a new type of cofactor, namely a prenylated flavin synthesized by the associated UbiX (or Pad1) protein. Thus, the real enzymatic activity of this PAD enzyme has been identified as the transformation of a flavin mononucleotide (FMN) cofactor with a prenyl moiety (from di-methyl-allyl-phosphate or pyrophosphate called DMAP or DMAPP). This reaction is shown in FIG. 1A.

Figure 1B:
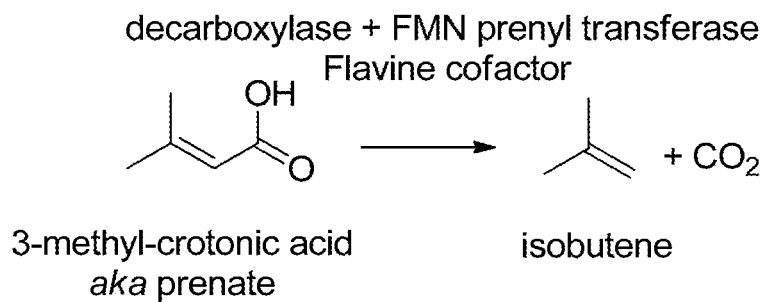

Accordingly, in contrast to the prior art's belief, the real decarboxylase is the Ferulic Acid Decarboxylase (FDC) in association with the modified FMN (prenylated-FMN). This reaction is shown in FIG. 1B. This mechanism of the Ferulic Acid Decarboxylase (FDC) in association with the modified FMN (prenylated-FMN) (the latter provided by the PAD enzyme) was recently described and involves a surprising enzymatic mechanism, i.e., an α,β-unsaturated acid decarboxylation via a 1,3-dipolar cyclo-addition. Moreover, the structure of this FDC decarboxylase has recently been elucidated (Nature 522 (2015), 497-501; Nature, 522 (2015), 502-505; Appl. Environ. Microbiol. 81 (2015), 4216-4223).

Although the above means and methods allow to produce isobutene from 2-methylcrotonic acid, there is still a need for improvements, in particular as regards a further increase in efficiency of the process so as to make it more suitable for industrial purposes.

The present application addresses this need by providing in a first part the embodiments as defined in the following items (1) to (12):

1. A variant of a 3-methylcrotonic acid decarboxylase (MDC) showing an improved activity in converting 3-methylcrotonic acid into isobutene over the corresponding MDC from which it is derived and having an amino acid sequence as shown in SEQ ID NO:1 or an amino acid sequence having at least 73% sequence identity to SEQ ID NO: 1, in which one or more amino acid residues at a position selected from the group consisting of positions 405, 2, 12, 13, 29, 31, 33, 35, 89, 114, 195, 197, 221, 293, 337, 351, 376, 381, 388, 420, 422, 435, 436, 439, 441, 447, 449, 500, 506 and 511 in the amino acid sequence shown in SEQ ID NO:1 or at a position corresponding to any of these positions, are substituted with another amino acid residue or deleted or wherein an insertion has been effected at one or more of these positions.

2. The MDC variant of item 1, wherein
   (1) an amino acid residue at position 2 in the amino acid sequence shown in SEQ ID NO:1 or at a position corresponding to this position, is deleted or substituted with alanine, aspartic acid, phenylalanine, lysine, leucine, asparagine, glutamine or valine; and/or
   (2) an amino acid residue at position 12 in the amino acid sequence shown in SEQ ID NO:1 or at a position corresponding to this position, is deleted or substituted with serine, alanine or asparagine; and/or
   (3) an amino acid residue at position 13 in the amino acid sequence shown in SEQ ID NO:1 or at a position corresponding to this position, is deleted or substituted with histidine, isoleucine, asparagine, serine, valine or tyrosine; and/or
   (4) an amino acid residue at position 29 in the amino acid sequence shown in SEQ ID NO:1 or at a position corresponding to this position, is deleted or substituted with asparagine, histidine or serine; and/or
   (5) an amino acid residue at position 31 in the amino acid sequence shown in SEQ ID NO:1 or at a position corresponding to this position, is deleted or substituted with glutamic acid or glycine; and/or
   (6) an amino acid residue at position 33 in the amino acid sequence shown in SEQ ID NO:1 or at a position corresponding to this position, is deleted or substituted with isoleucine; and/or
   (7) an amino acid residue at position 35 in the amino acid sequence shown in SEQ ID NO:1 or at a position corresponding to this position, is deleted or substituted with methionine, serine or threonine; and/or
   (8) an amino acid residue at position 89 in the amino acid sequence shown in SEQ ID NO:1 or at a position corresponding to this position, is deleted or substituted with serine or phenylalanine; and/or
   (9) an amino acid residue at position 114 in the amino acid sequence shown in SEQ ID NO:1 or at a position corresponding to this position, is deleted or substituted with serine; and/or
   (10) an amino acid residue at position 195 in the amino acid sequence shown in SEQ ID NO:1 or at a position corresponding to this position, is deleted or substituted with methionine, cysteine, phenylalanine, isoleucine, valine, tryptophan or tyrosine; and/or
   (11) an amino acid residue at position 197 in the amino acid sequence shown in SEQ ID NO:1 or at a position corresponding to this position, is deleted or substituted with phenylalanine or methionine; and/or
   (12) an amino acid residue at position 221 in the amino acid sequence shown in SEQ ID NO:1 or at a position corresponding to this position, is deleted or substituted with cysteine; and/or
   (13) an amino acid residue at position 293 in the amino acid sequence shown in SEQ ID NO:1 or at a position corresponding to this position, is deleted or substituted with leucine; and/or
   (14) an amino acid residue at position 337 in the amino acid sequence shown in SEQ ID NO:1 or at a position corresponding to this position, is deleted or substituted with methionine or leucine; and/or
   (15) an amino acid residue at position 351 in the amino acid sequence shown in SEQ ID NO:1 or at a position corresponding to this position, is deleted or substituted with arginine, asparagine, alanine, valine or glycine; and/or
   (16) an amino acid residue at position 376 in the amino acid sequence shown in SEQ ID NO:1 or at a position corresponding to this position, is deleted or substituted with isoleucine; and/or
   (17) an amino acid residue at position 381 in the amino acid sequence shown in SEQ ID NO:1 or at a position corresponding to this position, is deleted or substituted with arginine; and/or
   (18) an amino acid residue at position 388 in the amino acid sequence shown in SEQ ID NO:1 or at a position corresponding to this position, is deleted or substituted with glutamic acid; and/or
   (19) an amino acid residue at position 405 in the amino acid sequence shown in SEQ ID NO:1 or at a position corresponding to this position, is deleted or substituted with phenylalanine, leucine, methionine, proline or glutamine; and/or
   (20) an amino acid residue at position 420 in the amino acid sequence shown in SEQ ID NO:1 or at a position corresponding to this position, is deleted or substituted with leucine; and/or
   (21) an amino acid residue at position 422 in the amino acid sequence shown in SEQ ID NO:1 or at a position corresponding to this position, is deleted or substituted with methionine; and/or
   (22) an amino acid residue at position 435 in the amino acid sequence shown in SEQ ID NO:1 or at a position corresponding to this position, is deleted or substituted with methionine; and/or
   (23) an amino acid residue at position 436 in the amino acid sequence shown in SEQ ID NO:1 or at a position corresponding to this position, is deleted or substituted with asparagine; and/or
   (24) an amino acid residue at position 439 in the amino acid sequence shown in SEQ ID NO:1 or at a position corresponding to this position, is deleted or substituted with leucine; and/or
   (25) an amino acid residue at position 441 in the amino acid sequence shown in SEQ ID NO:1 or at a position corresponding to this position, is deleted or substituted with tyrosine; and/or
   (26) an amino acid residue at position 447 in the amino acid sequence shown in SEQ ID NO:1 or at a position corresponding to this position, is deleted or substituted with tryptophan, methionine or tyrosine; and/or
   (27) an amino acid residue at position 449 in the amino acid sequence shown in SEQ ID NO:1 or at a position corresponding to this position, is deleted or substituted with isoleucine, methionine or valine; and/or
   (28) an amino acid residue at position 500 in the amino acid sequence shown in SEQ ID NO:1 or at a position corresponding to this position, is deleted or substituted with alanine; and/or
   (29) an amino acid residue at position 506 in the amino acid sequence shown in SEQ ID NO:1 or at a position corresponding to this position, is deleted or substituted with isoleucine or tyrosine; and/or
   (30) an amino acid residue at position 511 in the amino acid sequence shown in SEQ ID NO:1 or at a position corresponding to this position, is deleted or substituted with methionine or isoleucine.

3. The MDC variant of item 1 or 2, wherein said variant furthermore shows at least one modification at positions 3, 4, 5, 6, 7, 8, 9, 10, 11, 14, 15, 25, 30, 34, 40, 43, 57, 60, 65, 67, 69, 70, 71, 72, 80, 84, 85, 86, 87, 90, 91, 99, 101, 102, 103, 105, 106, 108, 111, 117, 119, 120, 126, 132, 141, 146, 149, 154, 159, 160, 162, 175, 176, 187, 189, 193, 206, 211, 213, 214, 215, 216, 222, 228, 232, 244, 247, 264, 278, 284, 285, 303, 305, 306, 326, 338, 341, 342, 345, 349, 352, 375, 377, 384, 386, 392, 395, 399, 402, 404, 406, 414, 429, 440, 442, 443, 445, 448, 454, 460, 461, 462, 484, 488, 493, 494, 496, 501, 502, 509 and 512 in the amino acid sequence shown in SEQ ID NO:1.

4. The MDC variant of any one of items 1 to 3, wherein said variant furthermore shows at least one modification at positions 3, 4, 5, 6, 7, 8, 9, 10, 11, 14, 15, 25, 30, 34, 40, 43, 57, 60, 65, 67, 69, 70, 71, 72, 80, 84, 85, 86, 87, 90, 91, 99, 101, 102, 103, 105, 106, 108, 111, 117, 119, 120, 126, 132, 141, 146, 149, 154, 159, 160, 162, 175, 176, 187, 189, 193, 206, 211, 213, 214, 215, 216, 222, 228, 232, 244, 247, 264, 278, 284, 285, 303, 305, 306, 326, 338, 341, 342, 345, 349, 352, 375, 377, 384, 386, 392, 395, 399, 402, 404, 406, 414, 429, 440, 442, 443, 445, 448, 454, 460, 461, 462, 484, 488, 493, 494, 496, 501, 502, 509 and 512 in the amino acid sequence shown in SEQ ID NO:1 is an MDC variant, wherein (1) an amino acid residue at position 3 in the amino acid sequence shown in SEQ ID NO:1 or at a position corresponding to this position, is deleted or substituted with alanine, glutamic acid, glycine, lysine, proline, tryptophan, cysteine, aspartic acid or tyrosine; and/or (2) an amino acid residue at position 4 in the amino acid sequence shown in SEQ ID NO:1 or at a position corresponding to this position, is deleted or substituted with glutamic acid, leucine, methionine, alanine, serine or asparagine; and/or (3) an amino acid residue at position 5 in the amino acid sequence shown in SEQ ID NO:1 or at a position corresponding to this position, is deleted or substituted with serine; and/or (4) an amino acid residue at position 6 in the amino acid sequence shown in SEQ ID NO:1 or at a position corresponding to this position, is deleted or substituted with proline; and/or (5) an amino acid residue at position 7 in the amino acid sequence shown in SEQ ID NO:1 or at a position corresponding to this position, is deleted or substituted with arginine; and/or (6) an amino acid residue at position 8 in the amino acid sequence shown in SEQ ID NO:1 or at a position corresponding to this position, is deleted or substituted with asparagine; and/or (7) an amino acid residue at position 9 in the amino acid sequence shown in SEQ ID NO:1 or at a position corresponding to this position, is deleted or substituted with histidine, proline or tyrosine; and/or (8) an amino acid residue at position 10 in the amino acid sequence shown in SEQ ID NO:1 or at a position corresponding to this position, is deleted or substituted with histidine, phenylalanine, lysine, proline, threonine or leucine; and/or (9) an amino acid residue at position 11 in the amino acid sequence shown in SEQ ID NO:1 or at a position corresponding to this position, is deleted or substituted with leucine, tyrosine or proline; and/or

(10) an amino acid residue at position 14 in the amino acid sequence shown in SEQ ID NO:1 or at a position corresponding to this position, is deleted or substituted with aspartic acid; and/or

(11) an amino acid residue at position 15 in the amino acid sequence shown in SEQ ID NO:1 or at a position corresponding to this position, is deleted or substituted with threonine; and/or

(12) an amino acid residue at position 25 in the amino acid sequence shown in SEQ ID NO:1 or at a position corresponding to this position, is deleted or substituted with asparagine, serine or tryptophan; and/or

(13) an amino acid residue at position 30 in the amino acid sequence shown in SEQ ID NO:1 or at a position corresponding to this position, is deleted or substituted with glycine, histidine or arginine; and/or

(14) an amino acid residue at position 34 in the amino acid sequence shown in SEQ ID NO:1 or at a position corresponding to this position, is deleted or substituted with alanine or isoleucine; and/or

(15) an amino acid residue at position 40 in the amino acid sequence shown in SEQ ID NO:1 or at a position corresponding to this position, is deleted or substituted with isoleucine or methionine; and/or

(16) an amino acid residue at position 43 in the amino acid sequence shown in SEQ ID NO:1 or at a position corresponding to this position, is deleted or substituted with arginine; and/or

(17) an amino acid residue at position 57 in the amino acid sequence shown in SEQ ID NO:1 or at a position corresponding to this position, is deleted or substituted with asparagine; and/or

(18) an amino acid residue at position 60 in the amino acid sequence shown in SEQ ID NO:1 or at a position corresponding to this position, is deleted or substituted with valine; and/or

(19) an amino acid residue at position 65 in the amino acid sequence shown in SEQ ID NO:1 or at a position corresponding to this position, is deleted or substituted with leucine or tryptophan; and/or

(20) an amino acid residue at position 67 in the amino acid sequence shown in SEQ ID NO:1 or at a position corresponding to this position, is deleted or substituted with arginine or valine; and/or

(21) an amino acid residue at position 69 in the amino acid sequence shown in SEQ ID NO:1 or at a position corresponding to this position, is deleted or substituted with asparagine; and/or

(22) an amino acid residue at position 70 in the amino acid sequence shown in SEQ ID NO:1 or at a position corresponding to this position, is deleted or substituted with isoleucine or leucine; and/or

(23) an amino acid residue at position 71 in the amino acid sequence shown in SEQ ID NO:1 or at a position corresponding to this position, is deleted or substituted with glycine; and/or

(24) an amino acid residue at position 72 in the amino acid sequence shown in SEQ ID NO:1 or at a position corresponding to this position, is deleted or substituted with arginine; and/or

(25) an amino acid residue at position 80 in the amino acid sequence shown in SEQ ID NO:1 or at a position corresponding to this position, is deleted or substituted with leucine; and/or

(26) an amino acid residue at position 84 in the amino acid sequence shown in SEQ ID NO:1 or at a position corresponding to this position, is deleted or substituted with cysteine; and/or

(27) an amino acid residue at position 85 in the amino acid sequence shown in SEQ ID NO:1 or at a position corresponding to this position, is deleted or substituted with alanine or threonine; and/or

(28) an amino acid residue at position 86 in the amino acid sequence shown in SEQ ID NO:1 or at a position corresponding to this position, is deleted or substituted with asparagine or isoleucine; and/or
(29) an amino acid residue at position 87 in the amino acid sequence shown in SEQ ID NO:1 or at a position corresponding to this position, is deleted or substituted with alanine, cysteine, phenylalanine, isoleucine, leucine, methionine, valine or tryptophan; and/or
(30) an amino acid residue at position 90 in the amino acid sequence shown in SEQ ID NO:1 or at a position corresponding to this position, is deleted or substituted with leucine; and/or
(31) an amino acid residue at position 91 in the amino acid sequence shown in SEQ ID NO:1 or at a position corresponding to this position, is deleted or substituted with leucine; and/or
(32) an amino acid residue at position 99 in the amino acid sequence shown in SEQ ID NO:1 or at a position corresponding to this position, is deleted or substituted with asparagine or proline; and/or
(33) an amino acid residue at position 101 in the amino acid sequence shown in SEQ ID NO:1 or at a position corresponding to this position, is deleted or substituted with isoleucine or leucine; and/or
(34) an amino acid residue at position 102 in the amino acid sequence shown in SEQ ID NO:1 or at a position corresponding to this position, is deleted or substituted with leucine; and/or
(35) an amino acid residue at position 103 in the amino acid sequence shown in SEQ ID NO:1 or at a position corresponding to this position, is deleted or substituted with isoleucine, leucine or methionine; and/or
(36) an amino acid residue at position 105 in the amino acid sequence shown in SEQ ID NO:1 or at a position corresponding to this position, is deleted or substituted with phenylalanine, leucine or tryptophan; and/or
(37) an amino acid residue at position 106 in the amino acid sequence shown in SEQ ID NO:1 or at a position corresponding to this position, is deleted or substituted with threonine; and/or
(38) an amino acid residue at position 108 in the amino acid sequence shown in SEQ ID NO:1 or at a position corresponding to this position, is deleted or substituted with lysine, arginine or tryptophan; and/or
(39) an amino acid residue at position 111 in the amino acid sequence shown in SEQ ID NO:1 or at a position corresponding to this position, is deleted or substituted with cysteine; and/or
(40) an amino acid residue at position 117 in the amino acid sequence shown in SEQ ID NO:1 or at a position corresponding to this position, is deleted or substituted with alanine; and/or
(41) an amino acid residue at position 120 in the amino acid sequence shown in SEQ ID NO:1 or at a position corresponding to this position, is deleted or substituted with serine or lysine; and/or
(42) an amino acid residue at position 119 in the amino acid sequence shown in SEQ ID NO:1 or at a position corresponding to this position, is deleted or substituted with threonine; and/or
(43) an amino acid residue at position 126 in the amino acid sequence shown in SEQ ID NO:1 or at a position corresponding to this position, is deleted or substituted with proline; and/or
(44) an amino acid residue at position 132 in the amino acid sequence shown in SEQ ID NO:1 or at a position corresponding to this position, is deleted or substituted with cysteine; and/or
(45) an amino acid residue at position 141 in the amino acid sequence shown in SEQ ID NO:1 or at a position corresponding to this position, is deleted or substituted with aspartic acid; and/or
(46) an amino acid residue at position 146 in the amino acid sequence shown in SEQ ID NO:1 or at a position corresponding to this position, is deleted or substituted with serine; and/or
(47) an amino acid residue at position 149 in the amino acid sequence shown in SEQ ID NO:1 or at a position corresponding to this position, is deleted or substituted with valine or serine; and/or
(48) an amino acid residue at position 154 in the amino acid sequence shown in SEQ ID NO:1 or at a position corresponding to this position, is deleted or substituted with lysine; and/or
(49) an amino acid residue at position 159 in the amino acid sequence shown in SEQ ID NO:1 or at a position corresponding to this position, is deleted or substituted with cysteine; and/or
(50) an amino acid residue at position 160 in the amino acid sequence shown in SEQ ID NO:1 or at a position corresponding to this position, is deleted or substituted with phenylalanine; and/or
(51) an amino acid residue at position 162 in the amino acid sequence shown in SEQ ID NO:1 or at a position corresponding to this position, is deleted or substituted with proline, histidine or asparagine; and/or
(52) an amino acid residue at position 175 in the amino acid sequence shown in SEQ ID NO:1 or at a position corresponding to this position, is deleted or substituted with glycine, lysine, proline, glutamine, serine, threonine or tryptophan; and/or
(53) an amino acid residue at position 176 in the amino acid sequence shown in SEQ ID NO:1 or at a position corresponding to this position, is deleted or substituted with phenylalanine; and/or
(54) an amino acid residue at position 187 in the amino acid sequence shown in SEQ ID NO:1 or at a position corresponding to this position, is deleted or substituted with threonine; and/or
(55) an amino acid residue at position 189 in the amino acid sequence shown in SEQ ID NO:1 or at a position corresponding to this position, is deleted or substituted with isoleucine; and/or
(56) an amino acid residue at position 193 in the amino acid sequence shown in SEQ ID NO:1 or at a position corresponding to this position, is deleted or substituted with isoleucine, threonine or valine; and/or
(57) an amino acid residue at position 206 in the amino acid sequence shown in SEQ ID NO:1 or at a position corresponding to this position, is deleted or substituted with phenylalanine; and/or
(58) an amino acid residue at position 211 in the amino acid sequence shown in SEQ ID NO:1 or at a position corresponding to this position, is deleted or substituted with glutamic acid; and/or
(59) an amino acid residue at position 213 in the amino acid sequence shown in SEQ ID NO:1 or at a position corresponding to this position, is deleted or substituted with proline or leucine; and/or
(60) an amino acid residue at position 214 in the amino acid sequence shown in SEQ ID NO:1 or at a position corresponding to this position, is deleted or substituted with alanine, threonine or valine, histidine, glutamic acid, arginine or phenylalanine; and/or

(61) an amino acid residue at position 215 in the amino acid sequence shown in SEQ ID NO:1 or at a position corresponding to this position, is deleted or substituted with cysteine; and/or
(62) an amino acid residue at position 216 in the amino acid sequence shown in SEQ ID NO:1 or at a position corresponding to this position, is deleted or substituted with asparagine; and/or
(63) an amino acid residue at position 222 in the amino acid sequence shown in SEQ ID NO:1 or at a position corresponding to this position, is deleted or substituted with cysteine; and/or
(64) an amino acid residue at position 228 in the amino acid sequence shown in SEQ ID NO:1 or at a position corresponding to this position, is deleted or substituted with leucine, alanine, proline, threonine or valine; and/or
(65) an amino acid residue at position 232 in the amino acid sequence shown in SEQ ID NO:1 or at a position corresponding to this position, is deleted or substituted with valine; and/or
(66) an amino acid residue at position 244 in the amino acid sequence shown in SEQ ID NO:1 or at a position corresponding to this position, is deleted or substituted with phenylalanine; and/or
(67) an amino acid residue at position 247 in the amino acid sequence shown in SEQ ID NO:1 or at a position corresponding to this position, is deleted or substituted with alanine; and/or
(68) an amino acid residue at position 264 in the amino acid sequence shown in SEQ ID NO:1 or at a position corresponding to this position, is deleted or substituted with aspartic acid; and/or
(69) an amino acid residue at position 278 in the amino acid sequence shown in SEQ ID NO:1 or at a position corresponding to this position, is deleted or substituted with isoleucine; and/or
(70) an amino acid residue at position 284 in the amino acid sequence shown in SEQ ID NO:1 or at a position corresponding to this position, is deleted or substituted with tyrosine or leucine; and/or
(71) an amino acid residue at position 285 in the amino acid sequence shown in SEQ ID NO:1 or at a position corresponding to this position, is deleted or substituted with leucine; and/or
(72) an amino acid residue at position 303 in the amino acid sequence shown in SEQ ID NO:1 or at a position corresponding to this position, is deleted or substituted with serine or proline; and/or
(73) an amino acid residue at position 305 in the amino acid sequence shown in SEQ ID NO:1 or at a position corresponding to this position, is deleted or substituted with alanine or aspartic acid; and/or
(74) an amino acid residue at position 306 in the amino acid sequence shown in SEQ ID NO:1 or at a position corresponding to this position, is deleted or substituted with phenylalanine, arginine or serine; and/or
(75) an amino acid residue at position 326 in the amino acid sequence shown in SEQ ID NO:1 or at a position corresponding to this position, is deleted or substituted with alanine or proline; and/or
(76) an amino acid residue at position 338 in the amino acid sequence shown in SEQ ID NO:1 or at a position corresponding to this position, is deleted or substituted with proline, alanine or serine; and/or
(77) an amino acid residue at position 341 in the amino acid sequence shown in SEQ ID NO:1 or at a position corresponding to this position, is deleted or substituted with isoleucine; and/or
(78) an amino acid residue at position 342 in the amino acid sequence shown in SEQ ID NO:1 or at a position corresponding to this position, is deleted or substituted with glycine; and/or
(79) an amino acid residue at position 345 in the amino acid sequence shown in SEQ ID NO:1 or at a position corresponding to this position, is deleted or substituted with leucine; and/or
(80) an amino acid residue at position 349 in the amino acid sequence shown in SEQ ID NO:1 or at a position corresponding to this position, is deleted or substituted with serine; and/or
(81) an amino acid residue at position 352 in the amino acid sequence shown in SEQ ID NO:1 or at a position corresponding to this position, is deleted or substituted with glycine or leucine; and/or
(82) an amino acid residue at position 375 in the amino acid sequence shown in SEQ ID NO:1 or at a position corresponding to this position, is deleted or substituted with leucine; and/or
(83) an amino acid residue at position 377 in the amino acid sequence shown in SEQ ID NO:1 or at a position corresponding to this position, is deleted or substituted with histidine; and/or
(84) an amino acid residue at position 384 in the amino acid sequence shown in SEQ ID NO:1 or at a position corresponding to this position, is deleted or substituted with tyrosine; and/or
(85) an amino acid residue at position 386 in the amino acid sequence shown in SEQ ID NO:1 or at a position corresponding to this position, is deleted or substituted with asparagine; and/or
(86) an amino acid residue at position 392 in the amino acid sequence shown in SEQ ID NO:1 or at a position corresponding to this position, is deleted or substituted with leucine or alanine; and/or
(87) an amino acid residue at position 395 in the amino acid sequence shown in SEQ ID NO:1 or at a position corresponding to this position, is deleted or substituted with cysteine; and/or
(88) an amino acid residue at position 399 in the amino acid sequence shown in SEQ ID NO:1 or at a position corresponding to this position, is deleted or substituted with arginine or asparagine; and/or
(89) an amino acid residue at position 402 in the amino acid sequence shown in SEQ ID NO:1 or at a position corresponding to this position, is deleted or substituted with valine or histidine; and/or
(90) an amino acid residue at position 404 in the amino acid sequence shown in SEQ ID NO:1 or at a position corresponding to this position, is deleted or substituted with tyrosine or tryptophan; and/or
(91) an amino acid residue at position 406 in the amino acid sequence shown in SEQ ID NO:1 or at a position corresponding to this position, is deleted or substituted with glutamine; and/or
(92) an amino acid residue at position 414 in the amino acid sequence shown in SEQ ID NO:1 or at a position corresponding to this position, is deleted or substituted with asparagine; and/or

(93) an amino acid residue at position 440 in the amino acid sequence shown in SEQ ID NO:1 or at a position corresponding to this position, is deleted or substituted with valine; and/or

(94) an amino acid residue at position 443 in the amino acid sequence shown in SEQ ID NO:1 or at a position corresponding to this position, is deleted or substituted with asparagine; and/or

(95) an amino acid residue at position 448 in the amino acid sequence shown in SEQ ID NO:1 or at a position corresponding to this position, is deleted or substituted with serine, phenylalanine or trypophan; and/or

(96) an amino acid residue at position 454 in the amino acid sequence shown in SEQ ID NO:1 or at a position corresponding to this position, is deleted or substituted with glycine; and/or

(97) an amino acid residue at position 460 in the amino acid sequence shown in SEQ ID NO:1 or at a position corresponding to this position, is deleted or substituted with phenylalanine or proline; and/or

(98) an amino acid residue at position 461 in the amino acid sequence shown in SEQ ID NO:1 or at a position corresponding to this position, is deleted or substituted with valine, asparagine or methionine; and/or

(99) an amino acid residue at position 462 in the amino acid sequence shown in SEQ ID NO:1 or at a position corresponding to this position, is deleted or substituted with asparagine; and/or (100) an amino acid residue at position 484 in the amino acid sequence shown in SEQ ID NO:1 or at a position corresponding to this position, is deleted or substituted with alanine or glycine; and/or (101) an amino acid residue at position 488 in the amino acid sequence shown in SEQ ID NO:1 or at a position corresponding to this position, is deleted or substituted with alanine or asparagine; and/or (102) an amino acid residue at position 493 in the amino acid sequence shown in SEQ ID NO:1 or at a position corresponding to this position, is deleted or substituted with arginine; and/or (103) an amino acid residue at position 494 in the amino acid sequence shown in SEQ ID NO:1 or at a position corresponding to this position, is deleted or substituted with arginine; and/or (104) an amino acid residue at position 496 in the amino acid sequence shown in SEQ ID NO:1 or at a position corresponding to this position, is deleted or substituted with alanine or phenylalaine; and/or (105) an amino acid residue at position 429 in the amino acid sequence shown in SEQ ID NO:1 or at a position corresponding to this position, is deleted or substituted with alanine or serine; and/or (106) an amino acid residue at position 442 in the amino acid sequence shown in SEQ ID NO:1 or at a position corresponding to this position, is deleted or substituted with threonine; and/or (107) an amino acid residue at position 445 in the amino acid sequence shown in SEQ ID NO:1 or at a position corresponding to this position, is deleted or substituted with glutamic acid or proline; and/or (108) an amino acid residue at position 501 in the amino acid sequence shown in SEQ ID NO:1 or at a position corresponding to this position, is deleted or substituted with glutamic acid, methionine, glycine or lysine; and/or (109) an amino acid residue at position 502 in the amino acid sequence shown in SEQ ID NO:1 or at a position corresponding to this position, is deleted or substituted with asparagine; and/or (110) an amino acid residue at position 509 in the amino acid sequence shown in SEQ ID NO:1 or at a position corresponding to this position, is deleted or substituted with leucine; and/or (111) an amino acid residue at position 512 in the amino acid sequence shown in SEQ ID NO:1 or at a position corresponding to this position, is deleted or substituted with glutamic acid, histidine or serine.

5. A nucleic acid molecule encoding the MDC variant of any one of items 1 to 4.
6. A vector comprising the nucleic acid molecule of item 5.
7. A host cell comprising the nucleic acid molecule of item 5 or the vector of item 6.
8. Use of the MDC variant of any one of items 1 to 4 or the host cell of item 7 for the conversion of 3-methylcrotonic acid into isobutene.
9. A method for producing isobutene from 3-methylcrotonic acid by incubating 3-methylcrotonic acid with the MDC variant of any one of items 1 to 4.
10. The method of item 9, wherein the enzymatic conversion is carried out in vitro.
11. A composition comprising a variant of an MDC of any one of items 1 to 4, the nucleic acid molecule of item 5, the vector of item 6 or the host cell of item 7.
12. A composition comprising a variant of an MDC of any one of items 1 to 4, the nucleic acid molecule of item 5, the vector of item 6 or the host cell of item 7 and 3-methylcrotonic acid.

Thus, in a first aspect of the first part, the present invention provides a variant of a 3-methylcrotonic acid decarboxylase (MDC) showing an improved activity in converting 3-methylcrotonic acid into isobutene over the corresponding MDC from which it is derived.

An improved enzyme variant or an enzyme variant capable of catalyzing a reaction with increased activity is defined as an enzyme variant which differs from the wild-type enzyme and which catalyzes the conversion of 3-methylcrotonic acid into isobutene so that the specific activity of the enzyme variant is higher than the specific activity of the wildtype enzyme for at least one given concentration of a 3-methylcrotonic acid (preferably any 3-methylcrotonic acid higher than 0 M and up to 1 M). A specific activity is defined as the number of moles of substrate converted to moles of product by unit of time by mole of enzyme. $K_{cat}$ (turnover number) is the specific activity at saturating concentration of substrate.

In particular, in accordance with this first aspect of the first part, the present invention provides enzymes which are capable of converting 3-methylcrotonic acid into isobutene with a turnover rate of at least $1 \times 10^{-3}$ $s^{-1}$ of 3-methylcrotonic acid into isobutene. Such enzymes can be provided by effecting mutations at specific positions in an 3-methylcrotonic acid decarboxylase (MDC) and the variants obtained by effecting such mutations show an improved activity in catalyzing the conversion of 3-methylcrotonic acid into isobutene. In a preferred embodiment, the enzyme is capable of converting 3-methylcrotonic acid into isobutene with a turnover rate of at least $2 \times 10^{-3}$ $s^{-1}$ of 3-methylcrotonic acid into isobutene and in a particularly preferred embodiment of at least $4 \times 10^{-3}$ $s^{-1}$. In a most preferred embodiment, the enzyme has a turnover rate of at least $10 \times 10^{-3}$ $s^{-1}$ or at least 1 $s^{-1}$, or at least 10 $s^{-1}$ and even more preferably of at least 100 $s^{-1}$ of 3-methylcrotonic acid into isobutene. The corresponding wild-type enzyme has a turnover rate of about 1×10⁻³ s⁻¹ of 3-methylcrotonic acid into isobutene.

In the context of the first part of the present invention, an "improved activity" means that the activity of the enzyme in question is at least 10%, preferably at least 20%, more preferably at least 30% or 50%, even more preferably at least 70% or 80% and particularly preferred at least 90% or 100% higher than that of the enzyme from which the variant is derived, preferably higher than that of the enzyme represented by SEQ ID NO:1. In even more preferred embodiments the improved activity may be at least 150%, at least 200%, at least 300%, at least 750% or at least 1000% higher than that of the corresponding enzyme from which the variant is derived, preferably higher than that of the enzyme represented by SEQ ID NO:1. In a particularly preferred embodiment, the activity is measured by using an assay with purified enzyme and chemically synthesized substrates, as described below. The improved activity of a variant can be measured as a higher isobutene production in a given time under defined conditions, compared with the parent enzyme. This improved activity can result from a higher turnover number, e.g. a higher kcat value. It can also result from a lower Km value. It can also result from a higher kcat/Km value. Finally, it can result from a higher solubility, or stability of the enzyme. The degree of improvement can be measured as the improvement in isobutene production. The degree of improvement can also be measured in terms of kcat improvement, of kcat/Km improvement, or in terms of Km decrease, in terms of soluble protein production or in terms of protein stability.

In another embodiment, the enzyme variants which the present invention provides are capable of converting 3-methylcrotonic acid into isobutene with an activity which is at least 1.25 times as high compared to the turnover rate of the corresponding wild type enzyme having the amino acid sequence as shown in SEQ ID NO: 1. In a more preferred embodiment, the enzyme variants which are capable of converting 3-methylcrotonic acid into isobutene have a turnover rate (i.e., a $k_{cat}$-value) which is at least 2 times, at least 3 times, at least 5 times or even at least 10 times as high compared to the turnover rate of the corresponding wild type enzyme having the amino acid sequence as shown in SEQ ID NO: 1. In even more preferred embodiments, the turnover rate is at least 100 times or even at least 500 times as high compared to that of the corresponding wild type enzyme having the amino acid sequence as shown in SEQ ID NO:1.

Such enzyme variants are obtained by effecting mutations at specific positions in the amino acid sequence of an MDC and the variants obtained by effecting such mutations show an improved activity in catalyzing the conversion of 3-methylcrotonic acid into isobutene. The activity of an enzyme capable of converting 3-methylcrotonic acid into isobutene may be determined by methods known to the person skilled in the art. In one embodiment, this activity is determined as described in the Examples appended hereto. In a particular embodiment this activity can be measured by incubating the enzyme, preferably a cell lysate containing the overexpressed recombinant protein, in vitro. Alternatively, a purified enzyme can be used or an in vivo assay.

More specifically, the activity of the MDC variants for the conversion of 3-methylcrotonic acid into isobutene can be assessed by an enzymatic in vitro assay based on purified proteins and on the detection of isobutene by gas chromatography. The turnover rate of the enzyme to be assessed may be examined as outlined in the following: Michaelis-Menten $k_{cat}$ and $K_m$ steady state kinetic constants for the reaction of conversion of 3-methylcrotonic acid into isobutene may be determined using the following protocol:

The enzymatic assay for quantifying the conversion of 3-methylcrotonic acid into isobutene is carried out in a 2 ml glass vial at 30° C. in a 50 mM potassium phosphate pH 7.5 buffer; 20 mM NaCl, 3 mM MgCl₂, 5 mM DTT, 0.5 mg/ml of a purified enzyme of the MDC variant to be tested, 100 µl of a lysate containing a FMN prenyltransferase (i.e., a Flavin prenyltransferase UbiX protein from E. coli expressed and prepared as outlined further below) as well as different concentrations of the substrate 3-methylcrotonic acid ranging from 0 to 128 mM. A control without an MDC enzyme is performed in parallel. After 60 minutes, the reaction is stopped by incubating at 80° C. for 2 min. The rate of isobutene production is quantified by gas chromatography as follows.

The isobutene formed in the reaction headspace is analysed by gas chromatography (GC) equipped with a flame ionization detector (FID). For the GC headspace analysis, one ml of the headspace gas is separated in a Bruker GC-450 system equipped with a GS-alumina column (30 m×0.53 mm) (Agilent) using isothermal mode at 130° C. Nitrogen is used as carrier gas with a flow rate of 6 ml/min. The enzymatic reaction product is identified by comparison with an isobutene standard. Under these GC conditions, the retention time of isobutene is 2.42 min. From the rate of isobutene production, and using the Michaelis-Menten approximation, the enzyme catalytic efficiency can then be computed. The production rates of isobutene (mole of PV/mole enzyme/sec) are plotted as a function of the concentration of 3-methylcrotonic acid and the curve is fitted using the Michaelis Menten equation ($V=(V_{max}*(substrate))/(K_m+(substrate))$) to extract the $k_{cat}$ (s⁻¹) and the $K_m$ values (mM).

The MDC variant to be tested can be provided according to the following protocol: The MDC to be tested is subcloned into the pETDuet™-1 co-expression vector. The vector contains a stretch of 6 histidine codons after the methionine initiation codon of the ferulic acid decarboxylases in order to provide an affinity tag for purification.

Competent E. coli BL21 (DE3) cells (Novagen) are transformed with this vector according to standard heat shock procedures and plated out onto LB-agar plates supplemented with the appropriate antibiotic. Cells are grown overnight at 30° C. until individual colonies reach the desired size. A single colony is then picked and individually transferred into 5 ml of liquid LB medium supplemented with the appropriate antibiotic. Cell growth is carried out with shaking for 16 hours at 30° C. The LB culture of the transformed cells is used to inoculate a culture using ZYM-5052 auto-induction medium (Studier F W, Prot. Exp. Pur. 41, (2005), 207-234) and the culture is grown with shaking (160 rpm) at 30° C. during 24 h. The cells are collected by centrifugation at 4° C., 10,000 rpm for 20 min and the pellets are frozen and stored at −80° C. The pellets containing the overexpressed protein of a 500 ml of cultured cells is thawn on ice and resuspended in 15 ml of 50 mM potassium phosphate buffer containing 200 mM NaCl, 10 mM MgCl₂, 10 mM imidazole and 1 mM DTT. Twenty microliters of lysonase (Novagen) is added and the cells are incubated for 10 minutes at room temperature and then returned to ice for 20 minutes. Cell lysis is then completed by sonication for 2×15 seconds.

The bacterial extracts are then clarified by centrifugation at 4° C., 4000 rpm for 40 min. The clarified bacterial lysates are loaded onto a PROTINO-2000 Ni-TED column (Macherey-Nagel) allowing adsorption of 6-His tagged proteins.

Columns are washed and the enzymes of interest are eluted with 6 ml of 50 mM potassium phosphate buffer containing 250 mM imidazole. Eluates are then concentrated, desalted on a Amicon Ultra-4 10 kDa filter unit (Millipore) and enzymes are resuspended in 50 mM potassium phosphate buffer containing 1 mM DTT and 20 mM NaCl. Protein concentrations are determined by direct UV 280 nm measurement on a NanoDrop 1000 spectrophotometer (Thermo Scientific) or by a Bradford assay (BioRad).

Correspondingly, the cDNA of a Flavin prenyltransferase UbiX protein from *E. coli* is cloned and recombinantly expressed, purified and quantified.

As described in the above enzymatic in vitro assay for determining the activity of the MDC variants of the present invention, UbiX does not necessarily have to be provided in a recombinantly expressed and subsequently purified manner. Therefore, UbiX may alternatively also be provided in the form of a UbiX-containing cell lysate without purifying it as described in the following.

The Flavin prenyltransferase UbiX protein from *E. coli* is cloned in the vector pCAN. The Flavin prenyltransferase UbiX protein from *E. coli* was purchased from NAIST (Nara Institute of Science and Technology, Japan, ASKA collection).

Competent *E. coli* BL21 (DE3) cells (Novagen) are transformed with this vector according to standard heat shock procedures and plated out onto LB-agar plates supplemented with the appropriate antibiotic. Cells are grown overnight at 30° C. until individual colonies reach the desired size. A single colony is then picked and individually transferred into 5 ml of liquid LB medium supplemented with the appropriate antibiotic. Cell growth is carried out with shaking for 16 hours at 30° C. The LB culture of the transformed cells is used to inoculate a ZYM-5052 auto-induction medium (Studier F W, Prot. Exp. Pur. 41, (2005), 207-234) and the culture is grown with shaking (160 rpm) using at 30° C. during 24 h. The cells are collected by centrifugation at 4° C., 10,000 rpm for 20 min and the pellets are stored at −80° C. Pellets from 500 ml of cultured cells are thawed on ice and resuspended in 15 ml of 50 mM potassium phosphate buffer containing 200 mM NaCl, 10 mM $MgCl_2$, 10 mM imidazole and 1 mM DTT. Twenty microliters of lysonase (Novagen) is added. Cells are incubated 10 minutes at room temperature and then returned to ice for 20 minutes. Cell lysis is completed by sonication for 2×15 seconds. The cellular lysate containing the UbiX protein is kept on ice.

Alternatively to the above in vitro assays, the activity of the MDC variants for the conversion of 3-methylcrotonic acid into isobutene can be assessed by an in vivo testing. This coupled in vivo assay is based on the use of a bacterial strain transformed with an expression vector that contains the coding sequences leading to the production of the MDC variant and the Flavin prenyltransferase UbiX protein from *E. coli* (SEQ ID NO:2). Thus, the MDC variant to be tested is subcloned into a pETDuet™-1 co-expression vector (Novagen) in addition to the cDNA of the Flavin prenyltransferase UbiX protein from *E. coli*.

The MDC variant of the present invention to be tested is used to catalyze the decarboxylation reaction of 3-methylcrotonic acid into isobutene while the Flavin prenyltransferase UbiX protein from *E. coli* provides the modified flavin cofactor. Thus, in the coupled in vivo assay, a bacterial strain is used which is transformed with the above expression vector.

The transformed strain is first plated out onto LB-agar plates supplemented with the appropriate antibiotic. Cells are then grown overnight at 30° C. until individual colonies reach the desired size. Single colonies are then picked and individually transferred into either 50 or 500 µL of liquid LB medium supplemented with the appropriate antibiotic. Cell growth is carried out with shaking for 20 hours at 30° C. The LB cultures are used to inoculate 300 µL in 384 deepwell microplates or 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the two types of recombinant enzymes. The cell pellet containing these overexpressed recombinant enzymes is then resuspended in 40 µL of minimum medium (pH 7.5, Phosphate 100 mM, Glucose 10 g·$L^{-1}$, $MgSO_4$ 1 mM) supplemented with 10 mM 3-methylcrotonic acid in 384 deepwell microplates or in 400 µL of minimum medium (pH 7.5, Phosphate 100 mM, Glucose 10 g·$L^{-1}$, $MgSO_4$ 1 mM) supplemented with 10 mM 3-methylcrotonic acid in 96 deepwell microplates and incubated for a further 2 or 4 hours in a shaking incubator at 37° C., 700 rpm. During this step, the MDC variant catalyses the decarboxylation of 3-methylcrotonic acid into isobutene. After 5 min inactivation at 80° C., the isobutene produced is quantified by gas chromatography as follows. 100 µL of headspace gases from each enzymatic reaction are injected in a Brucker GC-450 system equipped with a Flame Ionization Detector (FID). Compounds present in samples are separated by chromatography using a RTX-1 column at 100° C. with a 1 mL/min constant flow of nitrogen as carrier gas. Upon injection, peak areas of isobutene are calculated.

By providing the above described enzyme variant, the first part of the present invention allows to dramatically increase the production efficiency of isobutene from 3-methylcrotonic acid.

The term "3-methylcrotonic acid decarboxylase (MDC)" refers to an enzyme which can catalyze the decarboxylation of 3-methylcrotonic acid into isobutene. A decarboxylation is a chemical reaction that removes a carboxyl group and releases carbon dioxide. This activity can be measured by methods known in the art and as described above. In a preferred embodiment, the MDC is a Ferulic Acid Decarboxylase (FDC) or is derived from such an enzyme. FDCs belong to the enzyme class EC 4.1.1.-. As mentioned above, it has originally been described that an FDC in association with a modified FMN (prenylated-FMN) is capable of catalyzing an α,β-unsaturated decarboxylation via a 1,3-dipolar cyclo-addition and, more specifically, capable of catalyzing the decarboxylation of 3-methylcrotonic acid into isobutene. Thus, in the context of the present invention, the term FDC relates to enzymes capable of catalyzing the decarboxylation of 3-methylcrotonic acid into isobutene, preferably when provided with a prenylated FMN.

FDC enzymes have, e.g., been described in *Saccharomyces cerevisiae*, *Enterobacter* sp., *Bacillus pumilus*, *Aspergillus niger* or *Candida dubliniensis*. Hence, in preferred embodiments, the FDC is derived from *Saccharomyces cerevisiae* (Uniprot accession number Q03034), *Enterobacter* sp. (Uniprot accession number V3P7U0), *Bacillus pumilus* (Uniprot accession number Q45361), *Aspergillus niger* (Uniprot accession number A2R0P7) or *Candida dubliniensis* (Uniprot accession number B9WJ66). In more preferred embodiments, the FDC is a 3-polyprenyl-4-hydroxybenzoate decarboxylase (UbiD). 3-polyprenyl-4-hydroxybenzoate decarboxylases have, e.g., been described in *Hypocrea atroviridis*, *Sphaerulina musiva*, *Penecillinum requeforti*, *Fusarium oxysporum* f. sp. *lycopersici*, *Saccharomyces kudriavzevii*, *Saccharomyces cerevisiae*, *Aspergillus*

*parasiticus, Candida albicans, Grosmannia clavigera, Escherichia coli, Bacillus megaterium, Methanothermobacter* sp. CaT2 or *Mycobacterium chelonae* 1518. Hence, in more preferred embodiments, the FDC enzyme variant capable of catalyzing the decarboxylation of 3-methylcrotonic acid into isobutene is derived from a 3-polyprenyl-4-hydroxybenzoate decarboxylase (UbiD) from *Hypocrea atroviridis* (UniProt Accession number G9NLP8), *Sphaerulina musiva* (UniProt Accession number M3DF95), *Penecillinum requeforti* (UniProt Accession number W6QKP7), *Fusarium oxysporum* f. sp. *lycopersici* (UniProt Accession number W9LTH3), *Saccharomyces kudriavzevii* (UniProt Accession number J8TRN5), *Saccaromyces cerevisiae, Aspergillus parasiticus, Candida albicans, Grosmannia clavigera, Escherichia coli* (Uniprot accession number POAAB4), *Bacillus megaterium* (Uniprot accession number D5DTL4), *Methanothermobacter* sp. CaT2 (Uniprot accession number T2GKK5) or *Mycobacterium chelonae* 1518 (Uniprot accession number X8EX86). Preferably, the MDC is an enzyme which is associated with and/or depends on an FMN prenyl transferase. As mentioned above, the enzymatic conversion of 3-methylcrotonic acid into isobutene utilizing an FMN-dependent decarboxylase is preferably associated with an FMN prenyl transferase and relies on a reaction of two consecutive steps catalyzed by the two enzymes, i.e., the FMN-dependent decarboxylase (catalyzing the actual decarboxylation of 3-methylcrotonic acid into isobutene) with an associated FMN prenyl transferase which provides the modified flavin cofactor. The flavin cofactor may preferably be FMN or FAD. FMN (flavin mononucleotide; also termed riboflavin-5'-phosphate) is a biomolecule produced from riboflavin (vitamin B2) by the enzyme riboflavin kinase and functions as prosthetic group of various reactions. FAD (flavin adenine dinucleotide) is a redox cofactor, more specifically a prosthetic group, involved in several important reactions in metabolism. The FMN prenyl transferases which may be associated with the MDC variants of the present invention are described in more detail further below.

The first part of the present invention provides now improved variants of enzymes which are capable of converting 3-methylcrotonic acid into isobutene. The inventors used as a model enzyme the FDC of *Hypocrea atroviridis* shown in SEQ ID NO: 1 and could show that it is possible to provide variants of this enzyme which show increased activity with respect to the conversion of 3-methylcrotonic acid into isobutene.

The model enzyme, i.e., the FDC of *Hypocrea atroviridis*, as used by the inventors has the amino acid sequence as shown in SEQ ID NO: 1.

In one preferred embodiment of the first part of the present invention, the variants of the present invention are characterized by the feature that they are derived from an MDC, more preferably from an MDC having the amino acid sequence shown in SEQ ID NO:1 or a highly related sequence (at least 60% identical) and in which mutations are effected at one or more of the above indicated positions and by the feature that they show the ability to convert 3-methylcrotonic acid into isobutene and that they can do this with an improved activity. In a preferred embodiment the variant according to the present invention is derived from a sequence which shows at least 70%, more preferably at least 80% sequence identity to SEQ ID NO:1 and in which one or more substitutions and/or deletions and/or insertions at the positions indicated herein have been effected.

However, the teaching of the present invention is not restricted to the MDC enzyme of *Hypocrea atroviridis* shown in SEQ ID NO: 1 which had been used as a model enzyme but can be extended to MDC enzymes from other organisms or to enzymes which are structurally related to SEQ ID NO:1 such as, e.g., truncated variants of the enzyme. Thus, the present invention also relates to variants of MDCs which are structurally related to the *Hypocrea atroviridis* sequence (SEQ ID NO: 1) and which show one or more substitutions and/or deletions and/or insertions at positions corresponding to any of the positions as indicated herein. The term "structurally related" refers to MDCs which show a sequence identity of at least n % to the sequence shown in SEQ ID NO: 1 with n being an integer between 60 and 100, preferably 60, 61, 62, 63, 64, 65, 66, 67, 68, 69, 70, 71, 72, 73, 74, 75, 80, 85, 90, 91, 92, 93, 94, 95, 96, 97, 98 or 99. In a preferred embodiment the structurally related MDC stems from a fungus, more preferably from an organism of the division of Ascomyceta, even more preferably from an organism of the class of Sordariomycetes, the order of Hypocreales, the family of Hypocreaceae or the genus *Hypocrea*, most preferably of the genus *Hypocrea*.

Thus, in one embodiment, the variant of an MDC according to the first part of the present invention has or preferably is derived from a sequence which is at least n % identical to SEQ ID NO: 1 with n being an integer between 60 and 100, preferably 60, 61, 62, 63, 64, 65, 66, 67, 68, 69, 70, 71, 72, 73, 74, 75, 80, 85, 90, 91, 92, 93, 94, 95, 96, 97, 98 or 99, and it has (a) substitution(s) and/or (a) deletion and/or (an) insertion(s) at a position as indicated herein. When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap. Preferably, the degree of identity is calculated over the complete length of the sequence.

Amino acid residues located at a position corresponding to a position as indicated herein in the amino acid sequence shown in SEQ ID NO:1 can be identified by the skilled person by methods known in the art. For example, such amino acid residues can be identified by aligning the sequence in question with the sequence shown in SEQ ID NO:1 and by identifying the positions which correspond to the above or below indicated positions of SEQ ID NO: 1.

The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

When the amino acid sequences of MDCs are aligned by means of such a method, regardless of insertions or deletions that occur in the amino acid sequences, the positions of the corresponding amino acid residues can be determined in each of the MDCs.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagine etc.). Naturally occurring modifications also encompass the change in the chemical structure by citrullination, carbamylation and disulphide bond formation between cysteine residues; attachment of co-factors (FMN or FAD that can be covalently attached) or the attachement of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi: 101016/jchembiol.2009.03.001).

In the context of the present invention, "deleted" or "deletion" means that the amino acid at the corresponding position is deleted.

In the context of the present invention, "inserted" or "insertion" means that at the respective position one or two, preferably one amino acid residue is inserted, preferably in front of the indicated position.

In a second aspect of the first part, the present invention provides a variant of a 3-methylcrotonic acid decarboxylase (MDC) showing an improved activity in converting 3-methylcrotonic acid into isobutene over the corresponding MDC from which it is derived, wherein the MDC variant is characterized in that it shows one or more substitutions, deletions and/or insertions in comparison to the corresponding sequence from which it is derived and wherein these substitutions, deletions and/or insertions occur at one or more of the positions corresponding to positions 405, 2, 12, 13, 29, 31, 33, 35, 89, 114, 195, 197, 221, 293, 337, 351, 376, 381, 388, 420, 422, 435, 436, 439, 441, 447, 449, 500, 506 and 511 in the amino acid sequence shown in SEQ ID NO: 1.

The present invention relates in a preferred embodiment to an MDC variant having an amino acid sequence as shown in SEQ ID NO:1 or an amino acid sequence having at least 60% sequence identity to SEQ ID NO:1, in which one or more amino acid residues at a position selected from the group consisting of positions 405, 2, 12, 13, 29, 31, 33, 35, 89, 114, 195, 197, 221, 293, 337, 351, 376, 381, 388, 420, 422, 435, 436, 439, 441, 447, 449, 500, 506 and 511 in the amino acid sequence shown in SEQ ID NO:1 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

According to one embodiment, the first part of the present invention relates to any of the above-described MDC variants having an amino acid sequence as shown in SEQ ID NO: 1 or an amino acid sequence having at least 60% sequence identity to SEQ ID NO: 1 in which (1) an amino acid residue at position 2 in the amino acid sequence shown in SEQ ID NO:1 or at a position corresponding to this position, is deleted or substituted with alanine, aspartic acid, phenylalanine, lysine, leucine, asparagine, glutamine or valine; and/or (2) an amino acid residue at position 12 in the amino acid sequence shown in SEQ ID NO:1 or at a position corresponding to this position, is deleted or substituted with serine, alanine or asparagine; and/or (3) an amino acid residue at position 13 in the amino acid sequence shown in SEQ ID NO:1 or at a position corresponding to this position, is deleted or substituted with histidine, isoleucine, asparagine, serine, valine or tyrosine; and/or (4) an amino acid residue at position 29 in the amino acid sequence shown in SEQ ID NO:1 or at a position corresponding to this position, is deleted or substituted with asparagine, histidine or serine; and/or (5) an amino acid residue at position 31 in the amino acid sequence shown in SEQ ID NO:1 or at a position corresponding to this position, is deleted or substituted with glutamic acid or glycine; and/or (6) an amino acid residue at position 33 in the amino acid sequence shown in SEQ ID NO:1 or at a position corresponding to this position, is deleted or substituted with isoleucine; and/or (7) an amino acid residue at position 35 in the amino acid sequence shown in SEQ ID NO:1 or at a position corresponding to this position, is deleted or substituted with methionine, serine or threonine; and/or (8) an amino acid residue at position 89 in the amino acid sequence shown in SEQ ID NO:1 or at a position corresponding to this position, is deleted or substituted with serine or phenylalanine; and/or (9) an amino acid residue at position 114 in the amino acid sequence shown in SEQ ID NO:1 or at a position corresponding to this position, is deleted or substituted with serine; and/or

(10) an amino acid residue at position 195 in the amino acid sequence shown in SEQ ID NO:1 or at a position corresponding to this position, is deleted or substituted with methionine, cysteine, phenylalanine, isoleucine, valine, tryptophan or tyrosine; and/or
(11) an amino acid residue at position 197 in the amino acid sequence shown in SEQ ID NO:1 or at a position corresponding to this position, is deleted or substituted with phenylalanine or methionine; and/or
(12) an amino acid residue at position 221 in the amino acid sequence shown in SEQ ID NO:1 or at a position corresponding to this position, is deleted or substituted with cysteine; and/or
(13) an amino acid residue at position 293 in the amino acid sequence shown in SEQ ID NO:1 or at a position corresponding to this position, is deleted or substituted with leucine; and/or
(14) an amino acid residue at position 337 in the amino acid sequence shown in SEQ ID NO:1 or at a position corresponding to this position, is deleted or substituted with methionine or leucine; and/or
(15) an amino acid residue at position 351 in the amino acid sequence shown in SEQ ID NO:1 or at a position corresponding to this position, is deleted or substituted with arginine, asparagine, alanine, valine or glycine; and/or
(16) an amino acid residue at position 376 in the amino acid sequence shown in SEQ ID NO:1 or at a position corresponding to this position, is deleted or substituted with isoleucine; and/or
(17) an amino acid residue at position 381 in the amino acid sequence shown in SEQ ID NO:1 or at a position corresponding to this position, is deleted or substituted with arginine; and/or
(18) an amino acid residue at position 388 in the amino acid sequence shown in SEQ ID NO:1 or at a position corresponding to this position, is deleted or substituted with glutamic acid; and/or
(19) an amino acid residue at position 405 in the amino acid sequence shown in SEQ ID NO:1 or at a position corresponding to this position, is deleted or substituted with phenylalanine, leucine, methionine, proline or glutamine; and/or
(20) an amino acid residue at position 420 in the amino acid sequence shown in SEQ ID NO:1 or at a position corresponding to this position, is deleted or substituted with leucine; and/or
(21) an amino acid residue at position 422 in the amino acid sequence shown in SEQ ID NO:1 or at a position corresponding to this position, is deleted or substituted with methionine; and/or
(22) an amino acid residue at position 435 in the amino acid sequence shown in SEQ ID NO:1 or at a position corresponding to this position, is deleted or substituted with methionine; and/or
(23) an amino acid residue at position 436 in the amino acid sequence shown in SEQ ID NO:1 or at a position corresponding to this position, is deleted or substituted with asparagine; and/or
(24) an amino acid residue at position 439 in the amino acid sequence shown in SEQ ID NO:1 or at a position corresponding to this position, is deleted or substituted with leucine; and/or
(25) an amino acid residue at position 441 in the amino acid sequence shown in SEQ ID NO:1 or at a position corresponding to this position, is deleted or substituted with tyrosine; and/or
(26) an amino acid residue at position 447 in the amino acid sequence shown in SEQ ID NO:1 or at a position corresponding to this position, is deleted or substituted with tryptophan, methionine or tyrosine; and/or
(27) an amino acid residue at position 449 in the amino acid sequence shown in SEQ ID NO:1 or at a position corresponding to this position, is deleted or substituted with isoleucine, methionine or valine; and/or
(28) an amino acid residue at position 500 in the amino acid sequence shown in SEQ ID NO:1 or at a position corresponding to this position, is deleted or substituted with alanine; and/or
(29) an amino acid residue at position 506 in the amino acid sequence shown in SEQ ID NO:1 or at a position corresponding to this position, is deleted or substituted with isoleucine or tyrosine; and/or
(30) an amino acid residue at position 511 in the amino acid sequence shown in SEQ ID NO:1 or at a position corresponding to this position, is deleted or substituted with methionine or isoleucine.

The invention also relates to variants as defined in (1) to (30) hereinabove, wherein the amino acid residue indicated as substituting the amino acid residue at the position in SEQ ID NO: 1 is not that particular amino acid residue but an amino acid residue which is conservative in relation to the indicated substituting amino acid.

Whether an amino acid is conservative with respect to another amino acid can be judged according to means and methods known in the art and as described herein above. One possibility is the PAM 250 matrix; alternatively, the Blosum Family Matrices can be used.

The present invention also relates to an MDC variant as described herein above which has an amino acid sequence as shown in SEQ ID NO:1 or an amino acid sequence having at least 60% sequence identity to SEQ ID NO: 1, in which one or more amino acid residues at a position selected from the group consisting of positions 405, 2, 12, 13, 29, 31, 33, 35, 89, 114, 195, 197, 221, 293, 337, 351, 376, 381, 388, 420, 422, 435, 436, 439, 441, 447, 449, 500, 506 and 511 in the amino acid sequence shown in SEQ ID NO: 1 or at a position corresponding to any of these positions, are substituted with another amino acid residue or deleted or wherein an insertion has been effected at one or more of these positions and which furthermore shows at least one modification at a position selected from the group consisting of 3, 4, 5, 6, 7, 8, 9, 10, 11, 14, 15, 25, 30, 34, 40, 43, 57, 60, 65, 67, 69, 70, 71, 72, 80, 84, 85, 86, 87, 90, 91, 99, 101, 102, 103, 105, 106, 108, 111, 117, 119, 120, 126, 132, 141, 146, 149, 154, 159, 160, 162, 175, 176, 187, 189, 193, 206, 211, 213, 214, 215, 216, 222, 228, 232, 244, 247, 264, 278, 284, 285, 303, 305, 306, 326, 338, 341, 342, 345, 349, 352, 375, 377, 384, 386, 392, 395, 399, 402, 404, 406, 414, 429, 440, 442, 443, 445, 448, 454, 460, 461, 462, 484, 488, 493, 494, 496, 501, 502, 509 and 512 in the amino acid sequence shown in SEQ ID NO: 1.

According to one embodiment, such an MDC variant as described herein above which furthermore shows at least one modification at a position selected from the group consisting of 3, 4, 5, 6, 7, 8, 9, 10, 11, 14, 15, 25, 30, 34, 40, 43, 57, 60, 65, 67, 69, 70, 71, 72, 80, 84, 85, 86, 87, 90, 91, 99, 101, 102, 103, 105, 106, 108, 111, 117, 119, 120, 126, 132, 141, 146, 149, 154, 159, 160, 162, 175, 176, 187, 189, 193, 206, 211, 213, 214, 215, 216, 222, 228, 232, 244, 247, 264, 278, 284, 285, 303, 305, 306, 326, 338, 341, 342, 345, 349, 352, 375, 377, 384, 386, 392, 395, 399, 402, 404, 406, 414, 429, 440, 442, 443, 445, 448, 454, 460, 461, 462, 484, 488, 493, 494, 496, 501, 502, 509 and 512 in the amino acid sequence shown in SEQ ID NO:1 or at a position corresponding to any of these positions is an MDC variant, wherein
- (1) an amino acid residue at position 3 in the amino acid sequence shown in SEQ ID NO:1 or at a position corresponding to this position, is deleted or substituted with alanine, glutamic acid, glycine, lysine, proline, tryptophan, cysteine, aspartic acid or tyrosine; and/or
- (2) an amino acid residue at position 4 in the amino acid sequence shown in SEQ ID NO:1 or at a position corresponding to this position, is deleted or substituted with glutamic acid, leucine, methionine, alanine, serine or asparagine; and/or
- (3) an amino acid residue at position 5 in the amino acid sequence shown in SEQ ID NO:1 or at a position corresponding to this position, is deleted or substituted with serine; and/or
- (4) an amino acid residue at position 6 in the amino acid sequence shown in SEQ ID NO:1 or at a position corresponding to this position, is deleted or substituted with proline; and/or
- (5) an amino acid residue at position 7 in the amino acid sequence shown in SEQ ID NO:1 or at a position corresponding to this position, is deleted or substituted with arginine; and/or
- (6) an amino acid residue at position 8 in the amino acid sequence shown in SEQ ID NO:1 or at a position corresponding to this position, is deleted or substituted with asparagine; and/or
- (7) an amino acid residue at position 9 in the amino acid sequence shown in SEQ ID NO:1 or at a position corresponding to this position, is deleted or substituted with histidine, proline or tyrosine; and/or
- (8) an amino acid residue at position 10 in the amino acid sequence shown in SEQ ID NO:1 or at a position corresponding to this position, is deleted or substituted with histidine, phenylalanine, lysine, proline, threonine or leucine; and/or
- (9) an amino acid residue at position 11 in the amino acid sequence shown in SEQ ID NO:1 or at a position corresponding to this position, is deleted or substituted with leucine, tyrosine or proline; and/or
- (10) an amino acid residue at position 14 in the amino acid sequence shown in SEQ ID NO:1 or at a position corresponding to this position, is deleted or substituted with aspartic acid; and/or
- (11) an amino acid residue at position 15 in the amino acid sequence shown in SEQ ID NO:1 or at a position corresponding to this position, is deleted or substituted with threonine; and/or
- (12) an amino acid residue at position 25 in the amino acid sequence shown in SEQ ID NO:1 or at a position corresponding to this position, is deleted or substituted with asparagine, serine or tryptophan; and/or
- (13) an amino acid residue at position 30 in the amino acid sequence shown in SEQ ID NO:1 or at a position corresponding to this position, is deleted or substituted with glycine, histidine or arginine; and/or
- (14) an amino acid residue at position 34 in the amino acid sequence shown in SEQ ID NO:1 or at a position corresponding to this position, is deleted or substituted with alanine or isoleucine; and/or
- (15) an amino acid residue at position 40 in the amino acid sequence shown in SEQ ID NO:1 or at a position corresponding to this position, is deleted or substituted with isoleucine or methionine; and/or
- (16) an amino acid residue at position 43 in the amino acid sequence shown in SEQ ID NO:1 or at a position corresponding to this position, is deleted or substituted with arginine; and/or
- (17) an amino acid residue at position 57 in the amino acid sequence shown in SEQ ID NO:1 or at a position corresponding to this position, is deleted or substituted with asparagine; and/or
- (18) an amino acid residue at position 60 in the amino acid sequence shown in SEQ ID NO:1 or at a position corresponding to this position, is deleted or substituted with valine; and/or
- (19) an amino acid residue at position 65 in the amino acid sequence shown in SEQ ID NO:1 or at a position corresponding to this position, is deleted or substituted with leucine or tryptophan; and/or
- (20) an amino acid residue at position 67 in the amino acid sequence shown in SEQ ID NO:1 or at a position corresponding to this position, is deleted or substituted with arginine or valine; and/or
- (21) an amino acid residue at position 69 in the amino acid sequence shown in SEQ ID NO:1 or at a position corresponding to this position, is deleted or substituted with asparagine; and/or
- (22) an amino acid residue at position 70 in the amino acid sequence shown in SEQ ID NO:1 or at a position corresponding to this position, is deleted or substituted with isoleucine or leucine; and/or
- (23) an amino acid residue at position 71 in the amino acid sequence shown in SEQ ID NO:1 or at a position corresponding to this position, is deleted or substituted with glycine; and/or
- (24) an amino acid residue at position 72 in the amino acid sequence shown in SEQ ID NO:1 or at a position corresponding to this position, is deleted or substituted with arginine; and/or
- (25) an amino acid residue at position 80 in the amino acid sequence shown in SEQ ID NO:1 or at a position corresponding to this position, is deleted or substituted with leucine; and/or
- (26) an amino acid residue at position 84 in the amino acid sequence shown in SEQ ID NO:1 or at a position corresponding to this position, is deleted or substituted with cysteine; and/or
- (27) an amino acid residue at position 85 in the amino acid sequence shown in SEQ ID NO:1 or at a position corresponding to this position, is deleted or substituted with alanine or threonine; and/or
- (28) an amino acid residue at position 86 in the amino acid sequence shown in SEQ ID NO:1 or at a position corresponding to this position, is deleted or substituted with asparagine or isoleucine; and/or
- (29) an amino acid residue at position 87 in the amino acid sequence shown in SEQ ID NO:1 or at a position corresponding to this position, is deleted or substituted with alanine, cysteine, phenylalanine, isoleucine, leucine, methionine, valine or tryptophan; and/or (30) an amino acid residue at position 90 in the amino acid sequence shown in SEQ ID NO:1 or at a position corresponding to this position, is deleted or substituted with leucine; and/or
- (31) an amino acid residue at position 91 in the amino acid sequence shown in SEQ ID NO:1 or at a position corresponding to this position, is deleted or substituted with leucine; and/or
- (32) an amino acid residue at position 99 in the amino acid sequence shown in SEQ ID NO:1 or at a position corresponding to this position, is deleted or substituted with asparagine or proline; and/or

(33) an amino acid residue at position 101 in the amino acid sequence shown in SEQ ID NO:1 or at a position corresponding to this position, is deleted or substituted with isoleucine or leucine; and/or

(34) an amino acid residue at position 102 in the amino acid sequence shown in SEQ ID NO:1 or at a position corresponding to this position, is deleted or substituted with leucine; and/or

(35) an amino acid residue at position 103 in the amino acid sequence shown in SEQ ID NO:1 or at a position corresponding to this position, is deleted or substituted with isoleucine, leucine or methionine; and/or

(36) an amino acid residue at position 105 in the amino acid sequence shown in SEQ ID NO:1 or at a position corresponding to this position, is deleted or substituted with phenylalanine, leucine or tryptophan; and/or

(37) an amino acid residue at position 106 in the amino acid sequence shown in SEQ ID NO:1 or at a position corresponding to this position, is deleted or substituted with threonine; and/or

(38) an amino acid residue at position 108 in the amino acid sequence shown in SEQ ID NO:1 or at a position corresponding to this position, is deleted or substituted with lysine, arginine or tryptophan; and/or

(39) an amino acid residue at position 111 in the amino acid sequence shown in SEQ ID NO:1 or at a position corresponding to this position, is deleted or substituted with cysteine; and/or

(40) an amino acid residue at position 117 in the amino acid sequence shown in SEQ ID NO:1 or at a position corresponding to this position, is deleted or substituted with alanine; and/or

(41) an amino acid residue at position 120 in the amino acid sequence shown in SEQ ID NO:1 or at a position corresponding to this position, is deleted or substituted with serine or lysine; and/or

(42) an amino acid residue at position 119 in the amino acid sequence shown in SEQ ID NO:1 or at a position corresponding to this position, is deleted or substituted with threonine; and/or

(43) an amino acid residue at position 126 in the amino acid sequence shown in SEQ ID NO:1 or at a position corresponding to this position, is deleted or substituted with proline; and/or

(44) an amino acid residue at position 132 in the amino acid sequence shown in SEQ ID NO:1 or at a position corresponding to this position, is deleted or substituted with cysteine; and/or

(45) an amino acid residue at position 141 in the amino acid sequence shown in SEQ ID NO:1 or at a position corresponding to this position, is deleted or substituted with aspartic acid; and/or

(46) an amino acid residue at position 146 in the amino acid sequence shown in SEQ ID NO:1 or at a position corresponding to this position, is deleted or substituted with serine; and/or

(47) an amino acid residue at position 149 in the amino acid sequence shown in SEQ ID NO:1 or at a position corresponding to this position, is deleted or substituted with valine or serine; and/or

(48) an amino acid residue at position 154 in the amino acid sequence shown in SEQ ID NO:1 or at a position corresponding to this position, is deleted or substituted with lysine; and/or

(49) an amino acid residue at position 159 in the amino acid sequence shown in SEQ ID NO:1 or at a position corresponding to this position, is deleted or substituted with cysteine; and/or

(50) an amino acid residue at position 160 in the amino acid sequence shown in SEQ ID NO:1 or at a position corresponding to this position, is deleted or substituted with phenylalanine; and/or

(51) an amino acid residue at position 162 in the amino acid sequence shown in SEQ ID NO:1 or at a position corresponding to this position, is deleted or substituted with proline, histidine or asparagine; and/or

(52) an amino acid residue at position 175 in the amino acid sequence shown in SEQ ID NO:1 or at a position corresponding to this position, is deleted or substituted with glycine, lysine, proline, glutamine, serine, threonine or tryptophan; and/or

(53) an amino acid residue at position 176 in the amino acid sequence shown in SEQ ID NO:1 or at a position corresponding to this position, is deleted or substituted with phenylalanine; and/or

(54) an amino acid residue at position 187 in the amino acid sequence shown in SEQ ID NO:1 or at a position corresponding to this position, is deleted or substituted with threonine; and/or

(55) an amino acid residue at position 189 in the amino acid sequence shown in SEQ ID NO:1 or at a position corresponding to this position, is deleted or substituted with isoleucine; and/or

(56) an amino acid residue at position 193 in the amino acid sequence shown in SEQ ID NO:1 or at a position corresponding to this position, is deleted or substituted with isoleucine, threonine or valine; and/or

(57) an amino acid residue at position 206 in the amino acid sequence shown in SEQ ID NO:1 or at a position corresponding to this position, is deleted or substituted with phenylalanine; and/or

(58) an amino acid residue at position 211 in the amino acid sequence shown in SEQ ID NO:1 or at a position corresponding to this position, is deleted or substituted with glutamic acid; and/or

(59) an amino acid residue at position 213 in the amino acid sequence shown in SEQ ID NO:1 or at a position corresponding to this position, is deleted or substituted with proline or leucine; and/or

(60) an amino acid residue at position 214 in the amino acid sequence shown in SEQ ID NO:1 or at a position corresponding to this position, is deleted or substituted with alanine, threonine or valine, histidine, glutamic acid, arginine or phenylalanine; and/or

(61) an amino acid residue at position 215 in the amino acid sequence shown in SEQ ID NO:1 or at a position corresponding to this position, is deleted or substituted with cysteine; and/or

(62) an amino acid residue at position 216 in the amino acid sequence shown in SEQ ID NO:1 or at a position corresponding to this position, is deleted or substituted with asparagine; and/or

(63) an amino acid residue at position 222 in the amino acid sequence shown in SEQ ID NO:1 or at a position corresponding to this position, is deleted or substituted with cysteine; and/or

(64) an amino acid residue at position 228 in the amino acid sequence shown in SEQ ID NO:1 or at a position corresponding to this position, is deleted or substituted with leucine, alanine, proline, threonine or valine; and/or

(65) an amino acid residue at position 232 in the amino acid sequence shown in SEQ ID NO:1 or at a position corresponding to this position, is deleted or substituted with valine; and/or
(66) an amino acid residue at position 244 in the amino acid sequence shown in SEQ ID NO:1 or at a position corresponding to this position, is deleted or substituted with phenylalanine; and/or
(67) an amino acid residue at position 247 in the amino acid sequence shown in SEQ ID NO:1 or at a position corresponding to this position, is deleted or substituted with alanine; and/or
(68) an amino acid residue at position 264 in the amino acid sequence shown in SEQ ID NO:1 or at a position corresponding to this position, is deleted or substituted with aspartic acid; and/or
(69) an amino acid residue at position 278 in the amino acid sequence shown in SEQ ID NO:1 or at a position corresponding to this position, is deleted or substituted with isoleucine; and/or
(70) an amino acid residue at position 284 in the amino acid sequence shown in SEQ ID NO:1 or at a position corresponding to this position, is deleted or substituted with tyrosine or leucine; and/or
(71) an amino acid residue at position 285 in the amino acid sequence shown in SEQ ID NO:1 or at a position corresponding to this position, is deleted or substituted with leucine; and/or
(72) an amino acid residue at position 303 in the amino acid sequence shown in SEQ ID NO:1 or at a position corresponding to this position, is deleted or substituted with serine or proline; and/or
(73) an amino acid residue at position 305 in the amino acid sequence shown in SEQ ID NO:1 or at a position corresponding to this position, is deleted or substituted with alanine or aspartic acid; and/or
(74) an amino acid residue at position 306 in the amino acid sequence shown in SEQ ID NO:1 or at a position corresponding to this position, is deleted or substituted with phenylalanine, arginine or serine; and/or
(75) an amino acid residue at position 326 in the amino acid sequence shown in SEQ ID NO:1 or at a position corresponding to this position, is deleted or substituted with alanine or proline; and/or
(76) an amino acid residue at position 338 in the amino acid sequence shown in SEQ ID NO:1 or at a position corresponding to this position, is deleted or substituted with proline, alanine or serine; and/or
(77) an amino acid residue at position 341 in the amino acid sequence shown in SEQ ID NO:1 or at a position corresponding to this position, is deleted or substituted with isoleucine; and/or
(78) an amino acid residue at position 342 in the amino acid sequence shown in SEQ ID NO:1 or at a position corresponding to this position, is deleted or substituted with glycine; and/or
(79) an amino acid residue at position 345 in the amino acid sequence shown in SEQ ID NO:1 or at a position corresponding to this position, is deleted or substituted with leucine; and/or
(80) an amino acid residue at position 349 in the amino acid sequence shown in SEQ ID NO:1 or at a position corresponding to this position, is deleted or substituted with serine; and/or
(81) an amino acid residue at position 352 in the amino acid sequence shown in SEQ ID NO:1 or at a position corresponding to this position, is deleted or substituted with glycine or leucine; and/or
(82) an amino acid residue at position 375 in the amino acid sequence shown in SEQ ID NO:1 or at a position corresponding to this position, is deleted or substituted with leucine; and/or
(83) an amino acid residue at position 377 in the amino acid sequence shown in SEQ ID NO:1 or at a position corresponding to this position, is deleted or substituted with histidine; and/or
(84) an amino acid residue at position 384 in the amino acid sequence shown in SEQ ID NO:1 or at a position corresponding to this position, is deleted or substituted with tyrosine; and/or
(85) an amino acid residue at position 386 in the amino acid sequence shown in SEQ ID NO:1 or at a position corresponding to this position, is deleted or substituted with asparagine; and/or
(86) an amino acid residue at position 392 in the amino acid sequence shown in SEQ ID NO:1 or at a position corresponding to this position, is deleted or substituted with leucine or alanine; and/or
(87) an amino acid residue at position 395 in the amino acid sequence shown in SEQ ID NO:1 or at a position corresponding to this position, is deleted or substituted with cysteine; and/or
(88) an amino acid residue at position 399 in the amino acid sequence shown in SEQ ID NO:1 or at a position corresponding to this position, is deleted or substituted with arginine or asparagine; and/or
(89) an amino acid residue at position 402 in the amino acid sequence shown in SEQ ID NO:1 or at a position corresponding to this position, is deleted or substituted with valine or histidine; and/or
(90) an amino acid residue at position 404 in the amino acid sequence shown in SEQ ID NO:1 or at a position corresponding to this position, is deleted or substituted with tyrosine or tryptophan; and/or
(91) an amino acid residue at position 406 in the amino acid sequence shown in SEQ ID NO:1 or at a position corresponding to this position, is deleted or substituted with glutamine; and/or
(92) an amino acid residue at position 414 in the amino acid sequence shown in SEQ ID NO:1 or at a position corresponding to this position, is deleted or substituted with asparagine; and/or
(93) an amino acid residue at position 440 in the amino acid sequence shown in SEQ ID NO:1 or at a position corresponding to this position, is deleted or substituted with valine; and/or
(94) an amino acid residue at position 443 in the amino acid sequence shown in SEQ ID NO:1 or at a position corresponding to this position, is deleted or substituted with asparagine; and/or
(95) an amino acid residue at position 448 in the amino acid sequence shown in SEQ ID NO:1 or at a position corresponding to this position, is deleted or substituted with serine, phenylalanine or trypophan; and/or
(96) an amino acid residue at position 454 in the amino acid sequence shown in SEQ ID NO:1 or at a position corresponding to this position, is deleted or substituted with glycine; and/or
(97) an amino acid residue at position 460 in the amino acid sequence shown in SEQ ID NO:1 or at a position corresponding to this position, is deleted or substituted with phenylalanine or proline; and/or

(98) an amino acid residue at position 461 in the amino acid sequence shown in SEQ ID NO:1 or at a position corresponding to this position, is deleted or substituted with valine, asparagine or methionine; and/or

(99) an amino acid residue at position 462 in the amino acid sequence shown in SEQ ID NO:1 or at a position corresponding to this position, is deleted or substituted with asparagine; and/or (100) an amino acid residue at position 484 in the amino acid sequence shown in SEQ ID NO:1 or at a position corresponding to this position, is deleted or substituted with alanine or glycine; and/or (101) an amino acid residue at position 488 in the amino acid sequence shown in SEQ ID NO:1 or at a position corresponding to this position, is deleted or substituted with alanine or asparagine; and/or (102) an amino acid residue at position 493 in the amino acid sequence shown in SEQ ID NO:1 or at a position corresponding to this position, is deleted or substituted with arginine; and/or (103) an amino acid residue at position 494 in the amino acid sequence shown in SEQ ID NO:1 or at a position corresponding to this position, is deleted or substituted with arginine; and/or (104) an amino acid residue at position 496 in the amino acid sequence shown in SEQ ID NO:1 or at a position corresponding to this position, is deleted or substituted with alanine or phenylalaine; and/or (105) an amino acid residue at position 429 in the amino acid sequence shown in SEQ ID NO:1 or at a position corresponding to this position, is deleted or substituted with alanine or serine; and/or (106) an amino acid residue at position 442 in the amino acid sequence shown in SEQ ID NO:1 or at a position corresponding to this position, is deleted or substituted with threonine; and/or (107) an amino acid residue at position 445 in the amino acid sequence shown in SEQ ID NO:1 or at a position corresponding to this position, is deleted or substituted with glutamic acid or proline; and/or (108) an amino acid residue at position 501 in the amino acid sequence shown in SEQ ID NO:1 or at a position corresponding to this position, is deleted or substituted with glutamic acid, methionine, glycine or lysine; and/or (109) an amino acid residue at position 502 in the amino acid sequence shown in SEQ ID NO:1 or at a position corresponding to this position, is deleted or substituted with asparagine; and/or (110) an amino acid residue at position 509 in the amino acid sequence shown in SEQ ID NO:1 or at a position corresponding to this position, is deleted or substituted with leucine; and/or (111) an amino acid residue at position 512 in the amino acid sequence shown in SEQ ID NO:1 or at a position corresponding to this position, is deleted or substituted with glutamic acid, histidine or serine.

The first part of the present invention also relates to an MDC variant having an amino acid sequence as shown in SEQ ID NO:1 or an amino acid sequence having at least 60% sequence identity to SEQ ID NO: 1, in which one or more amino acid residues at a position selected from the group consisting of positions 3, 4, 5, 6, 7, 8, 9, 10, 11, 14, 15, 30, 34, 40, 43, 57, 60, 65, 67, 69, 70, 71, 72, 80, 84, 85, 86, 87, 90, 91, 99, 101, 102, 103, 105, 106, 108, 111, 117, 119, 120, 126, 132, 146, 154, 159, 160, 162, 175, 176, 187, 189, 193, 206, 211, 213, 214, 215, 216, 222, 228, 232, 244, 247, 264, 278, 284, 285, 303, 305, 306, 326, 338, 341, 342, 345, 349, 352, 375, 377, 384, 386, 392, 395, 399, 402, 404, 406, 414, 429, 440, 442, 443, 445, 448, 454, 460, 461, 462, 484, 488, 493, 494, 496, 501, 502, 509 and 512 in the amino acid sequence shown in SEQ ID NO: 1 or at a position corresponding to any of these positions, are substituted with another amino acid residue or deleted, wherein said MDC variant has an improved activity in converting 3-methylcrotonic acid into isobutene and wherein (1) an amino acid residue at position 3 in the amino acid sequence shown in SEQ ID NO:1 or at a position corresponding to this position, is deleted or substituted with alanine, glutamic acid, glycine, lysine, proline, tryptophan, cysteine, aspartic acid or tyrosine; and/or (2) an amino acid residue at position 4 in the amino acid sequence shown in SEQ ID NO:1 or at a position corresponding to this position, is deleted or substituted with glutamic acid, leucine, methionine, alanine, serine or asparagine; and/or (3) an amino acid residue at position 5 in the amino acid sequence shown in SEQ ID NO:1 or at a position corresponding to this position, is deleted or substituted with serine; and/or (4) an amino acid residue at position 6 in the amino acid sequence shown in SEQ ID NO:1 or at a position corresponding to this position, is deleted or substituted with proline; and/or (5) an amino acid residue at position 7 in the amino acid sequence shown in SEQ ID NO:1 or at a position corresponding to this position, is deleted or substituted with arginine; and/or (6) an amino acid residue at position 8 in the amino acid sequence shown in SEQ ID NO:1 or at a position corresponding to this position, is deleted or substituted with asparagine; and/or (7) an amino acid residue at position 9 in the amino acid sequence shown in SEQ ID NO:1 or at a position corresponding to this position, is deleted or substituted with histidine, proline or tyrosine; and/or (8) an amino acid residue at position 10 in the amino acid sequence shown in SEQ ID NO:1 or at a position corresponding to this position, is deleted or substituted with histidine, phenylalanine, lysine, proline, threonine or leucine; and/or (9) an amino acid residue at position 11 in the amino acid sequence shown in SEQ ID NO:1 or at a position corresponding to this position, is deleted or substituted with leucine, tyrosine or proline; and/or

(10) an amino acid residue at position 14 in the amino acid sequence shown in SEQ ID NO:1 or at a position corresponding to this position, is deleted or substituted with aspartic acid; and/or

(11) an amino acid residue at position 15 in the amino acid sequence shown in SEQ ID NO:1 or at a position corresponding to this position, is deleted or substituted with threonine; and/or

(12) an amino acid residue at position 30 in the amino acid sequence shown in SEQ ID NO:1 or at a position corresponding to this position, is deleted or substituted with glycine, histidine or arginine; and/or

(13) an amino acid residue at position 34 in the amino acid sequence shown in SEQ ID NO:1 or at a position corresponding to this position, is deleted or substituted with alanine or isoleucine; and/or

(14) an amino acid residue at position 40 in the amino acid sequence shown in SEQ ID NO:1 or at a position corresponding to this position, is deleted or substituted with isoleucine or methionine; and/or
(15) an amino acid residue at position 43 in the amino acid sequence shown in SEQ ID NO:1 or at a position corresponding to this position, is deleted or substituted with arginine; and/or
(16) an amino acid residue at position 57 in the amino acid sequence shown in SEQ ID NO:1 or at a position corresponding to this position, is deleted or substituted with asparagine; and/or
(17) an amino acid residue at position 60 in the amino acid sequence shown in SEQ ID NO:1 or at a position corresponding to this position, is deleted or substituted with valine; and/or
(18) an amino acid residue at position 65 in the amino acid sequence shown in SEQ ID NO:1 or at a position corresponding to this position, is deleted or substituted with leucine or tryptophan; and/or
(19) an amino acid residue at position 67 in the amino acid sequence shown in SEQ ID NO:1 or at a position corresponding to this position, is deleted or substituted with arginine or valine; and/or
(20) an amino acid residue at position 69 in the amino acid sequence shown in SEQ ID NO:1 or at a position corresponding to this position, is deleted or substituted with asparagine; and/or
(21) an amino acid residue at position 70 in the amino acid sequence shown in SEQ ID NO:1 or at a position corresponding to this position, is deleted or substituted with isoleucine or leucine; and/or
(22) an amino acid residue at position 71 in the amino acid sequence shown in SEQ ID NO:1 or at a position corresponding to this position, is deleted or substituted with glycine; and/or
(23) an amino acid residue at position 72 in the amino acid sequence shown in SEQ ID NO:1 or at a position corresponding to this position, is deleted or substituted with arginine; and/or
(24) an amino acid residue at position 80 in the amino acid sequence shown in SEQ ID NO:1 or at a position corresponding to this position, is deleted or substituted with leucine; and/or
(25) an amino acid residue at position 84 in the amino acid sequence shown in SEQ ID NO:1 or at a position corresponding to this position, is deleted or substituted with cysteine; and/or
(26) an amino acid residue at position 85 in the amino acid sequence shown in SEQ ID NO:1 or at a position corresponding to this position, is deleted or substituted with alanine or threonine; and/or
(27) an amino acid residue at position 86 in the amino acid sequence shown in SEQ ID NO:1 or at a position corresponding to this position, is deleted or substituted with asparagine or isoleucine; and/or
(28) an amino acid residue at position 87 in the amino acid sequence shown in SEQ ID NO:1 or at a position corresponding to this position, is deleted or substituted with alanine, cysteine, phenylalanine, isoleucine, leucine, methionine, valine or tryptophan; and/or
(29) an amino acid residue at position 90 in the amino acid sequence shown in SEQ ID NO:1 or at a position corresponding to this position, is deleted or substituted with leucine; and/or
(30) an amino acid residue at position 91 in the amino acid sequence shown in SEQ ID NO:1 or at a position corresponding to this position, is deleted or substituted with leucine; and/or
(31) an amino acid residue at position 99 in the amino acid sequence shown in SEQ ID NO:1 or at a position corresponding to this position, is deleted or substituted with asparagine or proline; and/or
(31) an amino acid residue at position 101 in the amino acid sequence shown in SEQ ID NO:1 or at a position corresponding to this position, is deleted or substituted with isoleucine or leucine; and/or
(33) an amino acid residue at position 102 in the amino acid sequence shown in SEQ ID NO:1 or at a position corresponding to this position, is deleted or substituted with leucine; and/or
(34) an amino acid residue at position 103 in the amino acid sequence shown in SEQ ID NO:1 or at a position corresponding to this position, is deleted or substituted with isoleucine, leucine or methionine; and/or
(35) an amino acid residue at position 105 in the amino acid sequence shown in SEQ ID NO:1 or at a position corresponding to this position, is deleted or substituted with phenylalanine, leucine or tryptophan; and/or
(36) an amino acid residue at position 106 in the amino acid sequence shown in SEQ ID NO:1 or at a position corresponding to this position, is deleted or substituted with threonine; and/or
(37) an amino acid residue at position 108 in the amino acid sequence shown in SEQ ID NO:1 or at a position corresponding to this position, is deleted or substituted with lysine, arginine or tryptophan; and/or
(38) an amino acid residue at position 111 in the amino acid sequence shown in SEQ ID NO:1 or at a position corresponding to this position, is deleted or substituted with cysteine; and/or
(39) an amino acid residue at position 117 in the amino acid sequence shown in SEQ ID NO:1 or at a position corresponding to this position, is deleted or substituted with alanine; and/or
(40) an amino acid residue at position 120 in the amino acid sequence shown in SEQ ID NO:1 or at a position corresponding to this position, is deleted or substituted with serine or lysine; and/or
(41) an amino acid residue at position 119 in the amino acid sequence shown in SEQ ID NO:1 or at a position corresponding to this position, is deleted or substituted with threonine; and/or
(42) an amino acid residue at position 126 in the amino acid sequence shown in SEQ ID NO:1 or at a position corresponding to this position, is deleted or substituted with proline; and/or
(43) an amino acid residue at position 132 in the amino acid sequence shown in SEQ ID NO:1 or at a position corresponding to this position, is deleted or substituted with cysteine; and/or
(44) an amino acid residue at position 146 in the amino acid sequence shown in SEQ ID NO:1 or at a position corresponding to this position, is deleted or substituted with serine; and/or
(45) an amino acid residue at position 154 in the amino acid sequence shown in SEQ ID NO:1 or at a position corresponding to this position, is deleted or substituted with lysine; and/or
(46) an amino acid residue at position 159 in the amino acid sequence shown in SEQ ID NO:1 or at a position corresponding to this position, is deleted or substituted with cysteine; and/or

(47) an amino acid residue at position 160 in the amino acid sequence shown in SEQ ID NO:1 or at a position corresponding to this position, is deleted or substituted with phenylalanine; and/or
(48) an amino acid residue at position 162 in the amino acid sequence shown in SEQ ID NO:1 or at a position corresponding to this position, is deleted or substituted with proline, histidine or asparagine; and/or
(49) an amino acid residue at position 175 in the amino acid sequence shown in SEQ ID NO:1 or at a position corresponding to this position, is deleted or substituted with glycine, lysine, proline, glutamine, serine, threonine or tryptophan; and/or
(50) an amino acid residue at position 176 in the amino acid sequence shown in SEQ ID NO:1 or at a position corresponding to this position, is deleted or substituted with phenylalanine; and/or
(51) an amino acid residue at position 187 in the amino acid sequence shown in SEQ ID NO:1 or at a position corresponding to this position, is deleted or substituted with threonine; and/or
(52) an amino acid residue at position 189 in the amino acid sequence shown in SEQ ID NO:1 or at a position corresponding to this position, is deleted or substituted with isoleucine; and/or
(53) an amino acid residue at position 193 in the amino acid sequence shown in SEQ ID NO:1 or at a position corresponding to this position, is deleted or substituted with isoleucine, threonine or valine; and/or
(54) an amino acid residue at position 206 in the amino acid sequence shown in SEQ ID NO:1 or at a position corresponding to this position, is deleted or substituted with phenylalanine; and/or
(55) an amino acid residue at position 211 in the amino acid sequence shown in SEQ ID NO:1 or at a position corresponding to this position, is deleted or substituted with glutamic acid; and/or
(56) an amino acid residue at position 213 in the amino acid sequence shown in SEQ ID NO:1 or at a position corresponding to this position, is deleted or substituted with proline or leucine; and/or
(57) an amino acid residue at position 214 in the amino acid sequence shown in SEQ ID NO:1 or at a position corresponding to this position, is deleted or substituted with alanine, threonine or valine, histidine, glutamic acid, arginine or phenylalanine; and/or
(58) an amino acid residue at position 215 in the amino acid sequence shown in SEQ ID NO:1 or at a position corresponding to this position, is deleted or substituted with cysteine; and/or
(59) an amino acid residue at position 216 in the amino acid sequence shown in SEQ ID NO:1 or at a position corresponding to this position, is deleted or substituted with asparagine; and/or
(60) an amino acid residue at position 222 in the amino acid sequence shown in SEQ ID NO:1 or at a position corresponding to this position, is deleted or substituted with cysteine; and/or
(61) an amino acid residue at position 228 in the amino acid sequence shown in SEQ ID NO:1 or at a position corresponding to this position, is deleted or substituted with leucine, alanine, proline, threonine or valine; and/or
(62) an amino acid residue at position 232 in the amino acid sequence shown in SEQ ID NO:1 or at a position corresponding to this position, is deleted or substituted with valine; and/or
(63) an amino acid residue at position 244 in the amino acid sequence shown in SEQ ID NO:1 or at a position corresponding to this position, is deleted or substituted with phenylalanine; and/or
(64) an amino acid residue at position 247 in the amino acid sequence shown in SEQ ID NO:1 or at a position corresponding to this position, is deleted or substituted with alanine; and/or
(65) an amino acid residue at position 264 in the amino acid sequence shown in SEQ ID NO:1 or at a position corresponding to this position, is deleted or substituted with aspartic acid; and/or
(66) an amino acid residue at position 278 in the amino acid sequence shown in SEQ ID NO:1 or at a position corresponding to this position, is deleted or substituted with isoleucine; and/or
(67) an amino acid residue at position 284 in the amino acid sequence shown in SEQ ID NO:1 or at a position corresponding to this position, is deleted or substituted with tyrosine or leucine; and/or
(68) an amino acid residue at position 285 in the amino acid sequence shown in SEQ ID NO:1 or at a position corresponding to this position, is deleted or substituted with leucine; and/or
(69) an amino acid residue at position 303 in the amino acid sequence shown in SEQ ID NO:1 or at a position corresponding to this position, is deleted or substituted with serine or proline; and/or
(70) an amino acid residue at position 305 in the amino acid sequence shown in SEQ ID NO:1 or at a position corresponding to this position, is deleted or substituted with alanine or aspartic acid; and/or
(71) an amino acid residue at position 306 in the amino acid sequence shown in SEQ ID NO:1 or at a position corresponding to this position, is deleted or substituted with phenylalanine, arginine or serine; and/or
(72) an amino acid residue at position 326 in the amino acid sequence shown in SEQ ID NO:1 or at a position corresponding to this position, is deleted or substituted with alanine or proline; and/or
(73) an amino acid residue at position 338 in the amino acid sequence shown in SEQ ID NO:1 or at a position corresponding to this position, is deleted or substituted with proline, alanine or serine; and/or
(74) an amino acid residue at position 341 in the amino acid sequence shown in SEQ ID NO:1 or at a position corresponding to this position, is deleted or substituted with isoleucine; and/or
(75) an amino acid residue at position 342 in the amino acid sequence shown in SEQ ID NO:1 or at a position corresponding to this position, is deleted or substituted with glycine; and/or
(76) an amino acid residue at position 345 in the amino acid sequence shown in SEQ ID NO:1 or at a position corresponding to this position, is deleted or substituted with leucine; and/or
(77) an amino acid residue at position 349 in the amino acid sequence shown in SEQ ID NO:1 or at a position corresponding to this position, is deleted or substituted with serine; and/or
(78) an amino acid residue at position 352 in the amino acid sequence shown in SEQ ID NO:1 or at a position corresponding to this position, is deleted or substituted with glycine or leucine; and/or

(79) an amino acid residue at position 375 in the amino acid sequence shown in SEQ ID NO:1 or at a position corresponding to this position, is deleted or substituted with leucine; and/or
(80) an amino acid residue at position 377 in the amino acid sequence shown in SEQ ID NO:1 or at a position corresponding to this position, is deleted or substituted with histidine; and/or
(81) an amino acid residue at position 384 in the amino acid sequence shown in SEQ ID NO:1 or at a position corresponding to this position, is deleted or substituted with tyrosine; and/or
(82) an amino acid residue at position 386 in the amino acid sequence shown in SEQ ID NO:1 or at a position corresponding to this position, is deleted or substituted with asparagine; and/or
(83) an amino acid residue at position 392 in the amino acid sequence shown in SEQ ID NO:1 or at a position corresponding to this position, is deleted or substituted with leucine or alanine; and/or
(84) an amino acid residue at position 395 in the amino acid sequence shown in SEQ ID NO:1 or at a position corresponding to this position, is deleted or substituted with cysteine; and/or
(85) an amino acid residue at position 399 in the amino acid sequence shown in SEQ ID NO:1 or at a position corresponding to this position, is deleted or substituted with arginine or asparagine; and/or
(86) an amino acid residue at position 402 in the amino acid sequence shown in SEQ ID NO:1 or at a position corresponding to this position, is deleted or substituted with valine or histidine; and/or
(87) an amino acid residue at position 404 in the amino acid sequence shown in SEQ ID NO:1 or at a position corresponding to this position, is deleted or substituted with tyrosine or tryptophan; and/or
(88) an amino acid residue at position 406 in the amino acid sequence shown in SEQ ID NO:1 or at a position corresponding to this position, is deleted or substituted with glutamine; and/or
(89) an amino acid residue at position 414 in the amino acid sequence shown in SEQ ID NO:1 or at a position corresponding to this position, is deleted or substituted with asparagine; and/or
(90) an amino acid residue at position 440 in the amino acid sequence shown in SEQ ID NO:1 or at a position corresponding to this position, is deleted or substituted with valine; and/or
(91) an amino acid residue at position 443 in the amino acid sequence shown in SEQ ID NO:1 or at a position corresponding to this position, is deleted or substituted with asparagine; and/or
(92) an amino acid residue at position 448 in the amino acid sequence shown in SEQ ID NO:1 or at a position corresponding to this position, is deleted or substituted with serine, phenylalanine or trypophan; and/or
(93) an amino acid residue at position 454 in the amino acid sequence shown in SEQ ID NO:1 or at a position corresponding to this position, is deleted or substituted with glycine; and/or
(94) an amino acid residue at position 460 in the amino acid sequence shown in SEQ ID NO:1 or at a position corresponding to this position, is deleted or substituted with phenylalanine or proline; and/or
(95) an amino acid residue at position 461 in the amino acid sequence shown in SEQ ID NO:1 or at a position corresponding to this position, is deleted or substituted with valine, asparagine or methionine; and/or
(96) an amino acid residue at position 462 in the amino acid sequence shown in SEQ ID NO:1 or at a position corresponding to this position, is deleted or substituted with asparagine; and/or
(97) an amino acid residue at position 484 in the amino acid sequence shown in SEQ ID NO:1 or at a position corresponding to this position, is deleted or substituted with alanine or glycine; and/or
(98) an amino acid residue at position 488 in the amino acid sequence shown in SEQ ID NO:1 or at a position corresponding to this position, is deleted or substituted with alanine or asparagine; and/or
(99) an amino acid residue at position 493 in the amino acid sequence shown in SEQ ID NO:1 or at a position corresponding to this position, is deleted or substituted with arginine; and/or
(100) an amino acid residue at position 494 in the amino acid sequence shown in SEQ ID NO:1 or at a position corresponding to this position, is deleted or substituted with arginine; and/or
(101) an amino acid residue at position 496 in the amino acid sequence shown in SEQ ID NO:1 or at a position corresponding to this position, is deleted or substituted with alanine or phenylalaine; and/or
(102) an amino acid residue at position 429 in the amino acid sequence shown in SEQ ID NO:1 or at a position corresponding to this position, is deleted or substituted with alanine or serine; and/or
(103) an amino acid residue at position 442 in the amino acid sequence shown in SEQ ID NO:1 or at a position corresponding to this position, is deleted or substituted with threonine; and/or
(104) an amino acid residue at position 445 in the amino acid sequence shown in SEQ ID NO:1 or at a position corresponding to this position, is deleted or substituted with glutamic acid or proline; and/or
(105) an amino acid residue at position 501 in the amino acid sequence shown in SEQ ID NO:1 or at a position corresponding to this position, is deleted or substituted with glutamic acid, methionine, glycine or lysine; and/or
(106) an amino acid residue at position 502 in the amino acid sequence shown in SEQ ID NO:1 or at a position corresponding to this position, is deleted or substituted with asparagine; and/or
(107) an amino acid residue at position 509 in the amino acid sequence shown in SEQ ID NO:1 or at a position corresponding to this position, is deleted or substituted with leucine; and/or
(108) an amino acid residue at position 512 in the amino acid sequence shown in SEQ ID NO:1 or at a position corresponding to this position, is deleted or substituted with glutamic acid, histidine or serine.

The present invention also relates to an MDC variant having an amino acid sequence as shown in SEQ ID NO:1 or an amino acid sequence having at least 83%, at least 85%, or at least 87%, preferably at least 90% or at least 95%, even more preferred at least 98% sequence identity to SEQ ID NO:1, in which one or more amino acid residues at a position selected from the group consisting of positions 2, 3, 4, 7, 8, 10, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 111, 114, 117, 119, 120, 126, 141, 146, 154, 159, 160, 162, 176, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 381, 384, 386, 388, 395, 399, 402, 404, 405, 406, 414, 420, 422, 429, 435, 436, 439, 440, 441, 442, 443, 447, 449, 460, 462, 488, 493, 494, 496, 500, 501, 502, 506, 509, and 511 in the amino acid sequence shown in SEQ ID NO:1 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

According to one embodiment, the first part of the present invention relates to any of these MDC variants having an amino acid sequence as shown in SEQ ID NO:1 or an amino acid sequence having at least 83%, at least 85%, or at least 87%, preferably at least 90% or at least 95%, even more preferred at least 98% sequence identity to SEQ ID NO:1 in which (1) an amino acid residue at position 2 in the amino acid sequence shown in SEQ ID NO:1 or at a position corresponding to this position, is deleted or substituted with alanine, aspartic acid, phenylalanine, lysine, leucine, asparagine, glutamine, cysteine or valine; and/or (2) an amino acid residue at position 3 in the amino acid sequence shown in SEQ ID NO:1 or at a position corresponding to this position, is deleted or substituted with alanine, glutamic acid, glycine, lysine, proline, tryptophan, aspartic acid or tyrosine; and/or (3) an amino acid residue at position 4 in the amino acid sequence shown in SEQ ID NO:1 or at a position corresponding to this position, is deleted or substituted with glutamic acid, leucine, methionine, alanine, serine or asparagine; and/or (4) an amino acid residue at position 7 in the amino acid sequence shown in SEQ ID NO:1 or at a position corresponding to this position, is deleted or substituted with arginine; and/or (5) an amino acid residue at position 8 in the amino acid sequence shown in SEQ ID NO:1 or at a position corresponding to this position, is deleted or substituted with asparagine; and/or (6) an amino acid residue at position 10 in the amino acid sequence shown in SEQ ID NO:1 or at a position corresponding to this position, is deleted or substituted with histidine, phenylalanine, lysine, proline, threonine or leucine; and/or (7) an amino acid residue at position 12 in the amino acid sequence shown in SEQ ID NO:1 or at a position corresponding to this position, is deleted or substituted with serine or asparagine or alanine; and/or (8) an amino acid residue at position 13 in the amino acid sequence shown in SEQ ID NO:1 or at a position corresponding to this position, is deleted or substituted with histidine, isoleucine, asparagine, serine, valine or tyrosine; and/or (9) an amino acid residue at position 14 in the amino acid sequence shown in SEQ ID NO:1 or at a position corresponding to this position, is deleted or substituted with aspartic acid; and/or

(10) an amino acid residue at position 15 in the amino acid sequence shown in SEQ ID NO:1 or at a position corresponding to this position, is deleted or substituted with threonine; and/or

(11) an amino acid residue at position 25 in the amino acid sequence shown in SEQ ID NO:1 or at a position corresponding to this position, is deleted or substituted with asparagine, serine or tryptophan; and/or

(12) an amino acid residue at position 29 in the amino acid sequence shown in SEQ ID NO:1 or at a position corresponding to this position, is deleted or substituted with asparagine, histidine or serine; and/or

(13) an amino acid residue at position 30 in the amino acid sequence shown in SEQ ID NO:1 or at a position corresponding to this position, is deleted or substituted with glycine, histidine or arginine; and/or

(14) an amino acid residue at position 31 in the amino acid sequence shown in SEQ ID NO:1 or at a position corresponding to this position, is deleted or substituted with glutamic acid or glycine or lysine; and/or

(15) an amino acid residue at position 33 in the amino acid sequence shown in SEQ ID NO:1 or at a position corresponding to this position, is deleted or substituted with isoleucine; and/or

(16) an amino acid residue at position 34 in the amino acid sequence shown in SEQ ID NO:1 or at a position corresponding to this position, is deleted or substituted with alanine or isoleucine; and/or

(17) an amino acid residue at position 35 in the amino acid sequence shown in SEQ ID NO:1 or at a position corresponding to this position, is deleted or substituted with methionine, serine or threonine; and/or

(18) an amino acid residue at position 40 in the amino acid sequence shown in SEQ ID NO:1 or at a position corresponding to this position, is deleted or substituted with isoleucine or methionine; and/or

(19) an amino acid residue at position 43 in the amino acid sequence shown in SEQ ID NO:1 or at a position corresponding to this position, is deleted or substituted with arginine; and/or

(20) an amino acid residue at position 57 in the amino acid sequence shown in SEQ ID NO:1 or at a position corresponding to this position, is deleted or substituted with asparagine; and/or

(21) an amino acid residue at position 60 in the amino acid sequence shown in SEQ ID NO:1 or at a position corresponding to this position, is deleted or substituted with valine; and/or

(22) an amino acid residue at position 65 in the amino acid sequence shown in SEQ ID NO:1 or at a position corresponding to this position, is deleted or substituted with leucine or tryptophan; and/or

(23) an amino acid residue at position 67 in the amino acid sequence shown in SEQ ID NO:1 or at a position corresponding to this position, is deleted or substituted with arginine or valine; and/or

(24) an amino acid residue at position 69 in the amino acid sequence shown in SEQ ID NO:1 or at a position corresponding to this position, is deleted or substituted with asparagine; and/or

(25) an amino acid residue at position 70 in the amino acid sequence shown in SEQ ID NO:1 or at a position corresponding to this position, is deleted or substituted with isoleucine or leucine; and/or

(26) an amino acid residue at position 71 in the amino acid sequence shown in SEQ ID NO:1 or at a position corresponding to this position, is deleted or substituted with glycine; and/or

(27) an amino acid residue at position 72 in the amino acid sequence shown in SEQ ID NO:1 or at a position corresponding to this position, is deleted or substituted with arginine; and/or

(28) an amino acid residue at position 80 in the amino acid sequence shown in SEQ ID NO:1 or at a position corresponding to this position, is deleted or substituted with leucine; and/or
(29) an amino acid residue at position 84 in the amino acid sequence shown in SEQ ID NO:1 or at a position corresponding to this position, is deleted or substituted with cysteine; and/or
(30) an amino acid residue at position 85 in the amino acid sequence shown in SEQ ID NO:1 or at a position corresponding to this position, is deleted or substituted with alanine or threonine; and/or
(31) an amino acid residue at position 86 in the amino acid sequence shown in SEQ ID NO:1 or at a position corresponding to this position, is deleted or substituted with asparagine or isoleucine; and/or
(32) an amino acid residue at position 87 in the amino acid sequence shown in SEQ ID NO:1 or at a position corresponding to this position, is deleted or substituted with alanine, cysteine, phenylalanine, isoleucine, leucine, methionine, valine or tryptophan; and/or
(33) an amino acid residue at position 89 in the amino acid sequence shown in SEQ ID NO:1 or at a position corresponding to this position, is deleted or substituted with serine or phenylalanine; and/or
(34) an amino acid residue at position 90 in the amino acid sequence shown in SEQ ID NO:1 or at a position corresponding to this position, is deleted or substituted with leucine; and/or
(35) an amino acid residue at position 91 in the amino acid sequence shown in SEQ ID NO:1 or at a position corresponding to this position, is deleted or substituted with leucine; and/or
(36) an amino acid residue at position 99 in the amino acid sequence shown in SEQ ID NO:1 or at a position corresponding to this position, is deleted or substituted with asparagine or proline; and/or
(37) an amino acid residue at position 101 in the amino acid sequence shown in SEQ ID NO:1 or at a position corresponding to this position, is deleted or substituted with isoleucine or leucine; and/or
(38) an amino acid residue at position 102 in the amino acid sequence shown in SEQ ID NO:1 or at a position corresponding to this position, is deleted or substituted with leucine; and/or
(39) an amino acid residue at position 103 in the amino acid sequence shown in SEQ ID NO:1 or at a position corresponding to this position, is deleted or substituted with isoleucine, leucine or methionine; and/or
(40) an amino acid residue at position 105 in the amino acid sequence shown in SEQ ID NO:1 or at a position corresponding to this position, is deleted or substituted with phenylalanine, leucine or tryptophan; and/or
(41) an amino acid residue at position 111 in the amino acid sequence shown in SEQ ID NO:1 or at a position corresponding to this position, is deleted or substituted with cysteine; and/or
(42) an amino acid residue at position 117 in the amino acid sequence shown in SEQ ID NO:1 or at a position corresponding to this position, is deleted or substituted with alanine; and/or
(43) an amino acid residue at position 114 in the amino acid sequence shown in SEQ ID NO:1 or at a position corresponding to this position, is deleted or substituted with serine; and/or
(44) an amino acid residue at position 119 in the amino acid sequence shown in SEQ ID NO:1 or at a position corresponding to this position, is deleted or substituted with threonine; and/or
(45) an amino acid residue at position 120 in the amino acid sequence shown in SEQ ID NO:1 or at a position corresponding to this position, is deleted or substituted with serine; and/or
(46) an amino acid residue at position 126 in the amino acid sequence shown in SEQ ID NO:1 or at a position corresponding to this position, is deleted or substituted with proline; and/or
(47) an amino acid residue at position 141 in the amino acid sequence shown in SEQ ID NO:1 or at a position corresponding to this position, is deleted or substituted with aspartic acid; and/or
(48) an amino acid residue at position 146 in the amino acid sequence shown in SEQ ID NO:1 or at a position corresponding to this position, is deleted or substituted with serine; and/or
(49) an amino acid residue at position 159 in the amino acid sequence shown in SEQ ID NO:1 or at a position corresponding to this position, is deleted or substituted with cysteine; and/or
(50) an amino acid residue at position 160 in the amino acid sequence shown in SEQ ID NO:1 or at a position corresponding to this position, is deleted or substituted with phenylalanine; and/or
(51) an amino acid residue at position 162 in the amino acid sequence shown in SEQ ID NO:1 or at a position corresponding to this position, is deleted or substituted with proline, histidine or asparagine; and/or
(52) an amino acid residue at position 176 in the amino acid sequence shown in SEQ ID NO:1 or at a position corresponding to this position, is deleted or substituted with phenylalanine; and/or
(53) an amino acid residue at position 189 in the amino acid sequence shown in SEQ ID NO:1 or at a position corresponding to this position, is deleted or substituted with isoleucine; and/or
(54) an amino acid residue at position 193 in the amino acid sequence shown in SEQ ID NO:1 or at a position corresponding to this position, is deleted or substituted with isoleucine, threonine or valine; and/or
(55) an amino acid residue at position 195 in the amino acid sequence shown in SEQ ID NO:1 or at a position corresponding to this position, is deleted or substituted with methionine, cysteine, phenylalanine, isoleucine, valine, tryptophan or tyrosine; and/or
(56) an amino acid residue at position 197 in the amino acid sequence shown in SEQ ID NO:1 or at a position corresponding to this position, is deleted or substituted with phenylalanine or methionine; and/or
(57) an amino acid residue at position 206 in the amino acid sequence shown in SEQ ID NO:1 or at a position corresponding to this position, is deleted or substituted with phenylalanine; and/or
(58) an amino acid residue at position 211 in the amino acid sequence shown in SEQ ID NO:1 or at a position corresponding to this position, is deleted or substituted with glutamic acid; and/or
(59) an amino acid residue at position 213 in the amino acid sequence shown in SEQ ID NO:1 or at a position corresponding to this position, is deleted or substituted with proline or leucine; and/or
(60) an amino acid residue at position 214 in the amino acid sequence shown in SEQ ID NO:1 or at a position corresponding to this position, is deleted or substituted with alanine, threonine, histidine, glutamic acid, phenylalanine, arginine or valine; and/or
(61) an amino acid residue at position 215 in the amino acid sequence shown in SEQ ID NO:1 or at a position corresponding to this position, is deleted or substituted with cysteine; and/or
(62) an amino acid residue at position 216 in the amino acid sequence shown in SEQ ID NO:1 or at a position corresponding to this position, is deleted or substituted with asparagine; and/or
(63) an amino acid residue at position 221 in the amino acid sequence shown in SEQ ID NO:1 or at a position corresponding to this position, is deleted or substituted with cysteine; and/or
(64) an amino acid residue at position 222 in the amino acid sequence shown in SEQ ID NO:1 or at a position corresponding to this position, is deleted or substituted with cysteine; and/or
(65) an amino acid residue at position 228 in the amino acid sequence shown in SEQ ID NO:1 or at a position corresponding to this position, is deleted or substituted with leucine, alanine, proline, threonine or valine; and/or
(66) an amino acid residue at position 232 in the amino acid sequence shown in SEQ ID NO:1 or at a position corresponding to this position, is deleted or substituted with valine; and/or
(67) an amino acid residue at position 244 in the amino acid sequence shown in SEQ ID NO:1 or at a position corresponding to this position, is deleted or substituted with phenylalanine; and/or
(68) an amino acid residue at position 247 in the amino acid sequence shown in SEQ ID NO:1 or at a position corresponding to this position, is deleted or substituted with alanine; and/or
(69) an amino acid residue at position 264 in the amino acid sequence shown in SEQ ID NO:1 or at a position corresponding to this position, is deleted or substituted with aspartic acid; and/or
(70) an amino acid residue at position 278 in the amino acid sequence shown in SEQ ID NO:1 or at a position corresponding to this position, is deleted or substituted with isoleucine; and/or
(71) an amino acid residue at position 284 in the amino acid sequence shown in SEQ ID NO:1 or at a position corresponding to this position, is deleted or substituted with tyrosine or leucine; and/or
(72) an amino acid residue at position 285 in the amino acid sequence shown in SEQ ID NO:1 or at a position corresponding to this position, is deleted or substituted with leucine; and/or
(73) an amino acid residue at position 293 in the amino acid sequence shown in SEQ ID NO:1 or at a position corresponding to this position, is deleted or substituted with leucine; and/or
(74) an amino acid residue at position 303 in the amino acid sequence shown in SEQ ID NO:1 or at a position corresponding to this position, is deleted or substituted with serine or proline; and/or
(75) an amino acid residue at position 305 in the amino acid sequence shown in SEQ ID NO:1 or at a position corresponding to this position, is deleted or substituted with alanine or aspartic acid; and/or
(76) an amino acid residue at position 306 in the amino acid sequence shown in SEQ ID NO:1 or at a position corresponding to this position, is deleted or substituted with phenylalanine, arginine or serine; and/or
(77) an amino acid residue at position 326 in the amino acid sequence shown in SEQ ID NO:1 or at a position corresponding to this position, is deleted or substituted with alanine or proline; and/or
(78) an amino acid residue at position 337 in the amino acid sequence shown in SEQ ID NO:1 or at a position corresponding to this position, is deleted or substituted with methionine or leucine; and/or
(79) an amino acid residue at position 338 in the amino acid sequence shown in SEQ ID NO:1 or at a position corresponding to this position, is deleted or substituted with proline, alanine or serine; and/or
(80) an amino acid residue at position 341 in the amino acid sequence shown in SEQ ID NO:1 or at a position corresponding to this position, is deleted or substituted with isoleucine; and/or
(81) an amino acid residue at position 342 in the amino acid sequence shown in SEQ ID NO:1 or at a position corresponding to this position, is deleted or substituted with glycine; and/or
(82) an amino acid residue at position 345 in the amino acid sequence shown in SEQ ID NO:1 or at a position corresponding to this position, is deleted or substituted with leucine; and/or
(83) an amino acid residue at position 349 in the amino acid sequence shown in SEQ ID NO:1 or at a position corresponding to this position, is deleted or substituted with serine; and/or
(84) an amino acid residue at position 352 in the amino acid sequence shown in SEQ ID NO:1 or at a position corresponding to this position, is deleted or substituted with glycine or leucine; and/or
(85) an amino acid residue at position 351 in the amino acid sequence shown in SEQ ID NO:1 or at a position corresponding to this position, is deleted or substituted with arginine, asparagine, alaine or valine or glycine; and/or
(86) an amino acid residue at position 375 in the amino acid sequence shown in SEQ ID NO:1 or at a position corresponding to this position, is deleted or substituted with leucine; and/or
(88) an amino acid residue at position 376 in the amino acid sequence shown in SEQ ID NO:1 or at a position corresponding to this position, is deleted or substituted with isoleucine; and/or
(89) an amino acid residue at position 381 in the amino acid sequence shown in SEQ ID NO:1 or at a position corresponding to this position, is deleted or substituted with arginine; and/or
(90) an amino acid residue at position 384 in the amino acid sequence shown in SEQ ID NO:1 or at a position corresponding to this position, is deleted or substituted with tyrosine; and/or
(91) an amino acid residue at position 386 in the amino acid sequence shown in SEQ ID NO:1 or at a position corresponding to this position, is deleted or substituted with asparagine; and/or
(92) an amino acid residue at position 388 in the amino acid sequence shown in SEQ ID NO:1 or at a position corresponding to this position, is deleted or substituted with glutamic acid; and/or
(93) an amino acid residue at position 395 in the amino acid sequence shown in SEQ ID NO:1 or at a position corresponding to this position, is deleted or substituted with cysteine; and/or
(94) an amino acid residue at position 399 in the amino acid sequence shown in SEQ ID NO:1 or at a position corresponding to this position, is deleted or substituted with arginine or asparagine; and/or
(95) an amino acid residue at position 402 in the amino acid sequence shown in SEQ ID NO:1 or at a position corresponding to this position, is deleted or substituted with valine or histidine; and/or
(96) an amino acid residue at position 404 in the amino acid sequence shown in SEQ ID NO:1 or at a position corresponding to this position, is deleted or substituted with tyrosine or tryptophane; and/or
(97) an amino acid residue at position 405 in the amino acid sequence shown in SEQ ID NO:1 or at a position corresponding to this position, is deleted or substituted with phenylalanine, leucine, methionine, proline or glutamine; and/or
(98) an amino acid residue at position 406 in the amino acid sequence shown in SEQ ID NO:1 or at a position corresponding to this position, is deleted or substituted with glutamine; and/or
(99) an amino acid residue at position 414 in the amino acid sequence shown in SEQ ID NO:1 or at a position corresponding to this position, is deleted or substituted with asparagine; and/or
(100) an amino acid residue at position 420 in the amino acid sequence shown in SEQ ID NO:1 or at a position corresponding to this position, is deleted or substituted with leucine; and/or
(101) an amino acid residue at position 422 in the amino acid sequence shown in SEQ ID NO:1 or at a position corresponding to this position, is deleted or substituted with methionine; and/or
(102) an amino acid residue at position 429 in the amino acid sequence shown in SEQ ID NO:1 or at a position corresponding to this position, is deleted or substituted with alanine or serine; and/or
(103) an amino acid residue at position 435 in the amino acid sequence shown in SEQ ID NO:1 or at a position corresponding to this position, is deleted or substituted with methionine; and/or
(104) an amino acid residue at position 436 in the amino acid sequence shown in SEQ ID NO:1 or at a position corresponding to this position, is deleted or substituted with asparagine; and/or
(105) an amino acid residue at position 439 in the amino acid sequence shown in SEQ ID NO:1 or at a position corresponding to this position, is deleted or substituted with leucine; and/or
(106) an amino acid residue at position 440 in the amino acid sequence shown in SEQ ID NO:1 or at a position corresponding to this position, is deleted or substituted with valine; and/or
(107) an amino acid residue at position 441 in the amino acid sequence shown in SEQ ID NO:1 or at a position corresponding to this position, is deleted or substituted with tyrosine; and/or
(108) an amino acid residue at position 442 in the amino acid sequence shown in SEQ ID NO:1 or at a position corresponding to this position, is deleted or substituted with threonine; and/or
(109) an amino acid residue at position 443 in the amino acid sequence shown in SEQ ID NO:1 or at a position corresponding to this position, is deleted or substituted with asparagine; and/or
(110) an amino acid residue at position 447 in the amino acid sequence shown in SEQ ID NO:1 or at a position corresponding to this position, is deleted or substituted with tryptophan, methionine or tyrosine; and/or
(111) an amino acid residue at position 449 in the amino acid sequence shown in SEQ ID NO:1 or at a position corresponding to this position, is deleted or substituted with isoleucine, methionine or valine; and/or
(112) an amino acid residue at position 460 in the amino acid sequence shown in SEQ ID NO:1 or at a position corresponding to this position, is deleted or substituted with phenylalanine or proline; and/or
(113) an amino acid residue at position 462 in the amino acid sequence shown in SEQ ID NO:1 or at a position corresponding to this position, is deleted or substituted with asparagine; and/or
(114) an amino acid residue at position 488 in the amino acid sequence shown in SEQ ID NO:1 or at a position corresponding to this position, is deleted or substituted with alanine or asparagine; and/or
(115) an amino acid residue at position 493 in the amino acid sequence shown in SEQ ID NO:1 or at a position corresponding to this position, is deleted or substituted with arginine; and/or
(116) an amino acid residue at position 494 in the amino acid sequence shown in SEQ ID NO:1 or at a position corresponding to this position, is deleted or substituted with arginine; and/or
(117) an amino acid residue at position 496 in the amino acid sequence shown in SEQ ID NO:1 or at a position corresponding to this position, is deleted or substituted with alanine or phenylalaine; and/or
(118) an amino acid residue at position 500 in the amino acid sequence shown in SEQ ID NO:1 or at a position corresponding to this position, is deleted or substituted with alanine; and/or
(119) an amino acid residue at position 501 in the amino acid sequence shown in SEQ ID NO:1 or at a position corresponding to this position, is deleted or substituted with glutamic acid, glycine or methionine or lysine; and/or
(120) an amino acid residue at position 502 in the amino acid sequence shown in SEQ ID NO:1 or at a position corresponding to this position, is deleted or substituted with asparagine; and/or
(121) an amino acid residue at position 506 in the amino acid sequence shown in SEQ ID NO:1 or at a position corresponding to this position, is deleted or substituted with isoleucine or tyrosine; and/or
(122) an amino acid residue at position 509 in the amino acid sequence shown in SEQ ID NO:1 or at a position corresponding to this position, is deleted or substituted with leucine; and/or
(123) an amino acid residue at position 511 in the amino acid sequence shown in SEQ ID NO:1 or at a position corresponding to this position, is deleted or substituted with methionine or isoleucine.

The invention also relates to variants as defined in (1) to (123) hereinabove, wherein the amino acid residue indicated as substituting the amino acid residue at the position in SEQ ID NO: 1 is not that particular amino acid residue but an amino acid residue which is conservative in relation to the indicated substituting amino acid.

Whether an amino acid is conservative with respect to another amino acid can be judged according to means and methods known in the art and as described herein above. One possibility is the PAM 250 matrix; alternatively, the Blosum Family Matrices can be used.

The first part of the present invention also relates to an MDC variant having an amino acid sequence as shown in SEQ ID NO:1 or an amino acid sequence having at least 95%, preferably at least 97%, even more preferred at least 98% sequence identity to SEQ ID NO: 1, in which one or more amino acid residues at a position selected from the group consisting of positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

According to one embodiment, the first part of the present invention relates to any of these MDC variants having an amino acid sequence as shown in SEQ ID NO:1 or an amino acid sequence having at least 95%, preferably at least 97%, even more preferred at least 98% sequence identity to SEQ ID NO:1 in which (1) an amino acid residue at position 2 in the amino acid sequence shown in SEQ ID NO:1 or at a position corresponding to this position, is deleted or substituted with alanine, aspartic acid, phenylalanine, lysine, leucine, asparagine, glutamine, cysteine or valine; and/or
(2) an amino acid residue at position 3 in the amino acid sequence shown in SEQ ID NO:1 or at a position corresponding to this position, is deleted or substituted with alanine, glutamic acid, glycine, lysine, proline, tryptophan, aspartic acid or tyrosine; and/or
(3) an amino acid residue at position 4 in the amino acid sequence shown in SEQ ID NO:1 or at a position corresponding to this position, is deleted or substituted with glutamic acid, leucine, methionine, alanine, serine or asparagine; and/or
(4) an amino acid residue at position 5 in the amino acid sequence shown in SEQ ID NO:1 or at a position corresponding to this position, is deleted or substituted with serine; and/or
(5) an amino acid residue at position 6 in the amino acid sequence shown in SEQ ID NO:1 or at a position corresponding to this position, is deleted or substituted with proline; and/or
(6) an amino acid residue at position 7 in the amino acid sequence shown in SEQ ID NO:1 or at a position corresponding to this position, is deleted or substituted with arginine; and/or
(7) an amino acid residue at position 8 in the amino acid sequence shown in SEQ ID NO:1 or at a position corresponding to this position, is deleted or substituted with asparagine; and/or
(8) an amino acid residue at position 9 in the amino acid sequence shown in SEQ ID NO:1 or at a position corresponding to this position, is deleted or substituted with histidine, proline or tyrosine; and/or
(9) an amino acid residue at position 10 in the amino acid sequence shown in SEQ ID NO:1 or at a position corresponding to this position, is deleted or substituted with histidine, phenylalanine, lysine, proline, threonine or leucine; and/or
(10) an amino acid residue at position 11 in the amino acid sequence shown in SEQ ID NO:1 or at a position corresponding to this position, is deleted or substituted with leucine, tyrosine or proline; and/or
(11) an amino acid residue at position 12 in the amino acid sequence shown in SEQ ID NO:1 or at a position corresponding to this position, is deleted or substituted with serine or asparagine or alanine; and/or
(12) an amino acid residue at position 13 in the amino acid sequence shown in SEQ ID NO:1 or at a position corresponding to this position, is deleted or substituted with histidine, isoleucine, asparagine, serine, valine or tyrosine; and/or
(13) an amino acid residue at position 14 in the amino acid sequence shown in SEQ ID NO:1 or at a position corresponding to this position, is deleted or substituted with aspartic acid; and/or
(14) an amino acid residue at position 15 in the amino acid sequence shown in SEQ ID NO:1 or at a position corresponding to this position, is deleted or substituted with threonine; and/or
(15) an amino acid residue at position 25 in the amino acid sequence shown in SEQ ID NO:1 or at a position corresponding to this position, is deleted or substituted with asparagine, serine or tryptophan; and/or
(16) an amino acid residue at position 29 in the amino acid sequence shown in SEQ ID NO:1 or at a position corresponding to this position, is deleted or substituted with asparagine, histidine or serine; and/or
(17) an amino acid residue at position 30 in the amino acid sequence shown in SEQ ID NO:1 or at a position corresponding to this position, is deleted or substituted with glycine, histidine or arginine; and/or
(18) an amino acid residue at position 31 in the amino acid sequence shown in SEQ ID NO:1 or at a position corresponding to this position, is deleted or substituted with glutamic acid or glycine or lysine; and/or
(19) an amino acid residue at position 33 in the amino acid sequence shown in SEQ ID NO:1 or at a position corresponding to this position, is deleted or substituted with isoleucine; and/or
(20) an amino acid residue at position 34 in the amino acid sequence shown in SEQ ID NO:1 or at a position corresponding to this position, is deleted or substituted with alanine or isoleucine; and/or
(21) an amino acid residue at position 35 in the amino acid sequence shown in SEQ ID NO:1 or at a position corresponding to this position, is deleted or substituted with methionine, serine or threonine; and/or
(22) an amino acid residue at position 40 in the amino acid sequence shown in SEQ ID NO:1 or at a position corresponding to this position, is deleted or substituted with isoleucine or methionine; and/or
(23) an amino acid residue at position 43 in the amino acid sequence shown in SEQ ID NO:1 or at a position corresponding to this position, is deleted or substituted with arginine; and/or
(24) an amino acid residue at position 57 in the amino acid sequence shown in SEQ ID NO:1 or at a position corresponding to this position, is deleted or substituted with asparagine; and/or
(25) an amino acid residue at position 60 in the amino acid sequence shown in SEQ ID NO:1 or at a position corresponding to this position, is deleted or substituted with valine; and/or
(26) an amino acid residue at position 65 in the amino acid sequence shown in SEQ ID NO:1 or at a position corresponding to this position, is deleted or substituted with leucine or tryptophan; and/or
(27) an amino acid residue at position 67 in the amino acid sequence shown in SEQ ID NO:1 or at a position corresponding to this position, is deleted or substituted with arginine or valine; and/or
(28) an amino acid residue at position 69 in the amino acid sequence shown in SEQ ID NO:1 or at a position corresponding to this position, is deleted or substituted with asparagine; and/or
(29) an amino acid residue at position 70 in the amino acid sequence shown in SEQ ID NO:1 or at a position corresponding to this position, is deleted or substituted with isoleucine or leucine; and/or
(30) an amino acid residue at position 71 in the amino acid sequence shown in SEQ ID NO:1 or at a position corresponding to this position, is deleted or substituted with glycine; and/or
(31) an amino acid residue at position 72 in the amino acid sequence shown in SEQ ID NO:1 or at a position corresponding to this position, is deleted or substituted with arginine; and/or
(32) an amino acid residue at position 80 in the amino acid sequence shown in SEQ ID NO:1 or at a position corresponding to this position, is deleted or substituted with leucine; and/or
(33) an amino acid residue at position 84 in the amino acid sequence shown in SEQ ID NO:1 or at a position corresponding to this position, is deleted or substituted with cysteine; and/or
(34) an amino acid residue at position 85 in the amino acid sequence shown in SEQ ID NO:1 or at a position corresponding to this position, is deleted or substituted with alanine or threonine; and/or
(35) an amino acid residue at position 86 in the amino acid sequence shown in SEQ ID NO:1 or at a position corresponding to this position, is deleted or substituted with asparagine or isoleucine; and/or
(36) an amino acid residue at position 87 in the amino acid sequence shown in SEQ ID NO:1 or at a position corresponding to this position, is deleted or substituted with alanine, cysteine, phenylalanine, isoleucine, leucine, methionine, valine or tryptophan; and/or
(37) an amino acid residue at position 89 in the amino acid sequence shown in SEQ ID NO:1 or at a position corresponding to this position, is deleted or substituted with serine or phenylalanine; and/or
(38) an amino acid residue at position 90 in the amino acid sequence shown in SEQ ID NO:1 or at a position corresponding to this position, is deleted or substituted with leucine; and/or
(39) an amino acid residue at position 91 in the amino acid sequence shown in SEQ ID NO:1 or at a position corresponding to this position, is deleted or substituted with leucine; and/or
(40) an amino acid residue at position 99 in the amino acid sequence shown in SEQ ID NO:1 or at a position corresponding to this position, is deleted or substituted with asparagine or proline; and/or
(41) an amino acid residue at position 101 in the amino acid sequence shown in SEQ ID NO:1 or at a position corresponding to this position, is deleted or substituted with isoleucine or leucine; and/or
(42) an amino acid residue at position 102 in the amino acid sequence shown in SEQ ID NO:1 or at a position corresponding to this position, is deleted or substituted with leucine; and/or
(43) an amino acid residue at position 103 in the amino acid sequence shown in SEQ ID NO:1 or at a position corresponding to this position, is deleted or substituted with isoleucine, leucine or methionine; and/or
(44) an amino acid residue at position 105 in the amino acid sequence shown in SEQ ID NO:1 or at a position corresponding to this position, is deleted or substituted with phenylalanine, leucine or tryptophan; and/or
(45) an amino acid residue at position 106 in the amino acid sequence shown in SEQ ID NO:1 or at a position corresponding to this position, is deleted or substituted with threonine; and/or
(46) an amino acid residue at position 108 in the amino acid sequence shown in SEQ ID NO:1 or at a position corresponding to this position, is deleted or substituted with lysine, arginine or tryptophan; and/or
(47) an amino acid residue at position 111 in the amino acid sequence shown in SEQ ID NO:1 or at a position corresponding to this position, is deleted or substituted with cysteine; and/or
(48) an amino acid residue at position 117 in the amino acid sequence shown in SEQ ID NO:1 or at a position corresponding to this position, is deleted or substituted with alanine; and/or
(49) an amino acid residue at position 114 in the amino acid sequence shown in SEQ ID NO:1 or at a position corresponding to this position, is deleted or substituted with serine; and/or
(50) an amino acid residue at position 119 in the amino acid sequence shown in SEQ ID NO:1 or at a position corresponding to this position, is deleted or substituted with threonine; and/or
(51) an amino acid residue at position 120 in the amino acid sequence shown in SEQ ID NO:1 or at a position corresponding to this position, is deleted or substituted with serine; and/or
(52) an amino acid residue at position 126 in the amino acid sequence shown in SEQ ID NO:1 or at a position corresponding to this position, is deleted or substituted with proline; and/or
(53) an amino acid residue at position 132 in the amino acid sequence shown in SEQ ID NO:1 or at a position corresponding to this position, is deleted or substituted with cysteine; and/or
(54) an amino acid residue at position 141 in the amino acid sequence shown in SEQ ID NO:1 or at a position corresponding to this position, is deleted or substituted with aspartic acid; and/or
(55) an amino acid residue at position 146 in the amino acid sequence shown in SEQ ID NO:1 or at a position corresponding to this position, is deleted or substituted with serine; and/or
(56) an amino acid residue at position 149 in the amino acid sequence shown in SEQ ID NO:1 or at a position corresponding to this position, is deleted or substituted with valine or serine; and/or
(57) an amino acid residue at position 159 in the amino acid sequence shown in SEQ ID NO:1 or at a position corresponding to this position, is deleted or substituted with cysteine; and/or
(58) an amino acid residue at position 160 in the amino acid sequence shown in SEQ ID NO:1 or at a position corresponding to this position, is deleted or substituted with phenylalanine; and/or
(59) an amino acid residue at position 162 in the amino acid sequence shown in SEQ ID NO:1 or at a position corresponding to this position, is deleted or substituted with proline, histidine or asparagine; and/or
(60) an amino acid residue at position 175 in the amino acid sequence shown in SEQ ID NO:1 or at a position corresponding to this position, is deleted or substituted with glycine, lysine, proline, glutamine, serine, threonine, or tryptophan; and/or
(61) an amino acid residue at position 176 in the amino acid sequence shown in SEQ ID NO:1 or at a position corresponding to this position, is deleted or substituted with phenylalanine; and/or
(62) an amino acid residue at position 187 in the amino acid sequence shown in SEQ ID NO:1 or at a position corresponding to this position, is deleted or substituted with threonine; and/or
(63) an amino acid residue at position 189 in the amino acid sequence shown in SEQ ID NO:1 or at a position corresponding to this position, is deleted or substituted with isoleucine; and/or
(64) an amino acid residue at position 193 in the amino acid sequence shown in SEQ ID NO:1 or at a position corresponding to this position, is deleted or substituted with isoleucine, threonine or valine; and/or
(65) an amino acid residue at position 195 in the amino acid sequence shown in SEQ ID NO:1 or at a position corresponding to this position, is deleted or substituted with methionine, cysteine, phenylalanine, isoleucine, valine, tryptophan or tyrosine; and/or
(66) an amino acid residue at position 197 in the amino acid sequence shown in SEQ ID NO:1 or at a position corresponding to this position, is deleted or substituted with phenylalanine or methionine; and/or
(67) an amino acid residue at position 206 in the amino acid sequence shown in SEQ ID NO:1 or at a position corresponding to this position, is deleted or substituted with phenylalanine; and/or
(68) an amino acid residue at position 211 in the amino acid sequence shown in SEQ ID NO:1 or at a position corresponding to this position, is deleted or substituted with glutamic acid; and/or
(69) an amino acid residue at position 213 in the amino acid sequence shown in SEQ ID NO:1 or at a position corresponding to this position, is deleted or substituted with proline or leucine; and/or
(70) an amino acid residue at position 214 in the amino acid sequence shown in SEQ ID NO:1 or at a position corresponding to this position, is deleted or substituted with alanine, threonine, histidine, glutamic acid, phenylalanine, arginine or valine; and/or
(71) an amino acid residue at position 215 in the amino acid sequence shown in SEQ ID NO:1 or at a position corresponding to this position, is deleted or substituted with cysteine; and/or
(72) an amino acid residue at position 216 in the amino acid sequence shown in SEQ ID NO:1 or at a position corresponding to this position, is deleted or substituted with asparagine; and/or
(73) an amino acid residue at position 221 in the amino acid sequence shown in SEQ ID NO:1 or at a position corresponding to this position, is deleted or substituted with cysteine; and/or
(74) an amino acid residue at position 222 in the amino acid sequence shown in SEQ ID NO:1 or at a position corresponding to this position, is deleted or substituted with cysteine; and/or
(75) an amino acid residue at position 228 in the amino acid sequence shown in SEQ ID NO:1 or at a position corresponding to this position, is deleted or substituted with leucine, alanine, proline, threonine or valine; and/or
(76) an amino acid residue at position 232 in the amino acid sequence shown in SEQ ID NO:1 or at a position corresponding to this position, is deleted or substituted with valine; and/or
(77) an amino acid residue at position 244 in the amino acid sequence shown in SEQ ID NO:1 or at a position corresponding to this position, is deleted or substituted with phenylalanine; and/or
(78) an amino acid residue at position 247 in the amino acid sequence shown in SEQ ID NO:1 or at a position corresponding to this position, is deleted or substituted with alanine; and/or
(79) an amino acid residue at position 264 in the amino acid sequence shown in SEQ ID NO:1 or at a position corresponding to this position, is deleted or substituted with aspartic acid; and/or
(80) an amino acid residue at position 278 in the amino acid sequence shown in SEQ ID NO:1 or at a position corresponding to this position, is deleted or substituted with isoleucine; and/or
(81) an amino acid residue at position 284 in the amino acid sequence shown in SEQ ID NO:1 or at a position corresponding to this position, is deleted or substituted with tyrosine or leucine; and/or
(82) an amino acid residue at position 285 in the amino acid sequence shown in SEQ ID NO:1 or at a position corresponding to this position, is deleted or substituted with leucine; and/or
(83) an amino acid residue at position 293 in the amino acid sequence shown in SEQ ID NO:1 or at a position corresponding to this position, is deleted or substituted with leucine; and/or
(84) an amino acid residue at position 303 in the amino acid sequence shown in SEQ ID NO:1 or at a position corresponding to this position, is deleted or substituted with serine or proline; and/or
(85) an amino acid residue at position 305 in the amino acid sequence shown in SEQ ID NO:1 or at a position corresponding to this position, is deleted or substituted with alanine or aspartic acid; and/or
(86) an amino acid residue at position 306 in the amino acid sequence shown in SEQ ID NO:1 or at a position corresponding to this position, is deleted or substituted with phenylalanine, arginine or serine; and/or
(87) an amino acid residue at position 326 in the amino acid sequence shown in SEQ ID NO:1 or at a position corresponding to this position, is deleted or substituted with alanine or proline; and/or
(88) an amino acid residue at position 337 in the amino acid sequence shown in SEQ ID NO:1 or at a position corresponding to this position, is deleted or substituted with methionine or leucine; and/or
(89) an amino acid residue at position 338 in the amino acid sequence shown in SEQ ID NO:1 or at a position corresponding to this position, is deleted or substituted with proline, alanine or serine; and/or
(90) an amino acid residue at position 341 in the amino acid sequence shown in SEQ ID NO:1 or at a position corresponding to this position, is deleted or substituted with isoleucine; and/or
(91) an amino acid residue at position 342 in the amino acid sequence shown in SEQ ID NO:1 or at a position corresponding to this position, is deleted or substituted with glycine; and/or

(92) an amino acid residue at position 345 in the amino acid sequence shown in SEQ ID NO:1 or at a position corresponding to this position, is deleted or substituted with leucine; and/or
(93) an amino acid residue at position 349 in the amino acid sequence shown in SEQ ID NO:1 or at a position corresponding to this position, is deleted or substituted with serine; and/or
(94) an amino acid residue at position 352 in the amino acid sequence shown in SEQ ID NO:1 or at a position corresponding to this position, is deleted or substituted with glycine or leucine; and/or
(95) an amino acid residue at position 351 in the amino acid sequence shown in SEQ ID NO:1 or at a position corresponding to this position, is deleted or substituted with arginine, asparagine, alaine or valine or glycine; and/or
(96) an amino acid residue at position 375 in the amino acid sequence shown in SEQ ID NO:1 or at a position corresponding to this position, is deleted or substituted with leucine; and/or
(97) an amino acid residue at position 377 in the amino acid sequence shown in SEQ ID NO:1 or at a position corresponding to this position, is deleted or substituted with histidine; and/or
(98) an amino acid residue at position 376 in the amino acid sequence shown in SEQ ID NO:1 or at a position corresponding to this position, is deleted or substituted with isoleucine; and/or
(99) an amino acid residue at position 381 in the amino acid sequence shown in SEQ ID NO:1 or at a position corresponding to this position, is deleted or substituted with arginine; and/or
(100) an amino acid residue at position 384 in the amino acid sequence shown in SEQ ID NO:1 or at a position corresponding to this position, is deleted or substituted with tyrosine; and/or
(101) an amino acid residue at position 386 in the amino acid sequence shown in SEQ ID NO:1 or at a position corresponding to this position, is deleted or substituted with asparagine; and/or
(102) an amino acid residue at position 388 in the amino acid sequence shown in SEQ ID NO:1 or at a position corresponding to this position, is deleted or substituted with glutamic acid; and/or
(103) an amino acid residue at position 392 in the amino acid sequence shown in SEQ ID NO:1 or at a position corresponding to this position, is deleted or substituted with leucine or alanine; and/or
(104) an amino acid residue at position 395 in the amino acid sequence shown in SEQ ID NO:1 or at a position corresponding to this position, is deleted or substituted with cysteine; and/or
(105) an amino acid residue at position 399 in the amino acid sequence shown in SEQ ID NO:1 or at a position corresponding to this position, is deleted or substituted with arginine or asparagine; and/or
(106) an amino acid residue at position 402 in the amino acid sequence shown in SEQ ID NO:1 or at a position corresponding to this position, is deleted or substituted with valine or histidine; and/or
(107) an amino acid residue at position 404 in the amino acid sequence shown in SEQ ID NO:1 or at a position corresponding to this position, is deleted or substituted with tyrosine or tryptophane; and/or
(108) an amino acid residue at position 405 in the amino acid sequence shown in SEQ ID NO:1 or at a position corresponding to this position, is deleted or substituted with phenylalanine, leucine, methionine, proline or glutamine; and/or
(109) an amino acid residue at position 406 in the amino acid sequence shown in SEQ ID NO:1 or at a position corresponding to this position, is deleted or substituted with glutamine; and/or
(110) an amino acid residue at position 414 in the amino acid sequence shown in SEQ ID NO:1 or at a position corresponding to this position, is deleted or substituted with asparagine; and/or
(111) an amino acid residue at position 420 in the amino acid sequence shown in SEQ ID NO:1 or at a position corresponding to this position, is deleted or substituted with leucine; and/or
(112) an amino acid residue at position 422 in the amino acid sequence shown in SEQ ID NO:1 or at a position corresponding to this position, is deleted or substituted with methionine; and/or
(113) an amino acid residue at position 429 in the amino acid sequence shown in SEQ ID NO:1 or at a position corresponding to this position, is deleted or substituted with alanine or serine; and/or
(114) an amino acid residue at position 435 in the amino acid sequence shown in SEQ ID NO:1 or at a position corresponding to this position, is deleted or substituted with methionine; and/or
(115) an amino acid residue at position 436 in the amino acid sequence shown in SEQ ID NO:1 or at a position corresponding to this position, is deleted or substituted with asparagine; and/or
(116) an amino acid residue at position 439 in the amino acid sequence shown in SEQ ID NO:1 or at a position corresponding to this position, is deleted or substituted with leucine; and/or
(117) an amino acid residue at position 440 in the amino acid sequence shown in SEQ ID NO:1 or at a position corresponding to this position, is deleted or substituted with valine; and/or
(118) an amino acid residue at position 441 in the amino acid sequence shown in SEQ ID NO:1 or at a position corresponding to this position, is deleted or substituted with tyrosine; and/or
(119) an amino acid residue at position 442 in the amino acid sequence shown in SEQ ID NO:1 or at a position corresponding to this position, is deleted or substituted with threonine; and/or
(120) an amino acid residue at position 443 in the amino acid sequence shown in SEQ ID NO:1 or at a position corresponding to this position, is deleted or substituted with asparagine; and/or
(121) an amino acid residue at position 445 in the amino acid sequence shown in SEQ ID NO:1 or at a position corresponding to this position, is deleted or substituted with glutamic acid or proline; and/or
(122) an amino acid residue at position 447 in the amino acid sequence shown in SEQ ID NO:1 or at a position corresponding to this position, is deleted or substituted with tryptophan, methionine or tyrosine; and/or
(123) an amino acid residue at position 448 in the amino acid sequence shown in SEQ ID NO:1 or at a position corresponding to this position, is deleted or substituted with serine, phenylalanine or tryptophan; and/or
(124) an amino acid residue at position 449 in the amino acid sequence shown in SEQ ID NO:1 or at a position corresponding to this position, is deleted or substituted with isoleucine, methionine or valine; and/or (125) an amino acid residue at position 454 in the amino acid sequence shown in SEQ ID NO:1 or at a position corresponding to this position, is deleted or substituted with glycine; and/or
(126) an amino acid residue at position 460 in the amino acid sequence shown in SEQ ID NO:1 or at a position corresponding to this position, is deleted or substituted with phenylalanine or proline; and/or
(127) an amino acid residue at position 461 in the amino acid sequence shown in SEQ ID NO:1 or at a position corresponding to this position, is deleted or substituted with valine, asparagine or methionine; and/or
(128) an amino acid residue at position 462 in the amino acid sequence shown in SEQ ID NO:1 or at a position corresponding to this position, is deleted or substituted with asparagine; and/or
(129) an amino acid residue at position 484 in the amino acid sequence shown in SEQ ID NO:1 or at a position corresponding to this position, is deleted or substituted with alanine or glycine; and/or
(130) an amino acid residue at position 488 in the amino acid sequence shown in SEQ ID NO:1 or at a position corresponding to this position, is deleted or substituted with alanine or asparagine; and/or
(131) an amino acid residue at position 493 in the amino acid sequence shown in SEQ ID NO:1 or at a position corresponding to this position, is deleted or substituted with arginine; and/or
(132) an amino acid residue at position 494 in the amino acid sequence shown in SEQ ID NO:1 or at a position corresponding to this position, is deleted or substituted with arginine; and/or
(133) an amino acid residue at position 496 in the amino acid sequence shown in SEQ ID NO:1 or at a position corresponding to this position, is deleted or substituted with alanine or phenylalaine; and/or
(134) an amino acid residue at position 500 in the amino acid sequence shown in SEQ ID NO:1 or at a position corresponding to this position, is deleted or substituted with alanine; and/or
(135) an amino acid residue at position 501 in the amino acid sequence shown in SEQ ID NO:1 or at a position corresponding to this position, is deleted or substituted with glutamic acid, glycine or methionine or lysine; and/or
(136) an amino acid residue at position 502 in the amino acid sequence shown in SEQ ID NO:1 or at a position corresponding to this position, is deleted or substituted with asparagine; and/or
(137) an amino acid residue at position 506 in the amino acid sequence shown in SEQ ID NO:1 or at a position corresponding to this position, is deleted or substituted with isoleucine or tyrosine; and/or
(138) an amino acid residue at position 509 in the amino acid sequence shown in SEQ ID NO:1 or at a position corresponding to this position, is deleted or substituted with leucine; and/or
(139) an amino acid residue at position 511 in the amino acid sequence shown in SEQ ID NO:1 or at a position corresponding to this position, is deleted or substituted with methionine or isoleucine; and/or
(140) an amino acid residue at position 512 in the amino acid sequence shown in SEQ ID NO:1 or at a position corresponding to this position, is deleted or substituted with methionine, histidine or serine.

The invention also relates to variants as defined in (1) to 140) hereinabove, wherein the amino acid residue indicated as substituting the amino acid residue at the position in SEQ ID NO: 1 is not that particular amino acid residue but an amino acid residue which is conservative in relation to the indicated substituting amino acid.

Whether an amino acid is conservative with respect to another amino acid can be judged according to means and methods known in the art and as described herein above. One possibility is the PAM 250 matrix; alternatively, the Blosum Family Matrices can be used.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 405 in the amino acid sequence shown in SEQ ID NO:1 or at a position corresponding to this position.

Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: T405M, T405F, T405L, T405Q or T405P.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 2 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: S2Q, S2A, S2K, S2L, S2V, S2F, or S2N.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 195 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: L195M, L195C, L195I, L195W, L195Y, L195V, or L195F.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 3 in the amino acid sequence shown in SEQ ID NO:1 or at a position corresponding to this position and whereinsuch a variant further has one or more substitutions, deletions and/or insertions in comparison to the corresponding sequence from which it is derived and wherein these substitutions, deletions and/or insertions occur at one or more of the positions corresponding to positions 2, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: S3A, S3Y, S3W, S3G, S3P, or S3E.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 449 in the amino acid sequence shown in SEQ ID NO:1 or at a position corresponding to this position.

Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: L449I, L449M or L449V.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 4 in the amino acid sequence shown in SEQ ID NO:1 or at a position corresponding to this position and whereinsuch a variant further has one or more substitutions, deletions and/or insertions in comparison to the corresponding sequence from which it is derived and wherein these substitutions, deletions and/or insertions occur at one or more of the positions corresponding to positions 2, 3, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: T4E, T4M, or T4L.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 293 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: M293L.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 40 in the amino acid sequence shown in SEQ ID NO:1 or at a position corresponding to this position and whereinsuch a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: V40M or V40I.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 35 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: D35M, D35T or D35S.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 422 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: K422M.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 285 in the amino acid sequence shown in SEQ ID NO: 1 or at a position corresponding to this position and whereinsuch a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: A285L.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 448 in the amino acid sequence shown in SEQ ID NO: 1 or at a position corresponding to this position and whereinsuch a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: Q448W or Q448S.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 34 in the amino acid sequence shown in SEQ ID NO:1 or at a position corresponding to this position and whereinsuch a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: V34A or V34I.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 12 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: D12S.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 500 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: L500A.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 351 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: D351R.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 214 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: Q214T, Q214A or Q214V.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 9 in the amino acid sequence shown in SEQ ID NO:1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: E9Y, E9H or E9P.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 447 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: F447W or F447Y.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 114 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: L114S.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 13 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: P13N, P13I, P13Y, P13S or P13H.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 11 in the amino acid sequence shown in SEQ ID NO:1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: F11P, or F11L.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 43 in the amino acid sequence shown in SEQ ID NO:1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: D43R.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 420 in the amino acid sequence shown in SEQ ID NO:1 or at a position corresponding to this position.

Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: D420L.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 439 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: V439L.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 337 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: I337M.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 506 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 509, 511 and 512 in the amino acid sequence shown in SEQ ID NO:1.

Preferably, such a variant has the following substitution in the amino acid sequence shown in SEQ ID NO:1 or at positions corresponding to this position: L506I.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 120 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: P120S.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 429 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: T429S, or T429A.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 436 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: T436N.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 435 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: G435M.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 149 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: A149V.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 29 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: Q29N, or Q29S.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 10 in the amino acid sequence shown in SEQ ID NO:1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: A10H.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 31 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: N31G.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 25 in the amino acid sequence shown in SEQ ID NO:1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: E25N.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 501 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: N501K.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 197 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: I197F.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 146 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: A146S.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 442 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: D442T.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 445 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: V445P or V445E.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 33 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: L33I.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 381 in the amino acid sequence shown in SEQ ID NO:1 or at a position corresponding to this position.

Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: A381R.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 221 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: L221C.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 141 in the amino acid sequence shown in SEQ ID NO: 1 or at a position corresponding to this position and wherein such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: N141D.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 441 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitution in the amino acid sequence shown in SEQ ID NO:1 or at positions corresponding to this position: F441Y.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 3 in the amino acid sequence shown in SEQ ID NO: 1 or at a position corresponding to this position and another deletion/insertion/substitution is at position 511 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, and 512 in the amino acid sequence shown in SEQ ID NO:1.

Preferably, such a variant has the following substitutions in the amino acid sequence shown in SEQ ID NO:1 or at positions corresponding to these positions: S3K-L511M.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 4 in the amino acid sequence shown in SEQ ID NO: 1 or at a position corresponding to this position and another deletion/insertion/substitution is at position 91 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: T4N-F91L.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 3 in the amino acid sequence shown in SEQ ID NO: 1 or at a position corresponding to this position and another deletion/insertion/substitution is at position 284 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: S3K-M284Y.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 2 in the amino acid sequence shown in SEQ ID NO: 1 or at a position corresponding to this position and another deletion/insertion/substitution is at position 89 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: S2D-E89S.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 31 in the amino acid sequence shown in SEQ ID NO: 1 or at a position corresponding to this position and another deletion/insertion/substitution is at position 501 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: N31E-N501E.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 376 in the amino acid sequence shown in SEQ ID NO:1 or at a position corresponding to this position and another deletion/insertion/substitution is at position 388 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 377, 381, 384, 386, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: T376I-A388E.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 29 in the amino acid sequence shown in SEQ ID NO:1 or at a position corresponding to this position and another deletion/insertion/substitution is at position 351 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: Q29N-D351N.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 29 in the amino acid sequence shown in SEQ ID NO:1 or at a position corresponding to this position and another deletion/insertion/substitution is at position 448 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: Q29N-Q448W.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 405 in the amino acid sequence shown in SEQ ID NO:1 or at a position corresponding to this position and another deletion/insertion/substitution is at position 420 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: T405M-D420L.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 351 in the amino acid sequence shown in SEQ ID NO:1 or at a position corresponding to this position and another deletion/insertion/substitution is at position 405 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 352, 375, 376, 377, 381, 384, 386, 388, 392, 395, 399, 402, 404, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: D351N-T405M.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 29 in the amino acid sequence shown in SEQ ID NO: 1 or at a position corresponding to this position and another deletion/insertion/substitution is at position 405 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: Q29N-T405M.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 405 in the amino acid sequence shown in SEQ ID NO:1 or at a position corresponding to this position and another deletion/insertion/substitution is at position 448 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 429, 435, 436, 439, 440, 441, 442, 443, 445, 447, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: T405M-Q448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 351 in the amino acid sequence shown in SEQ ID NO:1 or at a position corresponding to this position, another deletion/insertion/substitution is at position 405 in the amino acid sequence shown in SEQ ID NO:1 or at a position corresponding to this position and another deletion/insertion/substitution is at position 445 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 352, 375, 376, 377, 381, 384, 386, 388, 392, 395, 399, 402, 404, 406, 414, 420, 422, 429, 435, 436, 439, 440, 441, 442, 443, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: D351R-T405M-V445P.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 351 in the amino acid sequence shown in SEQ ID NO:1 or at a position corresponding to this position, another deletion/insertion/substitution is at position 405 in the amino acid sequence shown in SEQ ID NO:1 or at a position corresponding to this position and another deletion/insertion/substitution is at position 448 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 352, 375, 376, 377, 381, 384, 386, 388, 392, 395, 399, 402, 404, 406, 414, 420, 422, 429, 435, 436, 439, 440, 441, 442, 443, 445, 447, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: D351R-T405M-Q448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 25 in the amino acid sequence shown in SEQ ID NO:1 or at a position corresponding to this position, another deletion/insertion/substitution is at position 31 in the amino acid sequence shown in SEQ ID NO:1 or at a position corresponding to this position and another deletion/insertion/substitution is at position 405 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 29, 30, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: E25N-N31G-T405M.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 29 in the amino acid sequence shown in SEQ ID NO:1 or at a position corresponding to this position, another deletion/insertion/substitution is at position 405 in the amino acid sequence shown in SEQ ID NO:1 or at a position corresponding to this position and another deletion/insertion/substitution is at position 429 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: Q29N-T405M-T429A.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 29 in the amino acid sequence shown in SEQ ID NO:1 or at a position corresponding to this position, another deletion/insertion/substitution is at position 405 in the amino acid sequence shown in SEQ ID NO:1 or at a position corresponding to this position and another deletion/insertion/substitution is at position 448 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 429, 435, 436, 439, 440, 441, 442, 443, 445, 447, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: Q29N-T405M-Q448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 31 in the amino acid sequence shown in SEQ ID NO:1 or at a position corresponding to this position, another deletion/insertion/substitution is at position 405 in the amino acid sequence shown in SEQ ID NO:1 or at a position corresponding to this position and another deletion/insertion/substitution is at position 445 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 429, 435, 436, 439, 440, 441, 442, 443, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: N31G-T405M-V445P.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 25 in the amino acid sequence shown in SEQ ID NO:1 or at a position corresponding to this position, another deletion/insertion/substitution is at position 405 in the amino acid sequence shown in SEQ ID NO:1 or at a position corresponding to this position and another deletion/insertion/substitution is at position 429 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: E25N-T405M-T429A.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 31 in the amino acid sequence shown in SEQ ID NO:1 or at a position corresponding to this position, another deletion/insertion/substitution is at position 405 in the amino acid sequence shown in SEQ ID NO:1 or at a position corresponding to this position and another deletion/insertion/substitution is at position 448 in the amino acid sequence shown in SEQ ID NO: 1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 406, 414, 420, 422, 429, 435, 436, 439, 440, 441, 442, 443, 445, 447, 449, 454, 460, 461, 462, 484, 488, 493, 494, 496, 500, 501, 502, 506, 509, 511 and 512 in the amino acid sequence shown in SEQ ID NO:1.

Preferably, such a variant has the following substitutions in the amino acid sequence shown in SEQ ID NO:1 or at positions corresponding to these positions: N31G-T405M-Q448W.

In other preferred embodiments, the MDC variant according to the invention showing an improved activity in converting 3-methylcrotonic acid into isobutene is characterized in that has multiple mutations. As it is exemplified in the examples further below, variants have been found bearing multiple mutations which exhibit an increase in the reaction rate of the conversion of 3-methylcrotonic acid into isobutene. These variants bearing multiple mutations are summarized in the following: Accordingly, in a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 351, 405, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: D351R-T405M-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 351, 405, 429, 445, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-D351R-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 405, 435, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-Q29N-T405M-G435M-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 31, 405, 435, and 445 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-Q29N-N31G-T405M-G435M-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 31, 405, and 429 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29H-N31G-T405M-T429A. In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 31, 351, 405, and 445 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-Q29N-N31G-D351R-T405M-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 351, 405, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-D351N-T405M-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 31, 351, 405, 429, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: N31G-D351R-T405M-T429A-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 31, 405, and 429 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-Q29N-N31G-T405M-T429A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 31, 351, 405, and 429 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-N31G-D351R-T405M-T429A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 31, 405, 420, 429, 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: N31G-T405M-D420L-T429A-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 351, 405, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-Q29H-D351R-T405M-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 351, 405, 435, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-D351R-T405M-G435M-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 86, 405, 429, 435, 445, and 448 in the amino acid sequence shown in SEQ ID NO:1 or at positions amino acid sequence shown in SEQ ID NO:1 or at positions corresponding to these positions: S86N-T405M-T429A-G435M-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 31, 351, 405, and 429 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-Q29N-N31G-D351R-T405M-T429A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 351, 405, 414, 429, 445, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-D351R-T405M-D414N-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 31, 351, 405, 429, 435, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: N31G-D351R-T405M-T429A-G435M-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 405, 429, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-T405M-T429A-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 351, 405, 429, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-D351R-T405M-T429A-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 405, 429, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-T405M-T429A-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 405, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-T405M-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 405, 429, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-Q29N-T405M-T429A-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 31, 351, 405, 429, 435, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-N31G-D351R-T405M-T429A-G435M-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 31, 405, 420, 429, 445, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: N31G-T405M-D420L-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 31, 351, 405, 429, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-N31G-D351G-T405M-T429A-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 405, 429, 435, 445, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-T405M-T429A-G435M-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 31, 405, 429, and 445 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-N31G-T405M-T429A-V445P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 435, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-G435M-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 31, 351, 405, 429, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: N31G-D351R-T405M-T429A-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 12, 29, 31, 405, 429, 445, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: D12N-Q29N-N31G-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 29, 31, 405, 429, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: Q29N-N31G-T405M-T429A-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 405, 429, 445, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 405, 429, 435, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-T405M-T429A-G435M-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 29, 31, 405, 429, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-Q29N-N31G-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 405, 429, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 120 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-P120K.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 303 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-H303S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445 and 448 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351G-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 264 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-N264D.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 392 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-R392L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 221 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-L221C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 305 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-G305A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 44, 448, and 85 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-S85A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 214 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-Q214V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 404 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 402 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-P402V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 228 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-T228L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 119 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-I119T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 10 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A10L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 484 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-S484A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 214 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-Q214E.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 214 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-Q214A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 211 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A211E.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 501 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-N501M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 214 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-Q214F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 228 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-T228V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 57 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-D57N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 512 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-D512E.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 484 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-S484G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 149 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A149V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 3, 86, 162, 384, and 392 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-D351R-T405M-T429A-V445P-Q448W-S3C-S86I-Q162P-T384Y-R392A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 162, 228, and 392 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-D351R-T405M-T429A-V445P-Q448W-Q162N-T228L-R392A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 162, and 392 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-D351R-T405M-T429A-V445P-Q448W-Q162N-R392A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 162, 228, 392, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-Q162N-T228L-R392A-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 162, 214, 228, 338, and 461 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85A-Q162N-Q214H-T228L-G338P-I461V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 175, 228, 392, 399, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-C175G-T228L-R392A-T399R-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 162, 175, 228, 338, 399, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85A-Q162N-C175G-T228L-G338P-T399R-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 162, 228, 338, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85A-Q162N-T228L-G338P-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 162, 175, 228, 338, 399, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85A-Q162N-C175G-T228L-G338P-T399R-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 162, 228, 338, 392, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85A-Q162N-T228L-G338P-R392A-I461M-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 162, 228, 338, 392, and 461 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-Q162N-T228L-G338P-R392A-I461V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 162, 175, 228, 338, 392, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-Q162N-C175G-T228L-G338P-R392A-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 175, 228, 338, 392, 399, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85A-C175G-T228L-G338P-R392A-T399R-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 162, 175, 228, 338, 392, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85A-Q162N-C175G-T228L-G338P-R392A-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 228, 338, 392, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-D351R-T405M-T429A-V445P-Q448W-T228L-G338P-R392A-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 305, and 402 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-D351R-T405M-T429A-V445P-Q448W-G305A-P402V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 305, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-D351R-T405M-T429A-V445P-Q448W-G305A-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 305, 402, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-D351R-T405M-T429A-V445P-Q448W-G305A-P402V-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 8 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-S8N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 10 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A1 OH.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 117 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-N117A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 132 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-V132C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 175 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-C175G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 175 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-C175K.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 175 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-C175S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 187 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-S187T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 193 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A193T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 197 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-I197M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448 and 222 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A222C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 228 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-T228A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 247 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-V247A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 342 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A342G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 399 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-T399N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 440 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-F440V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 460 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-A460P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 488 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-K488A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 501 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-N501G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 502 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-S502N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, and 506 in the amino acid sequence shown in SEQ ID NO:1 or at positions corresponding to these positions. Preferably, such a variant has the following substitutions in the amino acid sequence shown in SEQ ID NO: 1 or at positions corresponding to these positions: E25N-N31G-D351R-T405M-T429A-V445P-Q448W-L506Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 15 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P15T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 30 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-D30G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 30 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-D30H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 30 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-D30R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 65 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-N65W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 65 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-N65L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 70 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-K70L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 72 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-G72R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 80 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P80L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P87V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P87I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 90 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-R90L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 103 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-T103L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 105 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-

S85A-Q162N-C175G-T228L-G338P-D351R-R392A-T405M-T429A-V445P-Q448W-I461V-S494R-S105W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494 and 105 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-S105F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 108 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-D108R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 108 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-D108W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 126 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-I126P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175P-T228L-G338P-D351R-R392A-T405M-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 176 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-W176F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 213 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-G213L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 213 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-G213P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 305 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-G305D.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 306 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P306R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 306 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P306S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 326P in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-C326P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338S-D351R-R392A-T405M-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 341 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-A341I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351V-R392A-T405M-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 402 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P402H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 406 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-I406Q.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461N-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 103, and 111 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-T103I-D111C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 14, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-E14D-P87A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 176, and 511 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-W176F-L511I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 352 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25W-N31G-S85A-Q162N-C175G-T228L-G338P-D351R-R392A-T405M-T429A-V445P-Q448W-I461V-S494R-A352L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 352 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25S-N31G-S85A-Q162N-C175G-T228L-G338P-D351R-R392A-T405M-T429A-V445P-Q448W-I461V-S494R-A352G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 278, and 326 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-T278I-C326P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 341, 386, and 395 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-A341I-G386N-D395C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 349 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351A-R392A-T405M-T429A-V445P-Q448W-I461V-S494R-C349S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 7, and 176 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-K7R-W176F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 84, and 493 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-R84C-K493R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 87, and 159 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P87W-K159C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 87, 488, and 496 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P87C-K488N-Q496A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 89, and 496 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-E89F-Q496F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 377, 402, 404, 405, 429, 445, and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-K377H-P402V-F404Y-T405M-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 305, 377, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-G305A-K377H-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 305, 306, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-G305A-P306F-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 377, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-K377H-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 306, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P306F-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 306, and 377 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G338P-D351R-R392A-T405M-T429A-V445P-Q448W-I461V-S494R-P306F-K377H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 338, 351, 392, 405, 429, 445, 448, 461, 494, 306, 377, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions:

E25N-N31G-S85A-Q162N-C175G-T228L-G338P-D351R-R392A-T405M-T429A-V445P-Q448W-I461V-S494R-P306F-K377H-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 12 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-D12A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 35 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-D35T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 60 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A60V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 70 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-K70I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 70 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-K70L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P87F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448 and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P87L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P87M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P87V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P87W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 99 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A99P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 101 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P101I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 101 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P101L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 102 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P102L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 103 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-T103L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 105 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-S105L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 108 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-D108R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 189 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-K89I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 193 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A193I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 215 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-E215C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 244 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A244F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 326 in the amino acid sequence shown in SEQ ID NO: 1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-C326A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 375 in the amino acid sequence shown in SEQ ID NO: 1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-D375L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 443 in the amino acid sequence shown in SEQ ID NO: 1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-D443N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 460 in the amino acid sequence shown in SEQ ID NO: 1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A460F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, 102, and 484 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-P102L-S484A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, 108, and 160 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-D108K-Y160F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, 11, and 512 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-F11Y-D512S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 351, 405, 429, 445, 448, 85, 103, 162, 175, 228, 338, 392, and 461 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-D351R-T405M-T429A-V445P-Q448W-S85T-T103M-Q162H-C175W-T228P-G338A-R392A-I461M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 445, 448, and 87 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-V445P-Q448W-P87F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions E25, 31, 305, 351, 402, 404, 405, 429, 445, 448, and 3 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-S3G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 4 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-T4A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 5 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-T5S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 10 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A1 OF.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 10 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A10P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 10 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A1 OT.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 67 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-G305A-D351R-P402V-F404Y-T405M-T429A-V445P-Q448W-I67R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 67 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31 G-G305A-D351R-P402V-F404Y-T405M-T429A-V445P-Q448W-I67V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 71 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-D71G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 99 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A99N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 149 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A149S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 154 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-Q154K.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 193 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A193T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 193 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A193V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 206 in the amino acid sequence shown in SEQ ID NO: 1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-Q206F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 214 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-Q214R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 232 in the amino acid sequence shown in SEQ ID NO: 1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-A232V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 284 in the amino acid sequence shown in SEQ ID NO: 1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-M284L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 40, 404, 405, 429, 445, 448, and 303 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-H303P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 402, 404, 405, 429, 445, 448, and 462N in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-P402V-F404Y-T405M-T429A-V445P-Q448W-K462N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 494, 305, 402, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-S494R-G305A-P402V-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 461, 494, 305, 402, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-I461V-S494R-G305A-P402V-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 494, 228, 305, 402, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-S494R-L228T-G305A-P402V-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 494, 305, 377, 402, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-S494R-G305A-K377H-P402V-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 461, 494, 228, 305, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-I461V-S494R-L228T-G305A-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 461, 494, 305, 377, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-I461V-S494R-G305A-K377H-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 461, 494, 305, and 404 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-I461V-S494R-G305A-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 461, 494, 305, 377, 402, and 404Y in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-I461V-S494R-G305A-K377H-P402V-F404Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 351, 392, 405, 429, 445, 448, 461, 494, 305, and 377 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-D351R-R392A-T405M-T429A-V445P-Q448W-I461V-S494R-G305A-K377H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 2 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-S2N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 46, 494, and 10 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-A10K.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 13 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-P13S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 69 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-A69N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 106 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-A106T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175T-T228L-G305A-D351R-K377H-R392A-P402V-F404Y-T405M-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175K-T228L-G305A-D351R-K377H-R392A-P402V-F404Y-T405M-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175Q-T228L-G305A-D351R-K377H-R392A-P402V-F404Y-T405M-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 216 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-E216N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 345 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-I345L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 454 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-S454G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, 3, and 509 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-S3D-K509L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, 4, and 13 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-T4S-P13V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, 6, and 512 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-Y6P-D512H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405F-T429A-V445P-Q448W-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 454 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405F-T429A-V445P-Q448W-I461V-S494R-S454G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 447 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404W-T405M-T429A-V445P-Q448W-I461V-S494R-F447M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 337 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448W-I461V-S494R-I337L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, 494, and 197 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448F-I461V-S494R-I197M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 85, 162, 175, 228, 305, 351, 377, 392, 402, 404, 405, 429, 445, 448, 461, and 494 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-S85A-Q162N-C175G-T228L-G305A-D351R-K377H-R392A-P402V-F404Y-T405M-T429A-V445P-Q448F-I461V-S494R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 377, 402, 404, 405, 429, 445, 448 and 454 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-K377H-P402V-F404Y-T405M-T429A-V445P-Q448W-S454G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 377, 402, 404, 405, 429, 445 and 448 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-K377H-P402V-F404Y-T405F-T429A-V445P-Q448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 31, 305, 351, 377, 402, 404, 405, 429, 445, 448 and 454 in the amino acid sequence shown in SEQ ID NO:1 or at positions corresponding to these positions. Preferably, such a variant has the following substitutions in the amino acid sequence shown in SEQ ID NO:1 or at positions corresponding to these positions: E25N-N31G-G305A-D351R-K377H-P402V-F404Y-T405F-T429A-V445P-Q448W-S454G.

Preferably, any of the above described variants having multiple mutations further has one or more substitutions, deletions and/or insertions in comparison to the corresponding sequence from which it is derived and wherein these substitutions, deletions and/or insertions occur at one or more of the positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO: 1.

In a third aspect of the first part, the present invention provides a variant of a 3-methylcrotonic acid decarboxylase (MDC) showing an improved activity in converting 3-methylcrotonic acid into isobutene over the corresponding MDC from which it is derived, wherein the MDC variant is characterized in that it comprises a substitution, deletion and/or insertion in comparison to the corresponding sequence from which it is derived and wherein this substitution, deletion and/or insertion occurs at position 5 in the following amino acid motif of an MDC:

$$K\text{-}X_2\text{-}G\text{-}x_4\text{-}X_5\text{-}X_6\text{-}H\text{-}R\text{-}X_9\text{-}X_{10}\text{-}X_{11}\text{-}x_{12}\text{-}G, \quad \text{(SEQ ID NO: 16)}$$

wherein the amino acid $X_2$ at position 2 is an amino acid selected from the group consisting of A, P and V,
wherein the amino acid $x_4$ at position 4 is any amino acid,
wherein the amino acid $X_5$ at position 5 is an amino acid selected from the group consisting of A, P and T,
wherein the amino acid $X_6$ at position 6 is an amino acid selected from the group consisting of F, I and M,
wherein the amino acid $X_9$ at position 9 is an amino acid selected from the group consisting of I and L,
wherein the amino acid $X_{10}$ at position 10 is an amino acid selected from the group consisting of A, I, L and V,
wherein the amino acid $X_{11}$ at position 11 is an amino acid selected from the group consisting of I, L and V,
wherein the amino acid $x_{12}$ at position 12 is any amino acid and wherein the substitution at position 5 does not result in an A, P or T.

In another preferred embodiment, the above variant of a 3-methylcrotonic acid decarboxylase (MDC) is a variant having an amino acid sequence as shown in SEQ ID NO:1 or a sequence which is derived from SEQ ID NO:1 or an amino acid sequence having at least 60% sequence identity to SEQ ID NO: 1 or a sequence which is derived from SEQ ID NO:1, in which one amino acid is substituted, deleted and/or inserted at position 5 in the amino acid motif $K\text{-}X_2\text{-}G\text{-}x_4\text{-}X_5\text{-}X_6\text{-}H\text{-}R\text{-}X_9\text{-}X_{10}\text{-}X_{11}\text{-}x_{12}\text{-}G$ (SEQ ID NO: 15) in the amino acid sequence shown in SEQ ID NO: 1 or a sequence which is derived from SEQ ID NO:1 or at a position corresponding to this position and wherein said MDC variant has an improved activity in converting 3-methylcrotonic acid into isobutene.

The above variant of a 3-methylcrotonic acid decarboxylase (MDC) having an amino acid sequence as shown in SEQ ID NO:1 or a sequence which is derived from SEQ ID NO: 1 is not limited to a specific sequence. A sequence which is derived from SEQ ID NO:1 may be any sequence having the amino acid motif $K\text{-}X_2\text{-}G\text{-}x_4\text{-}X_5\text{-}X_6\text{-}H\text{-}R\text{-}X_9\text{-}X_{10}\text{-}X_{11}\text{-}x_{12}\text{-}G$ (SEQ ID NO:15) and having an activity in converting 3-methylcrotonic acid into isobutene. Examples for sequences which are derived from SEQ ID NO:1, having the amino acid motif $K\text{-}X_2\text{-}G\text{-}x_4\text{-}X_5\text{-}X_6\text{-}H\text{-}R\text{-}X_9\text{-}X_{10}\text{-}X_{11}\text{-}x_{12}\text{-}G$ (SEQ ID NO:15) and having an activity in converting 3-methylcrotonic acid into isobutene, are shown in Table 5.

In a preferred embodiment, the above variant of a 3-methylcrotonic acid decarboxylase (MDC) is a variant wherein an amino acid residue at position 5 in the amino acid motif of an MDC $K\text{-}X_2\text{-}G\text{-}x_4\text{-}X_5\text{-}X_6\text{-}H\text{-}R\text{-}X_9\text{-}X_{10}\text{-}X_{11}\text{-}x_{12}\text{-}G$ (SEQ ID NO:15) is deleted or substituted with an M or F.

In another preferred embodiment, the above variant of a 3-methylcrotonic acid decarboxylase (MDC) is a variant having at least n % sequence identity to an amino acid sequence as shown in the amino acid sequence of a protein having the UniProt accession number selected from the group consisting of the UniProt accession numbers shown in Table 5 with n being an integer between 60 and 100, preferably 60, 61, 62, 63, 64, 65, 66, 67, 68, 69, 70, 71, 72, 73, 74, 75, 80, 85, 90, 91, 92, 93, 94, 95, 96, 97, 98 or 99. As regards the determination of the sequence identity, the same applies as has been set forth above.

The present invention of the first part also relates to a method for providing a variant of an MDC wherein said variant shows an improved activity of converting 3-methylcrotonic acid into isobutene, said method comprising the step of effecting one or more changes in the sequence of the MDC wherein said change(s) is/are effected at one or more amino acid positions selected from the group consisting of the amino acid positions corresponding to positions 2, 3, 4, 5, 6, 7, 8, 9, 10, 11, 12, 13, 14, 15, 25, 29, 30, 31, 33, 34, 35, 40, 43, 57, 60, 65, 67, 69, 70, 71, 72, 80, 84, 85, 86, 87, 89, 90, 91, 99, 101, 102, 103, 105, 106, 108, 111, 114, 117, 119, 120, 126, 132, 141, 146, 149, 154, 159, 160, 162, 175, 176, 187, 189, 193, 195, 197, 206, 211, 213, 214, 215, 216, 221, 222, 228, 232, 244, 247, 264, 278, 284, 285, 293, 303, 305, 306, 326, 337, 338, 341, 342, 345, 349, 351, 352, 375, 376, 377, 381, 384, 386, 388, 392, 395, 399, 402, 404, 405, 406, 414, 420, 422, 429, 435, 436, 439, 440, 441, 442, 443, 445, 447, 448, 449, 454, 460, 461, 462, 484, 488, 493, 494, 496, 500, 501, 502, 506, 509, 511 and 512 in the amino acid sequence shown in SEQ ID NO:1. "Corresponding to" means corresponding to any of these positions in a related sequence.

As regards the preferred embodiments of an MDC to be mutated according to such a method, the same applies as has been set forth herein-above.

In one preferred embodiment the MDC from which the MDC variant is derived is an MDC which shows the amino acid sequence as shown in SEQ ID NO: 1 or an amino acid sequence having at least 60%, 70%, 80% or 90% sequence identity to SEQ ID NO:1 or any of the preferred degrees of sequence identity as specified herein above.

Moreover, as regards preferred embodiments of the degree of improvement in activity and the changes to be effected, the same applies as described herein above.

The change(s) which is/are effected at any of the above position(s) is/are substitution(s), deletion(s) and/or insertion (s) as defined herein above.

An MDC variant of the first part of the present invention can be fused to a homologous or heterologous polypeptide or protein, an enzyme, a substrate or a tag to form a fusion protein. Fusion proteins in accordance with the present invention will have the same improved activity as the MDC variant of the present invention. Polypeptides, enzymes, substrates or tags that can be added to another protein are known in the art. They may useful for purifying or detecting the proteins of the invention. For instance, tags that can be used for detection and/or purification are e.g. FLAG-tag, His6-tag or a Strep-tag. Alternatively, the protein of the invention can be fused to an enzyme e.g. luciferase, for the detection or localisation of said protein. Other fusion partners include, but are not limited to, bacterial β-galactosidase, trpE, Protein A, β-lactamase, alpha amylase, alcohol dehydrogenase or yeast alpha mating factor. It is also conceivable that the polypeptide, enzyme, substrate or tag is removed from the protein of the invention after e.g. purification. Fusion proteins can typically be made by either recombinant nucleic acid methods or by synthetic polypeptide methods known in art.

The first part of the present invention further relates to a nucleic acid molecule encoding an MDC variant of the present invention and to a vector comprising said nucleic acid molecules. Vectors that can be used in accordance with the present invention are known in the art. The vectors can further comprise expression control sequences operably linked to the nucleic acid molecules of the present invention contained in the vectors. These expression control sequences may be suited to ensure transcription and synthesis of a translatable RNA in bacteria or fungi. Expression control sequences can for instance be promoters. Promoters for use in connection with the nucleic acid molecules of the present invention may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

Preferably, the vector of the present invention is an expression vector. Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), lp1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-ß-D-thiogalactopyranoside) (deBoer et al., Proc. Natl. Acad. Sci. USA 80 (1983), 21-25). Termination signals for transcription are also described in the literature.

In addition, the first part of the present invention relates to a host cell comprising the nucleic acid molecule or the vector of the present invention.

In a preferred embodiment, the host cell according to the presenting invention is a microorganism, in particular a bacterium or a fungus. In a more preferred embodiment, the host cell of the present invention is E. coli, a bacterium of the genus Clostridium or a yeast cell, such as S. cerevisiae. In another preferred embodiment the host cell is a plant cell or a non-human animal cell.

The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

As mentioned above, the enzymatic conversion of 3-methylcrotonic acid into isobutene utilizing an MDC is preferably performed in the presence of an FMN prenyl transferase and relies on a reaction of two consecutive steps catalyzed by the two enzymes, i.e., the MDC (catalyzing the actual decarboxylation of 3-methylcrotonic acid into isobutene) with an FMN prenyl transferase which provides the modified flavin cofactor. The flavin cofactor may preferably be FMN or FAD. FMN (flavin mononucleotide; also termed riboflavin-5'-phosphate) is a biomolecule produced from riboflavin (vitamin B2) by the enzyme riboflavin kinase and functions as prosthetic group of various reactions. FAD (flavin adenine dinucleotide) is a redox cofactor, more specifically a prosthetic group, involved in several important reactions in metabolism. Thus, in a preferred embodiment, when producing isobutene from 3-methylcrotonic acid comprising the step of incubating an MDC variant of the invention with 3-methylcrotonic acid an FMN prenyl transferase is present which, in a first step, modifies a flavin cofactor (FMN or FAD) into a (modified) flavin-derived cofactor. FMN prenyl transferase prenylates the flavin ring of the flavin cofactor (FMN or FAD) into a (modified) prenylated flavin cofactor. This reaction is schematically illustrated in FIG. 1A.

In a second step, the actual conversion of 3-methylcrotonic acid into isobutene is catalyzed by said MDC variant via a 1,3-dipolar cycloaddition based mechanism wherein said FMN-dependent decarboxylase uses the prenylated flavin cofactor (FMN or FAD) provided by the associated FMN prenyl transferase. This reaction is schematically illustrated in FIG. 1B.

Thus, preferably, the host cell of the present invention is a cell which expresses an FMN prenyl transferase capable of modifying a flavin cofactor (FMN or FAD) into a (modified) flavin-derived cofactor. In a preferred embodiment, the host cell is a cell which naturally (endogenously) expresses an FMN prenyl transferase. In another preferred embodiment, the host cell is a cell which recombinantly expresses an FMN prenyl transferase by, e.g., introducing a nucleic acid molecule encoding an FMN prenyl transferase or a vector comprising such a nucleic acid molecule.

In a preferred embodiment, said FMN prenyl transferase which modifies the flavin cofactor (FMN or FAD) into a (modified) flavin-derived cofactor is a phenylacrylic acid decarboxylase (PAD)-type protein, or the closely related prokaryotic enzyme UbiX, an enzyme which is involved in ubiquinone biosynthesis in prokaryotes.

In Escherichia coli, the protein UbiX (also termed 3-octaprenyl-4-hydroxybenzoate carboxy-lyase) has been shown to be involved in the third step of ubiquinone biosynthesis.

It catalyses the reaction 3-octaprenyl-4-hydroxybenzoate $\rightleftarrows$ 2-octaprenylphenol+$CO_2$.

Thus, in a preferred embodiment, the modification of a flavin cofactor (FMN or FAD) into the corresponding (modified) flavin-derived cofactor is catalyzed by the FMN-containing protein phenylacrylic acid decarboxylase (PAD). The enzymes involved in the modification of the flavin cofactor (FMN or FAD) into the corresponding modified flavin-derived cofactor were initially annotated as decarboxylases (EC 4.1.1.-). Some phenylacrylic acid decarboxylases (PAD) are now annotated as flavin prenyl transferases as EC 2.5.1.-.

In a more preferred embodiment, the conversion of 3-methylcrotonic acid into isobutene makes use of a phenylacrylic acid decarboxylase (PAD)-type protein as the FMN prenyl transferase which modifies a flavin cofactor (FMN or FAD) into the corresponding (modified) flavin-derived cofactor wherein said phenylacrylic acid decarboxylase (PAD)-type protein is derived from *Candida albicans* (Uniprot accession number Q5A8L8), *Aspergillus niger* (Uniprot accession number A3F715), *Saccharomyces cerevisiae* (Uniprot accession number P33751) or *Cryptococcus gattii* (Uniprot accession number E6R9Z0).

In a preferred embodiment, the phenylacrylic acid decarboxylase (PAD)-type protein employed in the method of the present invention is a phenylacrylic acid decarboxylase (PAD)-type protein derived from *Candida albicans* (Uniprot accession number Q5A8L8; SEQ ID NO:3), *Aspergillus niger* (Uniprot accession number A3F715; SEQ ID NO:4), *Saccharomyces cerevisiae* (Uniprot accession number P33751; SEQ ID NO:5) or *Cryptococcus gattii* (Uniprot accession number E6R9Z0; SEQ ID NO:6) having the amino acid sequence as shown in SEQ ID NO:3, SEQ ID NO:4, SEQ ID NO:5 and SEQ ID NO:6, respectively.

In a preferred embodiment of the present invention the phenylacrylic acid decarboxylase (PAD)-type protein is an enzyme comprising an amino acid sequence selected from the group consisting of SEQ ID NOs: 3 to 6 or a sequence which is at least n % identical to any of SEQ ID NOs: 3 to 6 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor. As regards the determination of sequence identity, the same applies as has been set forth above.

In another preferred embodiment, the modification of a flavin cofactor (FMN or FAD) into the corresponding (modified) flavin-derived cofactor is catalyzed by the FMN-containing protein 3-octaprenyl-4-hydroxybenzoate carboxy-lyase also termed UbiX (initially annotated EC 4.1.1.-). As mentioned above, the enzymes involved in the modification of the flavin cofactor (FMN or FAD) into the corresponding modified flavin-derived cofactor were initially annotated as decarboxylases. Some phenylacrylic acid decarboxylases (PAD) are now annotated as flavin prenyl transferases as EC 2.5.1.-.

In a more preferred embodiment, the conversion of 3-methylcrotonic acid into isobutene makes use of a 3-octaprenyl-4-hydroxybenzoate carboxy-lyase (also termed UbiX) as the FMN prenyl transferase which modifies the flavin cofactor (FMN or FAD) into the corresponding (modified) flavin-derived cofactor wherein said 3-octaprenyl-4-hydroxybenzoate carboxy-lyase (also termed UbiX) is derived from *Escherichia coli* (Uniprot accession number P0AG03), *Bacillus subtilis* (Uniprot accession, number A0A086WXG4), *Pseudomonas aeruginosa* (Uniprot accession number A0A072ZCW8) or *Enterobacter* sp. DC4 (Uniprot accession number W7P6B1).

In an even more preferred embodiment, the 3-octaprenyl-4-hydroxybenzoate carboxy-lyase (also termed UbiX) employed in the method of the present invention is a 3-octaprenyl-4-hydroxybenzoate carboxy-lyase (also termed UbiX) derived from *Escherichia coli* (Uniprot accession number P0AG03; SEQ ID NO:2), *Bacillus subtilis* (Uniprot accession, number A0A086WXG4; SEQ ID NO:7), *Pseudomonas aeruginosa* (Uniprot accession number A0A072ZCW8; SEQ ID NO:8) or *Enterobacter* sp. DC4 (Uniprot accession number W7P6B1; SEQ ID NO:9) having the amino acid sequence as shown in SEQ ID NO:2, SEQ ID NO:7, SEQ ID NO:8 and SEQ ID NO:9, respectively.

In a preferred embodiment of the present invention the 3-octaprenyl-4-hydroxybenzoate carboxy-lyase is an enzyme comprising an amino acid sequence selected from the group consisting of SEQ ID NOs: 2 and 7 to 9 or a sequence which is at least n % identical to any of SEQ ID NOs: 2 and 7 to 9 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor. As regards the determination of the sequence identity, the same applies as has been set forth above.

The first part of the present invention also relates to a method for producing isobutene from 3-methylcrotonic acid comprising the step of incubating an MDC variant of the invention with 3-methylcrotonic acid under conditions allowing said conversion (preferably further in the presence of an FMN prenyl transferase as described above) or comprising the step of culturing a host cell of the present invention expressing an MDC variant (and preferably further expressing an FMN prenyl transferase as described above) in a suitable medium and recovering the produced isobutene.

It is also conceivable in this context that in such a method not only one enzyme according to the present invention is employed but a combination of two or more enzymes.

The first part of the present invention also relates to the use of an MDC variant or a host cell of the present invention as described above for the conversion of 3-methylcrotonic acid into isobutene, preferably in the presence of an FMN prenyl transferase or in the presence of a host co-expressing an FMN prenyl transferase as described herein above. Moreover, in a further embodiment, the present invention relates to a method for producing isobutene from 3-methylcrotonic acid by bringing 3-methylcrotonic acid into contact with the MDC variant of the present invention, preferably in the presence of an FMN prenyl transferase, or with a host cell comprising a nucleic acid molecule encoding the MDC variant of the present invention, wherein said host cell preferably expresses an FMN prenyl transferase. Thus, in a preferred embodiment, the present invention relates to a method for converting 3-methylcrotonic acid into isobutene comprising the steps of: (i) culturing the above-described host cell of the invention in a suitable medium; and (ii) achieving the production of isobutene from 3-methylcrotonic acid.

Thus, in a preferred embodiment, the present invention relates to methods and uses utilizing a host cell of the present invention which expresses an MDC variant of the present invention and, preferably, further expressing an FMN prenyl transferase as described herein above.

In another preferred embodiment, such a host cell is an organism which is capable of producing 3-methylcrotonic acid.

In another preferred embodiment, the method according to the invention is carried out in culture, in the presence of an organism, preferably a microorganism, producing an enzyme variant of the present invention and, preferably, also producing an FMN prenyl transferase. In such an embodiment of the invention, an organism, preferably a microorganism, that produces an enzyme of the present invention and, preferably, also producing an FMN prenyl transferase, is used. In a preferred embodiment, the (micro)organism is recombinant in that the enzyme produced by the host is heterologous relative to the production host. The method can thus be carried out directly in the culture medium, without the need to separate or purify the enzymes. In an especially advantageous manner, a (micro)organism is used having the natural or artificial property of endogenously producing 3-methylcrotonic acid so as to produce isobutene directly from the substrate already present in the culture in solution.

In connection with the above described methods and uses, the microorganisms are cultivated under suitable culture conditions allowing the occurrence of the enzymatic reaction of the MDC variants of the present invention (and, preferably, also the FMN prenyl transferases as described above). The specific culture conditions depend on the specific microorganism employed but are well known to the person skilled in the art. The culture conditions are generally chosen in such a manner that they allow the expression of the genes encoding the MDC variant of the present invention (and, preferably, also an FMN prenyl transferase as described above). Various methods are known to the person skilled in the art in order to improve and fine-tune the expression of certain genes at certain stages of the culture such as induction of gene expression by chemical inducers or by a temperature shift.

In another embodiment, the above described methods of the invention comprise the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical process like the method of the present invention is carried out which involves organisms, preferably microorganisms and/or biochemically active substances, i.e., the enzyme(s) described above derived from such organisms or organisms harboring the above described enzyme(s). In a bioreactor or a fermenter, this process can either be aerobic or anaerobic. These bioreactors are commonly cylindrical, and may range in size from litres to hundreds of cubic meters, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

In yet a further embodiment, the method according to the invention can be carried out in vitro, e.g. in the presence of isolated enzyme or of cell lysates comprising the enzyme or partially purified enzyme preparations comprising the MDC variant of the present invention (and, preferably, also an FMN prenyl transferase as described above). In vitro preferably means in a cell-free system.

In one embodiment, the enzyme(s) employed in the method is (are) used in purified form. However, such a method may be costly, since enzyme and substrate production and purification costs are high. Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

In an in vitro reaction the enzymes, native or recombinant, purified or not, are incubated in the presence of the substrate in physicochemical conditions allowing the enzymes to be active, and the incubation is allowed to proceed for a sufficient period of time allowing production of the desired product as described above. At the end of the incubation, one optionally measures the presence of isobutene by using any detection system known to one of skill in the art such as gas chromatography or colorimetric tests for measuring the formation of isobutene.

In a particularly preferred embodiment of the invention the method is carried out in vitro and the enzyme is immobilized. Means and methods for immobilizing enzymes on different supports are well-known to the person skilled in the art.

The method according to the invention furthermore comprises the step of collecting gaseous products, i.e. isobutene, degassing out of the reaction, i.e. recovering the product which degasses, e.g., out of the culture. Thus, in a preferred embodiment, the method is carried out in the presence of a system for collecting isobutene under gaseous form during the reaction.

As a matter of fact, isobutene adopts the gaseous state at room temperature and atmospheric pressure. Moreover, isobutene also adopts the gaseous state under culture conditions at 37° C. The method according to the invention therefore does not require extraction of isobutene from the liquid culture medium, a step which is always very costly when performed at industrial scale. The evacuation and storage of gaseous hydrocarbons, in particular of isobutene, and their possible subsequent physical separation and chemical conversion can be performed according to any method known to one of skill in the art.

Finally, the first part of the present invention relates to a composition comprising a variant of an MDC of the present invention, a nucleic acid molecule of the present invention, a vector of the present invention or a host cell of the present invention. As regards the variant of an MDC, the nucleic acid molecule, the vector or the host cell, the same applies as has been set forth above in connection with the methods according to the present invention.

As outlined above, methods for the production of isobutene comprising the enzymatic conversion of 3-methylcrotonic acid into isobutene utilizing the above enzymes has previously been described wherein corresponding enzymes have artificially been implemented in a pathway which ultimately leads to the production of isobutene (WO 2017/085176). In WO 2017/085176 FMN-dependent decarboxylase enzymes catalysing the decarboxylation of 3-methylcrotonic acid into isobutene have been described which belong to the 3-polyprenyl-4-hydroxybenzoate decarboxylase (UbiD) family of enzymes while, inter alia, an UbiD enzyme derived from *Hypocrea atroviridis* (UniProt Accession number Q9NLP8) has been described.

Moreover, as outlined above, the present invention relates in several aspects to improved variants of enzymes which are capable of converting 3-methylcrotonic acid into isobutene have been descried while the above FDC of *Hypocrea atroviridis* has been used as a model enzyme. These aspects are also disclosed in WO 2017/191239.

Although the above means and methods allow to produce isobutene from 3-methylcrotonic acid while means and methods which allow to increase the production of isobutene from 3-methylcrotonic acid have already been described, there is still a need for further improvements, in particular as regards a further increase in efficiency of the process so as to make it more suitable for industrial purposes.

The present application addresses this need by providing in a second part the embodiments as defined in the following items (14) to (26).

14. A variant of a 3-methylcrotonic acid decarboxylase (MDC) showing an improved activity in converting 3-methylcrotonic acid into isobutene over the corresponding MDC from which it is derived and having an amino acid sequence as shown in SEQ ID NO: 14 or an amino acid sequence having at least 63% sequence identity to SEQ ID NO:14, in which one or more amino acid residues at a position selected from the group consisting of positions 448, 2, 3, 5, 6, 24, 25, 35, 36, 64, 74, 80, 85, 86, 126, 129, 154, 166, 175, 195, 196, 197, 198, 204, 208, 214, 236, 237, 238, 240, 277, 298, 302, 339, 343, 347, 350, 359, 366, 368, 390, 391, 394, 395, 396, 398, 401, 402, 403, 404, 405, 406, 407, 408, 426, 439, 440, 441, 442, 444, 446, 447, 449, 450, 451, 452, 453, 454, 455, 456, 457, 458, 459, 460, 461, 462 and 473 in the amino acid sequence shown in SEQ ID NO: 14 or at a position corresponding to any of these positions, are substituted with another amino acid residue or deleted or wherein an insertion has been effected at one or more of these positions.

15. The MDC variant of item 14, wherein
    (1) an amino acid residue at position 2 in the amino acid sequence shown in SEQ ID NO:14 or at a position corresponding to this position, is deleted or substituted with asparagine; and/or
    (2) an amino acid residue at position 3 in the amino acid sequence shown in SEQ ID NO:14 or at a position corresponding to this position, is deleted or substituted with leucine or methionine; and/or
    (3) an amino acid residue at position 5 in the amino acid sequence shown in SEQ ID NO:14 or at a position corresponding to this position, is deleted or substituted with isoleucine; and/or
    (4) an amino acid residue at position 6 in the amino acid sequence shown in SEQ ID NO:14 or at a position corresponding to this position, is deleted or substituted with methionine; and/or
    (5) an amino acid residue at position 24 in the amino acid sequence shown in SEQ ID NO:14 or at a position corresponding to this position, is deleted or substituted with alanine, aspartic acid, leucine or valine; and/or
    (6) an amino acid residue at position 25 in the amino acid sequence shown in SEQ ID NO:14 or at a position corresponding to this position, is deleted or substituted with glutamic acid; and/or
    (7) an amino acid residue at position 35 in the amino acid sequence shown in SEQ ID NO:14 or at a position corresponding to this position, is deleted or substituted with isoleucine; and/or
    (8) an amino acid residue at position 36 in the amino acid sequence shown in SEQ ID NO:14 or at a position corresponding to this position, is deleted or substituted with tyrosine; and/or
    (9) an amino acid residue at position 64 in the amino acid sequence shown in SEQ ID NO: 14 or at a position corresponding to this position, is deleted or substituted with histidine; and/or
    (10) an amino acid residue at position 74 in the amino acid sequence shown in SEQ ID NO:14 or at a position corresponding to this position, is deleted or substituted with valine; and/or
    (11) an amino acid residue at position 80 in the amino acid sequence shown in SEQ ID NO:14 or at a position corresponding to this position, is deleted or substituted with serine; and/or
    (12) an amino acid residue at position 85 in the amino acid sequence shown in SEQ ID NO:14 or at a position corresponding to this position, is deleted or substituted with leucine; and/or
    (13) an amino acid residue at position 86 in the amino acid sequence shown in SEQ ID NO:14 or at a position corresponding to this position, is deleted or substituted with asparagine or tyrosine; and/or
    (14) an amino acid residue at position 126 in the amino acid sequence shown in SEQ ID NO:14 or at a position corresponding to this position, is deleted or substituted with valine; and/or
    (15) an amino acid residue at position 129 in the amino acid sequence shown in SEQ ID NO:14 or at a position corresponding to this position, is deleted or substituted with valine; and/or
    (16) an amino acid residue at position 154 in the amino acid sequence shown in SEQ ID NO: 14 or at a position corresponding to this position, is deleted or substituted with aspartic acid; and/or
    (17) an amino acid residue at position 166 in the amino acid sequence shown in SEQ ID NO: 14 or at a position corresponding to this position, is deleted or substituted with aspartic acid; and/or
    (18) an amino acid residue at position 175 in the amino acid sequence shown in SEQ ID NO: 14 or at a position corresponding to this position, is deleted or substituted with glutamic acid; and/or
    (19) an amino acid residue at position 195 in the amino acid sequence shown in SEQ ID NO: 14 or at a position corresponding to this position, is deleted or substituted with isoleucine or valine; and/or
    (20) an amino acid residue at position 196 in the amino acid sequence shown in SEQ ID NO: 14 or at a position corresponding to this position, is deleted or substituted with isoleucine; and/or
    (21) an amino acid residue at position 197 in the amino acid sequence shown in SEQ ID NO: 14 or at a position corresponding to this position, is deleted or substituted with valine; and/or
    (22) an amino acid residue at position 198 in the amino acid sequence shown in SEQ ID NO: 14 or at a position corresponding to this position, is deleted or substituted with glutamine or tryptophan; and/or
    (23) an amino acid residue at position 204 in the amino acid sequence shown in SEQ ID NO: 14 or at a position corresponding to this position, is deleted or substituted with arginine or serine; and/or
    (24) an amino acid residue at position 208 in the amino acid sequence shown in SEQ ID NO: 14 or at a position corresponding to this position, is deleted or substituted with leucine; and/or

(25) an amino acid residue at position 214 in the amino acid sequence shown in SEQ ID NO:14 or at a position corresponding to this position, is deleted or substituted with threonine; and/or
(26) an amino acid residue at position 236 in the amino acid sequence shown in SEQ ID NO:14 or at a position corresponding to this position, is deleted or substituted with leucine or valine; and/or
(27) an amino acid residue at position 237 in the amino acid sequence shown in SEQ ID NO: 14 or at a position corresponding to this position, is deleted or substituted with alanine, aspartic acid, asparagine or proline; and/or
(28) an amino acid residue at position 238 in the amino acid sequence shown in SEQ ID NO: 14 or at a position corresponding to this position, is deleted or substituted with histidine, arginine, serine or tryptophan; and/or
(29) an amino acid residue at position 240 in the amino acid sequence shown in SEQ ID NO: 14 or at a position corresponding to this position, is deleted or substituted with isoleucine or asparagine; and/or
(30) an amino acid residue at position 277 in the amino acid sequence shown in SEQ ID NO: 14 or at a position corresponding to this position, is deleted or substituted with tyrosine; and/or
(31) an amino acid residue at position 298 in the amino acid sequence shown in SEQ ID NO: 14 or at a position corresponding to this position, is deleted or substituted with serine; and/or
(32) an amino acid residue at position 302 in the amino acid sequence shown in SEQ ID NO: 14 or at a position corresponding to this position, is deleted or substituted with alanine, cysteine, phenylalanine, lysine, methionine, glutamine, arginine or serine; and/or
(33) an amino acid residue at position 339 in the amino acid sequence shown in SEQ ID NO: 14 or at a position corresponding to this position, is deleted or substituted with histidine; and/or
(34) an amino acid residue at position 343 in the amino acid sequence shown in SEQ ID NO: 14 or at a position corresponding to this position, is deleted or substituted with serine; and/or
(35) an amino acid residue at position 347 in the amino acid sequence shown in SEQ ID NO: 14 or at a position corresponding to this position, is deleted or substituted with cysteine; and/or
(36) an amino acid residue at position 350 in the amino acid sequence shown in SEQ ID NO: 14 or at a position corresponding to this position, is deleted or substituted with serine; and/or
(37) an amino acid residue at position 359 in the amino acid sequence shown in SEQ ID NO:14 or at a position corresponding to this position, is deleted or substituted with cysteine or valine; and/or
(38) an amino acid residue at position 366 in the amino acid sequence shown in SEQ ID NO:14 or at a position corresponding to this position, is deleted or substituted with isoleucine or phenylalanine; and/or
(39) an amino acid residue at position 368 in the amino acid sequence shown in SEQ ID NO: 14 or at a position corresponding to this position, is deleted or substituted with isoleucine or methionine; and/or
(40) an amino acid residue at position 390 in the amino acid sequence shown in SEQ ID NO: 14 or at a position corresponding to this position, is deleted or substituted with serine, aspartic acid, leucine, asparagine or glutamine; and/or
(41) an amino acid residue at position 391 in the amino acid sequence shown in SEQ ID NO: 14 or at a position corresponding to this position, is deleted or substituted with aspartic acid or tryptophan; and/or
(42) an amino acid residue at position 394 in the amino acid sequence shown in SEQ ID NO: 14 or at a position corresponding to this position, is deleted or substituted with cysteine, aspartic acid, glutamine or threonine; and/or
(43) an amino acid residue at position 395 in the amino acid sequence shown in SEQ ID NO: 14 or at a position corresponding to this position, is deleted or substituted with cysteine, glutamic acid or valine; and/or
(44) an amino acid residue at position 396 in the amino acid sequence shown in SEQ ID NO: 14 or at a position corresponding to this position, is deleted or substituted with isoleucine; and/or
(45) an amino acid residue at position 398 in the amino acid sequence shown in SEQ ID NO: 14 or at a position corresponding to this position, is deleted or substituted with cysteine or arginine; and/or
(46) an amino acid residue at position 401 in the amino acid sequence shown in SEQ ID NO: 14 or at a position corresponding to this position, is deleted or substituted with tyrosine; and/or
(47) an amino acid residue at position 402 in the amino acid sequence shown in SEQ ID NO: 14 or at a position corresponding to this position, is deleted or substituted with alanine; and/or
(48) an amino acid residue at position 403 in the amino acid sequence shown in SEQ ID NO: 14 or at a position corresponding to this position, is deleted or substituted with alanine, cysteine, glycine, histidine, isoleucine, asparagine, proline, glutamine, arginine or valine; and/or
(49) an amino acid residue at position 404 in the amino acid sequence shown in SEQ ID NO:14 or at a position corresponding to this position, is deleted or substituted with phenylalanine, leucine or methionine; and/or
(50) an amino acid residue at position 405 in the amino acid sequence shown in SEQ ID NO:14 or at a position corresponding to this position, is deleted or substituted with histidine, isoleucine, methionine, threonine or valine; and/or
(51) an amino acid residue at position 406 in the amino acid sequence shown in SEQ ID NO: 14 or at a position corresponding to this position, is deleted or substituted with glycine, alanine or serine; and/or
(52) an amino acid residue at position 407 in the amino acid sequence shown in SEQ ID NO: 14 or at a position corresponding to this position, is deleted or substituted with alanine, cysteine, isoleucine, lysine, arginine, serine or threonine; and/or
(53) an amino acid residue at position 408 in the amino acid sequence shown in SEQ ID NO: 14 or at a position corresponding to this position, is deleted or substituted with isoleucine, alanine, cysteine, leucine, or methionine; and/or
(54) an amino acid residue at position 426 in the amino acid sequence shown in SEQ ID NO: 14 or at a position corresponding to this position, is deleted or substituted with valine; and/or
(55) an amino acid residue at position 439 in the amino acid sequence shown in SEQ ID NO: 14 or at a position corresponding to this position, is deleted or substituted with cysteine; and/or

(56) an amino acid residue at position 440 in the amino acid sequence shown in SEQ ID NO: 14 or at a position corresponding to this position, is deleted or substituted with leucine; and/or

(57) an amino acid residue at position 441 in the amino acid sequence shown in SEQ ID NO: 14 or at a position corresponding to this position, is deleted or substituted with glycine, histidine, lysine, asparagine, proline, arginine, serine or threonine; and/or

(58) an amino acid residue at position 442 in the amino acid sequence shown in SEQ ID NO: 14 or at a position corresponding to this position, is deleted or substituted with alanine, cysteine, glutamic acid, glycine, histidine, leucine, methionine, asparagine, glutamine, arginine, serine or threonine; and/or

(59) an amino acid residue at position 444 in the amino acid sequence shown in SEQ ID NO: 14 or at a position corresponding to this position, is deleted or substituted with alanine, glutamic acid, phenylalanine, histidine, isoleucine, leucine, glutamine or threonine; and/or

(60) an amino acid residue at position 446 in the amino acid sequence shown in SEQ ID NO: 14 or at a position corresponding to this position, is deleted or substituted with alanine, cysteine, phenylalanine, isoleucine, methionine, asparagine, serine or valine; and/or

(61) an amino acid residue at position 447 in the amino acid sequence shown in SEQ ID NO:14 or at a position corresponding to this position, is deleted or substituted with glutamine; and/or

(62) an amino acid residue at position 448 in the amino acid sequence shown in SEQ ID NO:14 or at a position corresponding to this position, is deleted or substituted with phenylalanine, tryptophan or tyrosine; and/or

(63) an amino acid residue at position 449 in the amino acid sequence shown in SEQ ID NO: 14 or at a position corresponding to this position, is deleted or substituted with isoleucine, methionine or valine; and/or

(64) an amino acid residue at position 450 in the amino acid sequence shown in SEQ ID NO: 14 or at a position corresponding to this position, is deleted or substituted with alanine, histidine, methionine, asparagine, glutamine, serine or valine; and/or

(65) an amino acid residue at position 451 in the amino acid sequence shown in SEQ ID NO: 14 or at a position corresponding to this position, is deleted or substituted with asparagine or serine; and/or

(66) an amino acid residue at position 452 in the amino acid sequence shown in SEQ ID NO: 14 or at a position corresponding to this position, is deleted or substituted with phenylalanine; and/or

(67) an amino acid residue at position 453 in the amino acid sequence shown in SEQ ID NO: 14 or at a position corresponding to this position, is deleted or substituted with cysteine, glycine, leucine, asparagine, proline, arginine or serine; and/or

(68) an amino acid residue at position 454 in the amino acid sequence shown in SEQ ID NO: 14 or at a position corresponding to this position, is deleted or substituted with alanine, aspartic acid, glycine, histidine, lysine, leucine, methionine, glutamine, arginine, serine, threonine, valine or tryptophan; and/or

(69) an amino acid residue at position 455 in the amino acid sequence shown in SEQ ID NO: 14 or at a position corresponding to this position, is deleted or substituted with alanine, glutamic acid, histidine, lysine, asparagine, serine or valine; and/or

(70) an amino acid residue at position 456 in the amino acid sequence shown in SEQ ID NO: 14 or at a position corresponding to this position, is deleted or substituted with glutamine; and/or

(71) an amino acid residue at position 457 in the amino acid sequence shown in SEQ ID NO: 14 or at a position corresponding to this position, is deleted or substituted with lysine; and/or

(72) an amino acid residue at position 458 in the amino acid sequence shown in SEQ ID NO: 14 or at a position corresponding to this position, is deleted or substituted with glutamic acid, phenylalanine, glycine, leucine, methionine, asparagine, glutamine, arginine, serine or tyrosine; and/or

(73) an amino acid residue at position 459 in the amino acid sequence shown in SEQ ID NO:14 or at a position corresponding to this position, is deleted or substituted with aspartic acid, glutamic acid, glycine, methionine, asparagine, glutamine, arginine, threonine or tyrosine; and/or

(74) an amino acid residue at position 460 in the amino acid sequence shown in SEQ ID NO:14 or at a position corresponding to this position, is deleted or substituted with glutamic acid, phenylalanine, glycine, leucine, methionine, asparagine, glutamine or arginine; and/or

(75) an amino acid residue at position 461 in the amino acid sequence shown in SEQ ID NO: 14 or at a position corresponding to this position, is deleted or substituted with alanine, glycine, leucine, methionine, glutamine, serine or valine; and/or

(76) an amino acid residue at position 462 in the amino acid sequence shown in SEQ ID NO: 14 or at a position corresponding to this position, is deleted or substituted with cysteine or valine; and/or

(77) an amino acid residue at position 473 in the amino acid sequence shown in SEQ ID NO: 14 or at a position corresponding to this position, is deleted or substituted with serine.

16. The MDC variant of item 14 or 15, wherein in said variant one or more further amino acid residues at a position selected from the group consisting of 66, 168, 241, 296, 305, 349, 363, 443, 445, 479, and 496 in the amino acid sequence shown in SEQ ID NO: 14 or at a position corresponding to any of these positions, are substituted with another amino acid residue or deleted or wherein an insertion has been effected at one or more of these positions, and wherein said MDC variant has an improved activity in converting 3-methylcrotonic acid into isobutene over the corresponding MDC from which it is derived.

17. The MDC variant of any one of items 14 to 16, wherein
   (78) an amino acid residue at position 66 in the amino acid sequence shown in SEQ ID NO: 14 or at a position corresponding to this position, is deleted or substituted with histidine; and/or
   (79) an amino acid residue at position 168 in the amino acid sequence shown in SEQ ID NO: 14 or at a position corresponding to this position, is deleted or substituted with valine; and/or
   (80) an amino acid residue at position 241 in the amino acid sequence shown in SEQ ID NO: 14 or at a position corresponding to this position, is deleted or substituted with aspartic acid, asparagine or valine; and/or
   (81) an amino acid residue at position 296 in the amino acid sequence shown in SEQ ID NO:14 or at a position corresponding to this position, is deleted or substituted with glutamine; and/or

(82) an amino acid residue at position 305 in the amino acid sequence shown in SEQ ID NO:14 or at a position corresponding to this position, is deleted or substituted with isoleucine or threonine; and/or
(83) an amino acid residue at position 349 in the amino acid sequence shown in SEQ ID NO: 14 or at a position corresponding to this position, is deleted or substituted with methionine or serine; and/or
(84) an amino acid residue at position 363 in the amino acid sequence shown in SEQ ID NO: 14 or at a position corresponding to this position, is deleted or substituted with glycine; and/or
(85) an amino acid residue at position 443 in the amino acid sequence shown in SEQ ID NO: 14 or at a position corresponding to this position, is deleted or substituted with alanine, aspartic acid, phenylalanine, histidine, leucine, asparagine, arginine, serine, tryptophan or tyrosine; and/or
(86) an amino acid residue at position 445 in the amino acid sequence shown in SEQ ID NO: 14 or at a position corresponding to this position, is deleted or substituted with leucine, alanine, cysteine, serine or threonine; and/or
(87) an amino acid residue at position 479 in the amino acid sequence shown in SEQ ID NO: 14 or at a position corresponding to this position, is deleted or substituted with cysteine, isoleucine, leucine, methionine, serine, threonine or valine; and/or
(88) an amino acid residue at position 496 in the amino acid sequence shown in SEQ ID NO: 14 or at a position corresponding to this position, is deleted or substituted with leucine.
18. A nucleic acid molecule encoding the MDC variant of any one of items 14 to 17.
19. A host cell comprising the nucleic acid molecule of item 18.
20. A vector comprising the nucleic acid molecule of item 18.
21. A host cell comprising the vector of item 20.
22. Use of the MDC variant of any one of items 14 to 17 or the host cell of item 19 or 21 or the vector of item 20 for the conversion of 3-methylcrotonic acid into isobutene.
23. A method for producing isobutene from 3-methylcrotonic acid by incubating 3-methylcrotonic acid with the MDC variant of any one of items 14 to 17, or the host cell of item 19 or 21 or the vector of item 20.
24. The method of item 23, wherein the enzymatic conversion is carried out in vitro or by a host cell expressing the nucleic acid molecule.
25. A composition comprising the MDC variant of any one of items 14 to 17 or the host cell of item 19 or 21 or the vector of item 20.
26. A composition comprising the MDC variant of any one of items 14 to 17 or the host cell of item 19 or 21 or the vector of item 20 and 3-methylcrotonic acid.

In a first aspect of the second part of the present invention, the present invention provides a variant of a 3-methylcrotonic acid decarboxylase (MDC) showing an improved activity in converting 3-methylcrotonic acid into isobutene over the corresponding MDC from which it is derived.

An improved enzyme variant or an enzyme variant capable of catalyzing a reaction with increased activity is defined as an enzyme variant which differs from the wild-type enzyme and which catalyzes the conversion of 3-methylcrotonic acid into isobutene so that the specific activity of the enzyme variant is higher than the specific activity of the wildtype enzyme for at least one given concentration of a 3-methylcrotonic acid (preferably any 3-methylcrotonic acid higher than 0 M and up to 1 M). A specific activity is defined as the number of moles of substrate converted to moles of product by unit of time by mole of enzyme. $K_{cat}$ (turnover number) is the specific activity at saturating concentration of substrate.

In particular, in accordance with this first aspect of the second part of the present invention, the present invention provides enzymes which are capable of converting 3-methylcrotonic acid into isobutene with a turnover rate of at least $1\times10^{-3}$ $s^{-1}$ of 3-methylcrotonic acid into isobutene. Such enzymes can be provided by effecting mutations at specific positions in an 3-methylcrotonic acid decarboxylase (MDC) and the variants obtained by effecting such mutations show an improved activity in catalyzing the conversion of 3-methylcrotonic acid into isobutene. In a preferred embodiment, the enzyme is capable of converting 3-methylcrotonic acid into isobutene with a turnover rate of at least $2\times10^{-3}$ $s^{-1}$ of 3-methylcrotonic acid into isobutene and in a particularly preferred embodiment of at least $4\times10^{-3}$ $s^{-1}$. In a most preferred embodiment, the enzyme has a turnover rate of at least $10\times10^{-3}$ $s^{-1}$ or at least $1$ $s^{-1}$, or at least $10$ $s^{-1}$ and even more preferably of at least $100$ $s^{-1}$ of 3-methylcrotonic acid into isobutene. The corresponding wild-type enzyme has a turnover rate of about $1\times10^{-3}$ $s^{-1}$ of 3-methylcrotonic acid into isobutene.

In the context of the present invention, an "improved activity" means that the activity of the enzyme in question is at least 10%, preferably at least 20%, more preferably at least 30% or 50%, even more preferably at least 70% or 80% and particularly preferred at least 90% or 100% higher than that of the enzyme from which the variant is derived, preferably higher than that of the enzyme represented by SEQ ID NO: 14. In even more preferred embodiments the improved activity may be at least 150%, at least 200%, at least 300%, at least 750% or at least 1000% higher than that of the corresponding enzyme from which the variant is derived, preferably higher than that of the enzyme represented by SEQ ID NO: 14. In a particularly preferred embodiment, the activity is measured by using an assay with purified enzyme and chemically synthesized substrates, as described below. The improved activity of a variant can be measured as a higher isobutene production in a given time under defined conditions, compared with the parent enzyme. This improved activity can result from a higher turnover number, e.g. a higher kcat value. It can also result from a lower Km value. It can also result from a higher kcat/Km value. Finally, it can result from a higher solubility, or stability of the enzyme. The degree of improvement can be measured as the improvement in isobutene production. The degree of improvement can also be measured in terms of kcat improvement, of kcat/Km improvement, or in terms of Km decrease, in terms of soluble protein production or in terms of protein stability.

In another embodiment, the enzyme variants which the present invention provides are capable of converting 3-methylcrotonic acid into isobutene with an activity which is at least 1.25 times as high compared to the turnover rate of the corresponding wild type enzyme having the amino acid sequence as shown in SEQ ID NO: 14. In a more preferred embodiment, the enzyme variants which are capable of converting 3-methylcrotonic acid into isobutene have a turnover rate (i.e., a $k_{cat}$-value) which is at least 2 times, at least 3 times, at least 5 times or even at least 10 times as high compared to the turnover rate of the corresponding wild type enzyme having the amino acid sequence as shown in SEQ ID NO: 14. In even more preferred embodiments, the turnover rate is at least 100 times or even at least 500 times as high compared to that of the corresponding wild type enzyme having the amino acid sequence as shown in SEQ ID NO:14.

Such enzyme variants are obtained by effecting mutations at specific positions in the amino acid sequence of an MDC and the variants obtained by effecting such mutations show an improved activity in catalyzing the conversion of 3-methylcrotonic acid into isobutene. The activity of an enzyme capable of converting 3-methylcrotonic acid into isobutene may be determined by methods known to the person skilled in the art. In one embodiment, this activity is determined as described in the Examples appended hereto. In a particular embodiment this activity can be measured by incubating the enzyme, preferably a cell lysate containing the overexpressed recombinant protein, in vitro. Alternatively, a purified enzyme can be used or an in vivo assay.

More specifically, the activity of the MDC variants for the conversion of 3-methylcrotonic acid into isobutene can be assessed by an enzymatic in vitro assay based on purified proteins and on the detection of isobutene by gas chromatography. The turnover rate of the enzyme to be assessed may be examined as outlined in the following: Michaelis-Menten $k_{cat}$ and Km steady state kinetic constants for the reaction of conversion of 3-methylcrotonic acid into isobutene may be determined using the following protocol:

The enzymatic assay for quantifying the conversion of 3-methylcrotonic acid into isobutene is carried out in a 2 ml glass vial at 30° C. in a 50 mM potassium phosphate pH 7.5 buffer; 20 mM NaCl, 3 mM $MgCl_2$, 5 mM DTT, 0.5 mg/ml of a purified enzyme of the MDC variant to be tested, 100 µl of a lysate containing a FMN prenyltransferase (i.e., a Flavin prenyltransferase UbiX protein from E. coli expressed and prepared as outlined further below) as well as different concentrations of the substrate 3-methylcrotonic acid ranging from 0 to 128 mM. A control without an MDC enzyme is performed in parallel. After 60 minutes, the reaction is stopped by incubating at 80° C. for 2 min. The rate of isobutene production is quantified by gas chromatography as follows.

The isobutene formed in the reaction headspace is analysed by gas chromatography (GC) equipped with a flame ionization detector (FID). For the GC headspace analysis, one ml of the headspace gas is separated in a Bruker GC-450 system equipped with a GS-alumina column (30 m×0.53 mm) (Agilent) using isothermal mode at 130° C. Nitrogen is used as carrier gas with a flow rate of 6 ml/min. The enzymatic reaction product is identified by comparison with an isobutene standard. Under these GC conditions, the retention time of isobutene is 2.42 min. From the rate of isobutene production, and using the Michaelis-Menten approximation, the enzyme catalytic efficiency can then be computed. The production rates of isobutene (mole of PV/mole enzyme/sec) are plotted as a function of the concentration of 3-methylcrotonic acid and the curve is fitted using the Michaelis Menten equation ($V=(V_{max}*(\text{substrate}))/(K_m+(\text{substrate}))$) to extract the $k_{cat}$ ($s^{-1}$) and the $K_m$ values (mM).

The MDC variant to be tested can be provided according to the following protocol: The MDC to be tested is subcloned into the pETDuet™-1 co-expression vector. The vector contains a stretch of 6 histidine codons after the methionine initiation codon of the ferulic acid decarboxylases in order to provide an affinity tag for purification.

Competent E. coli BL21 (DE3) cells (Novagen) are transformed with this vector according to standard heat shock procedures and plated out onto LB-agar plates supplemented with the appropriate antibiotic. Cells are grown overnight at 30° C. until individual colonies reach the desired size. A single colony is then picked and individually transferred into 5 ml of liquid LB medium supplemented with the appropriate antibiotic. Cell growth is carried out with shaking for 16 hours at 30° C. The LB culture of the transformed cells is used to inoculate a culture using ZYM-5052 auto-induction medium (Studier F W, Prot. Exp. Pur. 41, (2005), 207-234) and the culture is grown with shaking (160 rpm) at 30° C. during 24 h. The cells are collected by centrifugation at 4° C., 10,000 rpm for 20 min and the pellets are frozen and stored at −80° C. The pellets containing the overexpressed protein of a 500 ml of cultured cells is thawn on ice and resuspended in 15 ml of 50 mM potassium phosphate buffer containing 200 mM NaCl, 10 mM $MgCl_2$, 10 mM imidazole and 1 mM DTT. Twenty microliters of lysonase (Novagen) is added and the cells are incubated for 10 minutes at room temperature and then returned to ice for 20 minutes. Cell lysis is then completed by sonication for 2×15 seconds.

The bacterial extracts are then clarified by centrifugation at 4° C., 4000 rpm for 40 min. The clarified bacterial lysates are loaded onto a PROTINO-2000 Ni-TED column (Macherey-Nagel) allowing adsorption of 6-His tagged proteins. Columns are washed and the enzymes of interest are eluted with 6 ml of 50 mM potassium phosphate buffer containing 250 mM imidazole. Eluates are then concentrated, desalted on a Amicon Ultra-4 10 kDa filter unit (Millipore) and enzymes are resuspended in 50 mM potassium phosphate buffer containing 1 mM DTT and 20 mM NaCl. Protein concentrations are determined by direct UV 280 nm measurement on a NanoDrop 1000 spectrophotometer (Thermo Scientific) or by a Bradford assay (BioRad).

Correspondingly, the cDNA of a Flavin prenyltransferase UbiX protein from E. coli is cloned and recombinantly expressed, purified and quantified.

As described in the above enzymatic in vitro assay for determining the activity of the MDC variants of the present invention, UbiX does not necessarily have to be provided in a recombinantly expressed and subsequently purified manner. Therefore, UbiX may alternatively also be provided in the form of a UbiX-containing cell lysate without purifying it as described in the following.

The Flavin prenyltransferase UbiX protein from E. coli is cloned in the vector pCAN. The Flavin prenyltransferase UbiX protein from E. coli was purchased from NAIST (Nara Institute of Science and Technology, Japan, ASKA collection).

Competent E. coli BL21 (DE3) cells (Novagen) are transformed with this vector according to standard heat shock procedures and plated out onto LB-agar plates supplemented with the appropriate antibiotic. Cells are grown overnight at 30° C. until individual colonies reach the desired size. A single colony is then picked and individually transferred into 5 ml of liquid LB medium supplemented with the appropriate antibiotic. Cell growth is carried out with shaking for 16 hours at 30° C. The LB culture of the transformed cells is used to inoculate a ZYM-5052 auto-induction medium (Studier F W, Prot. Exp. Pur. 41, (2005), 207-234) and the culture is grown with shaking (160 rpm) using at 30° C. during 24 h. The cells are collected by centrifugation at 4° C., 10,000 rpm for 20 min and the pellets are stored at −80° C. Pellets from 500 ml of cultured cells are thawed on ice and resuspended in 15 ml of 50 mM potassium phosphate buffer containing 200 mM NaCl, 10 mM $MgCl_2$, 10 mM imidazole and 1 mM DTT. Twenty microliters of lysonase (Novagen) is added. Cells are incubated 10 minutes at room temperature and then returned to ice for 20 minutes. Cell lysis is completed by sonication for 2×15 seconds. The cellular lysate containing the UbiX protein is kept on ice.

Alternatively to the above in vitro assays, the activity of the MDC variants for the conversion of 3-methylcrotonic acid into isobutene can be assessed by an in vivo testing. This coupled in vivo assay is based on the use of a bacterial strain transformed with an expression vector that contains the coding sequences leading to the production of the MDC variant and the Flavin prenyltransferase UbiX protein from *E. coli* (SEQ ID NO:2). Thus, the MDC variant to be tested is subcloned into a pETDuet™-1 co-expression vector (Novagen) in addition to the cDNA of the Flavin prenyltransferase UbiX protein from *E. coli*.

The MDC variant of the present invention to be tested is used to catalyze the decarboxylation reaction of 3-methylcrotonic acid into isobutene while the Flavin prenyltransferase UbiX protein from *E. coli* provides the modified flavin cofactor. Thus, in the coupled in vivo assay, a bacterial strain is used which is transformed with the above expression vector.

The transformed strain is first plated out onto LB-agar plates supplemented with the appropriate antibiotic. Cells are then grown overnight at 30° C. until individual colonies reach the desired size. Single colonies are then picked and individually transferred into either 50 or 500 µL of liquid LB medium supplemented with the appropriate antibiotic. Cell growth is carried out with shaking for 20 hours at 30° C. The LB cultures are used to inoculate 300 µL in 384 deepwell microplates or 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the two types of recombinant enzymes. The cell pellet containing these overexpressed recombinant enzymes is then resuspended in 40 µL of minimum medium (pH 7.5, Phosphate 100 mM, Glucose 10 g·L$^{-1}$, MgSO$_4$ 1 mM) supplemented with 10 mM 3-methylcrotonic acid in 384 deepwell microplates or in 400 µL of minimum medium (pH 7.5, Phosphate 100 mM, Glucose 10 g·L$^{-1}$, MgSO$_4$ 1 mM) supplemented with 10 mM 3-methylcrotonic acid in 96 deepwell microplates and incubated for a further 2 or 4 hours in a shaking incubator at 37° C., 700 rpm. During this step, the MDC variant catalyses the decarboxylation of 3-methylcrotonic acid into isobutene. After 5 min inactivation at 80° C., the isobutene produced is quantified by gas chromatography as follows. 100 µL of headspace gases from each enzymatic reaction are injected in a Brucker GC-450 system equipped with a Flame Ionization Detector (FID). Compounds present in samples are separated by chromatography using a RTX-1 column at 100° C. with a 1 mL/min constant flow of nitrogen as carrier gas. Upon injection, peak areas of isobutene are calculated.

By providing the above described enzyme variant of the second part of the present invention, the present invention allows to dramatically increase the production efficiency of isobutene from 3-methylcrotonic acid.

The term "3-methylcrotonic acid decarboxylase (MDC)" refers to an enzyme which can catalyze the decarboxylation of 3-methylcrotonic acid into isobutene. A decarboxylation is a chemical reaction that removes a carboxyl group and releases carbon dioxide. This activity can be measured by methods known in the art and as described above. In a preferred embodiment, the MDC is a Ferulic Acid Decarboxylase (FDC) or is derived from such an enzyme. FDCs belong to the enzyme class EC 4.1.1.-. As mentioned above, it has originally been described that an FDC in association with a modified FMN (prenylated-FMN) is capable of catalyzing an α,β-unsaturated decarboxylation via a 1,3-dipolar cyclo-addition and, more specifically, capable of catalyzing the decarboxylation of 3-methylcrotonic acid into isobutene. Thus, in the context of the present invention, the term FDC relates to enzymes capable of catalyzing the decarboxylation of 3-methylcrotonic acid into isobutene, preferably when provided with a prenylated FMN.

FDC enzymes have, e.g., been described in *Saccharomyces cerevisiae*, *Enterobacter* sp., *Bacillus pumilus*, *Aspergillus niger* or *Candida dubliniensis*. Hence, in preferred embodiments, the FDC is derived from *Saccharomyces cerevisiae* (Uniprot accession number Q03034), *Enterobacter* sp. (Uniprot accession number V3P7U0), *Bacillus pumilus* (Uniprot accession number Q45361), *Aspergillus niger* (Uniprot accession number A2R0P7) or *Candida dubliniensis* (Uniprot accession number B9WJ66). In more preferred embodiments, the FDC is a 3-polyprenyl-4-hydroxybenzoate decarboxylase (UbiD). 3-polyprenyl-4-hydroxybenzoate decarboxylases have, e.g., been described in *Hypocrea atroviridis*, *Sphaerulina musiva*, *Penecillinum requeforti*, *Fusarium oxysporum* f. sp. *lycopersici*, *Saccharomyces kudriavzevii*, *Saccharomyces cerevisiae*, *Aspergillus parasiticus*, *Candida albicans*, *Grosmannia clavigera*, *Escherichia coli*, *Bacillus megaterium*, *Methanothermobacter* sp. CaT2 or *Mycobacterium chelonae* 1518. Hence, in more preferred embodiments, the FDC enzyme variant capable of catalyzing the decarboxylation of 3-methylcrotonic acid into isobutene is derived from a 3-polyprenyl-4-hydroxybenzoate decarboxylase (UbiD) from *Hypocrea atroviridis* (UniProt Accession number G9NLP8), *Sphaerulina musiva* (UniProt Accession number M3DF95), *Penecillinum requeforti* (UniProt Accession number W6QKP7), *Fusarium oxysporum* f. sp. *lycopersici* (UniProt Accession number W9LTH3), *Saccharomyces kudriavzevii* (UniProt Accession number J8TRN5), *Saccharomyces cerevisiae*, *Aspergillus parasiticus*, *Candida albicans*, *Grosmannia clavigera*, *Escherichia coli* (Uniprot accession number P0AAB4), *Bacillus megaterium* (Uniprot accession number D5DTL4), *Methanothermobacter* sp. CaT2 (Uniprot accession number T2GKK5) or *Mycobacterium chelonae* 1518 (Uniprot accession number X8EX86). Preferably, the MDC is an enzyme which is associated with and/or depends on an FMN prenyl transferase. As mentioned above, the enzymatic conversion of 3-methylcrotonic acid into isobutene utilizing an FMN-dependent decarboxylase is preferably associated with an FMN prenyl transferase and relies on a reaction of two consecutive steps catalyzed by the two enzymes, i.e., the FMN-dependent decarboxylase (catalyzing the actual decarboxylation of 3-methylcrotonic acid into isobutene) with an associated FMN prenyl transferase which provides the modified flavin cofactor. The flavin cofactor may preferably be FMN or FAD. FMN (flavin mononucleotide; also termed riboflavin-5'-phosphate) is a biomolecule produced from riboflavin (vitamin B2) by the enzyme riboflavin kinase and functions as prosthetic group of various reactions. FAD (flavin adenine dinucleotide) is a redox cofactor, more specifically a prosthetic group, involved in several important reactions in metabolism. The FMN prenyl transferases which may be associated with the MDC variants of the present invention are described in more detail further below.

The second part of the present invention provides now improved variants of enzymes which are capable of converting 3-methylcrotonic acid into isobutene. The inventors used as a model enzyme the FDC, more specifically the UbiD-like decarboxylase of *Streptomyces* sp. 769 (UniProt Accession number A0A0A8EV26; the corresponding encoding gene GZL_07100) shown in SEQ ID NO: 14 and could show that it is possible to provide variants of this enzyme which show increased activity with respect to the conversion of 3-methylcrotonic acid into isobutene.

The model enzyme, i.e., the UbiD-like decarboxylase of *Streptomyces* sp. 769, as used by the inventors has the amino acid sequence as shown in SEQ ID NO: 14.

In one preferred embodiment the variants of the second part of the present invention are characterized by the feature that they are derived from an MDC, more preferably from an MDC having the amino acid sequence shown in SEQ ID NO: 14 or a highly related sequence (at least 63% identical) and in which mutations are effected at one or more of the below indicated positions and by the feature that they show the ability to convert 3-methylcrotonic acid into isobutene and that they can do this with an improved activity. In a preferred embodiment the variant according to the present invention is derived from a sequence which shows at least 70%, more preferably at least 80% sequence identity to SEQ ID NO:14 and in which one or more substitutions and/or deletions and/or insertions at the positions indicated herein have been effected.

However, the teaching of the present invention is not restricted to the MDC enzyme of *Streptomyces* sp. 769 shown in SEQ ID NO:14 which had been used as a model enzyme but can be extended to MDC enzymes from other organisms or to enzymes which are structurally related to SEQ ID NO:14 such as, e.g., truncated variants of the enzyme. Thus, the present invention also relates to variants of MDCs which are structurally related to the *Streptomyces* sp. 769 sequence (SEQ ID NO: 14) and which show one or more substitutions and/or deletions and/or insertions at positions corresponding to any of the positions as indicated herein. The term "structurally related" refers to MDCs which show a sequence identity of at least n % to the sequence shown in SEQ ID NO:14 with n being an integer between 60 and 100, preferably 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99. In a preferred embodiment the structurally related MDC stems from a bacteria, more preferably from an organism of the phylum of Actinobacteria, even more preferably from an organism of the class of Actinobacteria, the order of Actinomycetales, the family of Streptomycetaceae or the genus *Streptomyces* sp., most preferably *Streptomyces* sp. 769.

Thus, in one embodiment, the variant of an MDC according to the present invention has or preferably is derived from a sequence which is at least n % identical to SEQ ID NO: 14 with n being an integer between 60 and 100, preferably 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99, and it has (a) substitution(s) and/or (a) deletion and/or (an) insertion(s) at a position as indicated herein.

In more preferred embodiments, the variant of an MDC according to the present invention has or preferably is derived from a sequence which is at least n % identical to SEQ ID NO:14 with n being preferably 63, 64, 74, 77, 78, 94 or 97, and it has (a) substitution(s) and/or (a) deletion and/or (an) insertion(s) at a position as indicated herein.

When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap. Preferably, the degree of identity is calculated over the complete length of the sequence.

Amino acid residues located at a position corresponding to a position as indicated herein in the amino acid sequence shown in SEQ ID NO: 14 can be identified by the skilled person by methods known in the art. For example, such amino acid residues can be identified by aligning the sequence in question with the sequence shown in SEQ ID NO: 14 and by identifying the positions which correspond to the below indicated positions of SEQ ID NO:14. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

When the amino acid sequences of MDCs are aligned by means of such a method, regardless of insertions or deletions that occur in the amino acid sequences, the positions of the corresponding amino acid residues can be determined in each of the MDCs.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagine etc.). Naturally occurring modifications also encompass the change in the chemical structure by citrullination, carbamylation and disulphide bond formation between cysteine residues; attachment of co-factors (FMN or FAD that can be covalently attached) or the attachment of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi: 101016/jchembiol.2009.03.001).

In the context of the present invention, "deleted" or "deletion" means that the amino acid at the corresponding position is deleted.

In the context of the present invention, "inserted" or "insertion" means that at the respective position one or two, preferably one amino acid residue is inserted, preferably in front of the indicated position.

In a second aspect of the second part of the present invention, the present invention provides a variant of a 3-methylcrotonic acid decarboxylase (MDC) showing an improved activity in converting 3-methylcrotonic acid into isobutene over the corresponding MDC from which it is derived, wherein the MDC variant is characterized in that it shows one or more substitutions, deletions and/or insertions in comparison to the corresponding sequence from which it is derived and wherein these substitutions, deletions and/or insertions occur at one or more of the positions corresponding to positions 448, 2, 3, 5, 6, 24, 25, 35, 36, 64, 74, 80, 85, 86, 126, 129, 154, 166, 175, 195, 196, 197, 198, 204, 208, 214, 236, 237, 238, 240, 277, 298, 302, 339, 343, 347, 350, 359, 366, 368, 390, 391, 394, 395, 396, 398, 401, 402, 403, 404, 405, 406, 407, 408, 426, 439, 440, 441, 442, 444, 446, 447, 449, 450, 451, 452, 453, 454, 455, 456, 457, 458, 459, 460, 461, 462 and 473 in the amino acid sequence shown in SEQ ID NO:14.

The present invention relates in a preferred embodiment to an MDC variant having an amino acid sequence as shown in SEQ ID NO:14 or an amino acid sequence having at least 63% sequence identity to SEQ ID NO: 14, in which one or more amino acid residues at a position selected from the group consisting of positions 448, 2, 3, 5, 6, 24, 25, 35, 36, 64, 74, 80, 85, 86, 126, 129, 154, 166, 175, 195, 196, 197, 198, 204, 208, 214, 236, 237, 238, 240, 277, 298, 302, 339, 343, 347, 350, 359, 366, 368, 390, 391, 394, 395, 396, 398, 401, 402, 403, 404, 405, 406, 407, 408, 426, 439, 440, 441, 442, 444, 446, 447, 449, 450, 451, 452, 453, 454, 455, 456, 457, 458, 459, 460, 461, 462 and 473 in the amino acid sequence shown in SEQ ID NO: 14 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

The present invention relates in a preferred embodiment to an MDC variant having an amino acid sequence as shown in SEQ ID NO:14 or an amino acid sequence having at least 63% sequence identity to SEQ ID NO: 14, in which one or more amino acid residues at a position selected from the group consisting of positions 85, 198, 240, 241, 359, 390, 401, 402, 403, 404, 405, 406, 408, 443, 444, 445, 446, 448, 449 and 450 in the amino acid sequence shown in SEQ ID NO: 14 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

According to one embodiment, the second part of the present invention relates to any of the above-described MDC variants having an amino acid sequence as shown in SEQ ID NO: 14 or an amino acid sequence having at least 63% sequence identity to SEQ ID NO: 14 in which (1) an amino acid residue at position 2 in the amino acid sequence shown in SEQ ID NO:14 or at a position corresponding to this position, is deleted or substituted with asparagine; and/or (2) an amino acid residue at position 3 in the amino acid sequence shown in SEQ ID NO:14 or at a position corresponding to this position, is deleted or substituted with leucine or methionine; and/or (3) an amino acid residue at position 5 in the amino acid sequence shown in SEQ ID NO:14 or at a position corresponding to this position, is deleted or substituted with isoleucine; and/or (4) an amino acid residue at position 6 in the amino acid sequence shown in SEQ ID NO:14 or at a position corresponding to this position, is deleted or substituted with methionine; and/or (5) an amino acid residue at position 24 in the amino acid sequence shown in SEQ ID NO:14 or at a position corresponding to this position, is deleted or substituted with alanine, aspartic acid, leucine or valine; and/or (6) an amino acid residue at position 25 in the amino acid sequence shown in SEQ ID NO:14 or at a position corresponding to this position, is deleted or substituted with glutamic acid; and/or (7) an amino acid residue at position 35 in the amino acid sequence shown in SEQ ID NO:14 or at a position corresponding to this position, is deleted or substituted with isoleucine; and/or (8) an amino acid residue at position 36 in the amino acid sequence shown in SEQ ID NO:14 or at a position corresponding to this position, is deleted or substituted with tyrosine; and/or (9) an amino acid residue at position 64 in the amino acid sequence shown in SEQ ID NO: 14 or at a position corresponding to this position, is deleted or substituted with histidine; and/or

(10) an amino acid residue at position 74 in the amino acid sequence shown in SEQ ID NO: 14 or at a position corresponding to this position, is deleted or substituted with valine; and/or

(11) an amino acid residue at position 80 in the amino acid sequence shown in SEQ ID NO:14 or at a position corresponding to this position, is deleted or substituted with serine; and/or

(12) an amino acid residue at position 85 in the amino acid sequence shown in SEQ ID NO:14 or at a position corresponding to this position, is deleted or substituted with leucine; and/or

(13) an amino acid residue at position 86 in the amino acid sequence shown in SEQ ID NO:14 or at a position corresponding to this position, is deleted or substituted with asparagine or tyrosine; and/or

(14) an amino acid residue at position 126 in the amino acid sequence shown in SEQ ID NO:14 or at a position corresponding to this position, is deleted or substituted with valine; and/or

(15) an amino acid residue at position 129 in the amino acid sequence shown in SEQ ID NO: 14 or at a position corresponding to this position, is deleted or substituted with valine; and/or

(16) an amino acid residue at position 154 in the amino acid sequence shown in SEQ ID NO: 14 or at a position corresponding to this position, is deleted or substituted with aspartic acid; and/or

(17) an amino acid residue at position 166 in the amino acid sequence shown in SEQ ID NO: 14 or at a position corresponding to this position, is deleted or substituted with aspartic acid; and/or

(18) an amino acid residue at position 175 in the amino acid sequence shown in SEQ ID NO: 14 or at a position corresponding to this position, is deleted or substituted with glutamic acid; and/or

(19) an amino acid residue at position 195 in the amino acid sequence shown in SEQ ID NO:14 or at a position corresponding to this position, is deleted or substituted with isoleucine or valine; and/or

(20) an amino acid residue at position 196 in the amino acid sequence shown in SEQ ID NO:14 or at a position corresponding to this position, is deleted or substituted with isoleucine; and/or

(21) an amino acid residue at position 197 in the amino acid sequence shown in SEQ ID NO: 14 or at a position corresponding to this position, is deleted or substituted with valine; and/or

(22) an amino acid residue at position 198 in the amino acid sequence shown in SEQ ID NO: 14 or at a position corresponding to this position, is deleted or substituted with glutamine or tryptophan; and/or

(23) an amino acid residue at position 204 in the amino acid sequence shown in SEQ ID NO: 14 or at a position corresponding to this position, is deleted or substituted with arginine or serine; and/or

(24) an amino acid residue at position 208 in the amino acid sequence shown in SEQ ID NO: 14 or at a position corresponding to this position, is deleted or substituted with leucine; and/or

(25) an amino acid residue at position 214 in the amino acid sequence shown in SEQ ID NO: 14 or at a position corresponding to this position, is deleted or substituted with threonine; and/or

(26) an amino acid residue at position 236 in the amino acid sequence shown in SEQ ID NO: 14 or at a position corresponding to this position, is deleted or substituted with leucine or valine; and/or

(27) an amino acid residue at position 237 in the amino acid sequence shown in SEQ ID NO: 14 or at a position corresponding to this position, is deleted or substituted with alanine, aspartic acid, asparagine or proline; and/or

(28) an amino acid residue at position 238 in the amino acid sequence shown in SEQ ID NO: 14 or at a position corresponding to this position, is deleted or substituted with histidine, arginine, serine or tryptophan; and/or

(29) an amino acid residue at position 240 in the amino acid sequence shown in SEQ ID NO: 14 or at a position corresponding to this position, is deleted or substituted with isoleucine or asparagine; and/or

(30) an amino acid residue at position 277 in the amino acid sequence shown in SEQ ID NO: 14 or at a position corresponding to this position, is deleted or substituted with tyrosine; and/or

(31) an amino acid residue at position 298 in the amino acid sequence shown in SEQ ID NO:14 or at a position corresponding to this position, is deleted or substituted with serine; and/or

(32) an amino acid residue at position 302 in the amino acid sequence shown in SEQ ID NO:14 or at a position corresponding to this position, is deleted or substituted with alanine, cysteine, phenylalanine, lysine, methionine, glutamine, arginine or serine; and/or

(33) an amino acid residue at position 339 in the amino acid sequence shown in SEQ ID NO: 14 or at a position corresponding to this position, is deleted or substituted with histidine; and/or

(34) an amino acid residue at position 343 in the amino acid sequence shown in SEQ ID NO: 14 or at a position corresponding to this position, is deleted or substituted with serine; and/or

(35) an amino acid residue at position 347 in the amino acid sequence shown in SEQ ID NO: 14 or at a position corresponding to this position, is deleted or substituted with cysteine; and/or

(36) an amino acid residue at position 350 in the amino acid sequence shown in SEQ ID NO: 14 or at a position corresponding to this position, is deleted or substituted with serine; and/or

(37) an amino acid residue at position 359 in the amino acid sequence shown in SEQ ID NO: 14 or at a position corresponding to this position, is deleted or substituted with cysteine or valine; and/or

(38) an amino acid residue at position 366 in the amino acid sequence shown in SEQ ID NO: 14 or at a position corresponding to this position, is deleted or substituted with isoleucine or phenylalanine; and/or

(39) an amino acid residue at position 368 in the amino acid sequence shown in SEQ ID NO: 14 or at a position corresponding to this position, is deleted or substituted with isoleucine or methionine; and/or

(40) an amino acid residue at position 390 in the amino acid sequence shown in SEQ ID NO: 14 or at a position corresponding to this position, is deleted or substituted with serine, aspartic acid, leucine, asparagine or glutamine; and/or

(41) an amino acid residue at position 391 in the amino acid sequence shown in SEQ ID NO: 14 or at a position corresponding to this position, is deleted or substituted with aspartic acid or tryptophan; and/or

(42) an amino acid residue at position 394 in the amino acid sequence shown in SEQ ID NO: 14 or at a position corresponding to this position, is deleted or substituted with cysteine, aspartic acid, glutamine or threonine; and/or

(43) an amino acid residue at position 395 in the amino acid sequence shown in SEQ ID NO:14 or at a position corresponding to this position, is deleted or substituted with cysteine, glutamic acid or valine; and/or

(44) an amino acid residue at position 396 in the amino acid sequence shown in SEQ ID NO:14 or at a position corresponding to this position, is deleted or substituted with isoleucine; and/or

(45) an amino acid residue at position 398 in the amino acid sequence shown in SEQ ID NO: 14 or at a position corresponding to this position, is deleted or substituted with cysteine or arginine; and/or

(46) an amino acid residue at position 401 in the amino acid sequence shown in SEQ ID NO: 14 or at a position corresponding to this position, is deleted or substituted with tyrosine; and/or
(47) an amino acid residue at position 402 in the amino acid sequence shown in SEQ ID NO: 14 or at a position corresponding to this position, is deleted or substituted with alanine; and/or
(48) an amino acid residue at position 403 in the amino acid sequence shown in SEQ ID NO: 14 or at a position corresponding to this position, is deleted or substituted with alanine, cysteine, glycine, histidine, isoleucine, asparagine, proline, glutamine, arginine or valine; and/or
(49) an amino acid residue at position 404 in the amino acid sequence shown in SEQ ID NO: 14 or at a position corresponding to this position, is deleted or substituted with phenylalanine, leucine or methionine; and/or
(50) an amino acid residue at position 405 in the amino acid sequence shown in SEQ ID NO: 14 or at a position corresponding to this position, is deleted or substituted with histidine, isoleucine, methionine, threonine or valine; and/or
(51) an amino acid residue at position 406 in the amino acid sequence shown in SEQ ID NO: 14 or at a position corresponding to this position, is deleted or substituted with glycine, alanine or serine; and/or
(52) an amino acid residue at position 407 in the amino acid sequence shown in SEQ ID NO: 14 or at a position corresponding to this position, is deleted or substituted with alanine, cysteine, isoleucine, lysine, arginine, serine or threonine; and/or
(53) an amino acid residue at position 408 in the amino acid sequence shown in SEQ ID NO: 14 or at a position corresponding to this position, is deleted or substituted with isoleucine, alanine, cysteine, leucine, or methionine; and/or
(54) an amino acid residue at position 426 in the amino acid sequence shown in SEQ ID NO: 14 or at a position corresponding to this position, is deleted or substituted with valine; and/or
(55) an amino acid residue at position 439 in the amino acid sequence shown in SEQ ID NO:14 or at a position corresponding to this position, is deleted or substituted with cysteine; and/or
(56) an amino acid residue at position 440 in the amino acid sequence shown in SEQ ID NO:14 or at a position corresponding to this position, is deleted or substituted with leucine; and/or
(57) an amino acid residue at position 441 in the amino acid sequence shown in SEQ ID NO: 14 or at a position corresponding to this position, is deleted or substituted with glycine, histidine, lysine, asparagine, proline, arginine, serine or threonine; and/or
(58) an amino acid residue at position 442 in the amino acid sequence shown in SEQ ID NO: 14 or at a position corresponding to this position, is deleted or substituted with alanine, cysteine, glutamic acid, glycine, histidine, leucine, methionine, asparagine, glutamine, arginine, serine or threonine; and/or
(59) an amino acid residue at position 444 in the amino acid sequence shown in SEQ ID NO: 14 or at a position corresponding to this position, is deleted or substituted with alanine, glutamic acid, phenylalanine, histidine, isoleucine, leucine, glutamine or threonine; and/or
(60) an amino acid residue at position 446 in the amino acid sequence shown in SEQ ID NO: 14 or at a position corresponding to this position, is deleted or substituted with alanine, cysteine, phenylalanine, isoleucine, methionine, asparagine, serine or valine; and/or
(61) an amino acid residue at position 447 in the amino acid sequence shown in SEQ ID NO: 14 or at a position corresponding to this position, is deleted or substituted with glutamine; and/or
(62) an amino acid residue at position 448 in the amino acid sequence shown in SEQ ID NO: 14 or at a position corresponding to this position, is deleted or substituted with phenylalanine, tryptophan or tyrosine; and/or
(63) an amino acid residue at position 449 in the amino acid sequence shown in SEQ ID NO: 14 or at a position corresponding to this position, is deleted or substituted with isoleucine, methionine or valine; and/or
(64) an amino acid residue at position 450 in the amino acid sequence shown in SEQ ID NO: 14 or at a position corresponding to this position, is deleted or substituted with alanine, histidine, methionine, asparagine, glutamine, serine or valine; and/or
(65) an amino acid residue at position 451 in the amino acid sequence shown in SEQ ID NO: 14 or at a position corresponding to this position, is deleted or substituted with asparagine or serine; and/or
(66) an amino acid residue at position 452 in the amino acid sequence shown in SEQ ID NO:14 or at a position corresponding to this position, is deleted or substituted with phenylalanine; and/or
(67) an amino acid residue at position 453 in the amino acid sequence shown in SEQ ID NO:14 or at a position corresponding to this position, is deleted or substituted with cysteine, glycine, leucine, asparagine, proline, arginine or serine; and/or
(68) an amino acid residue at position 454 in the amino acid sequence shown in SEQ ID NO: 14 or at a position corresponding to this position, is deleted or substituted with alanine, aspartic acid, glycine, histidine, lysine, leucine, methionine, glutamine, arginine, serine, threonine, valine or tryptophan; and/or
(69) an amino acid residue at position 455 in the amino acid sequence shown in SEQ ID NO: 14 or at a position corresponding to this position, is deleted or substituted with alanine, glutamic acid, histidine, lysine, asparagine, serine or valine; and/or
(70) an amino acid residue at position 456 in the amino acid sequence shown in SEQ ID NO: 14 or at a position corresponding to this position, is deleted or substituted with glutamine; and/or
(71) an amino acid residue at position 457 in the amino acid sequence shown in SEQ ID NO: 14 or at a position corresponding to this position, is deleted or substituted with lysine; and/or
(72) an amino acid residue at position 458 in the amino acid sequence shown in SEQ ID NO: 14 or at a position corresponding to this position, is deleted or substituted with glutamic acid, phenylalanine, glycine, leucine, methionine, asparagine, glutamine, arginine, serine or tyrosine; and/or
(73) an amino acid residue at position 459 in the amino acid sequence shown in SEQ ID NO: 14 or at a position corresponding to this position, is deleted or substituted with aspartic acid, glutamic acid, glycine, methionine, asparagine, glutamine, arginine, threonine or tyrosine; and/or
(74) an amino acid residue at position 460 in the amino acid sequence shown in SEQ ID NO: 14 or at a position corresponding to this position, is deleted or substituted with glutamic acid, phenylalanine, glycine, leucine, methionine, asparagine, glutamine or arginine; and/or

(75) an amino acid residue at position 461 in the amino acid sequence shown in SEQ ID NO: 14 or at a position corresponding to this position, is deleted or substituted with alanine, glycine, leucine, methionine, glutamine, serine or valine; and/or

(76) an amino acid residue at position 462 in the amino acid sequence shown in SEQ ID NO: 14 or at a position corresponding to this position, is deleted or substituted with cysteine or valine; and/or

(77) an amino acid residue at position 473 in the amino acid sequence shown in SEQ ID NO:14 or at a position corresponding to this position, is deleted or substituted with serine.

The invention also relates to variants as defined in (1) to (77) hereinabove, wherein the amino acid residue indicated as substituting the amino acid residue at the position in SEQ ID NO:14 is not that particular amino acid residue but an amino acid residue which is conservative in relation to the indicated substituting amino acid.

Whether an amino acid is conservative with respect to another amino acid can be judged according to means and methods known in the art and as described herein above. One possibility is the PAM 250 matrix; alternatively, the Blosum Family Matrices can be used.

According to another embodiment, the present invention relates to any of the above-described MDC variants, wherein in said variant one or more further amino acid residues at a position selected from the group consisting of 66, 168, 241, 296, 305, 349, 363, 443, 445, 479, and 496 in the amino acid sequence shown in SEQ ID NO:14 or at a position corresponding to any of these positions, are substituted with another amino acid residue or deleted or wherein an insertion has been effected at one or more of these positions, and wherein said MDC variant has an improved activity in converting 3-methylcrotonic acid into isobutene over the corresponding MDC from which it is derived.

According to one embodiment, the present invention relates to any of the above-described MDC variants having one or more further amino acid residues at a position selected from the group consisting of 66, 168, 241, 296, 305, 349, 363, 443, 445, 479, and 496 in the amino acid sequence shown in SEQ ID NO:14 or at a position corresponding to any of these positions substituted with another amino acid residue or deleted or having effected an insertion at one or more of these positions and wherein said MDC has an improved activity in converting 3-methylcrotonic acid into isobutene over the corresponding MDC from which it is derived, in which

(78) an amino acid residue at position 66 in the amino acid sequence shown in SEQ ID NO:14 or at a position corresponding to this position, is deleted or substituted with histidine; and/or

(79) an amino acid residue at position 168 in the amino acid sequence shown in SEQ ID NO:14 or at a position corresponding to this position, is deleted or substituted with valine; and/or

(80) an amino acid residue at position 241 in the amino acid sequence shown in SEQ ID NO:14 or at a position corresponding to this position, is deleted or substituted with aspartic acid, asparagine or valine; and/or

(81) an amino acid residue at position 296 in the amino acid sequence shown in SEQ ID NO:14 or at a position corresponding to this position, is deleted or substituted with glutamine; and/or

(82) an amino acid residue at position 305 in the amino acid sequence shown in SEQ ID NO:14 or at a position corresponding to this position, is deleted or substituted with isoleucine or threonine; and/or

(83) an amino acid residue at position 349 in the amino acid sequence shown in SEQ ID NO: 14 or at a position corresponding to this position, is deleted or substituted with methionine or serine; and/or

(84) an amino acid residue at position 363 in the amino acid sequence shown in SEQ ID NO: 14 or at a position corresponding to this position, is deleted or substituted with glycine; and/or

(85) an amino acid residue at position 443 in the amino acid sequence shown in SEQ ID NO: 14 or at a position corresponding to this position, is deleted or substituted with alanine, aspartic acid, phenylalanine, histidine, leucine, asparagine, arginine, serine, tryptophan or tyrosine; and/or

(86) an amino acid residue at position 445 in the amino acid sequence shown in SEQ ID NO: 14 or at a position corresponding to this position, is deleted or substituted with leucine, alanine, cysteine, serine or threonine; and/or

(87) an amino acid residue at position 479 in the amino acid sequence shown in SEQ ID NO: 14 or at a position corresponding to this position, is deleted or substituted with cysteine, isoleucine, leucine, methionine, serine, threonine or valine; and/or

(88) an amino acid residue at position 496 in the amino acid sequence shown in SEQ ID NO: 14 or at a position corresponding to this position, is deleted or substituted with leucine.

The invention also relates to variants as defined in (78) to (88) hereinabove, wherein the amino acid residue indicated as substituting the amino acid residue at the position in SEQ ID NO: 14 is not that particular amino acid residue but an amino acid residue which is conservative in relation to the indicated substituting amino acid.

Whether an amino acid is conservative with respect to another amino acid can be judged according to means and methods known in the art and as described herein above. One possibility is the PAM 250 matrix; alternatively, the Blosum Family Matrices can be used.

The present invention relates in another preferred embodiment to an MDC variant having an amino acid sequence as shown in SEQ ID NO: 14 or an amino acid sequence having at least 78% sequence identity to SEQ ID NO: 14, in which one or more amino acid residues at a position selected from the group consisting of positions 448, 2, 3, 5, 6, 24, 25, 35, 36, 64, 74, 80, 85, 86, 126, 129, 154, 166, 175, 195, 196, 197, 198, 204, 208, 214, 236, 237, 238, 240, 277, 298, 302, 339, 343, 347, 350, 359, 366, 368, 390, 391, 394, 395, 396, 398, 401, 402, 403, 404, 405, 406, 407, 408, 426, 439, 440, 441, 442, 444, 446, 447, 449, 450, 451, 452, 453, 454, 455, 456, 457, 458, 459, 460, 461, 462 and 473 in the amino acid sequence shown in SEQ ID NO: 14 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

The present invention relates in another preferred embodiment to any of the above-described variants having an amino acid sequence as shown in SEQ ID NO:14 or an amino acid sequence having at least 78% sequence identity to SEQ ID NO:14, wherein in said variant one or more further amino acid residues at a position selected from the group consisting of 66, 168, 241, 296, 305, 349, 363, 443, 445, 479, and 496 in the amino acid sequence shown in SEQ ID NO: 14 or at a position corresponding to any of these positions, are substituted with another amino acid residue or deleted or wherein an insertion has been effected at one or more of these positions, and wherein said MDC variant has an improved activity in converting 3-methylcrotonic acid into isobutene over the corresponding MDC from which it is derived.

As regards the preferred embodiments of the substitutions, deletions or insertions for these variants, the same applies as described herein above. Thus, in preferred embodiments, the change(s) which are effected in these variants at any of the above position(s) is/are substitution(s), deletion(s) and/or insertion(s) as defined herein above.

The present invention relates in another preferred embodiment to an MDC variant having an amino acid sequence as shown in SEQ ID NO: 14 or an amino acid sequence having at least 77% sequence identity to SEQ ID NO: 14, in which one or more amino acid residues at a position selected from the group consisting of positions 2, 3, 5, 6, 25, 74, 80, 85, 154, 166, 175, 195, 196, 198, 204, 208, 236, 237, 238, 240, 277, 302, 347, 350, 366, 368, 390, 391, 394, 395, 402, 405, 406, 407, 408, 426, 439, 440, 441, 442, 444, 446, 448, 449, 450, 451, 452, 453, 456, 457, 459, 461, 462 and 473 in the amino acid sequence shown in SEQ ID NO: 14 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

The present invention relates in another preferred embodiment to any of the above-described variants having an amino acid sequence as shown in SEQ ID NO: 14 or an amino acid sequence having at least 77% sequence identity to SEQ ID NO:14, wherein in said variant one or more further amino acid residues at a position selected from the group consisting of 24, 35, 36, 64, 66, 86, 126, 129, 168, 197, 214, 241, 296, 298, 305, 339, 343, 349, 359, 363, 396, 398, 401, 403, 404, 443, 445, 447, 454, 455, 458, 460, 479, and 496 in the amino acid sequence shown in SEQ ID NO:14 or at a position corresponding to any of these positions, are substituted with another amino acid residue or deleted or wherein an insertion has been effected at one or more of these positions, and wherein said MDC variant has an improved activity in converting 3-methylcrotonic acid into isobutene over the corresponding MDC from which it is derived.

As regards the preferred embodiments of the substitutions, deletions or insertions for these variants, the same applies as described herein above. Thus, in preferred embodiments, the change(s) which are effected in these variants at any of the above position(s) is/are substitution(s), deletion(s) and/or insertion(s) as defined herein above.

The present invention relates in another preferred embodiment to an MDC variant having an amino acid sequence as shown in SEQ ID NO: 14 or an amino acid sequence having at least 74% sequence identity to SEQ ID NO: 14, in which one or more amino acid residues at a position selected from the group consisting of positions 2, 3, 5, 6, 25, 74, 80, 85, 154, 166, 175, 195, 196, 198, 204, 208, 236, 237, 238, 277, 347, 350, 366, 368, 390, 391, 395, 402, 405, 406, 408, 426, 440, 441, 442, 444, 446, 448, 449, 450, 451, 452, 456, 457, 459, 461, 462, and 473 in the amino acid sequence shown in SEQ ID NO: 14 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

The present invention relates in another preferred embodiment to any of the above-described variants having an amino acid sequence as shown in SEQ ID NO: 14 or an amino acid sequence having at least 74% sequence identity to SEQ ID NO:14, wherein in said variant one or more further amino acid residues at a position selected from the group consisting of 24, 35, 36, 64, 66, 86, 126, 129, 168, 197, 214, 240, 241, 296, 298, 302, 305, 339, 343, 349, 359, 363, 394, 396, 398, 401, 403, 404, 407, 439, 443, 445, 447, 453, 454, 455, 458, 460, 479, and 496 in the amino acid sequence shown in SEQ ID NO: 14 or at a position corresponding to any of these positions, are substituted with another amino acid residue or deleted or wherein an insertion has been effected at one or more of these positions, and wherein said MDC variant has an improved activity in converting 3-methylcrotonic acid into isobutene over the corresponding MDC from which it is derived.

As regards the preferred embodiments of the substitutions, deletions or insertions for these variants, the same applies as described herein above. Thus, in preferred embodiments, the change(s) which are effected in these variants at any of the above position(s) is/are substitution(s), deletion(s) and/or insertion(s) as defined herein above.

The present invention relates in another preferred embodiment to an MDC variant having an amino acid sequence as shown in SEQ ID NO: 14 or an amino acid sequence having at least 64% sequence identity to SEQ ID NO: 14, in which one or more amino acid residues at a position selected from the group consisting of positions 2, 3, 5, 6, 25, 74, 80, 85, 166, 175, 195, 196, 198, 204, 208, 238, 277, 350, 366, 390, 402, 405, 406, 408, 426, 440, 441, 444, 446, 448, 449, 451, 452, 456, 457, 459, 462, and 473 in the amino acid sequence shown in SEQ ID NO: 14 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

The present invention relates in another preferred embodiment to any of the above-described variants having an amino acid sequence as shown in SEQ ID NO:14 or an amino acid sequence having at least 64% sequence identity to SEQ ID NO:14, wherein in said variant one or more further amino acid residues at a position selected from the group consisting of 24, 35, 36, 64, 66, 86, 126, 129, 154, 168, 197, 214, 236, 237, 240, 241, 296, 298, 302, 305, 339, 343, 347, 349, 359, 363, 368, 391, 394, 395, 396, 398, 401, 403, 404, 407, 439, 442, 443, 445, 447, 450, 453, 454, 455, 458, 460, 461, 479, and 496 in the amino acid sequence shown in SEQ ID NO: 14 or at a position corresponding to any of these positions, are substituted with another amino acid residue or deleted or wherein an insertion has been effected at one or more of these positions, and wherein said MDC variant has an improved activity in converting 3-methylcrotonic acid into isobutene over the corresponding MDC from which it is derived.

As regards the preferred embodiments of the substitutions, deletions or insertions for these variants, the same applies as described herein above. Thus, in preferred embodiments, the change(s) which are effected in these variants at any of the above position(s) is/are substitution(s), deletion(s) and/or insertion(s) as defined herein above.

The present invention relates in another preferred embodiment to an MDC variant having an amino acid sequence as shown in SEQ ID NO: 14 or an amino acid sequence having at least 63% sequence identity to SEQ ID NO: 14, in which one or more amino acid residues at a position selected from the group consisting of positions 2, 3, 5, 6, 25, 74, 80, 85, 175, 195, 196, 277, 350, 366, 402, 408, 426, 441, 448, 449, 451, 452, 456, 457, and 473 in the amino acid sequence shown in SEQ ID NO:14 or at a position corresponding to any of these positions, are substituted with another amino acid residue or deleted or wherein an insertion has been effected at one or more of these positions and wherein said MDC variant has an improved activity in converting 3-methylcrotonic acid into isobutene.

The present invention relates in another preferred embodiment to any of the above-described variants having an amino acid sequence as shown in SEQ ID NO: 14 or an amino acid sequence having at least 63% sequence identity to SEQ ID NO:14, wherein in said variant one or more further amino acid residues at a position selected from the group consisting of 24, 35, 36, 64, 66, 86, 126, 129, 154, 166, 168, 197, 198, 204, 208, 214, 236, 237, 238, 240, 241, 296, 298, 302, 305, 339, 343, 347, 349, 359, 363, 368, 390, 391, 394, 395, 396, 398, 401, 403, 404, 405, 406, 407, 439, 440, 442, 443, 444, 445, 446, 447, 450, 453, 454, 455, 458, 459, 460, 461, 462, 479, and 496 in the amino acid sequence shown in SEQ ID NO: 14 or at a position corresponding to any of these positions, are substituted with another amino acid residue or deleted or wherein an insertion has been effected at one or more of these positions, and wherein said MDC variant has an improved activity in converting 3-methylcrotonic acid into isobutene over the corresponding MDC from which it is derived.

As regards the preferred embodiments of the substitutions, deletions or insertions for these variants, the same applies as described herein above. Thus, in preferred embodiments, the change(s) which are effected in these variants at any of the above position(s) is/are substitution(s), deletion(s) and/or insertion(s) as defined herein above.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 241 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 404, 405, 439, 440, 441, 442, 443, 444, 445, 446, 447, 448, 453, 459, 460, 461, 479 and 496 in the amino acid sequence shown in SEQ ID NO: 14.

Preferably, such a variant has the following substitution in the amino acid sequence shown in SEQ ID NO:14 or at positions corresponding to this position: A241D, A241N, or A241V.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 359 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 404, 405, 439, 440, 441, 442, 443, 444, 445, 446, 447, 448, 453, 459, 460, 461, 479 and 496 in the amino acid sequence shown in SEQ ID NO: 14.

Preferably, such a variant has the following substitution in the amino acid sequence shown in SEQ ID NO: 14 or at positions corresponding to this position: A359C.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 404 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 446, 447, 448, 453, 459, 460, 461, 479 and 496 in the amino acid sequence shown in SEQ ID NO: 14.

Preferably, such a variant has the following substitution in the amino acid sequence shown in SEQ ID NO: 14 or at positions corresponding to this position: C404F or C404L.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 404, 405, 439, 440, 441, 442, 443, 444, 445, 446, 447, 453, 459, 460, 461, 479 and 496 in the amino acid sequence shown in SEQ ID NO: 14.

Preferably, such a variant has the following substitution in the amino acid sequence shown in SEQ ID NO: 14 or at positions corresponding to this position: L448F, L448W or L448Y.

In a preferred embodiment, the MDC variant according to the invention showing an improved activity in converting 3-methylcrotonic acid into isobutene is characterized in that contains at least one deletion, substitution and/or insertion wherein the deletion/insertion/substitution is at position 406 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 404, 405, 439, 440, 441, 442, 443, 444, 445, 446, 447, 448, 453, 459, 460, 461, 479 and 496 in the amino acid sequence shown in SEQ ID NO: 14.

Preferably, such a variant has the following substitution in the amino acid sequence shown in SEQ ID NO: 14 or at positions corresponding to this position: P406A.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 390 in the amino acid sequence shown in SEQ ID NO: 14 or at a position corresponding to this position and another deletion/insertion/substitution is at position 448 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 404, 405, 439, 440, 441, 442, 443, 444, 445, 446, 447, 453, 459, 460, 461, 479 and 496 in the amino acid sequence shown in SEQ ID NO:14. Preferably, such a variant has the following substitutions in the amino acid sequence shown in SEQ ID NO: 14 or at positions corresponding to these positions: R390S-L448W or R390S-L448Y.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 241 in the amino acid sequence shown in SEQ ID NO: 14 or at a position corresponding to this position and another deletion/insertion/substitution is at position 404 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 405, 439, 440, 441, 442, 443, 444, 445, 446, 447, 448, 453, 459, 460, 461, 479 and 496 in the amino acid sequence shown in SEQ ID NO:14. Preferably, such a variant has the following substitutions in the amino acid sequence shown in SEQ ID NO:14 or at positions corresponding to these positions: A241D-C404F, A241D-C404L, A241N-C404F, or A241N-C404L.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 241 in the amino acid sequence shown in SEQ ID NO: 14 or at a position corresponding to this position and another deletion/insertion/substitution is at position 448 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 404, 405, 439, 440, 441, 442, 443, 444, 445, 446, 447, 453, 459, 460, 461, 479 and 496 in the amino acid sequence shown in SEQ ID NO:14. Preferably, such a variant has the following substitutions in the amino acid sequence shown in SEQ ID NO:14 or at positions corresponding to these positions: A241D-L448F, A241D-L448W, A241D-L448Y, A241N-L448F, A241N-L448W, or A241N-L448Y.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 241 in the amino acid sequence shown in SEQ ID NO: 14 or at a position corresponding to this position and another deletion/insertion/substitution is at position 406 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 404, 405, 439, 440, 441, 442, 443, 444, 445, 446, 447, 448, 453, 459, 460, 461, 479 and 496 in the amino acid sequence shown in SEQ ID NO:14. Preferably, such a variant has the following substitutions in the amino acid sequence shown in SEQ ID NO:14 or at positions corresponding to these positions: A241D-P406A or A241N-P406A.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 404 in the amino acid sequence shown in SEQ ID NO: 14 or at a position corresponding to this position and another deletion/insertion/substitution is at position 448 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 446, 447, 453, 459, 460, 461, 479 and 496 in the amino acid sequence shown in SEQ ID NO:14. Preferably, such a variant has the following substitutions in the amino acid sequence shown in SEQ ID NO:14 or at positions corresponding to these positions: C404L-L448F, C404L-L448W, C404M-L448F, C404M-L448W, C404F-L448F, C404F-L448W, C404F-L448Y or C404L-L448Y.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 404 in the amino acid sequence shown in SEQ ID NO: 14 or at a position corresponding to this position and another deletion/insertion/substitution is at position 406 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 446, 447, 448, 453, 459, 460, 461, 479 and 496 in the amino acid sequence shown in SEQ ID NO:14. Preferably, such a variant has the following substitutions in the amino acid sequence shown in SEQ ID NO: 14 or at positions corresponding to these positions: C404L-P406A or C404F-P406A.

In a preferred embodiment, the MDC variant according to the invention showing an improved activity in converting 3-methylcrotonic acid into isobutene is characterized in that contains at least two deletions, substitutions and/or insertions wherein one deletion/insertion/substitution is at position 406 in the amino acid sequence shown in SEQ ID NO: 14 or at a position corresponding to this position and another deletion/insertion/substitution is at position 448 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 404, 405, 439, 440, 441, 442, 443, 444, 445, 446, 447, 453, 459, 460, 461, 479 and 496 in the amino acid sequence shown in SEQ ID NO:14. Preferably, such a variant has the following substitutions in the amino acid sequence shown in SEQ ID NO:14 or at positions corresponding to these positions: P406A-L448F, P406A-L448W or P406A-L448Y.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 241 in the amino acid sequence shown in SEQ ID NO: 14 or at a position corresponding to this position, another deletion/insertion/substitution is at position 404 in the amino acid sequence shown in SEQ ID NO: 14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 405, 439, 440, 441, 442, 443, 444, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: A241D-C404F-L448F, A241D-C404F-L448Y, A241D-C404L-L448F, A241D-C404L-L448W, A241D-C404L-L448Y, A241N-C404F-L448F, A241N-C404F-L448W, A241N-C404F-L448Y, A241N-C404L-L448F, A241N-C404L-L448W, A241N-C404L-L448Y, A241D-C404F-L448W, A241N-C404M-L448W or A241D-C404M-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 241 in the amino acid sequence shown in SEQ ID NO: 14 or at a position corresponding to this position, another deletion/insertion/substitution is at position 404 in the amino acid sequence shown in SEQ ID NO:14 or at a position corresponding to this position and another deletion/insertion/substitution is at position 406 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 405, 439, 440, 441, 442, 443, 444, 445, 446, 447, 448, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: A241D-C404F-P406A, A241D-C404L-P406A, A241N-C404L-P406A or A241N-C404F-P406A.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 241 in the amino acid sequence shown in SEQ ID NO:14 or at a position corresponding to this position, another deletion/insertion/substitution is at position 406 in the amino acid sequence shown in SEQ ID NO: 14 or at a position corresponding to this position and another deletion/insertion/substitution is at position 448 in the amino acid sequence shown in SEQ ID NO:14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 404, 405, 439, 440, 441, 442, 443, 444, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: A241D-P406A-L448F, A241D-P406A-L448Y, A241N-P406A-L448F, A241N-P406A-L448W, A241N-P406A-L448Y or A241D-P406A-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 404 in the amino acid sequence shown in SEQ ID NO: 14 or at a position corresponding to this position, another deletion/insertion/substitution is at position 406 in the amino acid sequence shown in SEQ ID NO: 14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: C404F-P406A-L448F, C404F-P406A-L448W, C404F-P406A-L448Y, C404L-P406A-L448F, C404L-P406A-L448Y, C404M-P406A-L448W, C404M-P406S-L448W or C404L-P406A-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 404 in the amino acid sequence shown in SEQ ID NO: 14 or at a position corresponding to this position, another deletion/insertion/substitution is at position 446 in the amino acid sequence shown in SEQ ID NO: 14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: C404F-L446I-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 404 in the amino acid sequence shown in SEQ ID NO: 14 or at a position corresponding to this position, another deletion/insertion/substitution is at position 446 in the amino acid sequence shown in SEQ ID NO:14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: C404M-L446N-L448W or C404M-L446I-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 240 in the amino acid sequence shown in SEQ ID NO: 14 or at a position corresponding to this position, another deletion/insertion/substitution is at position 404 in the amino acid sequence shown in SEQ ID NO: 14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: V240I-C404M-L448F.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 404 in the amino acid sequence shown in SEQ ID NO: 14 or at a position corresponding to this position, another deletion/insertion/substitution is at position 448 in the amino acid sequence shown in SEQ ID NO:14 or at a position corresponding to this position and another deletion/insertion/substitution is at position 450 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 451, 452, 454, 455, 456, 457, 458, 462, 473, 2, 3, 5, 6, 24, 64, 66, 85, 154, 168, 175, 195, 197, 214, 241, 277, 296, 305, 339, 343, 347, 349, 350, 363, 391, 394, 398, 401, 403, 405, 439, 440, 441, 442, 443, 444, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO: 14 or at positions corresponding to these positions: C404M-L448W-T450A or C404M-L448W-T450H.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 241 in the amino acid sequence shown in SEQ ID NO: 14 or at a position corresponding to this position, another deletion/insertion/substitution is at position 401 in the amino acid sequence shown in SEQ ID NO: 14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 403, 404, 405, 439, 440, 441, 442, 443, 444, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: A241D-F401Y-L448W or A241N-F401Y-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 241 in the amino acid sequence shown in SEQ ID NO: 14 or at a position corresponding to this position, another deletion/insertion/substitution is at position 444 in the amino acid sequence shown in SEQ ID NO:14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 404, 405, 439, 440, 441, 442, 443, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: A241D-P444E-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 241 in the amino acid sequence shown in SEQ ID NO: 14 or at a position corresponding to this position, another deletion/insertion/substitution is at position 403 in the amino acid sequence shown in SEQ ID NO: 14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 404, 405, 439, 440, 441, 442, 443, 444, 445, 446, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: A241D-S403G-L448W, A241N-S403P-L448W, A241D-S403P-L448W or A241N-S403G-L448W.

In a preferred embodiment, the MDC variant according to the invention showing an improved activity in converting 3-methylcrotonic acid into isobutene is characterized in that contains at least three deletions, substitutions and/or insertions wherein one deletion/insertion/substitution is at position 241 in the amino acid sequence shown in SEQ ID NO: 14 or at a position corresponding to this position, another deletion/insertion/substitution is at position 446 in the amino acid sequence shown in SEQ ID NO:14 or at a position corresponding to this position and another deletion/insertion/substitution is at position 448 in the amino acid sequence shown in SEQ ID NO: 14 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 406, 25, 35, 36, 74, 80, 86, 126, 129, 166, 196, 198, 204, 208, 236, 237, 238, 240, 298, 302, 359, 366, 368, 390, 395, 396, 402, 407, 408, 426, 449, 450, 451, 452, 454, 455, 456, 457, 458, 462, 473, 2, 3, 5, 6, 24, 64, 66, 85, 154, 168, 175, 195, 197, 214, 277, 296, 305, 339, 343, 347, 349, 350, 363, 391, 394, 398, 401, 403, 404, 405, 439, 440, 441, 442, 443, 444, 445, 447, 453, 459, 460, 461, 479 and 496 in the amino acid sequence shown in SEQ ID NO: 14.

Preferably, such a variant has the following substitutions in the amino acid sequence shown in SEQ ID NO:14 or at positions corresponding to these positions: A241N-L446V-L448W.

In other preferred embodiments, the MDC variant according to the invention showing an improved activity in converting 3-methylcrotonic acid into isobutene is characterized in that has multiple mutations. As it is exemplified in the examples further below, variants have been found bearing multiple mutations which exhibit an increase in the reaction rate of the conversion of 3-methylcrotonic acid into isobutene. These variants bearing multiple mutations are summarized in the following: Accordingly, in a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406 and 448 in the amino acid sequence shown in SEQ ID NO:14 or at positions amino acid sequence shown in SEQ ID NO:14 or at positions corresponding to these positions: A241D-C404F-P406A-L448F, A241D-C404F-P406A-L448Y, A241D-C404L-P406A-L448F, A241D-C404L-P406A-L448Y, A241N-C404F-P406A-L448F, A241N-C404F-P406A-L448Y, A241N-C404L-P406A-L448F or A241N-C404L-P406A-L448Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 446 and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: C404M-P406A-L446I-L448W or C404M-P406S-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403R-C404M-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 446, 448, and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: C404M-L446I-L448W-T450A, C404M-L446I-L448W-T450H, C404M-L446I-L448W-T450M, C404M-L446I-L448W-T450N, C404M-L446I-L448W-T450S, C404M-L446N-L448W-T450A or C404M-L446N-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: C404M-P406A-L446N-L448W, C404M-P406S-L446N-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 446, 448, and 450 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: C404M-P406A-L446I-L448W-T450A, C404M-P406S-L446I-L448W-T450A, C404M-P406S-L446I-L448W-T450H, C404M-P406A-L446N-L448W-T450A, C404M-P406A-L446N-L448W-T450H, C404M-P406S-L446N-L448W-T450A, C404M-P406S-L446N-L448W-T450H, C404M-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-C404F-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-C404F-P406A-L448W, A241D-C404F-P406S-L448W, or A241D-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 443 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-C404L-P406A-G443D-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-C404L-P406A-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-C404L-P406A-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-C404M-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 404, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-F401Y-C404F-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 404 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-F401Y-C404F-L448W or A241D-F401Y-C404M-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 404, 406 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-F401Y-C404F-P406A-L448W, A241D-F401Y-C404M-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 403, 404, 446 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-F401Y-S403G-C404F-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 403, 404, and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-F401Y-S403G-C404F-L448W or A241D-F401Y-S403G-C404M-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 403, 404, 446 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-F401Y-S403P-C404F-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 403, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-F401Y-S403P-C404M-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 401, 403, 404 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-F401Y-S403P-C404F-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 404, 406, 446 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-G402A-C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 404, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-G402A-C404L-P406A-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 404, 406 and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A241D-G402A-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 404, 406, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-G402A-C404L-P406A-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-G402A-S403C-C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-G402A-S403C-C404L-P406A-L446V-L448W-T450M or A241D-G402A-S403V-C404L-P406A-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-G402A-S403C-C404L-P406A-L448W or A241D-G402A-S403V-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-G402A-S403C-C404L-P406A-L448W-T450M or A241D-G402A-S403V-C404L-P406A-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A 241 D-G402A-S403V-C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 446 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-S403C-C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406 and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A241D-S403C-C404L-P406A-L448W, A241D-S403G-C404F-P406A-L448W or A241D-S403G-C404M-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403P-C404F-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-S403C-C404L-P406A-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403G-C404F-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403G-C404F-L448W, A241D-S403P-C404F-L448W or A241D-S403P-C404M-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403P-C404F-P406A-L448W, A241D-S403P-C404M-P406A-L448W or A241D-S403V-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 446 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-S403V-C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403V-C404L-P406A-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403V-C404L-P406A-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 405, 406 and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A241N-C404F-L405H-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406 and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A241N-C404F-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 446, and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241N-C404L-P406A-L446C-L448W or A241N-C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241N-C404L-P406A-L448W or A241N-C404M-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 448 and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241N-C404L-P406A-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241N-C404L-P406A-L448W-T450M or A241N-C404L-P406A-L448W-T450Q.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406 and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A241N-S403C-C404L-P406A-L448W, A241N-S403N-C404L-P406A-L448W or A241N-S403V-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: C404L-P406A-L446F-L448W, C404L-P406A-L446S-L448W or C404L-P406A-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: C404L-P406A-L448W-T450M, C404M-P406A-L448W-T450A, C404M-P406S-L448W-T450A, C404M-P406A-L448W-T450H or C404M-P406S-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 444 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: C404L-P406A-P444H-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 85, 241, 404, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: P85L-A241N-C404M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403V-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-G443D-L448W, A241D-S403C-C404L-P406A-G443H-L448W or A241 D-S403C-C404L-P406A-G443N-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-S403C-C404L-P406A-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 444 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-P444A-L448W, A241D-S403C-C404L-P406A-P444H-L448W or A241 D-S403C-C404L-P406A-P444L-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406, 443 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-G402A-S403C-C404L-P406A-G443H-L448W, A241D-G402A-S403C-C404L-P406A-G443S-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-G402A-S403C-C404L-P406A-L446M-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 402, 403, 404, 406, 444 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-G402A-S403C-C404L-P406A-P444F-L448W or A241D-G402A-S403C-C404L-P406A-P444H-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403H-C404L-P406A-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443A-L448W-T450M, A241D-S403C-C404L-P406A-G443F-L448W-T450M, A241D-S403C-C404L-P406A-G443Y-L448W-T450M, A241D-S403V-C404L-P406A-G443A-L448W-T450M, A241D-S403V-C404L-P406A-G443D-L448W-T450M, A241D-S403V-C404L-P406A-G443F-L448W-T450M, A241D-S403V-C404L-P406A-G443N-L448W-T450M or A241D-S403V-C404L-P406A-G443S-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 444, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-P444A-L448W-T450M, A241D-S403C-C404L-P406A-P444F-L448W-T450M and A241D-S403C-C404L-P406A-P444T-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 446 and 448 in the amino acid sequence shown in SEQ ID NO:14 or at positions amino acid sequence shown in SEQ ID NO:14 or at positions corresponding to these positions: A241 D-S403V-C404L-P406A-G443D-L446V-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403V-C404L-P406A-G443D-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 445, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403V-C404L-P406A-V445L-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-C404L-P406A-G443F-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 406, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-C404L-P406A-L446V-L448W-T450A.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443A-L446V-L448W-T450M, A241D-S403C-C404L-P406A-G443S-L446V-L448W-T450M, A241D-S403C-C404L-P406A-G443W-L446V-L448W-T450M, A241D-S403C-C404L-P406A-G443Y-L446V-L448W-T450M, A241D-S403V-C404L-P406A-G443D-L446V-L448W-T450M, A241D-S403V-C404L-P406A-G443F-L446V-L448W-T450M or A241 D-S403V-C404L-P406A-G443Y-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 198, 241, 403, 404, 406, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: H198Q-A241D-S403C-C404L-P406A-G443F-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 444, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-P444H-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-V408I-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-L446M-L448W-T450M, A241D-S403V-C404L-P406A-L446V-L448W-T450H, A241D-S403A-C404L-P406A-L446V-L448W-T450M, A241D-S403G-C404L-P406A-L446V-L448W-T450M, A241D-S403V-C404L-P406A-L446A-L448W-T450M or A241D-S403V-C404L-P406A-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403V-C404L-P406A-V408I-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 443, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: C404M-P406A-G443W-L446I-L448W-T450H, C404M-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 405, 406, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: C404M-L405I-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 404, 406, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: M197V-C404M-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 407, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: C404M-P406A-Q407K-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S403C-C404M-P406A-L446I-L448W-T450H or S403P-C404M-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 405, 406, 448 and 450 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: C404M-L405I-P406A-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 405, 406, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404M-L405I-P406A-G443Y-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 448 and 450 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: S403C-C404M-P406A-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 405, 406, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404M-L405I-P406A-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 404, 405, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-C404M-L405I-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 404, 406, 448 and 450 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: M197V-C404M-P406A-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 405, 406, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S403C-C404M-L405I-P406A-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 405, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: C404M-L405I-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 404, 405, 406, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: M197V-C404M-L405I-P406A-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404M-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 405, 406, 443, 448 and 450 in the amino acid sequence shown in SEQ ID NO: 14 or at positions amino acid sequence shown in SEQ ID NO:14 or at positions corresponding to these positions: S403C-C404M-L405I-P406A-G443Y-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 406, 443, 448 and 450 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: C404M-P406A-G443Y-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404M-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S403C-C404M-P406A-G443Y-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 405, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404M-L405I-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 404, 405, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-C404M-L405I-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 405, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404M-L405I-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 404, 405, 406, 443, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: C404M-L405I-P406A-G443Y-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 405, 406, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404M-L405I-P406A-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-C404M-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 405, 406, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-L405I-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404M-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403 404, 406, 443, 448 and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443D-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 444, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448 and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443D-P444A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-S403C-C404L-P406A-G443Y-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443Y-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 25, 241, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A25E-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 241, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 80, 241, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A80S-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 24, 241, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: E24A-A241D-S403C-C404L-P406A-L448W, E24D-A241D-S403C-C404L-P406A-L448W, E24L-A241D-S403C-C404L-P406A-L448W, or E24V-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 237, 241, 403, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: G237D-A241D-S403C-C404L-P406A-L448W or G237P-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-S403C-C404L-P406A-G443A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 236, 241, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: I236L-A241D-S403C-C404L-P406A-L448W or I236V-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 296, 403, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-I296Q-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 241, 403, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: K214T-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 64, 241, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: N64H-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 448 and 479 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-L448W-P479C or A241D-S403C-C404L-P406A-L448W-P479I or A241D-S403C-C404L-P406A-L448W-P479L or A241D-S403C-C404L-P406A-L448W-P479M or A241D-S403C-C404L-P406A-L448W-P479S or A241D-S403C-C404L-P406A-L448W-P479T or A241D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 448 and 496 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-S403C-C404L-P406A-L448W-R496L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 175, 241, 403, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S175E-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 448 and 473 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-L448W-A473S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 86, 241, 403, 404, 406, and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S86N-A241D-S403C-C404L-P406A-L448W or S86Y-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 240, 241, 403, 404, 406 and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: V240N-A241 D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 240, 241, 403, 404, 406, 448 and 479 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: V240N-A241 D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 214, 237, 241, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-K214T-G237P-A241D-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 237, 241, 296, 403, 404, 406, and 448 in the amino acid sequence shown in SEQ ID NO:14 or at positions amino acid sequence shown in SEQ ID NO:14 or at positions corresponding to these positions: K214T-G237P-A241D-I296Q-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 237, 241, 296, 403, 404, 406, 448 and 479 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: K214T-G237P-A241D-I296Q-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 241, 403, 404, 406, 448 and 496 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: K214T-A241D-S403C-C404L-P406A-L448W-R496L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 240, 241, 403, 404, 406, 448 and 496 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: V240N-A241 D-S403C-C404L-P406A-L448W-R496L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 237, 240, 241, 296, 403, 404, 406 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: K214T-G237P-V240N-A241D-I296Q-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 241, 403, 404, 406, 448 and 479 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A66H-A241D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 214, 237, 240, 241, 403, 404, 406, 448 and 479 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-K214T-G237P-V240N-A241D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 214, 241, 403, 404, 406, 448 and 479 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-K214T-A241D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 237, 241, 296, 403, 404, 406, 448 and 479 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: G237P-A241 D-I296Q-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 214, 237, 241, 403, 404, 406, 448 and 479 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-K214T-G237P-A241 D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 296, 403, 404, 406, 448 and 479 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-I296Q-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 214, 241, 296, 403, 404, 406, and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-K214T-A241D-I296Q-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 241, 403, 404, 406, 443 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: K214T-A241D-S403C-C404L-P406A-G443N-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 241, 296, 403, 404, 406 and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A66H-A241 D-I296Q-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 241, 296, 403, 404, 406 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: K214T-A241D-I296Q-S403C-C404L-P406A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 237, 241, 403, 404, 406, 448 and 479 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: G237P-A241 D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 214, 241, 296, 403, 404, 406, 448 and 479 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-K214T-A241 D-I296Q-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 237, 240, 241, 403, 404, 406, 448 and 479 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-G237P-V240N-A241 D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 237, 241, 403, 404, 406, 448 and 479 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A66H-G237P-A241 D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 241, 296, 403, 404, 406, 448 and 479 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: K214T-A241D-I296Q-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 66, 241, 296, 403, 404, 406, 448 and 479 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: A66H-A241 D-I296Q-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 241, 403, 404, 406, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: K214T-A241D-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 214, 237, 241, 403, 404, 406, 448 and 479 in the amino acid sequence shown in SEQ ID NO:14 or at positions corresponding to these positions. Preferably, such a variant has the following substitutions in the amino acid sequence shown in SEQ ID NO:14 or at positions corresponding to these positions: K214T-G237P-A241D-S403C-C404L-P406A-L448W-P479V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-A241 D-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-V408C-G443F-L448W-T450M or A241D-S403C-C404L-P406A-V408L-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 445, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443F-V445L-L448W-T450M or A241D-S403C-C404L-P406A-G443F-V445S-L448W-T450M or A241D-S403C-C404L-P406A-G443F-V445T-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 445 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443D-V445T-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-A241 D-S403C-C404L-P406A-G443D-P444A-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 405, 406, 443, 448 and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-L405I-P406A-G443D-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: M197V-A241 D-S403C-C404L-P406A-G443D-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 445, 448 and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443D-V445L-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443A-P444H-L448W-L449I or A241D-S403C-C404L-P406A-G443F-P444H-L448W-L449I or A241D-S403C-C404L-P406A-G443L-P444H-L448W-L449I or A241 D-S403C-C404L-P406A-G443S-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-G443D-P444H-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448 and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443D-P444H-L448W-L449V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 404, 405, 406, 443, 446, 448, 449 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-C404L-L405M-P406A-G443F-L446V-L448W-L449M-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403Q-C404L-P406A-G443F-L446V-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 444, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P444H-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 444, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406S-P444H-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 195, 241, 403, 404, 406, 444, 448 and 450 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: L195I-A241 D-S403C-C404L-P406A-P444H-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 444, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-A241 D-S403C-C404L-P406A-P444H-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 407, 444, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-Q407R-P444H-L448W-T450M or A241 D-S403C-C404L-P406A-Q407S-P444H-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 448 and 450 in the amino acid sequence shown in SEQ ID NO: 14 or at positions amino acid sequence shown in SEQ ID NO:14 or at positions corresponding to these positions: A241 D-S403C-C404L-P406A-V408I-P444H-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 195, 241, 403, 404, 406, 408, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: L195I-A241D-S403C-C404L-P406A-V408I-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 408, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-V408I-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 445, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-P444H-V445C-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-G443Y-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448, and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-G443D-P444H-L448W-L449V or M197V-A241D-S403C-C404L-P406A-G443S-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 443, 446, 448, 450 and 455 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-P406A-G443Y-L446I-L448W-T450H-Q455H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403A-C404M-P406A-G443Y-L446I-L448W-T450H or S403I-C404M-P406A-G443Y-L446I-L448W-T450H or S403Q-C404M-P406A-G443Y-L446I-L448W-T450H or S403V-C404M-P406A-G443Y-L446I-L448W-T450H or S403C-C404M-P406G-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 442, 443, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S403C-C404M-P406A-D442A-G443Y-L446I-L448W-T450H or S403C-C404M-P406A-D442E-G443Y-L446I-L448W-T450H or S403C-C404M-P406A-D442G-G443Y-L446I-L448W-T450H or S403C-C404M-P406A-D442S-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 443, 444, 446, 448 and 450 in the amino acid sequence shown in SEQ ID NO:14 or at positions amino acid sequence shown in SEQ ID NO:14 or at positions corresponding to these positions: S403C-C404M-P406A-G443Y-P444H-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 443, 445, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S403C-C404M-P406A-G443Y-V445A-L446I-L448W-T450H or S403C-C404M-P406A-G443Y-V445C-L446I-L448W-T450H or S403C-C404M-P406A-G443Y-V445L-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 443, 446, 448, 450 and 451 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S403C-C404M-P406A-G443Y-L446I-L448W-T450H-C451N or S403C-C404M-P406A-G443Y-L446I-L448W-T450H-C451S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 196, 197, 403, 404, 406, 443, 446, and 448 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: V196I-M197V-S403C-C404M-P406A-G443Y-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 443, 446, and 448 in the amino acid sequence shown in SEQ ID NO:14 or at positions corresponding to these positions. Preferably, such a variant has the following substitutions in the amino acid sequence shown in SEQ ID NO:14 or at positions corresponding to these positions: M197V-S403C-C404M-P406G-G443Y-L446I-L448W or M197V-S403C-C404M-P406S-G443Y-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446 and 448 in the amino acid sequence shown in SEQ ID NO: 14 or at positions amino acid sequence shown in SEQ ID NO:14 or at positions corresponding to these positions: M197V-S403C-C404M-P406A-D442A-G443Y-L446I-L448W or M197V-S403C-C404M-P406A-D442C-G443Y-L446I-L448W or M197V-S403C-C404M-P406A-D442G-G443Y-L446I-L448W or M197V-S403C-C404M-P406A-D442H-G443Y-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 442, 443, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404M-P406A-D442H-G443Y-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446, and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404M-P406A-D442N-G443Y-L446I-L448W or M197V-S403C-C404M-P406A-D442S-G443Y-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 443, 445, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404M-P406A-G443Y-V445S-L446I-L448W or M197V-S403C-C404M-P406A-G443Y-V445T-L446I-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 442, 443, 445, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-D442A-G443Y-V445L-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-P406A-D442A-G443Y-L446I-L448W-T450H or M197V-S403C-C404M-P406A-D442Q-G443Y-L446I-L448W-T450H or M197V-S403C-C404M-P406A-D442N-G443Y-L446I-L448W-T450H or M197V-S403C-C404M-P406A-D442S-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 441, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-E441R-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 442, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-D442L-G443D-P444H-L448W-L449I or A241D-S403C-C404L-P406A-D442R-G443D-P444H-L448W-L449I or A241D-S403C-C404L-P406A-D442M-G443D-P444H-L448W-L449I or A241D-S403C-C404L-P406A-D442A-G443D-P444H-L448W-L449I or A241D-S403C-C404L-P406A-D442S-G443D-P444H-L448W-L449I or A241D-S403C-C404L-P406A-D442G-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 445, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-S403C-C404L-P406A-G443D-P444H-V445T-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 407, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-S403C-C404L-P406A-Q407C-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-G443D-P444H-L448W-L449I-P454A or A241D-S403C-C404L-P406A-G443D-P444H-L448W-L449I-P454W or A241D-S403C-C404L-P406A-G443D-P444H-L448W-L449I-P454V or A241D-S403C-C404L-P406A-G443D-P444H-L448W-L449I-P454M or A241D-S403C-C404L-P406A-G443D-P444H-L448W-L449I-P454H or A241D-S403C-C404L-P406A-G443D-P444H-L448W-L449I-P454T or A241D-S403C-C404L-P406A-G443D-P444H-L448W-L449I-P454G or A241D-S403C-C404L-P406A-G443D-P444H-L448W-L449I-P454K or A241D-S403C-C404L-P406A-G443D-P444H-L448W-L449I-P454R or A241D-S403C-C404L-P406A-G443D-P444H-L448W-L449I-P454Q or A241D-S403C-C404L-P406A-G443D-P444H-L448W-L449I-P454L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449 and 459 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-G443D-P444H-L448W-L449I-A459Y or A241D-S403C-C404L-P406A-G443D-P444H-L448W-L449I-A459N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449 and 460 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-G443D-P444H-L448W-L449I-A460N or A241D-S403C-C404L-P406A-G443D-P444H-L448W-L449I-A460L or A241D-S403C-C404L-P406A-G443D-P444H-L448W-L449I-A460M or A241D-S403C-C404L-P406A-G443D-P444H-L448W-L449I-A460R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449 and 461 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-G443D-P444H-L448W-L449I-R461V or A241D-S403C-C404L-P406A-G443D-P444H-L448W-L449I-R461 S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 154, 241, 339, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: E154D-A241 D-E339H-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 302, 339, 403, 404, 406, 443, 444, 448, and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-L302R-E339H-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 363, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-A363G-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 390, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-R390D-S403C-C404L-P406A-G443D-P444H-L448W-L449I or A241D-E339H-R390L-S403C-C404L-P406A-G443D-P444H-L448W-L449I or A241D-E339H-R390N-S403C-C404L-P406A-G443D-P444H-L448W-L449I or A241D-E339H-R390Q-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 391, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-R391D-S403C-C404L-P406A-G443D-P444H-L448W-L449I or A241D-E339H-R391W-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 394, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-E394Q-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 3, 241, 339, 394, 403, 404, 406, 443, 444, 448 or 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: V3M-A241 D-E339H-E394T-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 398, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-G398R-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 129, 241, 339, 398, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A129V-A241D-E339H-G398C-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 408, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-V408L-G443D-P444H-L448W-L449I or A241D-E339H-S403C-C404L-P406A-V408M-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 441, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-E339H-S403C-C404L-P406A-E441S-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-D442H-G443D-P444H-L448W-L449I or A241D-E339H-S403C-C404L-P406A-D442R-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 168, 241, 339, 403, 404, 406, 443, 444, 445, 448, and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: I168V-A241D-E339H-S403C-C404L-P406A-G443D-P444H-V445L-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 448, 449 and 452 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-G443D-P444H-L448W-L449I-Y452F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 448, 449 and 453 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-G443D-P444H-L448W-L449I-T453L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 448, 449, and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-G443D-P444H-L448W-L449I-P454H or A241D-E339H-S403C-C404L-P406A-G443D-P444H-L448W-L449I-P454K or A241D-E339H-S403C-C404L-P406A-G443D-P444H-L448W-L449I-P454R or A241D-E339H-S403C-C404L-P406A-G443D-P444H-L448W-L449I-P454S or A241D-E339H-S403C-C404L-P406A-G443D-P444H-L448W-L449I-P454T or A241D-E339H-S403C-C404L-P406A-G443D-P444H-L448W-L449I-P454W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 448, 449, 461 and 479 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-G443D-P444H-L448W-L449I-R461V-P479S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 407, 443 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-Q407A-G443N-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 442, 443 and 448 in the amino acid sequence shown in SEQ ID NO: 14 or at positions amino acid sequence shown in SEQ ID NO:14 or at positions corresponding to these positions: A241D-S403C-C404L-P406A-D442A-G443N-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443N-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448 and 453 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443N-L448W-T453R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 446 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443N-L446M-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 441, 443 444, 446, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-E441K-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 237, 241, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-G237A-A241D-S403C-C404L-P406A-G443F-L448W-T450M or M197V-G237D-A241D-S403C-C404L-P406A-G443F-L448W-T450M or M197V-G237N-A241D-S403C-C404L-P406A-G443F-L448W-T450M or M197V-G237P-A241D-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 238, 241, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-D238H-A241D-S403C-C404L-P406A-G443F-L448W-T450M or M197V-D238R-A241D-S403C-C404L-P406A-G443F-L448W-T450M or M197V-D238S-A241D-S403C-C404L-P406A-G443F-L448W-T450M or M197V-D238W-A241D-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 302, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-L302A-S403C-C404L-P406A-G443F-L448W-T450M or M197V-A241D-L302K-S403C-C404L-P406A-G443F-L448W-T450M or M197V-A241D-L302M-S403C-C404L-P406A-G443F-L448W-T450M or M197V-A241D-L302R-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 359, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-A359V-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 398, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-G398R-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 394, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-E394C-S403C-C404L-P406A-G443F-L448W-T450M or M197V-A241D-E394D-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 396, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-V396I-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 35, 197, 241, 403, 404, 406, 407, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: V35I-M197V-A241D-S403C-C404L-P406A-Q407I-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 408, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-V408A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 2, 197, 241, 403, 404, 406, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: Y2N-M197V-A241D-S403C-C404L-P406A-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 439, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-R439C-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 440, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-F440L-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 448, 450 and 460 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-G443F-L448W-T450M-A460F or M197V-A241D-

S403C-C404L-P406A-G443F-L448W-T450M-A460L or M197V-A241D-S403C-C404L-P406A-G443F-L448W-T450M-A460R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 448, 450 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-G443F-L448W-T450M-P454T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 448, 450 and 462 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-G443F-L448W-T450M-A462V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448 and 450 in the amino acid sequence shown in SEQ ID NO: 14 or at positions amino acid sequence shown in SEQ ID NO:14 or at positions corresponding to these positions: S403C-C404M-P406G-Q407T-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 5, 197, 403, 404, 406, 442, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M5I-M197V-S403C-C404M-P406G-D442N-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448, 449 and 459 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-G443D-P444H-L448W-L449V-A459D.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 449 and 459 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443D-L448W-L449I-A459G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448, 450 and 459 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-L446I-L448W-T450H-A459G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 443, 446, 448, 450 and 459 in the amino acid sequence shown in SEQ ID NO:14 or at positions corresponding to these positions. Preferably, such a variant has the following substitutions in the amino acid sequence shown in SEQ ID NO:14 or at positions corresponding to these positions: S403C-C404M-P406A-G443Y-L446I-L448W-T450H-A459G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 449 and 459 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443D-L448W-L449I-A459R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 450 and 460 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443Y-L448W-T450M-A460E.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448, 450 and 460 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-P444H-L446M-L448W-T450M-A460G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448, 449, 460 and 462 in the amino acid sequence shown in SEQ ID NO:14 or at positions corresponding to these positions. Preferably, such a variant has the following substitutions in the amino acid sequence shown in SEQ ID NO:14 or at positions corresponding to these positions: M197V-A241D-S403C-C404L-P406A-G443D-P444H-L448W-L449V-A460G-A462V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 450 and 460 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443Y-L448W-T450M-A460L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448, 450 and 460 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-L446I-L448W-T450H-A460L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448, 450 and 460 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-P444H-L446M-L448W-T450M-A460Q.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 450 and 462 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443Y-L448W-T450M-A462C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446, 448, 450 and 462 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-P406A-D442N-G443Y-L446I-L448W-T450H-A462C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 450 and 462 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241 D-S403C-C404L-P406A-G443Y-L448W-T450M-A462V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448, 450 and 462 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-L4461-L448W-T450H-A462V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448, 450, 454 and 462 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-L446I-L448W-T450H-P454Q-A462V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 198, 403, 404, 406, 407, 443, 446, 448, and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: H198W-S403V-C404M-P406A-Q407T-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 74, 198, 403, 404, 406, 407, 443, 446, 448, and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: L74V-H198W-S403V-C404M-P406A-Q407T-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 198, 403, 404, 406, 442, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: H198W-S403C-C404M-P406A-D442Q-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 441, 443, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-E441G-G443D-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 208, 241, 403, 404, 406, 408, 443, 444, 446, 448 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: Q208L-A241D-S403C-C404L-P406A-V408I-G443R-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 443, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-G443W-P444H-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 449 and 458 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-G443D-L448W-L449I-H458G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 195, 403, 404, 406, 407, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: L195V-S403C-C404M-P406A-Q407T-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 195, 403, 404, 406, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: L195V-S403C-C404M-P406A-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-A241 D-S403C-C404L-P406A-G443Y-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 407, 443, 446, 448, and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-P406A-Q407T-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446, 448, 450 and 456 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-P406A-D442N-G443Y-L446I-L448W-T450H-E456Q.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404F-P406A-Q407T-G443Y-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-P444F-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 449 and 454 in the amino acid sequence shown in SEQ ID NO: 14 or at positions amino acid sequence shown in SEQ ID NO:14 or at positions corresponding to these positions: A241 D-S403C-C404L-P406A-G443D-L448W-L449I-P454K.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-G443D-P444H-L448W-L449V-P454K.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 449 and 454 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443D-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-G443D-P444H-L448W-L449V-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403 404, 406, 443, 448, 449 and 455 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-S403C-C404L-P406A-G443D-L448W-L449I-Q455S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446, 448, 450 and 455 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-P406A-D442N-G443Y-L446I-L448W-T450H-Q455V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448, 450 and 457 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-L446I-L448W-T450H-R457K.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446, 448, 450, and 461 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404M-P406A-D442N-G443Y-L446I-L448W-T450H-R461G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448, 450, and 461 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-P444H-L446M-L448W-T450M-R461S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448, 449 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-G443D-P444H-L448W-L449V-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 448, 449 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406A-G443D-L448W-L449I-T450V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444, 448, 449 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-G443D-P444H-L448W-L449V-T450V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 36, 197, 403, 404, 406, 442, 443, 446, 448, 450 and 453 in the amino acid sequence shown in SEQ ID NO:14 or at positions corresponding to these positions. Preferably, such a variant has the following substitutions in the amino acid sequence shown in SEQ ID NO:14 or at positions corresponding to these positions: H36Y-M197V-S403C-C404M-P406A-D442N-G443Y-L446I-L448W-T450H-T453G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448, 450 and 453 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-L446I-L448W-T450H-T453N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 198, 403, 404, 406, 443, 446, 448, 450 and 453 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: H198W-S403C-C404M-P406A-G443Y-L446I-L448W-T450H-T453P.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448, 450 and 453 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-P444H-L446M-L448W-T450M-T453R or A241D-S403C-C404L-P406A-V408I-P444H-L446M-L448W-T450M-T453 S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 445, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404M-P406A-Q407T-G443Y-V445L-L446I-L448W-T450H or S403C-C404M-P406A-Q407T-G443Y-V445S-L446I-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 444 and 448 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-A241 D-S403C-C404L-P406A-G443D-P444H-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448, 450 and 452 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-V408I-P444H-L446M-L448W-T450M-Y452F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 5, 241, 403, 404, 406, 443, 448 and 450 in the amino acid sequence shown in SEQ ID NO: 14 or at positions corresponding to these positions. Preferably, such a variant has the following substitutions in the amino acid sequence shown in SEQ ID NO: 14 or at positions corresponding to these positions: M5I-A241 D-S403C-C404L-P406A-G443Y-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241D-S403C-C404L-P406A-G443F-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-S403C-C404L-P406A-D442N-G443Y-L446M-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 403, 404, 406, 442, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: M197V-S403C-C404L-P406A-D442N-G443Y-L448W-T450M or M197V-S403C-C404L-P406A-D442N-G443Y-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404L-P406A-Q407T-G443Y-L446M-L448W-T450H or S403C-C404L-P406A-Q407T-G443Y-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404L-P406A-Q407T-G443Y-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 343, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-A343S-S403C-C404L-P406A-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 350, 403, 404, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-A350S-S403C-C404L-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 395, 403, 404, 406, 426, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-A395E-S403C-C404L-P406A-A426V-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-P454R or A241D-E339H-S403C-C404L-P406A-D442S-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442T-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-G443H-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 441, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241 D-E339H-S403C-C404L-P406A-E441R-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 347, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-I347C-S403C-C404L-P406A-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 3, 241, 302, 339, 403, 404, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: V3L-A241D-L302Q-E339H-S403C-C404L-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 405, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-L405T-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 5, 241, 339, 403, 404, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: M5I-A241D-E339H-S403C-C404L-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 443, 444, 448, 449, 454 and 455 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-G443D-P444H-L448W-L449I-P454R-Q455A or A241D-E339H-S403C-C404L-P406A-G443D-P444H-L448W-L449I-P454R-Q455N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449, 454 and 459 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-G443D-P444H-L448W-L449I-P454R-A459E or A241D-S403C-C404L-P406A-G443D-P444H-L448W-L449I-P454R-A459M or A241D-S403C-C404L-P406A-G443D-P444H-L448W-L449I-P454R-A459Q or A241D-S403C-C404L-P406A-G443D-P444H-L448W-L449I-P454R-A459T.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-G443N-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 441, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-S403C-C404L-P406A-E441 G-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-S403C-C404L-P406A-G443D-P444F-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449, 454 and 458 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-

G443D-P444H-L448W-L449I-P454R-H458F or A241D-S403C-C404L-P406A-G443D-P444H-L448W-L449I-P454R-H458N.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 296, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-I296Q-S403C-C404L-P406A-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 302, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-L302A-S403C-C404L-P406A-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448, 449, 453 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-S403C-C404L-P406A-G443D-P444H-L448W-L449I-T453S-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 196, 241, 403, 404, 406, 443, 444, 448, 449 and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: V196I-A241D-S403C-C404L-P406A-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 305, 403, 404, 406, 443, 444, 448, 449, and 454 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-V305I-S403C-C404L-P406A-G443D-P444H-L448W-L449I-P454R or A241D-V305T-S403C-C404L-P406A-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 237, 241, 403, 404, 406, 441, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-G237A-A241D-S403C-C404L-P406A-E441G-G443F-L448W-T450M or M197V-G237A-A241D-S403C-C404L-P406A-E441H-G443F-L448W-T450M or M197V-G237A-A241D-S403C-C404L-P406A-E441T-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 440, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-F440L-G443F-L446M-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 277, 403, 404, 406, 440, 443, 448, 449 and 450 in the amino acid sequence shown in SEQ ID NO:14 or at positions corresponding to these positions. Preferably, such a variant has the following substitutions in the amino acid sequence shown in SEQ ID NO:14 or at positions corresponding to these positions: M197V-A241D-H277Y-S403C-C404L-P406A-F440L-G443F-L448W-L449I-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 237, 241, 403, 404, 406, 443, 444, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-G237A-A241D-S403C-C404L-P406A-G443F-P444H-L448W-T450M or M197V-G237A-A241 D-S403C-C404L-P406A-G443F-P444I-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 241, 403, 404, 406, 407, 440, 443, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-A241 D-S403C-C404L-P406A-Q407R-F440L-G443F-L448W-T450M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 6, 197, 238, 241, 403, 404, 406, 443, 448, 450 and 453 in the amino acid sequence shown in SEQ ID NO:14 or at positions corresponding to these positions. Preferably, such a variant has the following substitutions in the amino acid sequence shown in SEQ ID NO:14 or at positions corresponding to these positions: V6M-M197V-D238H-A241D-S403C-C404L-P406A-G443F-L448W-T450M-T453C.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 238, 241, 403, 404, 406, 443, 448, 450 and 453 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-D238H-A241D-S403C-C404L-P406A-G443F-L448W-T450M-T453R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 197, 238, 241, 403, 404, 406, 443, 448, 450 and 452 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M197V-D238H-A241D-S403C-C404L-P406A-G443F-L448W-T450M-Y452F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 444, 446, 448, 450 and 452 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241 D-S403C-C404L-P406A-P444H-L446M-L448W-T450M-Y452F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448, 450, 452 and 455 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-V408I-P444H-L446M-L448W-T450M-Y452F-Q455H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 447, 448, 450 and 460 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-V408I-P444H-L446M-P447Q-L448W-T450M-A460G.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 408, 444, 446, 448, 450, 455 and 461 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-S403C-C404L-P406A-V408I-P444H-L446M-L448W-T450M-Q455K-R461S or A241D-S403C-C404L-P406A-V408I-P444H-L446M-L448W-T450M-Q455V-R461S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 204, 403, 404, 406, 407, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: Q204R-S403C-C404L-P406A-Q407T-G443Y-L446F-L448W-T450H or Q204S-S403C-C404L-P406A-Q407T-G443Y-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 302, 403, 404, 406, 407, 443, 446, 448, and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: L302F-S403C-C404L-P406A-Q407T-G443Y-L446F-L448W-T450H or L302S-S403C-C404L-P406A-Q407T-G443Y-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 349, 403, 404, 406, 407, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: E349S-S403C-C404L-P406A-Q407T-G443Y-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 395, 403, 404, 406, 407, 443, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A395C-S403C-C404L-P406A-Q407T-G443Y-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 441, 443, 446, 448, and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404L-P406A-Q407T-E441P-G443Y-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448 and 450 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: S403C-C404L-P406A-Q407T-G443A-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 444, 446, 448 and 450 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404L-P406A-Q407T-G443Y-P444Q-L446F-L448W-T450H.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 403, 404, 406, 407, 443, 446, 448, 450 and 458 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: S403C-C404L-P406A-Q407T-G443Y-L446F-L448W-T450H-H458L or S403C-C404L-P406A-Q407T-G443Y-L446F-L448W-T450H-H458M.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 366, 403, 404, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-H366F-S403C-C404L-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 366, 403, 404, 406, 443, 444, 446 and 448 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-H366F-S403C-C404L-P406A-G443D-P444H-L446M-L448W.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 366, 403, 404, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-H366I-S403C-C404L-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 368, 403, 404, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-L368I-S403C-C404L-P406A-G443D-P444H-L446M-L448W-L449I or A241D-E339H-L368M-S403C-C404L-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 368, 403, 404, 405, 406, 443, 444, 446, 448 and 449 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-L368M-S403C-C404L-L405M-P406A-G443D-P444H-L446M-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 395, 403, 404, 406, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-A395V-S403C-C404L-P406A-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449, 454 and 460 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-P454R-A460F.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 349, 403, 404, 406, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-E349M-S403C-C404L-P406A-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 441, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-E441H-D442N-G443D-P444H-L448W-L449I-P454R or A241D-E339H-S403C-C404L-P406A-E441N-D442N-G443D-P444H-L448W-L449I-P454R or A241D-E339H-S403C-C404L-P406A-E441R-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 126, 241, 339, 403, 404, 406, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A126V-A241D-E339H-S403C-C404L-P406A-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449, 454 and 458 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-P454R-H458E or A241D-E339H-S403C-C404L-P406A-D442N-G443D-P444H-L448W-L449I-P454R-H458G or A241D-E339H-S403C-C404L-P406A-D442N-G443D-P444H-L448W-L449I-P454R-H458L or A241D-E339H-S403C-C404L-P406A-D442N-G443D-P444H-L448W-L449I-P454R-H458Q or A241D-E339H-S403C-C404L-P406A-D442N-G443D-P444H-L448W-L449I-P454R-H458R or A241D-E339H-S403C-C404L-P406A-D442N-G443D-P444H-L448W-L449I-P454R-H458S or A241D-E339H-S403C-C404L-P406A-D442N-G443D-P444H-L448W-L449I-P454R-H458Y.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449V-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 302, 339, 403, 404, 406, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-L302C-E339H-S403C-C404L-P406A-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 405, 406, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-L405V-P406A-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 407, 442, 443, 444, 448, 449 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-Q407R-D442N-G443D-P444H-L448W-L449I-P454R or A241D-E339H-S403C-C404L-P406A-Q407S-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449, 454 and 455 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-P454R-Q455E.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 36, 241, 298, 339, 403, 404, 406, 442, 443, 444, 448, 449 and 454 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: H36Y-A241D-R298S-E339H-S403C-C404L-P406A-D442N-G443D-P444H-L448W-L449I-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449, and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-P454A or A241D-E339H-S403C-C404L-P406A-D442N-G443D-P444H-L448W-L449I-P454D or A241D-E339H-S403C-C404L-P406A-D442N-G443D-P444H-L448W-L449I-P454L.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: A241D-E339H-S403C-C404L-P406A-D442N-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449, and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-P454S.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449, 454 and 461 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-P454R-R461A or A241 D-E339H-S403C-C404L-P406A-D442N-G443D-P444H-L448W-L449I-P454R-R461L or A241D-E339H-S403C-C404L-P406A-D442N-G443D-P444H-L448W-L449I-P454R-R461M or A241 D-E339H-S403C-C404L-P406A-D442N-G443D-P444H-L448W-L449I-P454R-R461Q or A241 D-E339H-S403C-C404L-P406A-D442N-G443D-P444H-L448W-L449I-P454R-R461S or A241 D-E339H-S403C-C404L-P406A-D442N-G443D-P444H-L448W-L449I-P454R-R461V.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 339, 403, 404, 406, 442, 443, 444, 448, 449, 450 and 454 in the amino acid sequence shown in SEQ ID NO:14 or at positions corresponding to these positions. Preferably, such a variant has the following substitutions in the amino acid sequence shown in SEQ ID NO:14 or at positions corresponding to these positions: A241D-E339H-S403C-C404L-P406A-D442N-G443D-P444H-L448W-L449I-T450S-P454R.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 241, 403, 404, 406, 443, 444, 448 and 449 in the amino acid sequence shown in SEQ ID NO: 14 or at positions corresponding to these positions. Preferably, such a variant has the following substitutions in the amino acid sequence shown in SEQ ID NO:14 or at positions corresponding to these positions: A241D-S403C-C404L-P406S-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 5, 241, 403, 404, 406, 443, 444, 448 and 449 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: M5I-A241D-S403C-C404L-P406A-G443D-P444H-L448W-L449I.

In a preferred embodiment, the MDC variant according to the invention showing an improved activity in converting 3-methylcrotonic acid into isobutene is characterized in that it comprises deletions, substitutions and/or insertions wherein the deletions/insertions/substitutions are at positions 166, 241, 403, 404, 406, 443, 444, 448, 449 and 452 in the amino acid sequence shown in SEQ ID NO:14 or at positions corresponding to these positions. Preferably, such a variant has the following substitutions in the amino acid sequence shown in SEQ ID NO: 14 or at positions corresponding to these positions: V166D-A241D-S403C-C404L-P406A-G443D-P444H-L448W-L449I-Y452F.

Preferably, any of the above described variants having multiple mutations further has one or more substitutions, deletions and/or insertions in comparison to the corresponding sequence from which it is derived and wherein these substitutions, deletions and/or insertions occur at one or more of the positions corresponding to positions 448, 2, 3, 5, 6, 24, 25, 35, 36, 64, 74, 80, 85, 86, 126, 129, 154, 166, 175, 195, 196, 197, 198, 204, 208, 214, 236, 237, 238, 240, 277, 298, 302, 339, 343, 347, 350, 359, 366, 368, 390, 391, 394, 395, 396, 398, 401, 402, 403, 404, 405, 406, 407, 408, 426, 439, 440, 441, 442, 444, 446, 447, 449, 450, 451, 452, 453, 454, 455, 456, 457, 458, 459, 460, 461, 462, 473, 66, 168, 241, 296, 305, 349, 363, 443, 445, 479, and 496 in the amino acid sequence shown in SEQ ID NO:14.

The second part of the present invention also relates to a method for providing a variant of an MDC wherein said variant shows an improved activity of converting 3-methylcrotonic acid into isobutene, said method comprising the step of effecting one or more changes in the sequence of the MDC wherein said change(s) is/are effected at one or more amino acid positions selected from the group consisting of the amino acid positions corresponding to positions 448, 2, 3, 5, 6, 24, 25, 35, 36, 64, 74, 80, 85, 86, 126, 129, 154, 166, 175, 195, 196, 197, 198, 204, 208, 214, 236, 237, 238, 240, 277, 298, 302, 339, 343, 347, 350, 359, 366, 368, 390, 391, 394, 395, 396, 398, 401, 402, 403, 404, 405, 406, 407, 408, 426, 439, 440, 441, 442, 444, 446, 447, 449, 450, 451, 452, 453, 454, 455, 456, 457, 458, 459, 460, 461, 462, 473, 66, 168, 241, 296, 305, 349, 363, 443, 445, 479, and 496 in the amino acid sequence shown in SEQ ID NO: 14. "Corresponding to" means corresponding to any of these positions in a related sequence.

As regards the preferred embodiments of an MDC to be mutated according to such a method, the same applies as has been set forth herein-above.

In one preferred embodiment the MDC from which the MDC variant is derived is an MDC which shows the amino acid sequence as shown in SEQ ID NO: 14 or an amino acid sequence having at least 63%, 64%, 70%, 74%, 77%, 78%, 80%, 90%, 94% or 97% sequence identity to SEQ ID NO: 14 or any of the preferred degrees of sequence identity as specified herein above.

Moreover, as regards preferred embodiments of the degree of improvement in activity and the changes to be effected, the same applies as described herein above.

The change(s) which is/are effected at any of the above position(s) is/are substitution(s), deletion(s) and/or insertion(s) as defined herein above.

An MDC variant of the second part of the present invention can be fused to a homologous or heterologous polypeptide or protein, an enzyme, a substrate or a tag to form a fusion protein. Fusion proteins in accordance with the present invention will have the same improved activity as the MDC variant of the present invention. Polypeptides, enzymes, substrates or tags that can be added to another protein are known in the art. They may useful for purifying or detecting the proteins of the invention. For instance, tags that can be used for detection and/or purification are e.g. FLAG-tag, His6-tag or a Strep-tag. Alternatively, the protein of the invention can be fused to an enzyme e.g. luciferase, for the detection or localisation of said protein. Other fusion partners include, but are not limited to, bacterial β-galactosidase, trpE, Protein A, β-lactamase, alpha amylase, alcohol dehydrogenase or yeast alpha mating factor. It is also conceivable that the polypeptide, enzyme, substrate or tag is removed from the protein of the invention after e.g. purification. Fusion proteins can typically be made by either recombinant nucleic acid methods or by synthetic polypeptide methods known in art.

The second part of the present invention further relates to a nucleic acid molecule encoding an MDC variant of the present invention and to a vector comprising said nucleic acid molecules. Vectors that can be used in accordance with the present invention are known in the art. The vectors can further comprise expression control sequences operably linked to the nucleic acid molecules of the present invention contained in the vectors. These expression control sequences may be suited to ensure transcription and synthesis of a translatable RNA in bacteria or fungi. Expression control sequences can for instance be promoters. Promoters for use in connection with the nucleic acid molecules of the present invention may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

Preferably, the vector of the present invention is an expression vector. Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), lp1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-1-D-thiogalactopyranoside) (deBoer et al., Proc. Natl. Acad. Sci. USA 80 (1983), 21-25). Termination signals for transcription are also described in the literature.

In addition, the second part of the present invention relates to a host cell comprising the nucleic acid molecule or the vector of the present invention.

In a preferred embodiment, the host cell according to the presenting invention is a microorganism, in particular a bacterium or a fungus. In a more preferred embodiment, the host cell of the present invention is E. coli, a bacterium of the genus Clostridium or a yeast cell, such as S. cerevisiae. In another preferred embodiment the host cell is a plant cell or a non-human animal cell.

The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

As mentioned above, the enzymatic conversion of 3-methylcrotonic acid into isobutene utilizing an MDC is preferably performed in the presence of an FMN prenyl transferase and relies on a reaction of two consecutive steps catalyzed by the two enzymes, i.e., the MDC (catalyzing the actual decarboxylation of 3-methylcrotonic acid into isobutene) with an FMN prenyl transferase which provides the modified flavin cofactor. The flavin cofactor may preferably be FMN or FAD. FMN (flavin mononucleotide; also termed riboflavin-5'-phosphate) is a biomolecule produced from riboflavin (vitamin B2) by the enzyme riboflavin kinase and functions as prosthetic group of various reactions. FAD (flavin adenine dinucleotide) is a redox cofactor, more specifically a prosthetic group, involved in several important reactions in metabolism. Thus, in a preferred embodiment, when producing isobutene from 3-methylcrotonic acid comprising the step of incubating an MDC variant of the invention with 3-methylcrotonic acid an FMN prenyl transferase is present which, in a first step, modifies a flavin cofactor (FMN or FAD) into a (modified) flavin-derived cofactor. FMN prenyl transferase prenylates the flavin ring of the flavin cofactor (FMN or FAD) into a (modified) prenylated flavin cofactor. This reaction is schematically illustrated in FIG. 1A.

In a second step, the actual conversion of 3-methylcrotonic acid into isobutene is catalyzed by said MDC variant via a 1,3-dipolar cycloaddition based mechanism wherein said FMN-dependent decarboxylase uses the prenylated flavin cofactor (FMN or FAD) provided by the associated FMN prenyl transferase. This reaction is schematically illustrated in FIG. 1B.

Thus, preferably, the host cell of the present invention is a cell which expresses an FMN prenyl transferase capable of modifying a flavin cofactor (FMN or FAD) into a (modified) flavin-derived cofactor. In a preferred embodiment, the host cell is a cell which naturally (endogenously) expresses an FMN prenyl transferase. In another preferred embodiment, the host cell is a cell which recombinantly expresses an FMN prenyl transferase by, e.g., introducing a nucleic acid molecule encoding an FMN prenyl transferase or a vector comprising such a nucleic acid molecule.

In a preferred embodiment, said FMN prenyl transferase which modifies the flavin cofactor (FMN or FAD) into a (modified) flavin-derived cofactor is a phenylacrylic acid decarboxylase (PAD)-type protein, or the closely related prokaryotic enzyme UbiX, an enzyme which is involved in ubiquinone biosynthesis in prokaryotes.

In *Escherichia coli*, the protein UbiX (also termed 3-octaprenyl-4-hydroxybenzoate carboxy-lyase) has been shown to be involved in the third step of ubiquinone biosynthesis.

It catalyses the reaction 3-octaprenyl-4-hydroxybenzoate $\rightleftharpoons$ 2-octaprenylphenol+$CO_2$.

Thus, in a preferred embodiment, the modification of a flavin cofactor (FMN or FAD) into the corresponding (modified) flavin-derived cofactor is catalyzed by the FMN-containing protein phenylacrylic acid decarboxylase (PAD). The enzymes involved in the modification of the flavin cofactor (FMN or FAD) into the corresponding modified flavin-derived cofactor were initially annotated as decarboxylases (EC 4.1.1.-). Some phenylacrylic acid decarboxylases (PAD) are now annotated as flavin prenyl transferases as EC 2.5.1.-.

In a more preferred embodiment, the conversion of 3-methylcrotonic acid into isobutene makes use of a phenylacrylic acid decarboxylase (PAD)-type protein as the FMN prenyl transferase which modifies a flavin cofactor (FMN or FAD) into the corresponding (modified) flavin-derived cofactor wherein said phenylacrylic acid decarboxylase (PAD)-type protein is derived from *Candida albicans* (Uniprot accession number Q5A8L8), *Aspergillus niger* (Uniprot accession number A3F715), *Saccharomyces cerevisiae* (Uniprot accession number P33751) or *Cryptococcus gattii* (Uniprot accession number E6R9Z0).

In a preferred embodiment, the phenylacrylic acid decarboxylase (PAD)-type protein employed in the method of the present invention is a phenylacrylic acid decarboxylase (PAD)-type protein derived from *Candida albicans* (Uniprot accession number Q5A8L8; SEQ ID NO:3), *Aspergillus niger* (Uniprot accession number A3F715; SEQ ID NO:4), *Saccharomyces cerevisiae* (Uniprot accession number P33751; SEQ ID NO:5) or *Cryptococcus gattii* (Uniprot accession number E6R9Z0; SEQ ID NO:6) having the amino acid sequence as shown in SEQ ID NO:3, SEQ ID NO:4, SEQ ID NO:5 and SEQ ID NO:6, respectively.

In a preferred embodiment of the present invention the phenylacrylic acid decarboxylase (PAD)-type protein is an enzyme comprising an amino acid sequence selected from the group consisting of SEQ ID NOs: 3 to 6 or a sequence which is at least n % identical to any of SEQ ID NOs: 3 to 6 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor. As regards the determination of sequence identity, the same applies as has been set forth above.

In another preferred embodiment, the modification of a flavin cofactor (FMN or FAD) into the corresponding (modified) flavin-derived cofactor is catalyzed by the FMN-containing protein 3-octaprenyl-4-hydroxybenzoate carboxy-lyase also termed UbiX (initially annotated EC 4.1.1.-). As mentioned above, the enzymes involved in the modification of the flavin cofactor (FMN or FAD) into the corresponding modified flavin-derived cofactor were initially annotated as decarboxylases. Some phenylacrylic acid decarboxylases (PAD) are now annotated as flavin prenyl transferases as EC 2.5.1.-.

In a more preferred embodiment, the conversion of 3-methylcrotonic acid into isobutene makes use of a 3-octaprenyl-4-hydroxybenzoate carboxy-lyase (also termed UbiX) as the FMN prenyl transferase which modifies the flavin cofactor (FMN or FAD) into the corresponding (modified) flavin-derived cofactor wherein said 3-octaprenyl-4-hydroxybenzoate carboxy-lyase (also termed UbiX) is derived from *Escherichia coli* (Uniprot accession number P0AG03), *Bacillus subtilis* (Uniprot accession, number A0A086WXG4), *Pseudomonas aeruginosa* (Uniprot accession number A0A072ZCW8) or *Enterobacter* sp. DC4 (Uniprot accession number W7P6B1).

In an even more preferred embodiment, the 3-octaprenyl-4-hydroxybenzoate carboxy-lyase (also termed UbiX) employed in the method of the present invention is a 3-octaprenyl-4-hydroxybenzoate carboxy-lyase (also termed UbiX) derived from *Escherichia coli* (Uniprot accession number P0AG03; SEQ ID NO:2), *Bacillus subtilis* (Uniprot accession, number A0A086WXG4; SEQ ID NO:7), *Pseudomonas aeruginosa* (Uniprot accession number A0A072ZCW8; SEQ ID NO:8) or *Enterobacter* sp. DC4 (Uniprot accession number W7P6B1; SEQ ID NO:9) having the amino acid sequence as shown in SEQ ID NO:2, SEQ ID NO:7, SEQ ID NO:8 and SEQ ID NO:9, respectively.

In a preferred embodiment of the present invention the 3-octaprenyl-4-hydroxybenzoate carboxy-lyase is an enzyme comprising an amino acid sequence selected from the group consisting of SEQ ID NOs: 2 and 7 to 9 or a sequence which is at least n % identical to any of SEQ ID NOs: 2 and 7 to 9 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor. As regards the determination of the sequence identity, the same applies as has been set forth above.

The second part of the present invention also relates to a method for producing isobutene from 3-methylcrotonic acid comprising the step of incubating an MDC variant of the invention with 3-methylcrotonic acid under conditions allowing said conversion (preferably further in the presence of an FMN prenyl transferase as described above) or comprising the step of culturing a host cell of the present invention expressing an MDC variant (and preferably further expressing an FMN prenyl transferase as described above) in a suitable medium and recovering the produced isobutene.

It is also conceivable in this context that in such a method not only one enzyme according to the present invention is employed but a combination of two or more enzymes.

The second part of the present invention also relates to the use of an MDC variant or a host cell of the present invention as described above for the conversion of 3-methylcrotonic acid into isobutene, preferably in the presence of an FMN prenyl transferase or in the presence of a host co-expressing an FMN prenyl transferase as described herein above. Moreover, in a further embodiment, the present invention relates to a method for producing isobutene from 3-methylcrotonic acid by bringing 3-methylcrotonic acid into contact with the MDC variant of the present invention, preferably in the presence of an FMN prenyl transferase, or with a host cell comprising a nucleic acid molecule encoding the MDC variant of the present invention, wherein said host cell preferably expresses an FMN prenyl transferase. Thus, in a preferred embodiment, the present invention relates to a method for converting 3-methylcrotonic acid into isobutene comprising the steps of: (i) culturing the above-described host cell of the invention in a suitable medium; and (ii) achieving the production of isobutene from 3-methylcrotonic acid.

Thus, in a preferred embodiment, the present invention relates to methods and uses utilizing a host cell of the present invention which expresses an MDC variant of the present invention and, preferably, further expressing an FMN prenyl transferase as described herein above.

In another preferred embodiment, such a host cell is an organism which is capable of producing 3-methylcrotonic acid.

In another preferred embodiment, the method according to the invention is carried out in culture, in the presence of an organism, preferably a microorganism, producing an enzyme variant of the present invention and, preferably, also producing an FMN prenyl transferase. In such an embodiment of the invention, an organism, preferably a microorganism, that produces an enzyme of the present invention and, preferably, also producing an FMN prenyl transferase, is used. In a preferred embodiment, the (micro)organism is recombinant in that the enzyme produced by the host is heterologous relative to the production host. The method can thus be carried out directly in the culture medium, without the need to separate or purify the enzymes. In an especially advantageous manner, a (micro)organism is used having the natural or artificial property of endogenously producing 3-methylcrotonic acid so as to produce isobutene directly from the substrate already present in the culture in solution.

In connection with the above described methods and uses, the microorganisms are cultivated under suitable culture conditions allowing the occurrence of the enzymatic reaction of the MDC variants of the present invention (and, preferably, also the FMN prenyl transferases as described above). The specific culture conditions depend on the specific microorganism employed but are well known to the person skilled in the art. The culture conditions are generally chosen in such a manner that they allow the expression of the genes encoding the MDC variant of the present invention (and, preferably, also an FMN prenyl transferase as described above). Various methods are known to the person skilled in the art in order to improve and fine-tune the expression of certain genes at certain stages of the culture such as induction of gene expression by chemical inducers or by a temperature shift.

In another embodiment, the above described methods of the invention comprise the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art.

A bioreactor or a fermenter refers to any manufactured or engineered device or system known in the art that supports a biologically active environment. Thus, a bioreactor or a fermenter may be a vessel in which a chemical/biochemical process like the method of the present invention is carried out which involves organisms, preferably microorganisms and/or biochemically active substances, i.e., the enzyme(s) described above derived from such organisms or organisms harbouring the above described enzyme(s). In a bioreactor or a fermenter, this process can either be aerobic or anaerobic. These bioreactors are commonly cylindrical, and may range in size from litres to hundreds of cubic meters, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

In yet a further embodiment, the method according to the invention can be carried out in vitro, e.g. in the presence of isolated enzyme or of cell lysates comprising the enzyme or partially purified enzyme preparations comprising the MDC variant of the present invention (and, preferably, also an FMN prenyl transferase as described above). In vitro preferably means in a cell-free system.

In one embodiment, the enzyme(s) employed in the method is (are) used in purified form. However, such a method may be costly, since enzyme and substrate production and purification costs are high.

Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

In an in vitro reaction the enzymes, native or recombinant, purified or not, are incubated in the presence of the substrate in physicochemical conditions allowing the enzymes to be active, and the incubation is allowed to proceed for a sufficient period of time allowing production of the desired product as described above. At the end of the incubation, one optionally measures the presence of isobutene by using any detection system known to one of skill in the art such as gas chromatography or colorimetric tests for measuring the formation of isobutene.

In a particularly preferred embodiment of the invention the method is carried out in vitro and the enzyme is immobilized. Means and methods for immobilizing enzymes on different supports are well-known to the person skilled in the art.

The method according to the invention furthermore comprises the step of collecting gaseous products, i.e. isobutene, degassing out of the reaction, i.e. recovering the product which degasses, e.g., out of the culture. Thus, in a preferred embodiment, the method is carried out in the presence of a system for collecting isobutene under gaseous form during the reaction.

As a matter of fact, isobutene adopts the gaseous state at room temperature and atmospheric pressure. Moreover, isobutene also adopts the gaseous state under culture conditions at 37° C. The method according to the invention therefore does not require extraction of isobutene from the liquid culture medium, a step which is always very costly when performed at industrial scale. The evacuation and storage of gaseous hydrocarbons, in particular of isobutene, and their possible subsequent physical separation and chemical conversion can be performed according to any method known to one of skill in the art.

Finally, the second part of the present invention relates to a composition comprising a variant of an MDC of the present invention, a nucleic acid molecule of the present invention, a vector of the present invention or a host cell of the present invention. As regards the variant of an MDC, the nucleic acid molecule, the vector or the host cell, the same applies as has been set forth above in connection with the methods according to the present invention.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

FIG. 1A: shows a schematic reaction of the enzymatic prenylation of a flavin mononucleotide (FMN) into the corresponding modified (prenylated) flavin cofactor.

FIG. 1B: Schematic reaction of the enzymatic conversion of 3-methylcrotonic acid into isobutene.

Figure 2:
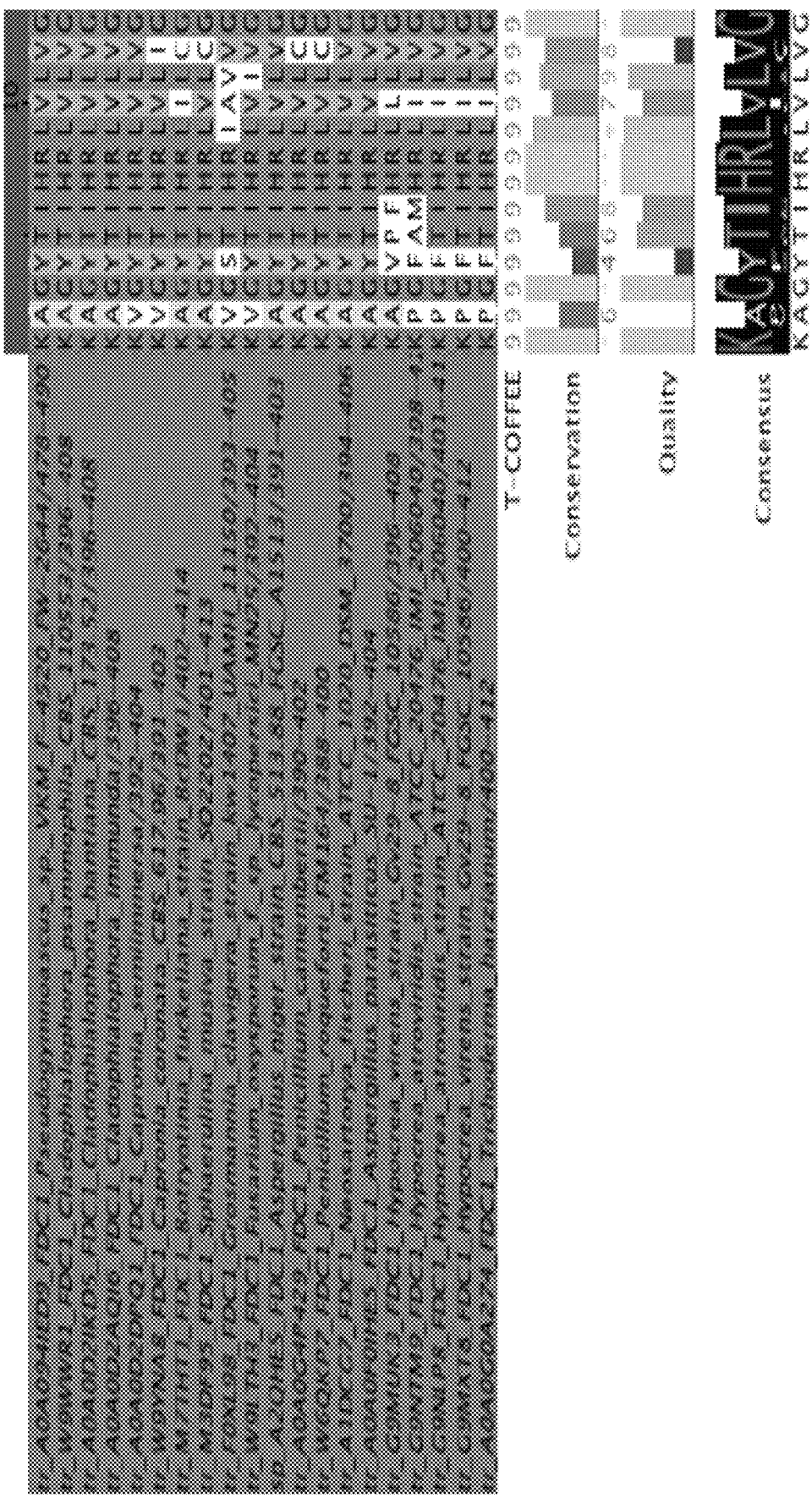

FIG. 2: Multiple Sequence Alignment of 19 protein homologues of the *Hypocrea atroviridis* Ferulic acid decarboxylase 1 (G9NLP8), focussing on the K401-G413 segment of G9NLP8.

Figure 3:
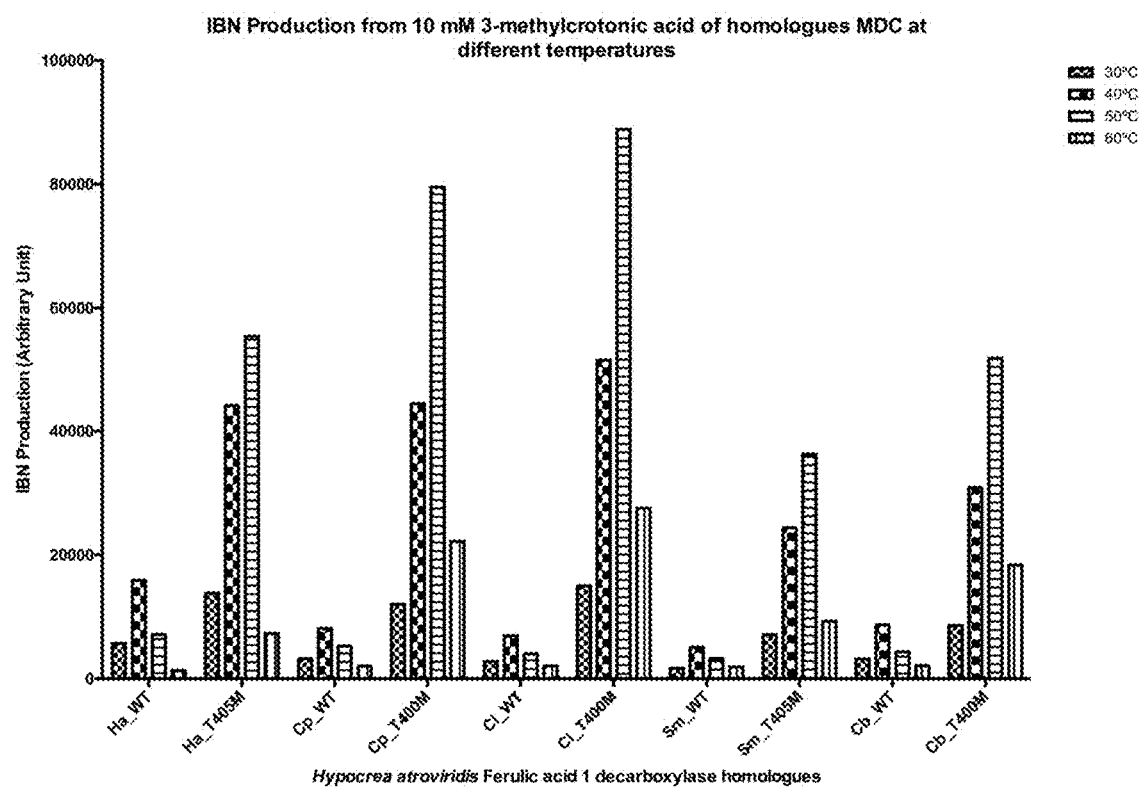

FIG. 3: Isobutene (IBN) production from 10 mM 3-methylcrotonic acid of homologues MDC and their T→M variants at different temperatures (30, 40, 50 and 60° C.).

Figure 4:
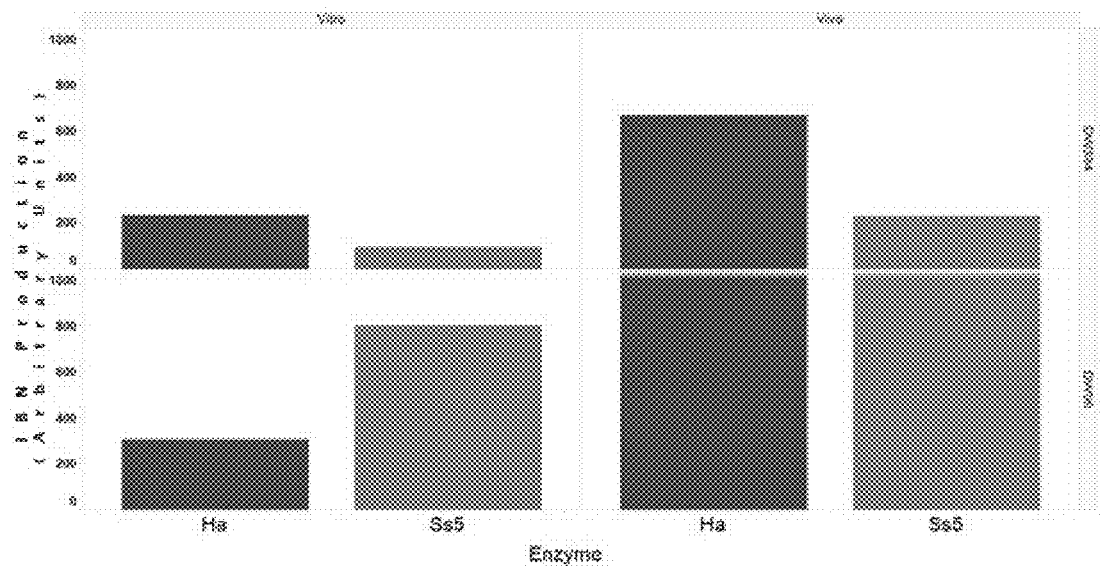

FIG. 4: Isobutene (IBN) production from 30 mM 3-methylcrotonic acid (3MC) after two hours of incubation with two 3-methylcrotonic acid decarboxylase (3-MDC) enzymes. Ss5: enzyme from *Streptomyces* sp. 769 (Uniprot Accession Number A0A0A8EV26); Ha: enzyme from *Hypocrea atroviridis* (Uniprot Accession Number G9NLP8). Tests are conducted in 384 or 96 microplates (DW384 and DW96), in vitro and in vivo.

Figure 5:
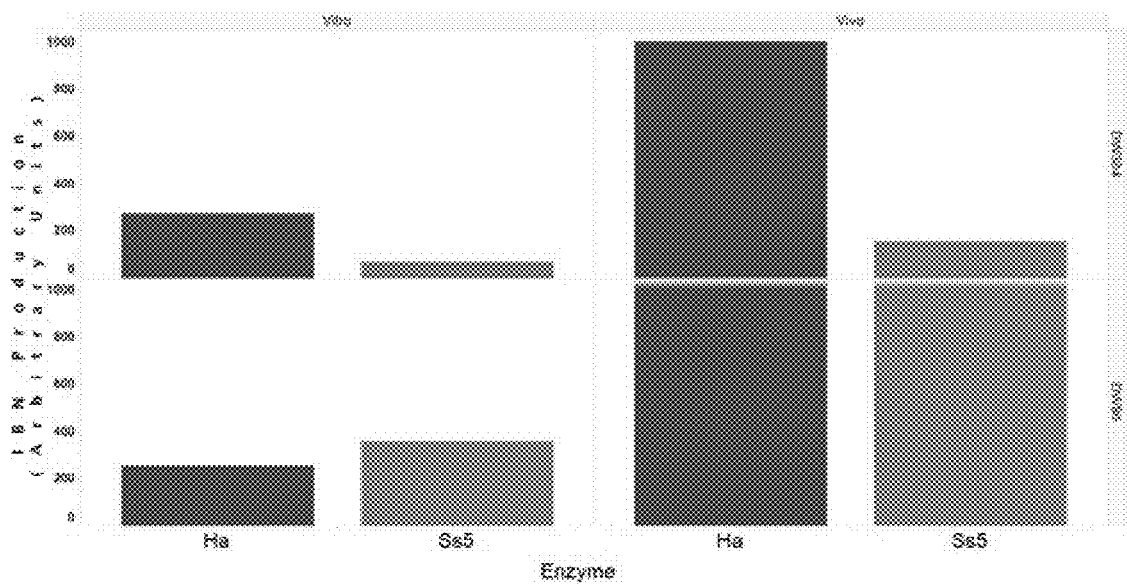

FIG. 5: Isobutene (IBN) production from 30 mM 3-methylcrotonic acid (3MC) after two hours of incubation with two 3-methylcrotonic acid decarboxylase (3MDC) enzymes (Ss5 and Ha) fused with a 6-His-tag. Ss5: enzyme from *Streptomyces* sp. 769 (Uniprot Accession Number A0A0A8EV26); Ha: enzyme from *Hypocrea atroviridis* (Uniprot Accession Number G9NLP8). Tests are conducted in 384 or 96 microplates (DW384 and DW96), in vitro and in vivo.

The invention will now be described by reference to the following examples which are merely illustrative and are not to be construed as a limitation of the scope of the present invention.

EXAMPLES—FIRST PART

Example 1: Directed Evolution Strategy

The enzyme *Hypocrea atroviridis* Ferulic acid decarboxylase 1 (SEQ ID NO:1) is capable of catalysing, amongst other reactions, the decarboxylation of 3-methylcrotonic acid (3MC) into isobutene (IBN). A directed evolution approach was used in order to specifically improve the catalytic efficiency of this reaction. This approach consisted in (1) the design of assay systems to test the activity of enzyme variants, (2) the generation of collections of single point or multiple mutants for *Hypocrea atroviridis* Ferulic acid decarboxylase 1, and (3) the use of the activity assays to screen the collection of mutants in order to identify variants with improved activity compared to the activity of the wild type *Hypocrea atroviridis* Ferulic acid decarboxylase 1.

This approach led to the identification and characterization of a collection of mutants with increased activity compared to the wild type enzyme.

Example 2: Construction of *Hypocrea atroviridis* Ferulic Acid Decarboxylase 1 Enzyme Mutants The polynucleotide sequences coding for the different mutants identified during the evolution of the *Hypocrea atroviridis* Ferulic acid decarboxylase 1 enzyme were generated using a range of standard molecular biology techniques. All these techniques used a codon-optimised polynucleotide sequence for expression in *Escherichia coli* as template. The sequence optimisation has been done by Geneart using their GeneOptimizer software.

Different PCR-based techniques known in the art were used for the construction of single-point mutants. For the generation of enzyme variants bearing multiple mutations (at least two mutations), either PCR-based techniques or other methods known in the art were used to introduce these mutations.

Following mutagenesis, the mutated polynucleotide sequence was inserted into a pETDuet™-1 co-expression vector (Novagen) (used for recombinant protein production in *E. coli* and screening) in addition to the cDNA of the Flavin prenyltransferase UbiX protein from *E. coli* either using standard ligase-based subcloning techniques, whole plasmid extension by PCR or ligase-independent cloning techniques.

Example 3: Selection of the Enzyme Mutants with Increased Activity

Two different screening methods were developed and used during the evolution of the *Hypocrea atroviridis* Ferulic acid decarboxylase 1 enzyme.

1.) In Vivo Assay in 384-Well Microplates Based on Exogenous 3MC (In Vivo 1)

This assay is based on the use of a bacterial strain (BL21(DE3), Novagen) transformed with the above expression vector that contain the above-described coding sequences leading to the production of the last two enzymes involved in the metabolic pathway converting 3MC into isobutene, namely the *Hypocrea atroviridis* Ferulic acid decarboxylase 1 variants and the Flavin prenyltransferase UbiX protein from *E. coli*. This strain is first plated out onto LB-agar plates supplemented with the appropriate antibiotic. Cells were grown overnight at 30° C. until individual colonies reach the desired size. Single colonies were then picked and individually transferred into 50 μL of liquid LB medium supplemented with the appropriate antibiotic. Cell growth is carried out with shaking for 20 hours at 30° C. The LB cultures were used to inoculate 300 μL in 384 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. in order to produce the two recombinant enzymes. The cell pellet containing these two overexpressed recombinant enzymes is then resuspended in 40 μL of minimum medium (pH 7.5, Phosphate 100 mM, Glucose 10 g·L$^{-1}$, MgSO$_4$ 1 mM) supplemented with 10 mM 3MC and incubated for a further 2 or 4 hours in a shaking incubator at 30° C., 700 rpm. During this step, the *Hypocrea atroviridis* Ferulic acid decarboxylase 1 variants catalyse the decarboxylation of 3MC into IBN. After 5 min inactivation at 80° C., the IBN produced is quantified by gas chromatography as described in the following. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL·min$^{-1}$ constant flow of nitrogen as carrier gas. Upon injection, peak areas of isobutene were calculated.

2.) In Vivo Assay in 96-Well Microplates Based on Exogenous 3MC (In Vivo 2)

This assay is based on the use of a bacterial strain (BL21(DE3), Novagen) transformed with the above expression vector that contains the coding sequences as described above, leading to the production of the last two enzymes involved in the metabolic pathway converting 3MC to isobutene; namely the *Hypocrea atroviridis* Ferulic acid decarboxylase 1 variants and the Flavin prenyltransferase UbiX protein from *E. coli*. This strain is first plated out onto LB-agar plates supplemented with the appropriate antibiotic. Cells were grown overnight at 30° C. until individual colonies reach the desired size. Single colonies were then picked and individually transferred into 500 μL of liquid LB medium supplemented with the appropriate antibiotic. Cell growth is carried out with shaking for 20 hours at 30° C. or 32° C. The LB cultures were used to inoculate 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C. or 32° C. in order to produce the two recombinant enzymes. The cell pellet containing these two overexpressed recombinant enzymes is then resuspended in 400 μL of minimum medium (pH 7.5, Phosphate 100 mM, Glucose 10 g·L$^{-1}$, MgSO$_4$ 1 mM) supplemented with 10 mM 3MC and incubated for a further 2 or 4 hours in a shaking incubator at 30° C. or 36° C., 700 rpm. During this step, the *Hypocrea atroviridis* Ferulic acid decarboxylase 1 variants catalyse the decarboxylation of 3MC into IBN. After 5 min inactivation at 80° C., the IBN produced is quantified by gas chromatography as described in the following. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL·min$^{-1}$ constant flow of nitrogen as carrier gas. Upon injection, peak areas of isobutene were calculated.

Example 4: Identification of Variants of *Hypocrea atroviridis* Ferulic Acid Decarboxylase 1 with Further Increased Activity for the Reaction of Conversion of 3-Methylcrotonic Acid into Isobutene A collection of mutants has been created by mutagenesis, using the *Hypocrea atroviridis* Ferulic acid decarboxylase 1 (SEQ ID NO: 1) as template. Several variants with an enhanced activity in converting 3-methylcrotonic acid into isobutene have been identified through in vivo screening assays as described above. A first round of screening with 59508 clones has been performed using the above IN VIVO 1 assay. The best 927 clones were then tested in 12-replicate using the same protocol. The plasmids of the best 95 variants were individually extracted, transformed into fresh competent BL21(DE3) cells and then tested in 8-replicate assays according to the above-described IN VIVO 2 assay.

The list of improved variants is presented in the following Table 1 and the list of the individual positions presenting an increase in activity is shown in Table 2. The improvement factor shown in the below Table 1 reflects the average value of 8 replicates of the relative quantity of isobutene which has been produced and measured according to the above-described IN VIVO 2 assay compared to the wild type enzyme.

TABLE 1

List of *Hypocrea atroviridis* Ferulic acid decarboxylase 1 variants presenting an increase in isobutene production from 3-methylcrotonic acid

| Mutations | Improvement Factor/WT | Mutations | Improvement Factor/WT |
|---|---|---|---|
| T405M | 7.9 | P13I | 1.8 |
| T405F | 4.7 | L195Y | 1.8 |
| S2Q | 4.4 | V439L | 1.8 |
| S2A | 4.3 | I337M | 1.8 |
| L195C | 4.3 | L506I | 1.8 |

TABLE 1-continued

List of *Hypocrea atroviridis* Ferulic acid decarboxylase 1 variants presenting an increase in isobutene production from 3-methylcrotonic acid

| Mutations | Improvement Factor/WT | Mutations | Improvement Factor/WT |
|---|---|---|---|
| L449I | 4.3 | F11L | 1.7 |
| S2K | 4.2 | P13Y | 1.7 |
| S2L | 4.1 | P120S | 1.7 |
| S2V | 4.0 | T429S | 1.7 |
| S3A | 3.9 | T436N | 1.7 |
| S3Y | 3.8 | G435M | 1.7 |
| S2F | 3.7 | L195V | 1.7 |
| S3K L511M | 3.7 | A149V | 1.6 |
| T4N F91L | 3.5 | F447Y | 1.6 |
| S2N | 3.5 | P13S | 1.6 |
| T4E | 3.5 | Q29N | 1.6 |
| S3K M284Y | 3.5 | A10H | 1.6 |
| S3W | 3.2 | N31G | 1.6 |
| S3G | 3.2 | Q214A | 1.5 |
| M293L | 3.2 | V40I | 1.5 |
| S3P | 3.1 | L195F | 1.5 |
| T4M | 3.1 | N31E N501E | 1.5 |
| S3E | 3.0 | E25N | 1.5 |
| T405L | 2.9 | T429A | 1.4 |
| S2D E89S | 2.8 | N501K | 1.4 |
| T4L | 2.7 | E9P | 1.4 |
| V40M | 2.6 | I197F | 1.4 |
| D35M | 2.5 | Q448S | 1.4 |
| K422M | 2.4 | D35T | 1.4 |
| Q448W | 2.3 | A146S | 1.4 |
| L195I | 2.3 | D442T | 1.4 |
| A285L | 2.3 | P13H | 1.3 |
| L195W | 2.2 | Q214V | 1.3 |
| V34A | 2.2 | V445P | 1.3 |
| D12S | 2.1 | V445E | 1.3 |
| L500A | 2.1 | L33I | 1.3 |
| D351R | 2.1 | A381R | 1.3 |
| V34I | 2.1 | L221C | 1.3 |
| Q214T | 2.1 | L449M | 1.2 |
| E9Y | 2.0 | T405Q | 1.2 |
| L195M | 2.0 | T405P | 1.2 |
| F447W | 2.0 | T376I A388E | 1.2 |
| L114S | 2.0 | D35S | 1.2 |
| P13N | 1.9 | L449V | 1.2 |
| E9H | 1.9 | Q29S | 1.2 |
| F11P | 1.8 | N141D | 1.2 |
| D43R | 1.8 | F441Y | 1.2 |
| D420L | 1.8 | | |

TABLE 2

List of the positions modified in the variants of *Hypocrea atroviridis* Ferulic acid decarboxylase 1 with increased activity

| Position | Wild-Type Amino Acid | Mutations |
|---|---|---|
| 2 | S | A, D, F, K, L, N, Q, V |
| 3 | S | A, E, G, K, P, W, Y, |
| 4 | T | E, L, M, N |
| 9 | E | H, P, Y |
| 10 | A | H |
| 11 | F | L, P |
| 12 | D | S |
| 13 | P | H, I, N, S, Y |
| 25 | E | N |
| 29 | Q | N, S |
| 31 | N | E, G |
| 33 | L | I |
| 34 | V | A, I |
| 35 | D | M, S, T |
| 40 | V | I, M |
| 43 | D | R |
| 89 | E | S |
| 91 | F | L |
| 114 | L | S |
| 120 | P | S |
| 141 | N | D |
| 146 | A | S |
| 149 | A | V |
| 195 | L | C, F, I, M, V, W, Y |
| 197 | I | F |
| 214 | Q | A, T, V |
| 221 | L | C |
| 284 | M | Y |
| 285 | A | L |
| 293 | M | L |
| 337 | I | M |
| 351 | D | R |
| 376 | T | I |
| 381 | A | R |
| 388 | A | E |
| 405 | T | F, L, M, P, Q |
| 420 | D | L |
| 422 | K | M |
| 429 | T | A, S |
| 435 | G | M |
| 436 | T | N |
| 439 | V | L |
| 441 | F | Y |
| 442 | D | T |
| 445 | V | E, P |
| 447 | F | W, Y |
| 448 | Q | S, W |
| 449 | L | I, M, V |
| 500 | L | A |
| 501 | N | E, K |
| 506 | L | I |
| 511 | L | M |

Example 5: In Vitro Activities of the *Hypocrea atroviridis* Ferulic Acid 1 Decarboxylase WT and T405M Mutant Gene Synthesis, Cloning, Expression and Purification of Ferulic Acid Decarboxylases The pETDuet™-1 co-expression vectors encoding *Hypocrea atroviridis* Ferulic acid 1 decarboxylase WT or T405M variant and the Flavin prenyltransferase UbiX protein from *E. coli* were obtained according to the procedure described in Example 2 and 3.

The provided vector contained a stretch of 6 histidine codons after the methionine initiation codon of the ferulic acid decarboxylases in order to specifically purify the ferulic acid decarboxylase.

Competent *E. coli* BL21 (DE3) cells (Novagen) were transformed with these vectors according to standard heat shock procedures. The transformed cells were grown with shaking (160 rpm) using ZYM-5052 auto-induction medium (Studier F W, Prot. Exp. Pur. 41, (2005), 207-234) at 30° C. during 24 h. The cells were collected by centrifugation at 4° C., 10,000 rpm for 20 min and the pellets were stored at −80° C. Pellets from 500 ml of culture cells were thawed on ice and resuspended in 15 ml of 50 mM potassium phosphate buffer containing 200 mM NaCl, 10 mM $MgCl_2$, 10 mM imidazole and 1 mM DTT. Twenty microliters of lysonase (Novagen) were added. Cells were incubated 10 minutes at room temperature and then returned to ice for 20 minutes. Cell lysis was completed by sonication for 2×15 seconds.

The bacterial extracts were then clarified by centrifugation at 4° C., 4000 rpm for 40 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of 50 mM potassium phosphate buffer containing 250 mM imidazole. Eluates were then concentrated, desalted on a Amicon Ultra-4 10 kDa filter unit (Millipore) and enzymes were resuspended in 50 mM potassium phosphate buffer containing 1 mM DTT and 20 mM NaCl. The purity of Ferulic acid decarboxylases thus purified varied from 80% to 90% as estimated by SDS-PAGE analysis. Protein concentrations were determined by direct UV 280 nm measurement on the NanoDrop 1000 spectrophotometer (Thermo Scientific) or by a Bradford assay (BioRad).

Production of Flavin Prenyltransferases

In order to perform enzymatic assays, the Flavin prenyltransferase UbiX protein from *E. coli* was also produced separately. Vector pCAN containing the gene coding for the Flavin prenyltransferase UbiX protein from *E. coli* was purchased from NAIST (Nara Institute of Science and Technology, Japan, ASKA collection).

Competent *E. coli* BL21 (DE3) cells (Novagen) were transformed with this vector according to standard heat shock procedures. The transformed cells were grown with shaking (160 rpm) using ZYM-5052 auto-induction medium (Studier F W, Prot. Exp. Pur. 41, (2005), 207-234) at 30° C. during 24 h. The cells were collected by centrifugation at 4° C., 10,000 rpm for 20 min and the pellets were stored at –80° C. Pellets from 500 ml of culture cells were thawed on ice and resuspended in 15 ml of 50 mM potassium phosphate buffer containing 200 mM NaCl, 10 mM $MgCl_2$, 10 mM imidazole and 1 mM DTT. Twenty microliters of lysonase (Novagen) were added. Cells were incubated 10 minutes at room temperature and then returned to ice for 20 minutes. Cell lysis was completed by sonication for 2×15 seconds. The cellular lysate containing the UbiX protein was kept on ice.

Enzymatic Assay

Enzymatic assays were performed with Ferulic acid decarboxylase purified as described above, supplemented with a fresh cellular lysate containing the UbiX protein (see above). 0.5 M stock solution of 3-methylcrotonic acid was prepared in water and adjusted to pH 7.0 with 10 M solution of NaOH. Enzymatic assays were carried out in 2 ml glass vials (Interchim) under the following conditions: 50 mM potassium phosphate pH 7.5; 20 mM NaCl; 3 mM $MgCl_2$; 5 mM DTT; 64 mM 3-methylcrotonic acid; 0.5 mg/ml purified of Ferulic acid decarboxylase (FDC) WT or T405M variant; 100 µl of the lysate contained the Flavin prenyltransferase UbiX protein; total volume of the assays were 300 µl.

The vials were sealed and incubated for 60 minutes at 30° C. A control without Ferulic acid decarboxylase was performed in parallel. The assays were stopped by incubating for 2 minute at 80° C. and the isobutene formed in the reaction headspace was analysed by Gas Chromatography (GC) equipped with a Flame Ionization Detector (FID). For the GC headspace analysis, one ml of the headspace gas was separated in a Bruker GC-450 system equipped with a GS-alumina column (30 m×0.53 mm) (Agilent) using isothermal mode at 130° C. Nitrogen was used as carrier gas with a flow rate of 6 ml/min. The enzymatic reaction product was identified by comparison with an isobutene standard. Under these GC conditions, the retention time of isobutene was 2.42 min.

Results

Under these conditions, the T405M variant of *Hypocrea atroviridis* Ferulic acid decarboxylase 1 is about 7 time more efficient than the WT corresponding enzyme for the conversion of 3-methylcrotonic acid into isobutene; see Table 3.

TABLE 3

|  | Isobutene peak area, arbitrary unit |
| --- | --- |
| FDC WT | 1680 |
| FDC T405M | 11550 |
| without FDC | 2 |

Example 6: Identification of a Signature Sequence Around Position 405 of *Hypocrea atroviridis* Ferulic Acid Decarboxylase 1 (SEQ ID NO:1)

The two variants of *Hypocrea atroviridis* Ferulic acid decarboxylase 1 (SEQ ID NO:1) having the highest increase in activity harbor a mutation at position 405.

*Hypocrea atroviridis* belongs to the Pezizomycotina subphylum of the Ascomycota phylum. Thus, the *Hypocrea atroviridis* Ferulic acid decarboxylase has been compared with 1 to 19 homologue proteins belonging to the Pezizomycotina subphylum (Table 4) which are capable of catalyzing the conversion of 3-methylcrotonic acid into isobutene.

These sequences have been compared in a multiple-sequence alignment using the T-Coffee software in "accurate" mode, combining sequence, structure and profile alignment (Notredame et al., JMB 302 (2000), 205-217). From this alignment, a conserved region around the T405 position of the *Hypocrea atroviridis* Ferulic acid decarboxylase 1 has been derived (K401-G413); (FIG. 2).

This block of aligned sequences was used to derive a pattern with the PRATT software (Jonassen et al., Protein Science 4(8) (1995), 1587-1595):
K-[APV]-G-x-[APT]-[FIM]-H-R-[IL]-[AILV]-[ILV]-x-G
(SEQ ID NO:16) where x represents any amino acid and [XYZ] represents either amino acid X or Y or Z.

This motif was then fed into the ScanProsite webtool (prosite.expasy.org/scanprosite/) to scan the UniProtKB database (Swiss-Prot including splice variants and TrEMBL). A total of 107 different proteins was found, including the original 20 from which the motif was derived (Table 5).

Among these 107 proteins, 3 are annotated as 3-octaprenyl-4-hydroxybenzoate carboxylyase, one as Phenolic acid decarboxylase, one as UbiD-domain-containing protein, 3 as Uncharacterized protein and 99 as Ferulic acid decarboxylase 1. Considering that these annotations represent the decarboxylation of aromatic acids, it is assumed that this motif is representative for the UbiD family.

Moreover, among these 107 proteins, 105 belong to the Dikarya sub-kingdom while 19 of these belong to the *Filobasidiella/Cryptococcus neoformans* species complex of the Agaricomycotina subphylum, 85 to the Pezizomycotina subphylum, one to the Saccharomycotina subphylum and two to the *Phytophthora* genus of the Peronosporales order.

Therefore, it is assumed that this motif is not only representative for the UbiD family of the Pezizomycotina subphylum from which it was derived, but also for the UbiD family of different fungi and fungus-like eukaryotic microorganisms.

TABLE 4

List of 19 proteins homologues to *Hypocrea atroviridis* Ferulic acid decarboxylase 1 (G9NLP8) presenting a 3-methylcrotonic acid decarboxylase activity

| Entry (UniProt) | Entry name | Protein names | Gene names | Organism | Length |
|---|---|---|---|---|---|
| A0A094IED9 | A0A094IED9_9PEZI | Ferulic acid decarboxylase 1 (EC 4.1.1.102) (Phenacrylate decarboxylase) | FDC1 V502_01403 | Pseudogymnoascus sp. VKM F-4520 (FW-2644) | 589 |
| W9WWR1 | W9WWR1_9EURO | Ferulic acid decarboxylase 1 (EC 4.1.1.102) (Phenacrylate decarboxylase) | FDC1 A1O5_04852 | Cladophialophora psammophila CBS 110553 | 503 |
| A0A0D2IKD5 | A0A0D2IKD5_XYLBA | Ferulic acid decarboxylase 1 (EC 4.1.1.102) (Phenacrylate decarboxylase) | FDC1 Z519_02676 | Cladophialophora bantiana CBS 173.52 | 503 |
| A0A0D2AQI6 | A0A0D2AQI6_9EURO | Ferulic acid decarboxylase 1 (EC 4.1.1.102) (Phenacrylate decarboxylase) | FDC1 PV07_07106 | Cladophialophora immunda | 505 |
| A0A0D2DPQ1 | A0A0D2DPQ1_9EURO | Ferulic acid decarboxylase 1 (EC 4.1.1.102) (Phenacrylate decarboxylase) | FDC1 PV04_09173 | Capronia semiimmersa | 499 |
| W9YNA8 | W9YNA8_9EURO | Ferulic acid decarboxylase 1 (EC 4.1.1.102) (Phenacrylate decarboxylase) | FDC1 A1O1_03830 | Capronia coronata CBS 617.96 | 498 |
| M7THT1 | M7THT1_BOTF1 | Ferulic acid decarboxylase 1 (EC 4.1.1.102) (Phenacrylate decarboxylase) | FDC1 BcDW1_8299 | Botryotinia fuckeliana (strain BcDW1) (Noble rot fungus) (Botrytis cinerea) | 513 |
| M3DF95 | M3DF95_SPHMS | Ferulic acid decarboxylase 1 (EC 4.1.1.102) (Phenacrylate decarboxylase) | FDC1 SEPMUDRAFT_154815 | Sphaerulina musiva (strain SO2202) (Poplar stem canker fungus) (Septoria musiva) | 508 |
| FOXL98 | FOXL98_GROCL | Ferulic acid decarboxylase 1 (EC 4.1.1.102) (Phenacrylate decarboxylase) | FDC1 CMQ_6352 | Grosmannia clavigera (strain kw1407/UAMH 11150) (Blue stain fungus) (Graphiocladiella clavigera) | 500 |
| W9LTH3 | W9LTH3_FUSOX | Ferulic acid decarboxylase 1 (EC 4.1.1.102) (Phenacrylate decarboxylase) | FDC1 FOWG_11397 | Fusarium oxysporum f. sp. lycopersici MN25 | 503 |
| A2QHE5 | FDC1_ASPNC | Ferulic acid decarboxylase 1 (EC 4.1.1.102) (Phenacrylate decarboxylase) | fdc1 An03g06590 | Aspergillus niger (strain CBS 513.88/FGSC A1513) | 500 |
| A0A0G4P429 | A0A0G4P429_PENCA | Ferulic acid decarboxylase 1 (EC 4.1.1.102) (Phenacrylate decarboxylase) | FDC1 PCAMFM013_S005g000265 | Penicillium camemberti FM 013 | 500 |
| W6QKP7 | W6QKP7_PENRF | Ferulic acid decarboxylase 1 (EC 4.1.1.102) (Phenacrylate decarboxylase) | FDC1 PROQFM164_S05g000853 | Penicillium roqueforti (strain FM164) | 498 |
| A1DCG7 | A1DCG7_NEOFI | Ferulic acid decarboxylase 1 (EC 4.1.1.102) (Phenacrylate decarboxylase) | FDC1 NFIA_026010 | Neosartorya fischeri (strain ATCC 1020/DSM 3700/ FGSC A1164/NRRL 181) (Aspergillus fischerianus) | 505 |
| A0A0F0IHE5 | A0A0F0IHE5_ASPPU | Ferulic acid decarboxylase 1 (EC 4.1.1.102) (Phenacrylate decarboxylase) | FDC1 P875_00128011 | Aspergillus parasiticus (strain ATCC 56775/NRRL 5862/SRRC 143/SU-1) | 503 |
| G9MUK3 | G9MUK3_HYPVG | Ferulic acid decarboxylase 1 (EC 4.1.1.102) (Phenacrylate decarboxylase) | FDC1 TRIVIDRAFT_53354 | Hypocrea virens (strain Gv29-8/FGSC 10586) (Gliocladium virens) (Trichoderma virens) | 507 |
| G9NTM9 | G9NTM9_HYPAI | Ferulic acid decarboxylase 1 (EC 4.1.1.102) (Phenacrylate decarboxylase) | FDC1 TRIATDRAFT_299540 | Hypocrea atroviridis (strain ATCC 20476/IMI 206040) (Gliocladium virens) (Trichoderma virens) | 510 |
| G9NLP8 | G9NLP8_HYPAI | Ferulic acid decarboxylase 1 (EC 4.1.1.102) (Phenacrylate decarboxylase) | FDC1 TRIATDRAFT_53567 | Hypocrea atroviridis (strain ATCC 20476/IMI 206040) (Trichoderma atroviride) | 512 |
| G9MXT8 | G9MXT8_HYPVG | Ferulic acid decarboxylase 1 (EC 4.1.1.102) (Phenacrylate decarboxylase) | FDC1 TRIVIDRAFT_69398 | Hypocrea virens (strain Gv29-8/FGSC 10586) (Gliocladium virens) (Trichoderma virens) | 511 |
| A0A0G0A274 | A0A0G0A274_TRIHA | Ferulic acid decarboxylase 1 (EC 4.1.1.102) (Phenacrylate decarboxylase) | FDC1 THAR02_01458 | Trichoderma harzianum (Hypocrea lixii) | 511 |

TABLE 5

List of the 107 proteins found in the UniProtKB database through ScanProsite, with the K-[APV]-G-x-[APT]-[FIM]-H-R-[IL]-[AILV]-[IILV]-x-G (SEQ ID NO: 16) motif.

| Entry (UniProt) | Entry name | Protein names | Gene names | Organism | Length |
|---|---|---|---|---|---|
| A0A0B4FU01 | A0A0B4FU01_9HYPO | 3-octaprenyl-4-hydroxybenzoate carboxylyase (Fragment) | MBR_10525 | Metarhizium brunneum ARSEF 3297 | 500 |
| A0A0B4ENF4 | A0A0B4ENF4_METAN | 3-octaprenyl-4-hydroxybenzoate carboxylyase (Fragment) | MAN_07756 | Metarhizium anisopliae ARSEF 549 | 500 |
| A0A0B8N4Y5 | A0A0B8N4Y5_9EURO | 3-octaprenyl-4-hydroxybenzoate carboxylyase | TCE0_047r17842 | Talaromyces cellulolyticus | 130 |
| A2QHE5 | FDC1_ASPNC | Ferulic acid decarboxylase 1 (EC 4.1.1.102) (Phenacrylate decarboxylase) | fdc1 An03g06590 | Aspergillus niger (strain CBS 513.88/FGSC A1513) | 500 |
| A0A0A2I5F4 | A0A0A2I5F4_PENEN | Ferulic acid decarboxylase 1 (EC 4.1.1.102) (Phenacrylate decarboxylase) | FDC1 PEX1_019400 PEX2_105470 PEXP_077520 | Penicillium expansum (Blue mold rot fungus) | 500 |
| A0A0D2YAR9 | A0A0D2YAR9_FUSO4 | Ferulic acid decarboxylase 1 (EC 4.1.1.102) (Phenacrylate decarboxylase) | FDC1 FOXG_13395 | Fusarium oxysporum f. sp. lycopersici (strain 4287/CBS 123668/FGSC 9935/NRRL 34936) (Fusarium vascular wilt of tomato) | 503 |
| A0A0J0DBQ6 | A0A0J0DBQ6_GIBFU | Ferulic acid decarboxylase 1 (EC 4.1.1.102) (Phenacrylate decarboxylase) | FDC1 LW94_13187 Y057_969 | Gibberella fujikuroi (Bakanae and foot rot disease fungus) (Fusarium fujikuroi) | 503 |
| R1EM06 | R1EM06_BOTPV | Ferulic acid decarboxylase 1 (EC 4.1.1.102) (Phenacrylate decarboxylase) | FDC1 UCRNP2_4413 | Botryosphaeria parva (strain UCR-NP2) (Grapevine canker fungus) (Neofusicoccum parvum) | 495 |
| A0A0G4P429 | A0A0G4P429_PENCA | Ferulic acid decarboxylase 1 (EC 4.1.1.102) (Phenacrylate decarboxylase) | FDC1 PCAMFM013_S005g000265 | Penicillium camemberti FM 013 | 500 |
| A0A014P6U4 | A0A014P6U4_9HYPO | Ferulic acid decarboxylase 1 (EC 4.1.1.102) (Phenacrylate decarboxylase) | FDC1 X797_008675 | Metarhizium robertsii | 508 |
| K9FXI0 | K9FXI0_PEND1 | Ferulic acid decarboxylase 1 (EC 4.1.1.102) (Phenacrylate decarboxylase) | FDC1 PDIP_44190 | Penicillium digitatum (strain Pd1/CECT 20795) (Green mold) | 499 |
| I8A854 | I8A854_ASPO3 | Ferulic acid decarboxylase 1 (EC 4.1.1.102) (Phenacrylate decarboxylase) | FDC1 Ao3042_02507 | Aspergillus oryzae (strain 3.042) (Yellow koji mold) | 503 |
| F9FQB3 | F9FQB3_FUSOF | Ferulic acid decarboxylase 1 (EC 4.1.1.102) (Phenacrylate decarboxylase) | FDC1 FOXB_08593 | Fusarium oxysporum (strain Fo5176) (Fusarium vascular wilt) | 506 |
| A0A0B7K683 | A0A0B7K683_BIOOC | Ferulic acid decarboxylase 1 (EC 4.1.1.102) (Phenacrylate decarboxylase) | FDC1 BN869_000007130_1 | Bionectria ochroleuca (Gliocladium roseum) | 496 |
| A0A0F9X6G5 | A0A0F9X6G5_TRIHA | Ferulic acid decarboxylase 1 (EC 4.1.1.102) (Phenacrylate decarboxylase) | FDC1 THAR02_07744 | Trichoderma harzianum (Hypocrea lixii) | 495 |
| A0A064B9K3 | A0A064B9K3_ASPOZ | Ferulic acid decarboxylase 1 (EC 4.1.1.102) (Phenacrylate decarboxylase) | FDC1 A01008_09897 | Aspergillus oryzae 100-8 | 503 |
| A0A0G0A274 | A0A0G0A274_TRIHA | Ferulic acid decarboxylase 1 (EC 4.1.1.102) (Phenacrylate decarboxylase) | FDC1 THAR02_01458 | Trichoderma harzianum (Hypocrea lixii) | 511 |
| A0A0D9QCX6 | A0A0D9QCX6_METAN | Ferulic acid decarboxylase 1 (EC 4.1.1.102) (Phenacrylate decarboxylase) | FDC1 H633G_00051 | Metarhizium anisopliae BRIP 53284 | 500 |
| H1VUR4 | H1VUR4_COLHI | Ferulic acid decarboxylase 1 (EC 4.1.1.102) (Phenacrylate decarboxylase) | FDC1 CH063_03208 | Colletotrichum higginsianum (strain IMI 349063) (Crucifer anthracnose fungus) | 506 |
| E6R9Z1 | E6R9Z1_CRYGW | Ferulic acid decarboxylase 1 (EC 4.1.1.102) (Phenacrylate decarboxylase) | FDC1 CGB_G5620W | Cryptococcus gattii serotype B (strain WM276/ATCC MYA-4071) (Filobasidiella gattii) (Cryptococcus bacillisporus) | 435 |
| A0A0D0U0M0 | A0A0D0U0M0_CRYGA | Ferulic acid decarboxylase 1 (EC 4.1.1.102) (Phenacrylate decarboxylase) | FDC1 I313_01913 | Cryptococcus gattii Ram5 | 501 |
| G9MUK3 | G9MUK3_HYPVG | Ferulic acid decarboxylase 1 (EC 4.1.1.102) (Phenacrylate decarboxylase) | FDC1 TRIVIDRAFT_53354 | Hypocrea virens (strain Gv29-8/FGSC 10586) (Gliocladium virens) (Trichoderma virens) | 507 |

TABLE 5-continued

List of the 107 proteins found in the UniProtKB database through ScanProsite, with the K-[APV]-G-x-[APT]-[FIM]-H-R-[IL]-[AILV]-[ILV]-x-G (SEQ ID NO: 16) motif.

| Entry (UniProt) | Entry name | Protein names | Gene names | Organism | Length |
|---|---|---|---|---|---|
| G9MXT8 | G9MXT8_HYPVG | Ferulic acid decarboxylase 1 (EC 4.1.1.102) (Phenacrylate decarboxylase) | FDC1 TRIVIDRAFT_69398 | Hypocrea virens (strain Gv29-8/FGSC 10586) (Gliocladium virens) (Trichoderma virens) | 511 |
| A0A0D0T0X7 | A0A0D0T0X7_CRYGA | Ferulic acid decarboxylase 1 (EC 4.1.1.102) (Phenacrylate decarboxylase) | FDC1 1309_02848 | Cryptococcus gattii LA55 | 501 |
| W6QKP7 | W6QKP7_PENRF | Ferulic acid decarboxylase 1 (EC 4.1.1.102) (Phenacrylate decarboxylase) | FDC1 PROQFM164_S05g000853 | Penicillium roqueforti (strain FM164) | 498 |
| A0A060T4A6 | A0A060T4A6_BLAAD | Ferulic acid decarboxylase 1 (EC 4.1.1.102) (Phenacrylate decarboxylase) | FDC1 GNLVRS02_ARAD1A15180g | Blastobotrys adeninivorans (Yeast) (Arxula adeninivorans) | 497 |
| W9LTH3 | W9LTH3_FUSOX | Ferulic acid decarboxylase 1 (EC 4.1.1.102) (Phenacrylate decarboxylase) | FDC1 FOWG_11397 | Fusarium oxysporum f. sp. lycopersici MN25 | 503 |
| W9LC23 | W9LC23_FUSOX | Ferulic acid decarboxylase 1 (EC 4.1.1.102) (Phenacrylate decarboxylase) | FDC1 FOWG_16734 | Fusarium oxysporum f. sp. lycopersici MN25 | 503 |
| W3XQA0 | W3XQA0_9PEZI | Ferulic acid decarboxylase 1 (EC 4.1.1.102) (Phenacrylate decarboxylase) | FDC1 PFICL_01973 | Pestalotiopsis fici W106-1 | 501 |
| A0A0F0IHE5 | A0A0F0IHE5_ASPPU | Ferulic acid decarboxylase 1 (EC 4.1.1.102) (Phenacrylate decarboxylase) | FDC1 P875_00128011 | Aspergillus parasiticus (strain ATCC 56775/NRRL 5862/SRRC 143 / SU-1) | 503 |
| A0A0D2JJA4 | A0A0D2JJA4_CRYGA | Ferulic acid decarboxylase 1 (EC 4.1.1.102) (Phenacrylate decarboxylase) | FDC1 1305_01613 | Cryptococcus gattii E566 | 435 |
| A0A0D0Y3D9 | A0A0D0Y3D9_CRYGA | Ferulic acid decarboxylase 1 (EC 4.1.1.102) (Phenacrylate decarboxylase) | FDC1 1306_05467 | Cryptococcus gattii EJB2 | 435 |
| W9WWR1 | W9WWR1_9EURO | Ferulic acid decarboxylase 1 (EC 4.1.1.102) (Phenacrylate decarboxylase) | FDC1 A105_04852 | Cladophialophora psammophila CBS 110553 | 503 |
| A0A0D2DPQ1 | A0A0D2DPQ1_9EURO | Ferulic acid decarboxylase 1 (EC 4.1.1.102) (Phenacrylate decarboxylase) | FDC1 PV04_09173 | Capronia semiimmersa | 499 |
| W9ZFW9 | W9ZFW9_FUSOX | Ferulic acid decarboxylase 1 (EC 4.1.1.102) (Phenacrylate decarboxylase) | FDC1 FOMG_16250 | Fusarium oxysporum f. sp. melonis 26406 | 503 |
| X0AT48 | X0AT48_FUSOX | Ferulic acid decarboxylase 1 (EC 4.1.1.102) (Phenacrylate decarboxylase) | FDC1 FOMG_09469 | Fusarium oxysporum f. sp. melonis 26406 | 503 |
| G7XVA2 | G7XVA2_ASPKW | Ferulic acid decarboxylase 1 (EC 4.1.1.102) (Phenacrylate decarboxylase) | FDC1 AKAW_08975 | Aspergillus kawachii (strain NBRC 4308) (White koji mold) (Aspergillus awamori var. kawachi) | 500 |
| N4TMS4 | N4TMS4_FUSC1 | Ferulic acid decarboxylase 1 (EC 4.1.1.102) (Phenacrylate decarboxylase) | FDC1 FOC1_g10005647 | Fusarium oxysporum f. sp. cubense (strain race 1) (Panama disease fungus) | 503 |
| G3Y7U5 | G3Y7U5_ASPNA | Ferulic acid decarboxylase 1 (EC 4.1.1.102) (Phenacrylate decarboxylase) | FDC1 ASPNIDRAFT_44615 | Aspergillus niger (strain ATCC 1015/CBS 113.46/ FGSC A1144/LSHB Ac4/NCTC 3858a/NRRL 328/USDA 3528.7) | 500 |
| A0A0D0XAE5 | A0A0D0XAE5_CRYGA | Ferulic acid decarboxylase 1 (EC 4.1.1.102) (Phenacrylate decarboxylase) | FDC1 1314_01406 | Cryptococcus gattii CA1873 | 435 |
| A0A0J0BVX6 | A0A0J0BVX6_GIBFU | Ferulic acid decarboxylase 1 (EC 4.1.1.102) (Phenacrylate decarboxylase) | FDC1 LW93_9666 | Gibberella fujikuroi (Bakanae and foot rot disease fungus) (Fusarium fujikuroi) | 503 |
| W9YNA8 | W9YNA8_9EURO | Ferulic acid decarboxylase 1 (EC 4.1.1.102) (Phenacrylate decarboxylase) | FDC1 A101_03830 | Capronia coronata CBS 617.96 | 498 |
| M7THT1 | M7THT1_BOTF1 | Ferulic acid decarboxylase 1 (EC 4.1.1.102) (Phenacrylate decarboxylase) | FDC1 BcDW1_8299 | Botryotinia fuckeliana (strain BcDW1) (Noble rot fungus) (Botrytis cinerea) | 513 |
| X0MQQ9 | X0MQQ9_FUSOX | Ferulic acid decarboxylase 1 (EC 4.1.1.102) (Phenacrylate decarboxylase) | FDC1 FOTG_09622 | Fusarium oxysporum f. sp. vasinfectum 25433 | 503 |
| X0FER4 | X0FLR4_FUSOX | Ferulic acid decarboxylase 1 (EC 4.1.1.102) (Phenacrylate decarboxylase) | FDC1 FOCG_08056 | Fusarium oxysporum f. sp. radicis-lycopersici 26381 | 503 |

TABLE 5-continued

List of the 107 proteins found in the UniProtKB database through ScanProsite, with the K-[APV]-G-x-[APT]-[FM]-H-R-[IL]-[AILV]-[ILV]-x-G (SEQ ID NO: 16) motif.

| Entry (UniProt) | Entry name | Protein names | Gene names | Organism | Length |
|---|---|---|---|---|---|
| X0BC97 | X0BC97_FUSOX | Ferulic acid decarboxylase 1 (EC 4.1.1.102) (Phenacrylate decarboxylase) | FDC1 FOQG_15695 | Fusarium oxysporum f. sp. raphani 54005 | 503 |
| X0HNC2 | X0HNC2_FUSOX | Ferulic acid decarboxylase 1 (EC 4.1.1.102) (Phenacrylate decarboxylase) | FDC1 FOPG_11348 | Fusarium oxysporum f. sp. conglutinans race 2 54008 | 503 |
| X0I4B9 | X0I4B9_FUSOX | Ferulic acid decarboxylase 1 (EC 4.1.1.102) (Phenacrylate decarboxylase) | FDC1 FOIG_11524 | Fusarium oxysporum f. sp. cubense tropical race 4 54006 | 503 |
| A0A0D9NTQ8 | A0A0D9NTQ8_METAN | Ferulic acid decarboxylase 1 (EC 4.1.1.102) (Phenacrylate decarboxylase) | FDC1 H634G_07518 | Metarhizium anisopliae BRIP 53293 | 500 |
| A0A0D0YJS6 | A0A0D0YJS6_CRYGA | Ferulic acid decarboxylase 1 (EC 4.1.1.102) (Phenacrylate decarboxylase) | FDC1 L804_03800 | Cryptococcus gattii 2001/935-1 | 501 |
| E9ENN2 | E9ENN2_METRA | Ferulic acid decarboxylase 1 (EC 4.1.1.102) (Phenacrylate decarboxylase) | FDC1 MAA_01631 | Metarhizium robertsii (strain ARSEF 23/ATCC MYA-3075) (Metarhizium anisopliae (strain ARSEF 23)) | 500 |
| G2XWX0 | G2XWX0_BOTF4 | Ferulic acid decarboxylase 1 (EC 4.1.1.102) (Phenacrylate decarboxylase) | FDC1 BofuT4_P051470.1 | Botryotinia fuckeliana (strain T4) (Noble rot fungus) (Botrytis cinerea) | 513 |
| A0A0F7U117 | A0A0F7U117_9EURO | Ferulic acid decarboxylase 1 (EC 4.1.1.102) (Phenacrylate decarboxylase) | FDC1 PMG11_09885 | Penicillium brasilianum | 503 |
| A0A010QFR6 | A0A010QFR6_9PEZI | Ferulic acid decarboxylase 1 (EC 4.1.1.102) (Phenacrylate decarboxylase) | FDC1 CFI001_10372 | Colletotrichum fioriniae PJ7 | 503 |
| K9FG02 | K9FG02_PEND2 | Ferulic acid decarboxylase 1 (EC 4.1.1.102) (Phenacrylate decarboxylase) | FDC1 PDIG_73710 | Penicillium digitatum (strain PHI26/CECT 20796) (Green mold) | 499 |
| A0A0G2EQF2 | A0A0G2EQF2_9EURO | Ferulic acid decarboxylase 1 (EC 4.1.1.102) (Phenacrylate decarboxylase) | FDC1 UCRPC4_g02163 | Phaeomoniella chlamydospora | 498 |
| A0A0D2AQI6 | A0A0D2AQI6_9EURO | Ferulic acid decarboxylase 1 (EC 4.1.1.102) (Phenacrylate decarboxylase) | FDC1 PV07_07106 | Cladophialophora immunda | 505 |
| S0E299 | S0E299_GIBF5 | Ferulic acid decarboxylase 1 (EC 4.1.1.102) (Phenacrylate decarboxylase) | FDC FFUJ_14803 | Gibberella fujikuroi (strain CBS 195.34/IMI 58289/NRRL A-6831) (Bakanae and foot rot disease fungus) (Fusarium fujikuroi) | 503 |
| B8NJ67 | B8NJ67_ASPFN | Ferulic acid decarboxylase 1 (EC 4.1.1.102) (Phenacrylate decarboxylase) | FDC1 AFLA_064990 | Aspergillus flavus (strain ATCC 200026/FGSC A1120/NRRL 3357/JCM 12722/SRRC 167) | 503 |
| K2RUE8 | K2RUE8_MACPH | Ferulic acid decarboxylase 1 (EC 4.1.1.102) (Phenacrylate decarboxylase) | FDC1 MPH_04225 | Macrophomina phaseolina (strain M56) (Charcoal rot fungus) | 494 |
| A1DCG7 | A1DCG7_NEOFI | Ferulic acid decarboxylase 1 (EC 4.1.1.102) (Phenacrylate decarboxylase) | FDC1 NFIA_026010 | Neosartorya fischeri (strain ATCC 1020/DSM 3700/FGSC_A1164/NRRL 181) (Aspergillus fischerianus) | 505 |
| A0A0D2IKD5 | A0A0D2IKD5_XYLBA | Ferulic acid decarboxylase 1 (EC 4.1.1.102) (Phenacrylate decarboxylase) | FDC1 Z519_02676 | Cladophialophora bantiana CBS 173.52 | 503 |
| A0A0D0VRV5 | A0A0D0VRV5_CRYGA | Ferulic acid decarboxylase 1 (EC 4.1.1.102) (Phenacrylate decarboxylase) | FDC1 I310_03088 | Cryptococcus gattii CA1014 | 501 |
| A0A017SAW2 | A0A017SAW2_9EURO | Ferulic acid decarboxylase 1 (EC 4.1.1.102) (Phenacrylate decarboxylase) | FDC1 EURHEDRAFT_503163 | Aspergillus ruber CBS 135680 | 500 |
| W9JNI1 | W9JNI1_FUSOX | Ferulic acid decarboxylase 1 (EC 4.1.1.102) (Phenacrylate decarboxylase) | FDC1 FOZG_15347 | Fusarium oxysporum Fo47 | 503 |
| M3DF95 | M3DF95_SPHMS | Ferulic acid decarboxylase 1 (EC 4.1.1.102) (Phenacrylate decarboxylase) | FDC1 SEPMUDRAFT_154815 | Sphaerulina musiva (strain SO2202) (poplar stem canker fungus) (Septoria musiva) | 508 |
| W9JP63 | W9JP63_FUSOX | Ferulic acid decarboxylase 1 (EC 4.1.1.102) (Phenacrylate decarboxylase) | FDC1 FOZG_14585 | Fusarium oxysporum Fo47 | 503 |

TABLE 5-continued

List of the 107 proteins found in the UniProtKB database through ScanProsite, with the K-[APV]-G-x-[APT]-[FM]-H-R-[IL]-[AILV]-[ILV]-x-G (SEQ ID NO: 16) motif.

| Entry (UniProt) | Entry name | Protein names | Gene names | Organism | Length |
|---|---|---|---|---|---|
| A0A094IED9 | A0A094IED9_9PEZI | Ferulic acid decarboxylase 1 (EC 4.1.1.102) (Phenacrylate decarboxylase) | FDC1 V502_01403 | Pseudogymnoascus sp. VKM F-4520 (FW-2644) | 589 |
| B6HRC8 | B6HRC8_PENRW | Ferulic acid decarboxylase 1 (EC 4.1.1.102) (Phenacrylate decarboxylase) | FDC1 Pc22g03390 PCH_Pc22g03390 | Penicillium rubens (strain ATCC 28089/DSM 1075/NRRL 1951/Wisconsin 54-1255) (Penicillium chrysogenum) | 500 |
| W7MPM7 | W7MPM7_GIBM7 | Ferulic acid decarboxylase 1 (EC 4.1.1.102) (Phenacrylate decarboxylase) | FDC1 FVEG_11829 | Gibberella moniliformis (strain M3125/FGSC 7600) (Maize ear and stalk rot fungus) (Fusarium verticillioides) | 503 |
| G9NLP8 | G9NLP8_HYPAI | Ferulic acid decarboxylase 1 (EC 4.1.1.102) (Phenacrylate decarboxylase) | FDC1 TRIATDRAFT_53567 | Hypocrea atroviridis (strain ATCC 20476/IMI 206040) (Trichoderma atroviride) | 512 |
| G9NTM9 | G9NTM9_HYPAI | Ferulic acid decarboxylase 1 (EC 4.1.1.102) (Phenacrylate decarboxylase) | FDC1 TRIATDRAFT_299540 | Hypocrea atroviridis (strain ATCC 20 476/IMI 206040) (Trichoderma atroviride) | 510 |
| G9P0U1 | G9P0U1_HYPAI | Ferulic acid decarboxylase 1 (EC 4.1.1.102) (Phenacrylate decarboxylase) | FDC1 TRIATDRAFT_35115 | Hypocrea atroviridis (strain ATCC 20476/IMI 206040) (Trichoderma atroviride) | 507 |
| T0K816 | T0K816_COLGC | Ferulic acid decarboxylase 1 (EC 4.1.1.102) (Phenacrylate decarboxylase) | FDC1 CGLO_11546 | Colletotrichum gloeosporioides (strain Cg-14) (Anthracnose fungus) (Glomerella cingulata) | 506 |
| N1RLH9 | N1RLH9_FUSC4 | Ferulic acid decarboxylase 1 | FOC4_g10005518 | Fusarium oxysporum f. sp. cubense (strain race 4) (Panama disease fungus) | 167 |
| N1RYW4 | N1RYW4_FUSC4 | Ferulic acid decarboxylase 1 (EC 4.1.1.102) (Phenacrylate decarboxylase) | FDC1 FOC4_g10005520 | Fusarium oxysporum f. sp. cubense (strain race 4) (Panama disease fungus) | 503 |
| A0A0D0VVI5 | A0A0D0VVI5_CRYGA | Ferulic acid decarboxylase 1 (EC 4.1.1.102) (Phenacrylate decarboxylase) | FDC1 1312_01590 | Cryptococcus gattii CA1280 | 435 |
| FOXL98 | FOXL98_GROCL | Ferulic acid decarboxylase 1 (EC 4.1.1.102) (Phenacrylate decarboxylase) | FDC1 CMQ_6352 | Grosmannia clavigera (strain kw1407/UAMH 11150) (Blue stain fungus) (Graphiocladiella clavigera) | 500 |
| FOXKQ3 | FOXKQ3_GROCL | Ferulic acid decarboxylase 1 (EC 4.1.1.102) (Phenacrylate decarboxylase) | FDC1 CMQ_8261 | Grosmannia clavigera (strain kw1407/UAMH 11150) (Blue stain fungus) (Graphiocladiella clavigera) | 482 |
| A0A0D0U7G3 | A0A0D0U7G3_CRYGA | Ferulic acid decarboxylase 1 (EC 4.1.1.102) (Phenacrylate decarboxylase) | FDC1 1315_02568 | Cryptococcus gattii Ru294 | 435 |
| A0A0D0X8C8 | A0A0D0X8C8_CRYGA | Ferulic acid decarboxylase 1 (EC 4.1.1.102) (Phenacrylate decarboxylase) | FDC1 1304_04581 | Cryptococcus gattii CBS 10090 | 501 |
| A0A0D0X028 | A0A0D0X028_CRYGA | Ferulic acid decarboxylase 1 (EC 4.1.1.102) (Phenacrylate decarboxylase) | FDC1 1308_01018 | Cryptococcus gattii IND107 | 435 |
| W9HNN8 | W9HNN8_FUSOX | Ferulic acid decarboxylase 1 (EC 4.1.1.102) (Phenacrylate decarboxylase) | FDC1 FOYG_14553 | Fusarium oxysporum FOSC 3-a | 503 |
| A0A0D9M9B3 | A0A0D9M9B3_9EURO | Ferulic acid decarboxylase 1 (EC 4.1.1.102) (Phenacrylate decarboxylase) | FDC1 U727_0043148038I | Penicillium solitum | 500 |
| W9HU82 | W9HU82_FUSOX | Ferulic acid decarboxylase 1 (EC 4.1.1.102) (Phenacrylate decarboxylase) | FDC1 FOYG_10553 | Fusarium oxysporum FOSC 3-a | 503 |
| C7ZIA7 | C7ZIA7_NECH7 | Ferulic acid decarboxylase 1 (EC 4.1.1.102) (Phenacrylate decarboxylase) | FDC1 NECHADRAFT_52948 | Nectria haematococca (strain 77-13-4/ATCC MYA-4622/FGSC 9596/MPVI) (Fusarium solani subsp. pisi) | 474 |
| C7ZC09 | C7ZC09_NECH7 | Ferulic acid decarboxylase 1 (EC 4.1.1.102) (Phenacrylate decarboxylase) | FDC1 NECHADRAFT_73218 | Nectria haematococca (strain 77-13-4/ATCC MYA-4622/FGSC 9596/MPVI) (Fusarium solani subsp. pisi) | 489 |
| A0A0D0ILU3 | A0A0D0ILU3_CRYGA | Ferulic acid decarboxylase 1 (EC 4.1.1.102) (Phenacrylate decarboxylase) | FDC1 1352_04272 | Cryptococcus gattii MMRL2647 | 501 |

TABLE 5-continued

List of the 107 proteins found in the UniProtKB database through ScanProsite, with the K-[APV]-G-x-[APT]-[FM]-H-R-[IL]-[AILV]-[ILV]-x-G (SEQ ID NO: 16) motif.

| Entry (UniProt) | Entry name | Protein names | Gene names | Organism | Length |
|---|---|---|---|---|---|
| A0A095C6V3 | A0A095C6V3_CRYGA | Ferulic acid decarboxylase 1 (EC 4.1.1.102) (Phenacrylate decarboxylase) | FDC1 CNBG_2095 | Cryptococcus gattii R265 | 501 |
| L2G6I9 | L2G6I9_COLGN | Ferulic acid decarboxylase 1 (EC 4.1.1.102) (Phenacrylate decarboxylase) | FDC1 CGGC5_6473 | Colletotrichum gloeosporioides (strain Nara gc5) (Anthracnose fungus) (Glomerella cingulata) | 506 |
| W9P9H8 | W9P9H8_FUSOX | Ferulic acid decarboxylase 1 (EC 4.1.1.102) (Phenacrylate decarboxylase) | FDC1 FOVG_12484 | Fusarium oxysporum f. sp. pisi HDV247 | 503 |
| W9NGN5 | W9NGN5_FUSOX | Ferulic acid decarboxylase 1 (EC 4.1.1.102) (Phenacrylate decarboxylase) | FDC1 FOVG_19288 | Fusarium oxysporum f. sp. pisi HDV247 | 517 |
| A0A086NHZ2 | A0A086NHZ2_METAN | Ferulic acid decarboxylase 1 (EC 4.1.1.102) (Phenacrylate decarboxylase) | FDC1 MANI_006214 | Metarhizium anisopliae (Entomophthora anisopliae) | 500 |
| A0A0D2LEN2 | A0A0D2LFN2_CRYGA | Ferulic acid decarboxylase 1 (EC 4.1.1.102) (Phenacrylate decarboxylase) | FDC1 I307_00579 | Cryptococcus gattii 99/473 | 501 |
| T2BN22 | T2BN22_CRYNH | Ferulic acid decarboxylase 1 (EC 4.1.1.102) (Phenacrylate decarboxylase) | FDC1 CNAG_03519 | Cryptococcus neoformans var. grubii serotype A (strain H99/ATCC 208821/CBS 10515/FGSC 9487) (Filobasidiella neoformans var. grubii) | 405 |
| T2BN40 | T2BN40_CRYNH | Ferulic acid decarboxylase 1 (EC 4.1.1.102) (Phenacrylate decarboxylase) | FDC1 CNAG_03519 | Cryptococcus neoformans var. grubii serotype A (strain H99/ATCC 208821/CBS 10515/FGSC 9487) (Filobasidiella neoformans var. grubii) | 447 |
| J9VVU7 | J9VVU7_CRYNH | Ferulic acid decarboxylase 1 (EC 4.1.1.102) (Phenacrylate decarboxylase) | FDC1 CNAG_03519 | Cryptococcus neoformans var. grubii serotype A (strain H99/ATCC 208821/CBS 10515/FGSC 9487) (Filobasidiella neoformans var. grubii) | 532 |
| S3D5R7 | S3D5R7_OPHP1 | Ferulic acid decarboxylase 1 (EC 4.1.1.102) (Phenacrylate decarboxylase) | FDC1 F503_04312 | Ophiostoma piceae (strain UAMH 11346) (Sap stain fungus) | 500 |
| Q2UP67 | Q2UP67_ASPOR | Ferulic acid decarboxylase 1 (EC 4.1.1.102) (Phenacrylate decarboxylase) | FDC1 AO090001000093 | Aspergillus oryzae (strain ATCC 42149/RIB 40) (Yellow koji mold) | 503 |
| A0A0D2WZP7 | A0A0D2WZP7CRYGA | Ferulic acid decarboxylase 1 (EC 4.1.1.102) (Phenacrylate decarboxylase) | FDC1 I311_00741 | Cryptococcus gattii NT-10 | 435 |
| G4YRJ8 | G4YRJ8_PHYSP | Ferulic acid decarboxylase 1 (EC 4.1.1.102) (Phenacrylate decarboxylase) | FDC1 PHYSODRAFT_258069 | Phytophthora sojae (strain P6497) (Soybean stem and root rot agent) (Phytophthora megasperma f. sp. glycines) | 468 |
| H3H3G9 | H3H3G9_PHYRM | Ferulic acid decarboxylase 1 (EC 4.1.1.102) (Phenacrylate decarboxylase) | FDC1 | Phytophthora ramorum (Sudden oak death agent) | 545 |
| A0A0AOWBD5 | A0A0AOWBD5_9PEZI | Phenolic acid decarboxylase (Fragment) | padB3 | Phomopsis liquidambaris | 180 |
| Q8I0Q7 | Q8I0Q7_NECHA | Putative uncharacterized protein (Fragment) | | Nectria haematococca | 489 |
| A0A074VCH2 | A0A074VCH2_9PEZI | UbiD-domain-containing protein | M437DRAFT_79329 | Aureobasidium melanogenum CBS 110374 | 375 |
| A0A0D2BJ27 | A0A0D2BJ27_9EURO | Uncharacterized protein | PV08_02858 | Exophiala spinifera | 282 |
| W9NFR4 | W9NFR4_FUSOX | Uncharacterized protein | FOVG_17226 | Fusarium oxysporum f. sp. pisi HDV247 | 177 |

Example 7: Selection of the Enzyme Mutants with Increased Activity by an In Vivo Assay in 96-Well Microplates Based on Exogenous 3MC 1.) In Vivo Assay in 96-Well Microplates Based on Exogenous 3MC (In Vivo 3)

This assay (IN VIVO 3) is based on the use of a bacterial strain (BL21(DE3), Novagen) transformed with the above expression vector that contains the coding sequences and lead to the production of the last two enzymes involved in the metabolic pathway converting 3-methylcrotonic acid into isobutene, i.e., the *Hypocrea atroviridis* Ferulic acid decarboxylase 1 variants and the Flavin prenyltransferase UbiX protein from *E. coli*. This transformed strain was first plated out onto LB-agar plates supplemented with the appropriate antibiotic. Cells were grown overnight at 30° C. until individual colonies reach the desired size. Single colonies were then picked and individually transferred into 500 µL of liquid LB medium supplemented with the appropriate antibiotic. Cell growth was carried out with shaking for 20 hours at 30° C. or 32° C. The LB cultures were used to inoculate 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 30° C., 32° C. or 36° C. in order to produce the two types of recombinant enzymes. The cell pellet containing these two overexpressed recombinant enzymes was then resuspended in 400 µL of minimum medium (MS pH 7.5, Phosphate 100 mM, Glucose 10 g·L$^{-1}$, MgSO$_4$ 1 mM) supplemented with 0.3 or 1 mM 3MC and incubated for a further 1 or 2 hours in a shaking incubator at 34° C. or 36° C., 700 rpm. During this step, the *Hypocrea atroviridis* Ferulic acid decarboxylase 1 variants catalyse the decarboxylation of 3-methylcrotonic acid into isobutene. After 5 min inactivation at 80° C., the isobutene produced was quantified by gas chromatography as followed. 100 µL of headspace gases from each enzymatic reaction are injected in a Brucker GC-450 system equipped with a Flame Ionization Detector (FID). Compounds present in samples were separated by chromatography using a RTX-1 column at 100° C. with a 1 mL·min$^{-1}$ constant flow of nitrogen as carrier gas. Upon injection, peak areas of isobutene were calculated.

2.) In Vivo Assay in 96-Well Microplates Based on Exogenous 3MC (In Vivo 4)

This assay is based on the use of a bacterial strain (BL21(DE3), Novagen) transformed with an expression vector pET25b (Novagen) that contains the coding sequences and lead to the production of the last enzyme involved in the metabolic pathway converting 3MC to isobutene; namely the *Hypocrea atroviridis* Ferulic acid decarboxylase 1 variants. In another variant, it can be co-transformed with an expression vector pRSFDuet (Novagen) that contains the coding sequences and lead to the production of the Flavin prenyltransferase UbiX protein from *E. coli*. This strain is first plated out onto LB-agar plates supplemented with the appropriate antibiotic. Cells were grown overnight at 32° C. until individual colonies reach the desired size. Single colonies were then picked and individually transferred into 500 µL of liquid LB medium supplemented with the appropriate antibiotic. Cell growth is carried out with shaking for 20 hours at 32° C. The LB cultures were used to inoculate 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 32° C. in order to produce the two types of recombinant enzymes. The cell pellet containing these overexpressed recombinant enzyme is then resuspended in 400 µL of minimum medium (MS pH 7.5, Phosphate 100 mM, Glucose 10 g·L–1, MgSO4 1 mM) supplemented with 1 mM or 10 mM 3MC and incubated for a further 30 minutes or 4 hours in a shaking incubator at 34° C. or 36° C., 700 rpm. During this step, the *Hypocrea atroviridis* Ferulic acid decarboxylase 1 variants catalyse the decarboxylation of 3MC into IBN. After 5 min inactivation at 80° C., the IBN produced is quantified by gas chromatography as followed. 100 µL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL·min-1 constant flow of nitrogen as carrier gas. Upon injection, peak areas of isobutene were calculated.

Example 8: Identification of Variants with Multiple Mutations of *Hypocrea atroviridis* Ferulic Acid Decarboxylase 1 with Further Increased Activity for the Reaction of Conversion of 3-Methylcrotonic Acid into Isobutene Libraries of mutants have been created by mutagenesis, using the *Hypocrea atroviridis* Ferulic acid decarboxylase 1 (SEQ ID NO: 1) as template. Several variants with an enhanced activity in converting 3-methylcrotonic acid into isobutene have been identified through in vivo screening assays as described above, using either the IN VIVO 2, the IN VIVO 3 or the IN VIVO 4 assay.

The list showing improving variants is presented in the following Table 6. The increase in activity is described relative to the wild-type enzyme (with "+" representing a low increase in activity and "+++++" representing a high increase in activity).

The mutations involved in the variants of the *Hypocrea atroviridis* Ferulic acid decarboxylase 1 with increased activity are summarized in Table 7.

TABLE 6

List of *Hypocrea atroviridis* Ferulic acid decarboxylase 1 variants with multiple mutations presenting an increase in isobutene production from 3-methylcrotonic acid.

| Mutations | Activity relative to WT | Assay |
|---|---|---|
| Q29N-D351N | + | IN VIVO 2 |
| Q29N-Q448W | + | IN VIVO 2 |
| T405M-D420L | + | IN VIVO 2 |
| D351N-T405M | + | IN VIVO 2 |
| Q29N-T405M | + | IN VIVO 2 |
| D351R-T405M-V445P-Q448W | + | IN VIVO 2 |
| D351R-T405M-V445P | + | IN VIVO 2 |
| T405M-Q448W | + | IN VIVO 2 |
| D351R-T405M-Q448W | + | IN VIVO 2 |
| E25N-N31G-T405M | + | IN VIVO 2 |
| Q29N-T405M-T429A | + | IN VIVO 2 |
| Q29N-D351R-T405M-T429A-V445P-Q448W | + | IN VIVO 2 |
| E25N-Q29N-T405M-G435M-V445P | + | IN VIVO 2 |
| Q29N-T405M-Q448W | + | IN VIVO 2 |
| E25N-Q29N-N31G-T405M-G435M-V445P | + | IN VIVO 2 |
| Q29H-N31G-T405M-T429A | + | IN VIVO 2 |
| E25N-Q29N-N31G-D351R-T405M-V445P | + | IN VIVO 2 |
| Q29N-D351N-T405M-Q448W | + | IN VIVO 2 |
| N31G-T405M-V445P | + | IN VIVO 2 |
| N31G-D351R-T405M-T429A-V445P | + | IN VIVO 2 |
| E25N-Q29N-N31G-T405M-T429A | + | IN VIVO 2 |
| Q29N-N31G-D351R-T405M-T429A | + | IN VIVO 2 |
| N31G-T405M-D420L-T429A-V445P | + | IN VIVO 2 |
| E25N-Q29H-D351R-T405M-V445P-Q448W | + | IN VIVO 2 |
| E25N-D351R-T405M-G435M-V445P-Q448W | + | IN VIVO 2 |
| S86N-T405M-T429A-G435M-V445P-Q448W | + | IN VIVO 2 |
| E25N-T405M-T429A | + | IN VIVO 2 |
| E25N-Q29N-N31G-D351R-T405M-T429A | + | IN VIVO 2 |
| Q29N-D351R-T405M-D414N-T429A-V445P-Q448W | + | IN VIVO 2 |
| N31G-D351R-T405M-T429A-G435M-V445P | + | IN VIVO 2 |
| E25N-N31G-T405M-T429A-V445P | + | IN VIVO 2 |
| E25N-D351R-T405M-T429A-V445P | + | IN VIVO 2 |
| E25N-N31G-T405M-T429A-Q448W | + | IN VIVO 2 |
| E25N-N31G-T405M-Q448W | + | IN VIVO 2 |
| E25N-Q29N-T405M-T429A-Q448W | + | IN VIVO 2 |
| Q29N-N31G-D351R-T405M-T429A-G435M-V445P | + | IN VIVO 2 |
| N31G-T405M-Q448W | + | IN VIVO 2 |
| N31G-T405M-D420L-T429A-V445P-Q448W | + | IN VIVO 2 |
| Q29N-N31G-D351G-T405M-T429A-V445P | + | IN VIVO 2 |
| Q29N-T405M-T429A-G435M-V445P-Q448W | + | IN VIVO 2 |
| E25N-N31G-D351R-T405M-V445P-Q448W | + | IN VIVO 2 |
| Q29N-N31G-T405M-T429A-V445P | + | IN VIVO 2 |
| E25N-N31G-D351R-T405M-G435M-V445P-Q448W | + | IN VIVO 2 |
| N31G-D351R-T405M-T429A-Q448W | + | IN VIVO 2 |
| D12N-Q29N-N31G-T405M-T429A-V445P-Q448W | + | IN VIVO 2 |

TABLE 6-continued

List of *Hypocrea atroviridis* Ferulic acid decarboxylase 1 variants with multiple mutations presenting an increase in isobutene production from 3-methylcrotonic acid.

| Mutations | Activity relative to WT | Assay |
|---|---|---|
| Q29N-N31G-T405M-T429A-Q448W | + | IN VIVO 2 |
| E25N-T405M-T429A-V445P-Q448W | + | IN VIVO 2 |
| E25N-N31G-T405M-T429A-G435M-V445P-Q448W | + | IN VIVO 2 |
| E25N-Q29N-N31G-T405M-T429A-V445P-Q448W | + | IN VIVO 2 |
| E25N-N31G-T405M-T429A-V445P-Q448W | + | IN VIVO 2 |
| E25N-N31G-D351R-T405M-T429A-V445P-Q448W | ++ | IN VIVO 3 |
| E25N-N31G-D351R-T405M-T429A-V445P-Q448W-P120K | ++ | IN VIVO 3 |
| E25N-N31G-D351R-T405M-T429A-V445P-Q448W-H303S | ++ | IN VIVO 3 |
| E25N-N31G-D351G-T405M-T429A-V445P-Q448W | ++ | IN VIVO 3 |
| E25N-N31G-D351R-T405M-T429A-V445P-Q448W-N264D | ++ | IN VIVO 3 |
| E25N-N31G-D351R-T405M-T429A-V445P-Q448W-R392L | ++ | IN VIVO 3 |
| E25N-N31G-D351R-T405M-T429A-V445P-Q448W-L221C | ++ | IN VIVO 3 |
| E25N-N31G-D351R-T405M-T429A-V445P-Q448W-G305A | ++ | IN VIVO 3 |
| E25N-N31G-D351R-T405M-T429A-V445P-Q448W-S85A | ++ | IN VIVO 3 |
| E25N-N31G-D351R-T405M-T429A-V445P-Q448W-Q214V | ++ | IN VIVO 3 |
| E25N-N31G-D351R-T405M-T429A-V445P-Q448W-F404Y | ++ | IN VIVO 3 |
| E25N-N31G-D351R-T405M-T429A-V445P-Q448W-P402V | ++ | IN VIVO 3 |
| E25N-N31G-D351R-T405M-T429A-V445P-Q448W-T228L | ++ | IN VIVO 3 |
| E25N-N31G-D351R-T405M-T429A-V445P-Q448W-I119T | ++ | IN VIVO 3 |
| E25N-N31G-D351R-T405M-T429A-V445P-Q448W-A10L | ++ | IN VIVO 3 |
| E25N-N31G-D351R-T405M-T429A-V445P-Q448W-S484A | ++ | IN VIVO 3 |
| E25N-N31G-D351R-T405M-T429A-V445P-Q448W-Q214E | ++ | IN VIVO 3 |
| E25N-N31G-D351R-T405M-T429A-V445P-Q448W-Q214A | ++ | IN VIVO 3 |
| E25N-N31G-D351R-T405M-T429A-V445P-Q448W-A211E | ++ | IN VIVO 3 |
| E25N-N31G-D351R-T405M-T429A-V445P-Q448W-N501M | ++ | IN VIVO 3 |
| E25N-N31G-D351R-T405M-T429A-V445P-Q448W-Q214F | ++ | IN VIVO 3 |
| E25N-N31G-D351R-T405M-T429A-V445P-Q448W-T228V | ++ | IN VIVO 3 |
| E25N-N31G-D351R-T405M-T429A-V445P-Q448W-D57N | ++ | IN VIVO 3 |
| E25N-N31G-D351R-T405M-T429A-V445P-Q448W-D512E | ++ | IN VIVO 3 |
| E25N-N31G-D351R-T405M-T429A-V445P-Q448W-S484G | ++ | IN VIVO 3 |
| E25N-N31G-D351R-T405M-T429A-V445P-Q448W-A149V | ++ | IN VIVO 3 |
| E25N-N31G-D351R-T405M-T429A-V445P-Q448W-S8N | ++ | IN VIVO 3 |
| E25N-N31G-D351R-T405M-T429A-V445P-Q448W-A10H | ++ | IN VIVO 3 |
| E25N-N31G-D351R-T405M-T429A-V445P-Q448W-N117A | ++ | IN VIVO 3 |
| E25N-N31G-D351R-T405M-T429A-V445P-Q448W-V132C | ++ | IN VIVO 3 |
| E25N-N31G-D351R-T405M-T429A-V445P-Q448W-C175G | ++ | IN VIVO 3 |
| E25N-N31G-D351R-T405M-T429A-V445P-Q448W-C175K | ++ | IN VIVO 3 |
| E25N-N31G-D351R-T405M-T429A-V445P-Q448W-C175S | ++ | IN VIVO 3 |
| E25N-N31G-D351R-T405M-T429A-V445P-Q448W-S187T | ++ | IN VIVO 3 |
| E25N-N31G-D351R-T405M-T429A-V445P-Q448W-A193T | ++ | IN VIVO 3 |
| E25N-N31G-D351R-T405M-T429A-V445P-Q448W-I197M | ++ | IN VIVO 3 |
| E25N-N31G-D351R-T405M-T429A-V445P-Q448W-A222C | ++ | IN VIVO 3 |
| E25N-N31G-D351R-T405M-T429A-V445P-Q448W-T228A | ++ | IN VIVO 3 |
| E25N-N31G-D351R-T405M-T429A-V445P-Q448W-V247A | ++ | IN VIVO 3 |
| E25N-N31G-D351R-T405M-T429A-V445P-Q448W-A342G | ++ | IN VIVO 3 |
| E25N-N31G-D351R-T405M-T429A-V445P-Q448W-T399N | ++ | IN VIVO 3 |
| E25N-N31G-D351R-T405M-T429A-V445P-Q448W-F440V | ++ | IN VIVO 3 |

TABLE 6-continued

List of *Hypocrea atroviridis* Ferulic acid decarboxylase 1 variants with multiple mutations presenting an increase in isobutene production from 3-methylcrotonic acid.

| Mutations | Activity relative to WT | Assay |
|---|---|---|
| E25N-N3IG-D351R-T405M-T429A-V445P-Q448W-A460P | ++ | IN VIVO 3 |
| E25N-N3IG-D351R-T405M-T429A-V445P-Q448W-K488A | ++ | IN VIVO 3 |
| E25N-N3IG-D351R-T405M-T429A-V445P-Q448W-N501G | ++ | IN VIVO 3 |
| E25N-N3IG-D351R-T405M-T429A-V445P-Q448W-S502N | ++ | IN VIVO 3 |
| E25N-N3IG-D351R-T405M-T429A-V445P-Q448W-L506Y | ++ | IN VIVO 3 |
| E25N-N3IG-D351R-T405M-T429A-V445P-Q448W-S3C-S861-Q162P-T384Y-R392A | +++ | IN VIVO 3 |
| E25N-N3IG-D351R-T405M-T429A-V445P-Q448W-Q162N-T228L-R392A | +++ | IN VIVO 3 |
| E25N-N3IG-D351R-T405M-T429A-V445P-Q448W-Q162N-R392A | +++ | IN VIVO 3 |
| E25N-N3IG-D351R-T405M-T429A-V445P-Q448W-Q162N-T228L-R392A-I461V-S494R | +++ | IN VIVO 3 |
| E25N-N3IG-D351R-T405M-T429A-V445P-Q448W-S85A-Q162N-Q214H-T228L-G338P-I461V | +++ | IN VIVO 3 |
| E25N-N3IG-D351R-T405M-T429A-V445P-Q448W-C175G-T228L-R392A-T399R-S494R | +++ | IN VIVO 3 |
| E25N-N3IG-D351R-T405M-T429A-V445P-Q448W-S85A-Q162N-C175G-T228L-G338P-T399R-S494R | +++ | IN VIVO 3 |
| E25N-N3IG-D351R-T405M-T429A-V445P-Q448W-S85A-Q162N-T228L-G338P-S494R | +++ | IN VIVO 3 |
| E25N-N3IG-D351R-T405M-T429A-V445P-Q448W-S85A-Q162N-C175G-T228L-G338P-T399R-I461V-S494R | +++ | IN VIVO 3 |
| E25N-N3IG-D351R-T405M-T429A-V445P-Q448W-S85A-Q162N-C175G-T228L-G338P-R392A-I461M-S494R | +++ | IN VIVO 3 |
| E25N-N3IG-D351R-T405M-T429A-V445P-Q448W-Q162N-T228L-G338P-R392A-I461V | +++ | IN VIVO 3 |
| E25N-N3IG-D351R-T405M-T429A-V445P-Q448W-S85A-Q162N-C175G-T228L-G338P-R392A-I461V-S494R | +++ | IN VIVO 3 |
| E25N-N3IG-D351R-T405M-T429A-V445P-Q448W-S85A-C175G-T228L-G338P-R392A-T399R-I461V-S494R | +++ | IN VIVO 3 |
| E25N-N3IG-D351R-T405M-T429A-V445P-Q448W-S85A-Q162N-C175G-T228L-G338P-R392A-I461V-S494R | +++ | IN VIVO 3 |
| E25N-N3IG-D351R-T405M-T429A-V445P-Q448W-T228L-G338P-R392A-I461V | +++ | IN VIVO 3 |
| E25N-N3IG-D351R-T405M-T429A-V445P-Q448W-G305A-P402V | +++ | IN VIVO 3 |
| E25N-N3IG-D351R-T405M-T429A-V445P-Q448W-G305A-F404Y | +++ | IN VIVO 3 |
| E25N-N3IG-D351R-T405M-T429A-V445P-Q448W-G305A-P402V-F404Y | +++ | IN VIVO 3 |
| E25N-N3IG-D351R-T405M-T429A-V445P-Q448W-I461V-S494R-P15T | ++++ | IN VIVO 4 |
| E25N-N3IG-S85A-Q162N-C175G-T228L-G338P-D351R-R392A-T405M-T429A-V445P-Q448W-I461V-S494R-D30G | ++++ | IN VIVO 4 |
| E25N-N3IG-S85A-Q162N-C175G-T228L-G338P-D351R-R392A-T405M-T429A-V445P-Q448W-I461V-S494R-D30H | ++++ | IN VIVO 4 |
| E25N-N3IG-S85A-Q162N-C175G-T228L-G338P-D351R-R392A-T405M-T429A-V445P-Q448W-I461V-S494R-D30R | ++++ | IN VIVO 4 |
| E25N-N3IG-S85A-Q162N-C175G-T228L-G338P-D351R-R392A-T405M-T429A-V445P-Q448W-I461V-S494R-N65W | ++++ | IN VIVO 4 |
| E25N-N3IG-S85A-Q162N-C175G-T228L-G338P-D351R-R392A-T405M-T429A-V445P-Q448W-I461V-S494R-N65L | ++++ | IN VIVO 4 |
| E25N-N3IG-S85A-Q162N-C175G-T228L-G338P-D351R-R392A-T405M-T429A-V445P-Q448W-I461V-S494R-K70L | ++++ | IN VIVO 4 |
| E25N-N3IG-S85A-Q162N-C175G-T228L-G338P-D351R-R392A-T405M-T429A-V445P-Q448W-I461V-S494R-G72R | ++++ | IN VIVO 4 |
| E25N-N3IG-S85A-Q162N-C175G-T228L-G338P-D351R-R392A-T405M-T429A-V445P-Q448W-I461V-S494R-P80L | ++++ | IN VIVO 4 |
| E25N-N3IG-S85A-Q162N-C175G-T228L-G338P-D351R-R392A-T405M-T429A-V445P-Q448W-I461V-S494R-P87V | ++++ | IN VIVO 4 |
| E25N-N3IG-S85A-Q162N-C175G-T228L-G338P-D351R-R392A-T405M-T429A-V445P-Q448W-I461V-S494R-P87I | ++++ | IN VIVO 4 |
| E25N-N3IG-S85A-Q162N-C175G-T228L-G338P-D351R-R392A-T405M-T429A-V445P-Q448W-I461V-S494R-R90L | ++++ | IN VIVO 4 |
| E25N-N3IG-S85A-Q162N-C175G-T228L-G338P-D351R-R392A-T405M-T429A-V445P-Q448W-I461V-S494R-T103L | ++++ | IN VIVO 4 |
| E25N-N3IG-S85A-Q162N-C175G-T228L-G338P-D351R-R392A-T405M-T429A-V445P-Q448W-I461V-S494R-S105W | ++++ | IN VIVO 4 |
| E25N-N3IG-S85A-Q162N-C175G-T228L-G338P-D351R-R392A-T405M-T429A-V445P-Q448W-I461V-S494R-S105F | ++++ | IN VIVO 4 |
| E25N-N3IG-S85A-Q162N-C175G-T228L-G338P-D351R-R392A-T405M-T429A-V445P-Q448W-I461V-S494R-D108R | ++++ | IN VIVO 4 |
| E25N-N3IG-S85A-Q162N-C175G-T228L-G338P-D351R-R392A-T405M-T429A-V445P-Q448W-I461V-S494R-D108W | ++++ | IN VIVO 4 |
| E25N-N3IG-S85A-Q162N-C175G-T228L-G338P-D351R-R392A-T405M-T429A-V445P-Q448W-I461V-S494R-I126P | ++++ | IN VIVO 4 |
| E25N-N3IG-S85A-Q162N-C175P-T228L-G338P-D351R-R392A-T405M-T429A-V445P-Q448W-I461V-S494R | ++++ | IN VIVO 4 |
| E25N-N3IG-S85A-Q162N-C175G-T228L-G338P-D351R-R392A-T405M-T429A-V445P-Q448W-I461V-S494R-W176F | ++++ | IN VIVO 4 |
| E25N-N3IG-S85A-Q162N-C175G-T228L-G338P-D351R-R392A-T405M-T429A-V445P-Q448W-I461V-S494R-G213L | ++++ | IN VIVO 4 |
| E25N-N3IG-S85A-Q162N-C175G-T228L-G338P-D351R-R392A-T405M-T429A-V445P-Q448W-I461V-S494R-G213P | ++++ | IN VIVO 4 |
| E25N-N3IG-S85A-Q162N-C175G-T228L-G338P-D351R-R392A-T405M-T429A-V445P-Q448W-I461V-S494R-G305D | ++++ | IN VIVO 4 |
| E25N-N3IG-S85A-Q162N-C175G-T228L-G338P-D351R-R392A-T405M-T429A-V445P-Q448W-I461V-S494R-G305R | ++++ | IN VIVO 4 |
| E25N-N3IG-S85A-Q162N-C175G-T228L-G338P-D351R-R392A-T405M-T429A-V445P-Q448W-I461V-S494R-P306R | ++++ | IN VIVO 4 |

TABLE 6-continued

List of *Hypocrea atroviridis* Ferulic acid decarboxylase 1 variants with multiple mutations presenting an increase in isobutene production from 3-methylcrotonic acid.

| Mutations | Activity relative to WT | Assay |
|---|---|---|
| E25N-N31G-S85A-Q162N-C175G-T228L-G338P-D351R-R392A-T405M-T429A-V445P-Q448W-I461V-S494R-P306S | ++++ | IN VIVO 4 |
| E25N-N31G-S85A-Q162N-C175G-T228L-G338P-D351R-R392A-T405M-T429A-V445P-Q448W-I461V-S494R-C326P | ++++ | IN VIVO 4 |
| E25N-N31G-S85A-Q162N-C175G-T228L-G338S-D351R-R392A-T405M-T429A-V445P-Q448W-I461V-S494R | ++++ | IN VIVO 4 |
| E25N-N31G-S85A-Q162N-C175G-T228L-D351R-R392A-T405M-T429A-V445P-Q448W-I461V-S494R | ++++ | IN VIVO 4 |
| E25N-N31G-S85A-Q162N-C175G-T228L-G338P-D351R-R392A-T405M-T429A-V445P-Q448W-I461V-S494R-A341I | ++++ | IN VIVO 4 |
| E25N-N31G-S85A-Q162N-C175G-T228L-G338P-D351V-R392A-T405M-T429A-V445P-Q448W-I461V-S494R | ++++ | IN VIVO 4 |
| E25N-N31G-S85A-Q162N-C175G-T228L-G338P-D351R-R392A-T405M-T429A-V445P-Q448W-I461V-S494R | ++++ | IN VIVO 4 |
| E25N-N31G-S85A-Q162N-C175G-T228L-G338P-D351R-R392A-T405M-T429A-V445P-Q448W-I461V-S494R-P402H | ++++ | IN VIVO 4 |
| E25N-N31G-S85A-Q162N-C175G-T228L-G338P-D351R-R392A-T405M-T429A-V445P-Q448W-I461V-S494R-I406Q | ++++ | IN VIVO 4 |
| E25N-N31G-S85A-Q162N-C175G-T228L-G338P-D351R-R392A-T405M-T429A-V445P-Q448W-I461N-S494R | ++++ | IN VIVO 4 |
| E25N-N31G-S85A-Q162N-C175G-T228L-G338P-D351R-R392A-T405M-T429A-V445P-Q448W-I461V-S494R-T103I-D111C | ++++ | IN VIVO 4 |
| E25N-N31G-S85A-Q162N-C175G-T228L-G338P-D351R-R392A-T405M-T429A-V445P-Q448W-I461V-S494R-E14D-P87A | ++++ | IN VIVO 4 |
| E25N-N31G-S85A-Q162N-C175G-T228L-G338P-D351R-R392A-T405M-T429A-V445P-Q448W-I461V-S494R-W176F-L511I | ++++ | IN VIVO 4 |
| E25N-N31G-S85A-Q162N-C175G-T228L-G338P-D351R-R392A-T405M-T429A-V445P-Q448W-I461V-S494R-A352L | ++++ | IN VIVO 4 |
| E25N-N31G-S85A-Q162N-C175G-T228L-G338P-D351R-R392A-T405M-T429A-V445P-Q448W-I461V-S494R-A352G | ++++ | IN VIVO 4 |
| E25N-N31G-S85A-Q162N-C175G-T228L-G338P-D351R-R392A-T405M-T429A-V445P-Q448W-I461V-S494R-T278I-C326P | ++++ | IN VIVO 4 |
| E25N-N31G-S85A-Q162N-C175G-T228L-G338P-D351R-R392A-T405M-T429A-V445P-Q448W-I461V-S494R-A341I-G386N-D395C | ++++ | IN VIVO 4 |
| E25N-N31G-S85A-Q162N-C175G-T228L-G338P-D351A-R392A-T405M-T429A-V445P-Q448W-I461V-S494R-C349S | ++++ | IN VIVO 4 |
| E25N-N31G-S85A-Q162N-C175G-T228L-G338P-D351R-R392A-T405M-T429A-V445P-Q448W-I461V-S494R-K7R-W176F | ++++ | IN VIVO 3 |
| E25N-N31G-S85A-Q162N-C175G-T228L-G338P-D351R-R392A-T405M-T429A-V445P-Q448W-I461V-S494R-R84C-K493R | +++++ | IN VIVO 2 |
| E25N-N31G-S85A-Q162N-C175G-T228L-G338P-D351R-R392A-T405M-T429A-V445P-Q448W-I461V-S494R-P87W-K159C | ++++ | IN VIVO 2 |
| E25N-N31G-S85A-Q162N-C175G-T228L-G338P-D351R-R392A-T405M-T429A-V445P-Q448W-I461V-S494R-P87C-K488N-Q496A | ++++ | IN VIVO 2 |
| E25N-N31G-S85A-Q162N-C175G-T228L-G338P-D351R-R392A-T405M-T429A-V445P-Q448W-I461V-S494R-E89F-Q496F | ++++ | IN VIVO 2 |
| E25N-N31G-S85A-Q162N-C175G-T228L-G338P-D351R-K377H-P402V-F404Y-T405M-T429A-V445P-Q448W | ++++ | IN VIVO 4 |
| E25N-N31G-S85A-Q162N-C175G-T228L-G338P-D351R-P402V-F404Y-T405M-T429A-V445P-Q448W-I461V-S494R-F404Y | ++++ | IN VIVO 4 |
| E25N-N31G-S85A-Q162N-C175G-T228L-G338P-D351R-P402V-F404Y-T405M-T429A-V445P-Q448W-I461V-S494R-G305A-K377H-F404Y | ++++ | IN VIVO 4 |
| E25N-N31G-S85A-Q162N-C175G-T228L-G338P-D351R-P402V-F404Y-T405M-T429A-V445P-Q448W-I461V-S494R-G305A-P306F-F404Y | ++++ | IN VIVO 4 |
| E25N-N31G-S85A-Q162N-C175G-T228L-G338P-D351R-P402V-F404Y-T405M-T429A-V445P-Q448W-I461V-S494R-K377H-F404Y | ++++ | IN VIVO 4 |
| E25N-N31G-S85A-Q162N-C175G-T228L-G338P-D351R-P402V-F404Y-T405M-T429A-V445P-Q448W-I461V-S494R-P306F-F404Y | ++++ | IN VIVO 4 |
| E25N-N31G-S85A-Q162N-C175G-T228L-G338P-D351R-P402V-F404Y-T405M-T429A-V445P-Q448W-I461V-S494R-P306F-K377H | ++++ | IN VIVO 4 |
| E25N-N31G-S85A-G305A-D351R-P402V-F404Y-T405M-T429A-V445P-Q448W-I461V-S494R-P306F-K377H-F404Y | ++++ | IN VIVO 4 |
| E25N-N31G-S85A-G305A-D351R-P402V-F404Y-T405M-T429A-V445P-Q448W-D12A | ++++ | IN VIVO 4 |
| E25N-N31G-S85A-G305A-D351R-P402V-F404Y-T405M-T429A-V445P-Q448W-D35T | ++++ | IN VIVO 4 |
| E25N-N31G-S85A-G305A-D351R-P402V-F404Y-T405M-T429A-V445P-Q448W-A60V | ++++ | IN VIVO 4 |
| E25N-N31G-S85A-G305A-D351R-P402V-F404Y-T405M-T429A-V445P-Q448W-K70I | ++++ | IN VIVO 4 |
| E25N-N31G-S85A-G305A-D351R-P402V-F404Y-T405M-T429A-V445P-Q448W-K70L | ++++ | IN VIVO 4 |
| E25N-N31G-S85A-G305A-D351R-P402V-F404Y-T405M-T429A-V445P-Q448W-P87F | ++++ | IN VIVO 4 |
| E25N-N31G-S85A-G305A-D351R-P402V-F404Y-T405M-T429A-V445P-Q448W-P87L | ++++ | IN VIVO 4 |
| E25N-N31G-S85A-G305A-D351R-P402V-F404Y-T405M-T429A-V445P-Q448W-P87M | ++++ | IN VIVO 4 |
| E25N-N31G-S85A-G305A-D351R-P402V-F404Y-T405M-T429A-V445P-Q448W-P87V | ++++ | IN VIVO 4 |
| E25N-N31G-S85A-G305A-D351R-P402V-F404Y-T405M-T429A-V445P-Q448W-P87W | ++++ | IN VIVO 4 |
| E25N-N31G-S85A-G305A-D351R-P402V-F404Y-T405M-T429A-V445P-Q448W-A99P | ++++ | IN VIVO 4 |
| E25N-N31G-S85A-G305A-D351R-P402V-F404Y-T405M-T429A-V445P-Q448W-P101I | ++++ | IN VIVO 4 |
| E25N-N31G-S85A-G305A-D351R-P402V-F404Y-T405M-T429A-V445P-Q448W-P101L | ++++ | IN VIVO 4 |
| E25N-N31G-S85A-G305A-D351R-P402V-F404Y-T405M-T429A-V445P-Q448W-P102L | ++++ | IN VIVO 4 |
| E25N-N31G-S85A-G305A-D351R-P402V-F404Y-T405M-T429A-V445P-Q448W-T103L | ++++ | IN VIVO 4 |
| E25N-N31G-S85A-G305A-D351R-P402V-F404Y-T405M-T429A-V445P-Q448W-S105L | ++++ | IN VIVO 4 |
| E25N-N31G-S85A-G305A-D351R-P402V-F404Y-T405M-T429A-V445P-Q448W-D108R | ++++ | IN VIVO 4 |

TABLE 6-continued

List of *Hypocrea atroviridis* Ferulic acid decarboxylase 1 variants with multiple mutations presenting an increase in isobutene production from 3-methylcrotonic acid.

| Mutations | Activity relative to WT | Assay |
|---|---|---|
| E25N-N3IG-G305A-D351R-P402V-F404Y-T405M-T429A-V445P-Q448W-K189I | ++++ | IN VIVO 4 |
| E25N-N3IG-G305A-D351R-P402V-F404Y-T405M-T429A-V445P-Q448W-A193I | ++++ | IN VIVO 4 |
| E25N-N3IG-G305A-D351R-P402V-F404Y-T405M-T429A-V445P-Q448W-E215C | ++++ | IN VIVO 4 |
| E25N-N3IG-G305A-D351R-P402V-F404Y-T405M-T429A-V445P-Q448W-A244F | ++++ | IN VIVO 4 |
| E25N-N3IG-G305A-D351R-P402V-F404Y-T405M-T429A-V445P-Q448W-C326A | ++++ | IN VIVO 4 |
| E25N-N3IG-G305A-D351R-P402V-F404Y-T405M-T429A-V445P-Q448W-D375L | ++++ | IN VIVO 4 |
| E25N-N3IG-G305A-D351R-P402V-F404Y-T405M-T429A-V445P-Q448W-D443N | ++++ | IN VIVO 4 |
| E25N-N3IG-G305A-D351R-P402V-F404Y-T405M-T429A-V445P-Q448W-A460F | ++++ | IN VIVO 4 |
| E25N-N3IG-G305A-D351R-P402V-F404Y-T405M-T429A-V445P-Q448W-P102L-S484A | ++++ | IN VIVO 4 |
| E25N-N3IG-G305A-D351R-P402V-F404Y-T405M-T429A-V445P-Q448W-D108K-Y160F | ++++ | IN VIVO 4 |
| E25N-N3IG-G305A-D351R-P402V-F404Y-T405M-T429A-V445P-Q448W-F11Y-D512S | ++++ | IN VIVO 4 |
| E25N-N3IG-D351R-T405M-T429A-V445P-Q448W-S85T-T103M-Q162H-C175W-T228P-G338A-R392A-I461M | ++++ | IN VIVO 4 |
| E25N-N3IG-G305A-D351R-P402V-F404Y-T405M-T429A-V445P-Q448W-P87F | ++++ | IN VIVO 4 |
| E25N-N3IG-G305A-D351R-P402V-F404Y-T405M-T429A-V445P-Q448W-S3G | ++++ | IN VIVO 4 |
| E25N-N3IG-G305A-D351R-P402V-F404Y-T405M-T429A-V445P-Q448W-T4A | ++++ | IN VIVO 4 |
| E25N-N3IG-G305A-D351R-P402V-F404Y-T405M-T429A-V445P-Q448W-T5S | ++++ | IN VIVO 4 |
| E25N-N3IG-G305A-D351R-P402V-F404Y-T405M-T429A-V445P-Q448W-A10F | ++++ | IN VIVO 4 |
| E25N-N3IG-G305A-D351R-P402V-F404Y-T405M-T429A-V445P-Q448W-A10P | ++++ | IN VIVO 4 |
| E25N-N3IG-G305A-D351R-P402V-F404Y-T405M-T429A-V445P-Q448W-A10T | ++++ | IN VIVO 4 |
| E25N-N3IG-G305A-D351R-P402V-F404Y-T405M-T429A-V445P-Q448W-I67R | ++++ | IN VIVO 4 |
| E25N-N3IG-G305A-D351R-P402V-F404Y-T405M-T429A-V445P-Q448W-I67V | ++++ | IN VIVO 4 |
| E25N-N3IG-G305A-D351R-P402V-F404Y-T405M-T429A-V445P-Q448W-D71G | ++++ | IN VIVO 4 |
| E25N-N3IG-G305A-D351R-P402V-F404Y-T405M-T429A-V445P-Q448W-A99N | ++++ | IN VIVO 4 |
| E25N-N3IG-G305A-D351R-P402V-F404Y-T405M-T429A-V445P-Q448W-A149S | ++++ | IN VIVO 4 |
| E25N-N3IG-G305A-D351R-P402V-F404Y-T405M-T429A-V445P-Q448W-Q154K | ++++ | IN VIVO 4 |
| E25N-N3IG-G305A-D351R-P402V-F404Y-T405M-T429A-V445P-Q448W-A193T | ++++ | IN VIVO 4 |
| E25N-N3IG-G305A-D351R-P402V-F404Y-T405M-T429A-V445P-Q448W-A193V | ++++ | IN VIVO 4 |
| E25N-N3IG-G305A-D351R-P402V-F404Y-T405M-T429A-V445P-Q448W-Q206F | ++++ | IN VIVO 4 |
| E25N-N3IG-G305A-D351R-P402V-F404Y-T405M-T429A-V445P-Q448W-Q214R | ++++ | IN VIVO 4 |
| E25N-N3IG-G305A-D351R-P402V-F404Y-T405M-T429A-V445P-Q448W-A232V | ++++ | IN VIVO 4 |
| E25N-N3IG-G305A-D351R-P402V-F404Y-T405M-T429A-V445P-Q448W-M284L | ++++ | IN VIVO 4 |
| E25N-N3IG-G305A-D351R-P402V-F404Y-T405M-T429A-V445P-Q448W-H303P | ++++ | IN VIVO 4 |
| E25N-N3IG-G305A-D351R-P402V-F404Y-T405M-T429A-V445P-Q448W-K462N | ++++ | IN VIVO 4 |
| E25N-N3IG-G305A-D351R-P402V-F404Y-T405M-T429A-V445P-Q448W-S494R-G305A-P402V-F404Y | ++++ | IN VIVO 4 |
| E25N-N3IG-S85A-Q162N-C175G-T228L-D351R-R392A-T405M-T429A-V445P-Q448W-I461V-S494R-G305A-P402V-F404Y | +++++ | IN VIVO 2 |
| E25N-N3IG-S85A-Q162N-C175G-T228L-D351R-R392A-T405M-T429A-V445P-Q448W-I461V-S494R-L228T-G305A-P402V-F404Y | +++++ | IN VIVO 2 |
| E25N-N3IG-S85A-Q162N-C175G-T228L-D351R-R392A-T405M-T429A-V445P-Q448W-I461V-S494R-G305A-K377H-P402V-F404Y | +++++ | IN VIVO 2 |
| E25N-N3IG-S85A-Q162N-C175G-T228L-D351R-R392A-T405M-T429A-V445P-Q448W-I461V-S494R-L228T-G305A-F404Y | +++++ | IN VIVO 2 |
| E25N-N3IG-S85A-Q162N-C175G-T228L-D351R-R392A-T405M-T429A-V445P-Q448W-I461V-S494R-G305A-K377H-F404Y | +++++ | IN VIVO 2 |
| E25N-N3IG-S85A-Q162N-C175G-T228L-D351R-R392A-T405M-T429A-V445P-Q448W-I461V-S494R-G305A-F404Y | +++++ | IN VIVO 2 |
| E25N-N3IG-S85A-Q162N-C175G-T228L-D351R-R392A-T405M-T429A-V445P-Q448W-I461V-S494R-G305A-K377H-P402V-F404Y | +++++ | IN VIVO 2 |
| E25N-N3IG-S85A-Q162N-C175G-T228L-D351R-G305A-D351R-R392A-T405M-T429A-V445P-Q448W-I461V-S494R-K377H | +++++ | IN VIVO 2 |
| E25N-N3IG-S85A-Q162N-C175G-T228L-G305A-D351R-R392A-T405M-T429A-V445P-Q448W-I461V-S494R-S2N | +++++ | IN VIVO 3 |
| E25N-N3IG-S85A-Q162N-C175G-T228L-G305A-D351R-R392A-T405M-T429A-V445P-Q448W-I461V-S494R-A10K | +++++ | IN VIVO 3 |
| E25N-N3IG-S85A-Q162N-C175G-T228L-G305A-D351R-R392A-T405M-T429A-V445P-Q448W-I461V-S494R-P13S | +++++ | IN VIVO 2 |
| E25N-N3IG-S85A-Q162N-C175G-T228L-G305A-D351R-R392A-T405M-T429A-V445P-Q448W-I461V-S494R-A69N | +++++ | IN VIVO 3 |
| E25N-N3IG-S85A-Q162N-C175G-T228L-G305A-D351R-R392A-T405M-T429A-V445P-Q448W-I461V-S494R-A106T | +++++ | IN VIVO 3 |

TABLE 6-continued

List of *Hypocrea atroviridis* Ferulic acid decarboxylase 1 variants with multiple mutations presenting an increase in isobutene production from 3-methylcrotonic acid.

| Mutations | Activity relative to WT | Assay |
|---|---|---|
| E25N-N31G-S85A-Q162N-C175T-T228L-G305A-D351R-K377H-R392A-P402V-F404Y-T405M-T429A-V445P-Q448W-I461V-S494R | +++++ | IN VIVO 3 |
| E25N-N31G-S85A-Q162N-C175K-T228L-G305A-D351R-K377H-R392A-P402V-F404Y-T405M-T429A-V445P-Q448W-I461V-S494R | +++++ | IN VIVO 3 |
| E25N-N31G-S85A-Q162N-C175Q-T228L-G305A-D351R-K377H-R392A-P402V-F404Y-T405M-T429A-V445P-Q448W-I461V-S494R | +++++ | IN VIVO 3 |
| E25N-N31G-S85A-Q162N-C175G-T228L-G305A-D351R-K377H-R392A-P402V-F404Y-T405M-T429A-V445P-Q448W-I461V-S494R-E216N | +++++ | IN VIVO 3 |
| E25N-N31G-S85A-Q162N-C175G-T228L-G305A-D351R-K377H-R392A-P402V-F404Y-T405M-T429A-V445P-Q448W-I461V-S494R-I345L | +++++ | IN VIVO 3 |
| E25N-N31G-S85A-Q162N-C175G-T228L-G305A-D351R-K377H-R392A-P402V-F404Y-T405M-T429A-V445P-Q448W-I461V-S494R-S454G | +++++ | IN VIVO 3 |
| E25N-N31G-S85A-Q162N-C175G-T228L-G305A-D351R-K377H-R392A-P402V-F404Y-T405M-T429A-V445P-Q448W-I461V-S494R-S3D-K509L | +++++ | IN VIVO 3 |
| E25N-N31G-S85A-Q162N-C175G-T228L-G305A-D351R-K377H-R392A-P402V-F404Y-T405M-T429A-V445P-Q448W-I461V-S494R-T4S-P13V | +++++ | IN VIVO 3 |
| E25N-N31G-S85A-Q162N-C175G-T228L-G305A-D351R-K377H-R392A-P402V-F404Y-T405M-T429A-V445P-Q448W-I461V-S494R-Y6P-D512H | +++++ | IN VIVO 3 |
| E25N-N31G-S85A-Q162N-C175G-T228L-G305A-D351R-K377H-R392A-P402V-F404Y-T405F-T429A-V445P-Q448W-I461V-S494R | +++++ | IN VIVO 3 |
| E25N-N31G-S85A-Q162N-C175G-T228L-G305A-D351R-K377H-R392A-P402V-F404Y-T405F-T429A-V445P-Q448W-I461V-S494R-S454G | +++++ | IN VIVO 3 |
| E25N-N31G-S85A-Q162N-C175G-T228L-G305A-D351R-K377H-R392A-P402V-F404W-T429A-V445P-Q448W-I461V-S494R-F447M | +++++ | IN VIVO 3 |
| E25N-N31G-S85A-Q162N-C175G-T228L-G305A-D351R-K377H-R392A-P402V-F404Y-T405M-T429A-V445P-Q448W-I461V-S494R-I337L | +++++ | IN VIVO 3 |
| E25N-N31G-S85A-Q162N-C175G-T228L-G305A-D351R-K377H-R392A-P402V-F404Y-T405M-T429A-V445P-Q448F-I461V-S494R-I197M | +++++ | IN VIVO 3 |
| E25N-N31G-G305A-D351R-K377H-P402V-F404Y-T405M-T429A-V445P-Q448W-S454G | +++++ | IN VIVO 3 |
| E25N-N31G-G305A-D351R-K377H-P402V-F404Y-T405F-T429A-V445P-Q448W | +++++ | IN VIVO 3 |
| E25N-N31G-G305A-D351R-K377H-P402V-F404Y-T405F-T429A-V445P-Q448W-S454G | +++++ | IN VIVO 3 |
| E25N-N31G-S85A-Q162N-C175G-T228L-G305A-D351R-K377H-R392A-P402V-F404Y-T405M-T429A-V445P-Q448F-I461V-S494R | +++++ | IN VIVO 3 |

TABLE 7

List of mutations involved in the variants of the *Hypocrea atroviridis* Ferulic acid decarboxylase 1 with increased activity

| Mutant | Wild-Type Amino Acid | Sequence Number | Mutation |
|---|---|---|---|
| S2A | S | 2 | A |
| S2D | S | 2 | D |
| S2F | S | 2 | F |
| S2K | S | 2 | K |
| S2L | S | 2 | L |
| S2N | S | 2 | N |
| S2Q | S | 2 | Q |
| S2V | S | 2 | V |
| S3A | S | 3 | A |
| S3C | S | 3 | C |
| S3D | S | 3 | D |
| S3E | S | 3 | E |
| S3G | S | 3 | G |
| S3K | S | 3 | K |
| S3P | S | 3 | P |
| S3W | S | 3 | W |
| S3Y | S | 3 | Y |
| T4A | T | 4 | A |
| T4E | T | 4 | E |
| T4L | T | 4 | L |
| T4M | T | 4 | M |
| T4N | T | 4 | N |
| T4S | T | 4 | S |
| T5S | T | 5 | S |
| Y6P | Y | 6 | P |
| K7R | K | 7 | R |
| S8N | S | 8 | N |
| E9H | E | 9 | H |
| E9P | E | 9 | P |
| E9Y | E | 9 | Y |
| A10F | A | 10 | F |
| A10H | A | 10 | H |
| A10K | A | 10 | K |
| A10L | A | 10 | L |
| A10P | A | 10 | P |
| A10T | A | 10 | T |
| F11L | F | 11 | L |
| F11P | F | 11 | P |
| F11Y | F | 11 | Y |
| D12A | D | 12 | A |
| D12N | D | 12 | N |
| D12S | D | 12 | S |
| P13H | P | 13 | H |
| P13I | P | 13 | I |
| P13N | P | 13 | N |
| P13S | P | 13 | S |
| P13V | P | 13 | V |
| P13Y | P | 13 | Y |
| E14D | E | 14 | D |
| P15T | P | 15 | T |
| E25N | E | 25 | N |
| E25S | E | 25 | S |
| E25W | E | 25 | W |
| Q29H | Q | 29 | H |
| Q29N | Q | 29 | N |
| Q29S | Q | 29 | S |
| D30G | D | 30 | G |
| D30H | D | 30 | H |
| D30R | D | 30 | R |
| N31E | N | 31 | E |
| N31G | N | 31 | G |
| L33I | L | 33 | I |
| V34A | V | 34 | A |
| V34I | V | 34 | I |
| D35M | D | 35 | M |
| D35S | D | 35 | S |
| D35T | D | 35 | T |
| V40I | V | 40 | I |
| V40M | V | 40 | M |
| D43R | D | 43 | R |
| D57N | D | 57 | N |
| A60V | A | 60 | V |
| N65L | N | 65 | L |
| N65W | N | 65 | W |
| I67R | I | 67 | R |
| I67V | I | 67 | V |
| A69N | A | 69 | N |
| K70I | K | 70 | I |
| K70L | K | 70 | L |
| D71G | D | 71 | G |
| G72R | G | 72 | R |
| P80L | P | 80 | L |
| R84C | R | 84 | C |
| S85A | S | 85 | A |
| S85T | S | 85 | T |
| S86I | S | 86 | I |
| S86N | S | 86 | N |
| P87A | P | 87 | A |
| P87C | P | 87 | C |
| P87F | P | 87 | F |
| P87I | P | 87 | I |
| P87L | P | 87 | L |
| P87M | P | 87 | M |
| P87V | P | 87 | V |
| P87W | P | 87 | W |
| E89F | E | 89 | F |
| E89S | E | 89 | S |
| R90L | R | 90 | L |
| F91L | F | 91 | L |
| A99N | A | 99 | N |
| A99P | A | 99 | P |
| P101I | P | 101 | I |
| P101L | P | 101 | L |
| P102L | P | 102 | L |
| T103I | T | 103 | I |
| T103L | T | 103 | L |
| T103M | T | 103 | M |
| S105F | S | 105 | F |
| S105L | S | 105 | L |
| S105W | S | 105 | W |
| A106T | A | 106 | T |
| D108K | D | 108 | K |
| D108R | D | 108 | R |
| D108W | D | 108 | W |
| D111C | D | 111 | C |
| L114S | L | 114 | S |
| N117A | N | 117 | A |
| I119T | I | 119 | T |
| P120K | P | 120 | K |
| P120S | P | 120 | S |
| I126P | I | 126 | P |
| V132C | V | 132 | C |
| N141D | N | 141 | D |
| A146S | A | 146 | S |
| A149S | A | 149 | S |
| A149V | A | 149 | V |
| Q154K | Q | 154 | K |
| K159C | K | 159 | C |
| Y160F | Y | 160 | F |
| Q162H | Q | 162 | H |
| Q162N | Q | 162 | N |
| Q162P | Q | 162 | P |
| C175G | C | 175 | G |
| C175K | C | 175 | K |
| C175P | C | 175 | P |
| C175Q | C | 175 | Q |
| C175S | C | 175 | S |
| C175T | C | 175 | T |
| C175W | C | 175 | W |
| W176F | W | 176 | F |
| S187T | S | 187 | T |
| K189I | K | 189 | I |
| A193I | A | 193 | I |
| A193T | A | 193 | T |
| A193V | A | 193 | V |
| L195C | L | 195 | C |
| L195F | L | 195 | F |
| L195I | L | 195 | I |

TABLE 7-continued

List of mutations involved in the variants of the *Hypocrea atroviridis* Ferulic acid decarboxylase 1 with increased activity

| Mutant | Wild-Type Amino Acid | Sequence Number | Mutation |
|---|---|---|---|
| L195V | L | 195 | V |
| L195W | L | 195 | W |
| L195Y | L | 195 | Y |
| I197F | I | 197 | F |
| I197M | I | 197 | M |
| Q206F | Q | 206 | F |
| A211E | A | 211 | E |
| G213L | G | 213 | L |
| G213P | G | 213 | P |
| Q214A | Q | 214 | A |
| Q214E | Q | 214 | E |
| Q214F | Q | 214 | F |
| Q214H | Q | 214 | H |
| Q214R | Q | 214 | R |
| Q214T | Q | 214 | T |
| Q214V | Q | 214 | V |
| E215C | E | 215 | C |
| E216N | E | 216 | N |
| L221C | L | 221 | C |
| A222C | A | 222 | C |
| T228A | T | 228 | A |
| T228L | T | 228 | L |
| T228P | T | 228 | P |
| L228T | L | 228 | T |
| T228V | T | 228 | V |
| A232V | A | 232 | V |
| A244F | A | 244 | F |
| V247A | V | 247 | A |
| N264D | N | 264 | D |
| T278I | T | 278 | I |
| M284L | M | 284 | L |
| M284Y | M | 284 | Y |
| A285L | A | 285 | L |
| M293L | M | 293 | L |
| H303P | H | 303 | P |
| H303S | H | 303 | S |
| G305A | G | 305 | A |
| G305D | G | 305 | D |
| P306F | P | 306 | F |
| P306R | P | 306 | R |
| P306S | P | 306 | S |
| C326A | C | 326 | A |
| C326P | C | 326 | P |
| I337L | I | 337 | L |
| I337M | I | 337 | M |
| G338A | G | 338 | A |
| G338P | G | 338 | P |
| G338S | G | 338 | S |
| A341I | A | 341 | I |
| A342G | A | 342 | G |
| I345L | I | 345 | L |
| C349S | C | 349 | S |
| D351A | D | 351 | A |
| D351G | D | 351 | G |
| D351N | D | 351 | N |
| D351R | D | 351 | R |
| D351V | D | 351 | V |
| A352G | A | 352 | G |
| A352L | A | 352 | L |
| D375L | D | 375 | L |
| T376I | T | 376 | I |
| K377H | K | 377 | H |
| A381R | A | 381 | R |
| T384Y | T | 384 | Y |
| G386N | G | 386 | N |
| A388E | A | 388 | E |
| R392A | R | 392 | A |
| R392L | R | 392 | L |
| D395C | D | 395 | C |
| T399N | T | 399 | N |
| T399R | T | 399 | R |
| P402H | P | 402 | H |
| P402V | P | 402 | V |
| F404W | F | 404 | W |
| F404Y | F | 404 | Y |
| T405F | T | 405 | F |
| T405L | T | 405 | L |
| T405M | T | 405 | M |
| T405P | T | 405 | P |
| T405Q | T | 405 | Q |
| I406Q | I | 406 | Q |
| D414N | D | 414 | N |
| D420L | D | 420 | L |
| K422M | K | 422 | M |
| T429A | T | 429 | A |
| T429S | T | 429 | S |
| G435M | G | 435 | M |
| T436N | T | 436 | N |
| V439L | V | 439 | L |
| F440V | F | 440 | V |
| F441Y | F | 441 | Y |
| D442T | D | 442 | T |
| D443N | D | 443 | N |
| V445E | V | 445 | E |
| V445P | V | 445 | P |
| F447M | F | 447 | M |
| F447W | F | 447 | W |
| F447Y | F | 447 | Y |
| Q448F | Q | 448 | F |
| Q448S | Q | 448 | S |
| Q448W | Q | 448 | W |
| L449I | L | 449 | I |
| L449M | L | 449 | M |
| L449V | L | 449 | V |
| S454G | S | 454 | G |
| A460F | A | 460 | F |
| A460P | A | 460 | P |
| I461M | I | 461 | M |
| I461N | I | 461 | N |
| I461V | I | 461 | V |
| K462N | K | 462 | N |
| S484A | S | 484 | A |
| S484G | S | 484 | G |
| K488A | K | 488 | A |
| K488N | K | 488 | N |
| K493R | K | 493 | R |
| S494R | S | 494 | R |
| Q496A | Q | 496 | A |
| Q496F | Q | 496 | F |
| L500A | L | 500 | A |
| N501E | N | 501 | E |
| N501G | N | 501 | G |
| N501K | N | 501 | K |
| N501M | N | 501 | M |
| S502N | S | 502 | N |
| L506I | L | 506 | I |
| L506Y | L | 506 | Y |
| K509L | K | 509 | L |
| L511I | L | 511 | I |
| L511M | L | 511 | M |
| D512E | D | 512 | E |
| D512H | D | 512 | H |
| D512S | D | 512 | S |

Example 9: In Vitro Activities of Homologues of the *Hypocrea atroviridis* Ferulic Acid 1 Decarboxylase at Different Temperatures (Wild-Type and T→M Mutants)

As described in Example 5, the T405M variant of *Hypocrea atroviridis* Ferulic acid 1 decarboxylase presents a very significant increase in the production of Isobutene from 3-methylcrotonic acid. To assess the general effect of this mutation on different Ferulic acid decarboxylases, we selected 4 homologues of the *Hypocrea atroviridis* Ferulic acid 1 decarboxylase and made the corresponding T→M mutation (Table 8).

TABLE 8

List of homologues of the *Hypocrea atroviridis* Ferulic acid decarboxylase 1 and their T−>M mutation

| Organism | Uniprot Accession Number | SEQ ID NO | T−>M Mutation |
|---|---|---|---|
| *Hypocrea atroviridis* (Ha) | G9NLP8 | 1 | T405M |
| *Cladophialophora psammophila* (Cp) | W9WWR1 | 10 | T400M |
| *Cladophialophora immunda* (Ci) | A0A0D2AQI6 | 11 | T400M |
| *Sphaerulina musiva* (Sm) | M3DF95 | 12 | T405M |
| *Cladophialophora bantiana* (Cb) | A0A0D2IKD5 | 13 | T400M |

The in vitro assay was performed as described in Example 5 with 10 mM 3-methylcrotonic acid, an incubation time of 120 min and an incubation temperature varying between 30 and 60° C. In all cases, the T→M mutation shows an increase in activity and in the optimal catalytic temperature (FIG. 3).

Example 10: Identification of Variants of Homologues of *Hypocrea atroviridis* Ferulic Acid Decarboxylase 1 with Increased Activity for the Reaction of Conversion of 3-Methylcrotonic Acid into Isobutene As was described in Example 9, we showed that the T→M mutation found in position 405 of the *Hypocrea atroviridis* Ferulic acid 1 decarboxylase increases the activity of 4 different homologues (Table 8 and FIG. 3). We decided to further evolve two of these homologues, namely the Ferulic Acid decarboxylase 1 of *Cladophialophora psammophila* (Uniprot Accession Number W9WWR1, SEQ ID NO: 10) and of *Cladophialophora bantiana* (Uniprot Accession Number A0A0D2IKD5, SEQ ID NO: 13).

The assay is based on the use of a bacterial strain (BL21(DE3), Novagen) transformed with the above expression vector that contains the coding sequences as described above, leading to the production of the last two enzymes involved in the metabolic pathway converting 3MC to isobutene; namely the Ferulic acid decarboxylase 1 of *Cladophialophora psammophila* (Uniprot Accession Number W9WWR1, SEQ ID NO: 10) or the Ferulic acid decarboxylase 1 of *Cladophialophora* bantiana (Uniprot Accession Number A0A0D2IKD5, SEQ ID NO: 13) variants and the Flavin prenyltransferase UbiX protein from *E. coli*. This strain is first plated out onto LB-agar plates supplemented with the appropriate antibiotic. Cells were grown overnight at 32° C. until individual colonies reach the desired size. Single colonies were then picked and individually transferred into 500 µL of liquid LB medium supplemented with the appropriate antibiotic. Cell growth is carried out with shaking for 20 hours at 32° C. The LB cultures were used to inoculate 1 mL in 96 deepwell microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 32° C. in order to produce the two recombinant enzymes. The cell pellet containing these two overexpressed recombinant enzymes is then resuspended in 400 µL of minimum medium (pH 7.5, Phosphate 100 mM, Glucose 10 g·L$^{-1}$, MgSO$_4$ 1 mM) supplemented with 10 mM 3MC and incubated for a further 2 or 4 hours in a shaking incubator at 36° C., 700 rpm. During this step, the Ferulic acid decarboxylase 1 variants catalyse the decarboxylation of 3MC into IBN. After 5 min inactivation at 80° C., the IBN produced is quantified by gas chromatography as described in the following. 100 µL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL·min$^{-1}$ constant flow of nitrogen as carrier gas. Upon injection, peak areas of isobutene were calculated.

The list of improving variants of the Ferulic acid decarboxylase 1 of *Cladophialophora psammophila* (Uniprot Accession Number W9WWR1, SEQ ID NO: 10) is presented in the following Table 9 and the list of improving variants of the Ferulic acid decarboxylase 1 of *Cladophialophora bantiana* (Uniprot Accession Number A0A0D2IKD5, SEQ ID NO: 13) is presented in the following Table 10. The increase in activity is described relative to the wild-type enzyme (with "+" representing a low increase in activity and "++" representing a high increase in activity).

The list of mutations involved in the variants of the *Cladophialophora psammophila* Ferulic acid decarboxylase 1 (Uniprot Accession Number W9WWR1, SEQ ID NO: 10) with increased activity is described in Table 11 and the list of mutations involved in the variants of the *Cladophialophora psammophila* Ferulic acid decarboxylase 1 (Uniprot Accession Number A0A0D2IKD5, SEQ ID NO: 13) with increased activity is described in Table 12.

TABLE 9

List of *Cladophialophora psammophila* Ferulic acid decarboxylase 1 variants presenting an increase in isobutene production from 3-methylcrotonic acid.

| Mutations | Activity relative to WT |
|---|---|
| T400M | + |
| T400M-Y393F-G394N-Y399F | ++ |
| T400M-Y393F | ++ |
| T400M-Y393F-G394N | ++ |
| T400M-Y393F-Y399F | ++ |
| T400M-Y393F-A397V-Y399F | ++ |
| T400M-Y393F-A397V | ++ |

TABLE 10

List of *Cladophialophora bantiana* Ferulic acid decarboxylase 1 variants presenting an increase in isobutene production from 3-methylcrotonic acid.

| Mutations | Activity relative to WT |
|---|---|
| T400M | + |
| T400M-Y393F-G394N | ++ |
| T400M-Y393F-G394N-Y399F | ++ |
| T400M-Y393F-A397V | ++ |
| T400M-Y393F | ++ |
| T400M-Y393F-Y399F | ++ |
| T400M-A14T-Y393F-H395Q | ++ |
| T400M-Y393F-G394N-A397V | ++ |
| T400M-Y393F-A397V-Y399F | ++ |
| T400M-Y393F-G394N-A397V-Y399F | ++ |

TABLE 11

List of mutations involved in the variants of the *Cladophialophora psammophila* Ferulic acid decarboxylase 1 with increased activity.

| Mutant | Wild-Type Amino Acid | Sequence Number | Mutation |
|---|---|---|---|
| Y393F | Y | 393 | F |
| G394N | G | 394 | N |
| A397V | A | 397 | V |
| Y399F | Y | 399 | F |
| T400M | T | 400 | M |

TABLE 12

List of mutations involved in the variants of the *Cladophialophora bantiana* Ferulic acid decarboxylase 1 with increased activity.

| Mutant | Wild-Type Amino Acid | Sequence Number | Mutation |
|---|---|---|---|
| A14T | A | 14 | T |
| Y393F | Y | 393 | F |
| G394N | G | 394 | N |
| H395Q | H | 395 | Q |
| A397V | A | 397 | V |
| Y399F | Y | 399 | F |
| T400M | T | 400 | M |

EXAMPLES—SECOND PART

Material and Methods: Methods Used to Assess Isobutene Production Activities a) Cloning of 3-Methylcrotonic Acid Decarboxylase (3-MDC) Enzymes All the 3-methylcrotonic acid decarboxylase (3-MDC) polynucleotide sequences were codon-optimized for the expression in *Escherichia coli* and subsequently chemically synthesized. They were then cloned in a pET25 (Novagen) expression vector or fused with a polynucleotide tag in 5' coding for a 6-His purification tag before being cloned in a pET25 expression vector, resulting in 2 expression vectors for each 3-MDC sequence.

b) Construction of 3-Methylcrotonic Acid Decarboxylase (3-MDC) Mutants

The polynucleotide sequences coding for the different mutants identified during the evolution of the selected 3-MDC enzymes were generated using a range of standard molecular biology techniques.

Different PCR-based techniques known in the art were used for the construction of single-point mutants. For the generation of enzyme variants bearing multiple mutations (at least two mutations), either PCR-based techniques or other methods known in the art were used to introduce these mutations.

Following mutagenesis, the mutated polynucleotide sequence was inserted into a pET25 expression vector with or without being fused to a tag as described above either using standard ligase-based subcloning techniques, whole plasmid extension by PCR or ligase-independent cloning techniques.

c) Screening of 3-Methylcrotonic Acid Decarboxylase (3-MDC) Enzymes Activity

A total of four different screening methods were developed and used during the evolution of the *Streptomyes* sp. 769 MDC enzyme.

c1) In Vivo Assay in 384-Well Microplates Based on Exogenous 3-Methylcrotonic Acid (3MC) (VIVO384)

This assay is based on the use of a bacterial strain (BL21(DE3), Novagen) transformed with two expression vectors leading to the production of the last two enzymes involved in the metabolic pathway converting 3MC to isobutene; namely the prenylated FMN Synthase UbiX protein from *E. coli* cloned in a pRSF-Duet™ (Novagen) expression vector and the respective 3-MDC enzyme cloned in one of the above expression vectors. This strain is first plated out onto LB-agar plates supplemented with the appropriate antibiotic. Cells were grown overnight at 32° C. until individual colonies reach the desired size. Single colonies were then picked and individually transferred into 50 μL of liquid LB medium supplemented with the appropriate antibiotics. Cell growth is carried out with shaking for 20 hours at 32° C. The LB cultures were used to inoculate 300 μL in 384 deep well microplates of auto-induction medium (Studier F W, Prat. Exp. Pur. 41, (2005), 207-234) supplemented with the appropriate antibiotics and grown in a shaking incubator set at 700 rpm and 85% humidity for 24 h at 32° C. in order to produce the two types of recombinant enzymes. The cell pellet containing these two overexpressed recombinant enzymes is then resuspended in 40 μL of minimum medium (pH 7.5, Phosphate 100 mM, Glucose 10 $g \cdot L^{-1}$, $MgSO_4$ 1 mM) supplemented with 3, 10 or 30 mM 3MC and incubated for a further 2 or 4 hours in a shaking incubator at 36° C., 700 rpm. During this step, the 3-MDC enzyme catalyzes the decarboxylation of 3MC into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 $mL \cdot min^{-1}$ constant flow of nitrogen as carrier gas. Upon injection, peak areas of isobutene were calculated.

c2) In vivo assay in 96-well microplates based on exogenous 3-methylcrotonic acid (3MC) (VIVO96)

This assay is based on the use of a bacterial strain (BL21(DE3), Novagen) transformed with two expression vectors leading to the production of the last two enzymes involved in the metabolic pathway converting 3MC to isobutene; namely the prenylated FMN Synthase UbiX protein from *E. coli* cloned in a pRSF-Duet™ (Novagen) expression vector and the respective 3-MDC enzyme cloned in one of the above expression vectors. This strain is first plated out onto LB-agar plates supplemented with the appropriate antibiotics. Cells were grown overnight at 32° C. until individual colonies reach the desired size. Single colonies were then picked and individually transferred into 50 μL of liquid LB medium supplemented with the appropriate antibiotics. Cell growth is carried out with shaking for 20 hours at 32° C. The LB cultures were used to inoculate 1 mL in 96 deep well microplates of auto-induction medium (Studier F W, Prat. Exp. Pur. 41, (2005), 207-234) supplemented with the appropriate antibiotics and grown in a shaking incubator set at 700 rpm and 85% humidity for 24 h at 32° C. in order to produce the two types of recombinant enzymes. The cell pellet containing these two overexpressed recombinant enzymes is then resuspended in 400 μL of minimum medium (pH 7.5, Phosphate 100 mM, Glucose 10 g·L$^{-1}$, MgSO$_4$ 1 mM) supplemented with 3, 10 or 30 mM 3MC and incubated for a further 2 or 4 hours in a shaking incubator at 36° C., 700 rpm. During this step, the 3-MDC enzyme catalyzes the decarboxylation of 3MC into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL·min$^{-1}$ constant flow of nitrogen as carrier gas. Upon injection, peak areas of isobutene were calculated.

c3) In Vitro Assay in 384-Well Microplates Based on Exogenous 3-Methylcrotonic Acid (3MC) (VITRO384)

This assay is based on the use of a bacterial strain (BL21(DE3), Novagen) transformed with two expression vectors leading to the production of the last two enzymes involved in the metabolic pathway converting 3MC to isobutene; namely the prenylated FMN Synthase UbiX protein from *E. coli* cloned in a pRSF-Duet™ (Novagen) expression vector and the respective 3-MDC enzyme cloned in one of the above expression vectors. This strain is first plated out onto LB-agar plates supplemented with the appropriate antibiotics. Cells were grown overnight at 32° C. until individual colonies reach the desired size. Single colonies were then picked and individually transferred into 50 μL of liquid LB medium supplemented with the appropriate antibiotic. Cell growth is carried out with shaking for 20 hours at 32° C. The LB cultures were used to inoculate 300 μL in 384 deep well microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 32° C. in order to produce the two types of recombinant enzymes. The cell pellet containing these two overexpressed recombinant enzymes is then resuspended in 30 μL of lysis mix (pH 7.5, Phosphate 50 mM, NaCl 20 mM, MgCl$_2$ 2 mM, Lysozyme 1 mg/mL, DNAse 0.03 mg/mL) and incubated for 1 hour in a shaking incubator at 36° C., 700 rpm. The mix is then supplemented with 10 L of reaction mix (final composition: pH 7.5, Phosphate 50 mM, NaCl 20 mM, MgCl$_2$ 2 mM, Lysozyme 0.75 mg/mL, DNAse 0.0225 mg/mL, KCl 100 mM) supplemented with 3, 10 or 30 mM (final) 3MC and incubated for a further 2 or 4 hours in a shaking incubator at 36° C., 700 rpm. During this step, the 3-MDC enzyme catalyzes the decarboxylation of 3MC into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL·min$^{-1}$ constant flow of nitrogen as carrier gas. Upon injection, peak areas of isobutene were calculated.

c4) In Vitro Assay in 96-Well Microplates Based on Exogenous 3-Methylcrotonic Acid (3MC) (VITRO96)

This assay is based on the use of a bacterial strain (BL21(DE3), Novagen) transformed with two expression vectors leading to the production of the last two enzymes involved in the metabolic pathway converting 3MC to isobutene; namely the prenylated FMN Synthase UbiX protein from *E. coli* cloned in a pRSF-Duet™ (Novagen) expression vector and the respective 3-MDC enzyme cloned in one of the above expression vectors. This strain is first plated out onto LB-agar plates supplemented with the appropriate antibiotics. Cells were grown overnight at 32° C. until individual colonies reach the desired size. Single colonies were then picked and individually transferred into 50 μL of liquid LB medium supplemented with the appropriate antibiotic. Cell growth is carried out with shaking for 20 hours at 32° C. The LB cultures were used to inoculate 1 mL in 96 deep well microplates of auto-induction medium (Studier F W, Prat. Exp. Pur. 41, (2005), 207-234) supplemented with the appropriate antibiotic and grown in a shaking incubator set at 700 rpm and 85% humidity for 24 h at 32° C. in order to produce the two types of recombinant enzymes. The cell pellet containing these two overexpressed recombinant enzymes is then resuspended in 150 μL of lysis mix (pH 7.5, Phosphate 50 mM, NaCl 20 mM, MgCl$_2$ 2 mM, Lysozyme 1 mg/mL, DNAse 0.03 mg/mL) and incubated for 1 hour in a shaking incubator at 36° C., 700 rpm. The mix is then supplemented with 50 μL of reaction mix (final composition: pH 7.5, Phosphate 50 mM, NaCl 20 mM, MgCl$_2$ 2 mM, Lysozyme 0.75 mg/mL, DNAse 0.0225 mg/mL, KCl 100 mM) supplemented with 3, 10 or 30 mM (final) 3MC and incubated for a further 2 or 4 hours in a shaking incubator at 36° C., 700 rpm. During this step, the 3-MDC enzyme catalyzes the decarboxylation of 3MC into IBN. After 5 min inactivation at 80° C., the IBN produced is quantified by gas chromatography as followed. 100 μL of headspace gases from each enzymatic reaction are injected in a Brucker GC-450 system equipped with a Flame Ionization Detector (FID). Compounds present in samples were separated by chromatography using a RTX-1 columns at 100° C. with a 1 mL·min$^{-1}$ constant flow of nitrogen as carrier gas. Upon injection, peak areas of isobutene were calculated.

Example 1: Identification of a *Streptomyces* sp. 769 UbiD-Like Decarboxylase Enzyme Presenting an Activity for the Reaction of Conversion of 3-Methylcrotonic Acid (3MC) into Isobutene (IBN)

We tested a UbiD-like decarboxylase enzyme from *Streptomyces* sp. 769 (UniProt ID A0A0A8EV26, gene GZL_07100, herein called Ss5; SEQ ID NO:14) for its capacity to catalyze the reaction of conversion of 3MC into IBN. The gene was codon-optimized for expression in *Escherichia Coli*, synthesized, fused to a 6-His-tag or not fused to a 6-His-tag, and then subcloned into a pET25 expression vector, as described above. The expression vectors were then screened for the production of isobutene (IBN) from 3-methylcrotonic acid (3MC) in microplate 96 and 384-wells, using both an in vivo and an in vitro assay, as described above. An 3-methylcrotonic acid decarboxylase (3-MDC) enzyme from *Hypocrea atroviridis* (herein called Ha, Uniprot Accession Number G9NLP8) described above in the context of the first, second and third aspect of the present invention and previously described in WO2017085167 (see Example 8, Table G; example 12 Table J therein) and in WO2017191239 (SEQ ID NO:1 therein) was added as a control (FIG. 4 and FIG. 5).

Example 2: Identification of Variants of a 3-Methylcrotonic Acid Decarboxylase (3-MDC) Enzyme from *Streptomyces* sp. 769 with Increased Activity for the Reaction of Conversion of 3-Methylcrotonic Acid (3MC) into Isobutene (IBN)

The above 3-methylcrotonic acid decarboxylase (3-MDC) gene presenting a capacity to catalyze the reaction of conversion of 3MC into IBN (UniProt ID A0A0A8EV26, gene GZL_07100 from *Streptomyces* sp. 769) was submitted to directed mutagenesis in order to create single point mutations or multiple mutations variants. Each of these variants was subsequently tested for their increased activity to convert 3MC into IBN, using one or more of the previously described assays. 230 variants presented an increased capacity in converting 3MC into IBN.

The list of improved variants is presented in the following Table 13. The increase in activity is described relative to the wild-type enzyme (with "+" representing a low increase in activity and "+++" representing a high increase in activity).

The list of mutations involved in the variants of the *Streptomyces* sp. 769 3-MethylCrotonate Decarboxylase with increased activity is described in Table 14.

TABLE 13

List of *Streptomyces* sp. 769 3-MethylCrotonate Decarboxylase variants presenting an increase in isobutene production from 3-methylcrotonic acid.

| Mutants | Activity relative to WT |
| --- | --- |
| A241D | + |
| A241N | + |
| A241V | + |
| A359C | + |
| C404F | + |
| C404L | + |
| L448F | + |
| L448W | + |
| L448Y | + |
| P406A | + |
| R390S-L448W | + |
| R390S-L448Y | + |
| A241D-C404F | ++ |
| A241D-C404F-L448F | ++ |
| A241D-C404F-L448Y | ++ |
| A241D-C404F-P406A | ++ |
| A241D-C404F-P406A-L448F | ++ |
| A241D-C404F-P406A-L448Y | ++ |
| A241D-C404L | ++ |
| A241D-C404L-L448F | ++ |
| A241D-C404L-L448W | ++ |
| A241D-C404L-L448Y | ++ |
| A241D-C404L-P406A | ++ |
| A241D-C404L-P406A-L448F | ++ |
| A241D-C404L-P406A-L448Y | ++ |
| A241D-L448F | ++ |
| A241D-L448W | ++ |
| A241D-L448Y | ++ |
| A241D-P406A | ++ |
| A241D-P406A-L448F | ++ |
| A241D-P406A-L448Y | ++ |
| A241N-C404F | ++ |
| A241N-C404F-L448F | ++ |
| A241N-C404F-L448W | ++ |
| A241N-C404F-L448Y | ++ |
| A241N-C404F-P406A | ++ |
| A241N-C404F-P406A-L448F | ++ |
| A241N-C404F-P406A-L448Y | ++ |
| A241N-C404L | ++ |
| A241N-C404L-L448F | ++ |
| A241N-C404L-L448W | ++ |
| A241N-C404L-L448Y | ++ |
| A241N-C404L-P406A | ++ |
| A241N-C404L-P406A-L448F | ++ |
| A241N-C404L-P406A-L448Y | ++ |
| A241N-L448F | ++ |
| A241N-L448W | ++ |
| A241N-L448Y | ++ |
| A241N-P406A | ++ |
| A241N-P406A-L448F | ++ |
| A241N-P406A-L448W | ++ |
| A241N-P406A-L448Y | ++ |
| C404F-L446I-L448W | ++ |
| C404F-L448F | ++ |
| C404F-L448W | ++ |
| C404F-L448Y | ++ |
| C404F-P406A | ++ |
| C404F-P406A-L448F | ++ |
| C404F-P406A-L448W | ++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
| --- | --- |
| C404F-P406A-L448Y | ++ |
| C404L-L448F | ++ |
| C404L-L448W | ++ |
| C404L-L448Y | ++ |
| C404L-P406A | ++ |
| C404L-P406A-L448F | ++ |
| C404L-P406A-L448Y | ++ |
| C404M-L446I-L448W | ++ |
| C404M-L448F | ++ |
| C404M-L448W | ++ |
| P406A-L448F | ++ |
| P406A-L448W | ++ |
| P406A-L448Y | ++ |
| V240I-C404M-L448F | ++ |
| C404M-L446N-L448W | ++ |
| C404M-P406A-L446I-L448W | ++ |
| C404M-P406S-L446I-L448W | ++ |
| S403R-C404M-L446I-L448W | ++ |
| C404M-L446I-L448W-T450A | ++ |
| C404M-L446I-L448W-T450H | ++ |
| C404M-L446I-L448W-T450M | ++ |
| C404M-L446I-L448W-T450N | ++ |
| C404M-L446I-L448W-T450S | ++ |
| C404M-P406A-L446N-L448W | ++ |
| C404M-P406A-L448W | ++ |
| C404M-P406A-L446I-L448W-T450A | ++ |
| C404M-P406S-L446N-L448W | ++ |
| C404M-P406S-L448W | ++ |
| C404M-P406S-L446I-L448W-T450A | ++ |
| C404M-P406S-L446I-L448W-T450H | ++ |
| C404M-L446N-L448W-T450A | ++ |
| C404M-L446N-L448W-T450H | ++ |
| C404M-L448W-T450A | ++ |
| C404M-L448W-T450H | ++ |
| C404M-P406A-L446N-L448W-T450A | ++ |
| C404M-P406A-L448W-T450A | ++ |
| C404M-P406A-L446N-L448W-T450H | ++ |
| C404M-P406S-L446N-L448W-T450A | ++ |
| C404M-P406S-L448W-T450A | ++ |
| C404M-P406S-L446N-L448W-T450H | ++ |
| C404M-P406A-L446I-L448W-T450H | +++ |
| C404M-P406A-L448W-T450H | +++ |
| C404M-P406S-L448W-T450H | +++ |
| A241D-C404F-L446I-L448W | +++ |
| A241D-C404F-L448W | +++ |
| A241D-C404F-P406A-L448W | +++ |
| A241D-C404F-P406S-L448W | +++ |
| A241D-C404L-P406A-G443D-L448W | +++ |
| A241D-C404L-P406A-L446V-L448W | +++ |
| A241D-C404L-P406A-L446V-L448W-T450M | +++ |
| A241D-C404L-P406A-L448W | +++ |
| A241D-C404L-P406A-L448W-T450M | +++ |
| A241D-C404M-L448W | +++ |
| A241D-C404M-P406A-L448W | +++ |
| A241D-F401Y-C404F-L446I-L448W | +++ |
| A241D-F401Y-C404F-L448W | +++ |
| A241D-F401Y-C404F-P406A-L448W | +++ |
| A241D-F401Y-C404M-L448W | +++ |
| A241D-F401Y-C404M-P406A-L448W | +++ |
| A241D-F401Y-L448W | +++ |
| A241D-F401Y-S403G-C404F-L446I-L448W | +++ |
| A241D-F401Y-S403G-C404F-L448W | +++ |
| A241D-F401Y-S403G-C404M-L448W | +++ |
| A241D-F401Y-S403P-C404F-L446I-L448W | +++ |
| A241D-F401Y-S403P-C404F-L448W | +++ |
| A241D-F401Y-S403P-C404M-P406A-L448W | +++ |
| A241D-G402A-C404L-P406A-L446V-L448W | +++ |
| A241D-G402A-C404L-P406A-L446V-L448W-T450M | +++ |
| A241D-G402A-C404L-P406A-L448W | +++ |
| A241D-G402A-C404L-P406A-L448W-T450M | +++ |
| A241D-G402A-S403C-C404L-P406A-L446V-L448W | +++ |
| A241D-G402A-S403C-C404L-P406A-L446V-L448W-T450M | +++ |
| A241D-G402A-S403C-C404L-P406A-L448W | +++ |
| A241D-G402A-S403C-C404L-P406A-L448W-T450M | +++ |
| A241D-G402A-S403V-C404L-P406A-L446V-L448W | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
| --- | --- |
| A241D-G402A-S403V-C404L-P406A-L446V-L448W-T450M | +++ |
| A241D-G402A-S403V-C404L-P406A-L448W | +++ |
| A241D-G402A-S403V-C404L-P406A-L448W-T450M | +++ |
| A241D-P406A-L448W | +++ |
| A241D-P444E-L448W | +++ |
| A241D-S403C-C404L-P406A-L446V-L448W | +++ |
| A241D-S403C-C404L-P406A-L446V-L448W-T450M | +++ |
| A241D-S403C-C404L-P406A-L448W | +++ |
| A241D-S403C-C404L-P406A-L448W-T450M | +++ |
| A241D-S403G-C404F-L446I-L448W | +++ |
| A241D-S403G-C404F-L448W | +++ |
| A241D-S403G-C404F-P406A-L448W | +++ |
| A241D-S403G-C404M-P406A-L448W | +++ |
| A241D-S403G-L448W | +++ |
| A241D-S403P-C404F-L446I-L448W | +++ |
| A241D-S403P-C404F-L448W | +++ |
| A241D-S403P-C404F-P406A-L448W | +++ |
| A241D-S403P-C404M-L448W | +++ |
| A241D-S403P-C404M-P406A-L448W | +++ |
| A241D-S403P-L448W | +++ |
| A241D-S403V-C404L-P406A-L446V-L448W | +++ |
| A241D-S403V-C404L-P406A-L446V-L448W-T450M | +++ |
| A241D-S403V-C404L-P406A-L448W | +++ |
| A241D-S403V-C404L-P406A-L448W-T450M | +++ |
| A241N-C404F-L405H-P406A-L448W | +++ |
| A241N-C404F-P406A-L448W | +++ |
| A241N-C404L-P406A-L446C-L448W | +++ |
| A241N-C404L-P406A-L446V-L448W | +++ |
| A241N-C404L-P406A-L448W | +++ |
| A241N-C404L-P406A-L448W-L449I | +++ |
| A241N-C404L-P406A-L448W-T450M | +++ |
| A241N-C404L-P406A-L448W-T450Q | +++ |
| A241N-C404M-L448W | +++ |
| A241N-C404M-P406A-L448W | +++ |
| A241N-F401Y-L448W | +++ |
| A241N-L446V-L448W | +++ |
| A241N-S403C-C404L-P406A-L448W | +++ |
| A241N-S403G-L448W | +++ |
| A241N-S403N-C404L-P406A-L448W | +++ |
| A241N-S403P-L448W | +++ |
| A241N-S403V-C404L-P406A-L448W | +++ |
| C404L-P406A-L446F-L448W | +++ |
| C404L-P406A-L446S-L448W | +++ |
| C404L-P406A-L446V-L448W | +++ |
| C404L-P406A-L448W | +++ |
| C404L-P406A-L448W-T450M | +++ |
| C404L-P406A-P444H-L448W | +++ |
| P85L-A241N-C404M-L448W-T450M | +++ |
| S403V-C404L-P406A-L448W | +++ |
| A241D-S403C-C404L-P406A-G443D-L448W | +++ |
| A241D-S403C-C404L-P406A-G443H-L448W | +++ |
| A241D-S403C-C404L-P406A-G443N-L448W | +++ |
| A241D-S403C-C404L-P406A-L448W-L449I | +++ |
| A241D-S403C-C404L-P406A-P444A-L448W | +++ |
| A241D-S403C-C404L-P406A-P444H-L448W | +++ |
| A241D-S403C-C404L-P406A-P444L-L448W | +++ |
| A241D-G402A-S403C-C404L-P406A-G443H-L448W | +++ |
| A241D-G402A-S403C-C404L-P406A-G443S-L448W | +++ |
| A241D-G402A-S403C-C404L-P406A-L446M-L448W | +++ |
| A241D-G402A-S403C-C404L-P406A-P444F-L448W | +++ |
| A241D-G402A-S403C-C404L-P406A-P444H-L448W | +++ |
| A241D-S403H-C404L-P406A-L448W-T450M | +++ |
| A241D-S403C-C404L-P406A-G443A-L448W-T450M | +++ |
| A241D-S403C-C404L-P406A-G443F-L448W-T450M | +++ |
| A241D-S403C-C404L-P406A-G443Y-L448W-T450M | +++ |
| A241D-S403C-C404L-P406A-P444A-L448W-T450M | +++ |
| A241D-S403C-C404L-P406A-P444F-L448W-T450M | +++ |
| A241D-S403C-C404L-P406A-P444T-L448W-T450M | +++ |
| A241D-S403V-C404L-P406A-G443D-L446V-L448W | +++ |
| A241D-S403V-C404L-P406A-G443D-L448W | +++ |
| A241D-S403V-C404L-P406A-G443A-L448W-T450M | +++ |
| A241D-S403V-C404L-P406A-G443D-L448W-T450M | +++ |
| A241D-S403V-C404L-P406A-G443F-L448W-T450M | +++ |
| A241D-S403V-C404L-P406A-G443N-L448W-T450M | +++ |
| A241D-S403V-C404L-P406A-G443S-L448W-T450M | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
|---|---|
| A241D-S403V-C404L-P406A-V445L-L448W-T450M | +++ |
| A241D-C404L-P406A-G443F-L446V-L448W-T450M | +++ |
| A241D-C404L-P406A-L446V-L448W-T450A | +++ |
| A241D-S403C-C404L-P406A-G443A-L446V-L448W-T450M | +++ |
| A241D-S403C-C404L-P406A-G443S-L446V-L448W-T450M | +++ |
| A241D-S403C-C404L-P406A-G443W-L446V-L448W-T450M | +++ |
| A241D-S403C-C404L-P406A-G443Y-L446V-L448W-T450M | +++ |
| H198Q-A241D-S403C-C404L-P406A-G443F-L446V-L448W-T450M | +++ |
| A241D-S403C-C404L-P406A-P444H-L446V-L448W-T450M | +++ |
| A241D-S403C-C404L-P406A-V408I-L446V-L448W-T450M | +++ |
| A241D-S403C-C404L-P406A-L446M-L448W-T450M | +++ |
| A241D-S403V-C404L-P406A-G443D-L446V-L448W-T450M | +++ |
| A241D-S403V-C404L-P406A-G443F-L446V-L448W-T450M | +++ |
| A241D-S403V-C404L-P406A-G443Y-L446V-L448W-T450M | +++ |
| A241D-S403V-C404L-P406A-L446V-L448W-T450H | +++ |
| A241D-S403A-C404L-P406A-L446V-L448W-T450M | +++ |
| A241D-S403G-C404L-P406A-L446V-L448W-T450M | +++ |
| A241D-S403V-C404L-P406A-V408I-L446V-L448W-T450M | +++ |
| A241D-S403V-C404L-P406A-L446A-L448W-T450M | +++ |
| A241D-S403V-C404L-P406A-L446M-L448W-T450M | +++ |
| C404M-P406A-G443W-L446I-L448W-T450H | +++ |
| C404M-P406A-G443Y-L446I-L448W-T450H | +++ |
| C404M-L405I-P406A-L446I-L448W-T450H | +++ |
| M197V-C404M-P406A-L446I-L448W-T450H | +++ |
| C404M-P406A-Q407K-L446I-L448W-T450H | +++ |
| S403C-C404M-P406A-L446I-L448W-T450H | +++ |
| S403P-C404M-P406A-L446I-L448W-T450H | +++ |
| C404M-L405I-P406A-L448W-T450H | +++ |
| M197V-S403C-C404M-L405I-P406A-G443Y-L448W-T450H | +++ |
| S403C-C404M-P406A-L448W-T450H | +++ |
| M197V-S403C-C404M-L405I-P406A-L448W-T450H | +++ |
| M197V-C404M-L405I-P406A-L446I-L448W-T450H | +++ |
| M197V-C404M-P406A-L448W-T450H | +++ |
| S403C-C404M-L405I-P406A-L448W-T450H | +++ |
| C404M-L405I-P406A-G443Y-L446I-L448W-T450H | +++ |
| M197V-C404M-L405I-P406A-L448W-T450H | +++ |
| M197V-S403C-C404M-P406A-L446I-L448W-T450H | +++ |
| S403C-C404M-L405I-P406A-G443Y-L448W-T450H | +++ |
| C404M-P406A-G443Y-L448W-T450H | +++ |
| S403C-C404M-P406A-G443Y-L446I-L448W-T450H | +++ |
| S403C-C404M-P406A-G443Y-L448W-T450H | +++ |
| S403C-C404M-L405I-P406A-L446I-L448W-T450H | +++ |
| M197V-C404M-L405I-P406A-G443Y-L446I-L448W-T450H | +++ |
| S403C-C404M-L405I-P406A-G443Y-L446I-L448W-T450H | +++ |
| C404M-L405I-P406A-G443Y-L448W-T450H | +++ |
| M197V-S403C-C404M-L405I-P406A-L446I-L448W-T450H | +++ |
| M197V-C404M-P406A-G443Y-L446I-L448W-T450H | +++ |
| M197V-S403C-C404M-L405I-P406A-G443Y-L446I-L448W-T450H | +++ |
| M197V-S403C-C404M-P406A-G443Y-L446I-L448W-T450I | +++ |
| A241D-S403C-C404L-P406A-G443D-L448W-L449I | +++ |
| A241D-S403C-C404L-P406A-P444H-L446M-L448W-T450M | +++ |
| A241D-S403C-C404L-P406A-G443D-P444H-L448W-L449I | +++ |
| A241D-S403C-C404L-P406A-G443D-P444A-L448W | +++ |
| A241D-S403C-C404L-P406A-G443Y-P444H-L446M-L448W-T450M | +++ |
| A241D-S403C-C404L-P406A-V408I-P444H-L446M-L448W-T450M | +++ |
| A241D-S403C-C404L-P406A-G443Y-L446M-L448W-T450M | +++ |
| A25E-A241D-S403C-C404L-P406A-L448W | +++ |
| A66H-A241D-S403C-C404L-P406A-L448W | +++ |
| A80S-A241D-S403C-C404L-P406A-L448W | +++ |
| E24A-A241D-S403C-C404L-P406A-L448W | +++ |
| E24D-A241D-S403C-C404L-P406A-L448W | +++ |
| E24L-A241D-S403C-C404L-P406A-L448W | +++ |
| E24V-A241D-S403C-C404L-P406A-L448W | +++ |
| G237D-A241D-S403C-C404L-P406A-L448W | +++ |
| G237P-A241D-S403C-C404L-P406A-L448W | +++ |
| A241D-S403C-C404L-P406A-G443A-L448W | +++ |
| I236L-A241D-S403C-C404L-P406A-L448W | +++ |
| I236V-A241D-S403C-C404L-P406A-L448W | +++ |
| A241D-I296Q-S403C-C404L-P406A-L448W | +++ |
| K214T-A241D-S403C-C404L-P406A-L448W | +++ |
| N64H-A241D-S403C-C404L-P406A-L448W | +++ |
| A241D-S403C-C404L-P406A-L448W-P479C | +++ |
| A241D-S403C-C404L-P406A-L448W-P479I | +++ |
| A241D-S403C-C404L-P406A-L448W-P479L | +++ |
| A241D-S403C-C404L-P406A-L448W-P479M | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
|---|---|
| A241D-S403C-C404L-P406A-L448W-P479S | +++ |
| A241D-S403C-C404L-P406A-L448W-P479T | +++ |
| A241D-S403C-C404L-P406A-L448W-P479V | +++ |
| A241D-S403C-C404L-P406A-L448W-R496L | +++ |
| S175E-A241D-S403C-C404L-P406A-L448W | +++ |
| A241D-S403C-C404L-P406A-L448W-A473S | +++ |
| S86N-A241D-S403C-C404L-P406A-L448W | +++ |
| S86Y-A241D-S403C-C404L-P406A-L448W | +++ |
| V240N-A241D-S403C-C404L-P406A-L448W | +++ |
| V240N-A241D-S403C-C404L-P406A-L448W-P479V | +++ |
| A66H-K214T-G237P-A241D-S403C-C404L-P406A-L448W | +++ |
| K214T-G237P-A241D-I296Q-S403C-C404L-P406A-L448W | +++ |
| K214T-G237P-A241D-I296Q-S403C-C404L-P406A-L448W-P479V | +++ |
| K214T-A241D-S403C-C404L-P406A-L448W-R496L | +++ |
| V240N-A241D-S403C-C404L-P406A-L448W-R496L | +++ |
| K214T-G237P-V240N-A241D-I296Q-S403C-C404L-P406A-L448W | +++ |
| A66H-A241D-S403C-C404L-P406A-L448W-P479V | +++ |
| A66H-K214T-G237P-V240N-A241D-S403C-C404L-P406A-L448W-P479V | +++ |
| A66H-K214T-A241D-S403C-C404L-P406A-L448W-P479V | +++ |
| G237P-A241D-I296Q-S403C-C404L-P406A-L448W-P479V | +++ |
| A66H-K214T-G237P-A241D-S403C-C404L-P406A-L448W-P479V | +++ |
| A241D-I296Q-S403C-C404L-P406A-L448W-P479V | +++ |
| A66H-K214T-A241D-I296Q-S403C-C404L-P406A-L448W | +++ |
| K214T-A241D-S403C-C404L-P406A-G443N-L448W | +++ |
| A66H-A241D-I296Q-S403C-C404L-P406A-L448W | +++ |
| K214T-A241D-I296Q-S403C-C404L-P406A-L448W | +++ |
| G237P-A241D-S403C-C404L-P406A-L448W-P479V | +++ |
| A66H-K214T-A241D-I296Q-S403C-C404L-P406A-L448W-P479V | +++ |
| A66H-G237P-V240N-A241D-S403C-C404L-P406A-L448W-P479V | +++ |
| A66H-G237P-A241D-S403C-C404L-P406A-L448W-P479V | +++ |
| K214T-A241D-I296Q-S403C-C404L-P406A-L448W-P479V | +++ |
| A66H-A241D-I296Q-S403C-C404L-P406A-L448W-P479V | +++ |
| K214T-A241D-S403C-C404L-P406A-G443F-L448W-T450M | +++ |
| K214T-G237P-A241D-S403C-C404L-P406A-L448W-P479V | +++ |
| M197V-A241D-S403C-C404L-P406A-G443F-L448W-T450M | +++ |
| A241D-S403C-C404L-P406A-V408G-G443F-L448W-T450M | +++ |
| A241D-S403C-C404L-P406A-V408L-G443F-L448W-T450M | +++ |
| A241D-S403C-C404L-P406A-G443F-V445L-L448W-T450M | +++ |
| A241D-S403C-C404L-P406A-G443F-V445S-L448W-T450M | +++ |
| A241D-S403C-C404L-P406A-G443F-V445T-L448W-T450M | +++ |
| A241D-S403C-C404L-P406A-G443D-V445T-L448W | +++ |
| M197V-A241D-S403C-C404L-P406A-G443D-P444A-L448W | +++ |
| A241D-S403C-C404L-L405I-P406A-G443D-L448W-L449I | +++ |
| M197V-A241D-S403C-C404L-P406A-G443D-L448W-L449I | +++ |
| A241D-S403C-C404L-P406A-G443D-V445L-L448W-L449I | +++ |
| A241D-S403C-C404L-P406A-G443A-P444H-L448W-L449I | +++ |
| A241D-S403C-C404L-P406A-G443F-P444H-L448W-L449I | +++ |
| A241D-S403C-C404L-P406A-G443L-P444H-L448W-L449I | +++ |
| A241D-S403C-C404L-P406A-G443S-P444H-L448W-L449I | +++ |
| A241D-S403C-C404L-P406A-G443D-P444H-L448W | +++ |
| A241D-S403C-C404L-P406A-G443D-P444H-L448W-L449V | +++ |
| M197V-A241D-S403C-C404L-P406A-G443F-P444H-L448W-L449I | +++ |
| A241D-C404L-L405M-P406A-G443F-L446V-L448W-L449M-T450M | +++ |
| A241D-S403Q-C404L-P406A-G443F-L446V-L448W-T450M | +++ |
| A241D-S403C-C404L-P444H-L448W-T450M | +++ |
| A241D-S403C-C404L-P406S-P444H-L448W-T450M | +++ |
| L195I-A241D-S403C-C404L-P406A-P444H-L448W-T450M | +++ |
| M197V-A241D-S403C-C404L-P406A-P444H-L448W-T450M | +++ |
| A241D-S403C-C404L-P406A-Q407R-P444H-L448W-T450M | +++ |
| A241D-S403C-C404L-P406A-Q407S-P444H-L448W-T450M | +++ |
| A241D-S403C-C404L-P406A-V408I-P444H-L448W-T450M | +++ |
| L195I-A241D-S403C-C404L-P406A-V408I-P444H-L446M-L448W-T450M | +++ |
| M197V-A241D-S403C-C404L-P406A-V408I-P444H-L446M-L448W-T450M | +++ |
| A241D-S403C-C404L-P406A-V408I-P444H-V445C-L446M-L448W-T450M | +++ |
| M197V-A241D-S403C-C404L-P406A-G443Y-P444H-L446M-L448W-T450M | +++ |
| M197V-A241D-S403C-C404L-P406A-G443D-P444H-L448W-L449V | +++ |
| M197V-A241D-S403C-C404L-P406A-G443S-P444H-L448W-L449I | +++ |
| A241D-E339H-S403C-C404L-P406A-G443D-P444H-L448W-L449I | +++ |
| M197V-S403C-C404M-P406A-G443Y-L446I-L448W-T450H-Q455H | +++ |
| S403A-C404M-P406A-G443Y-L446I-L448W-T450H | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
|---|---|
| S403I-C404M-P406A-G443Y-L446I-L448W-T450H | +++ |
| S403Q-C404M-P406A-G443Y-L446I-L448W-T450H | +++ |
| S403V-C404M-P406A-G443Y-L446I-L448W-T450H | +++ |
| S403C-C404M-P406G-G443Y-L446I-L448W-T450H | +++ |
| S403C-C404M-P406A-D442A-G443Y-L446I-L448W-T450H | +++ |
| S403C-C404M-P406A-D442E-G443Y-L446I-L448W-T450H | +++ |
| S403C-C404M-P406A-D442G-G443Y-L446I-L448W-T450H | +++ |
| S403C-C404M-P406A-D442S-G443Y-L446I-L448W-T450H | +++ |
| S403C-C404M-P406A-G443Y-P444H-L446I-L448W-T450H | +++ |
| S403C-C404M-P406A-G443Y-V445A-L446I-L448W-T450H | +++ |
| S403C-C404M-P406A-G443Y-V445C-L446I-L448W-T450H | +++ |
| S403C-C404M-P406A-G443Y-V445L-L446I-L448W-T450H | +++ |
| S403C-C404M-P406A-G443Y-L446I-L448W-T450H-C451N | +++ |
| S403C-C404M-P406A-G443Y-L446I-L448W-T450H-C451S | +++ |
| V196I-M197V-S403C-C404M-P406A-G443Y-L446I-L448W | +++ |
| M197V-S403C-C404M-P406G-G443Y-L446I-L448W | +++ |
| M197V-S403C-C404M-P406S-G443Y-L446I-L448W | +++ |
| M197V-S403C-C404M-P406A-D442A-G443Y-L446I-L448W | +++ |
| M197V-S403C-C404M-P406A-D442C-G443Y-L446I-L448W | +++ |
| M197V-S403C-C404M-P406A-D442G-G443Y-L446I-L448W | +++ |
| M197V-S403C-C404M-P406A-D442H-G443Y-L446I-L448W | +++ |
| S403C-C404M-P406A-D442H-G443Y-L446I-L448W | +++ |
| M197V-S403C-C404M-P406A-D442N-G443Y-L446I-L448W | +++ |
| M197V-S403C-C404M-P406A-D442S-G443Y-L446I-L448W | +++ |
| M197V-S403C-C404M-P406A-G443Y-V445S-L446I-L448W | +++ |
| M197V-S403C-C404M-P406A-G443Y-V445T-L446I-L448W | +++ |
| S403C-C404M-P406A-D442A-G443Y-V445L-L446I-L448W-T450H | +++ |
| M197V-S403C-C404M-P406A-D442A-G443Y-L446I-L448W-T450H | +++ |
| M197V-S403C-C404M-P406A-D442Q-G443Y-L446I-L448W-T450H | +++ |
| M197V-S403C-C404M-P406A-D442N-G443Y-L446I-L448W-T450H | +++ |
| M197V-S403C-C404M-P406A-D442S-G443Y-L446I-L448W-T450H | +++ |
| A241D-S403C-C404L-P406A-E441R-G443D-P444H-L448W-L449I | +++ |
| A241D-S403C-C404L-P406A-D442L-G443D-P444H-L448W-L449I | +++ |
| A241D-S403C-C404L-P406A-D442R-G443D-P444H-L448W-L449I | +++ |
| A241D-S403C-C404L-P406A-D442M-G443D-P444H-L448W-L449I | +++ |
| A241D-S403C-C404L-P406A-D442A-G443D-P444H-L448W-L449I | +++ |
| A241D-S403C-C404L-P406A-D442S-G443D-P444H-L448W-L449I | +++ |
| A241D-S403C-C404L-P406A-D442G-G443D-P444H-L448W-L449I | +++ |
| A241D-S403C-C404L-P406A-G443D-P444H-V445T-L448W-L449I | +++ |
| A241D-S403C-C404L-P406A-Q407C-G443D-P444H-L448W-L449I | +++ |
| A241D-S403C-C404L-P406A-G443D-P444H-L448W-L449I-P454A | +++ |
| A241D-S403C-C404L-P406A-G443D-P444H-L448W-L449I-P454W | +++ |
| A241D-S403C-C404L-P406A-G443D-P444H-L448W-L449I-P454V | +++ |
| A241D-S403C-C404L-P406A-G443D-P444H-L448W-L449I-P454M | +++ |
| A241D-S403C-C404L-P406A-G443D-P444H-L448W-L449I-P454H | +++ |
| A241D-S403C-C404L-P406A-G443D-P444H-L448W-L449I-P454T | +++ |
| A241D-S403C-C404L-P406A-G443D-P444H-L448W-L449I-P454G | +++ |
| A241D-S403C-C404L-P406A-G443D-P444H-L448W-L449I-P454K | +++ |
| A241D-S403C-C404L-P406A-G443D-P444H-L448W-L449I-P454R | +++ |
| A241D-S403C-C404L-P406A-G443D-P444H-L448W-L449I-P454Q | +++ |
| A241D-S403C-C404L-P406A-G443D-P444H-L448W-L449I-P454L | +++ |
| A241D-S403C-C404L-P406A-G443D-P444H-L448W-L449I-A459Y | +++ |
| A241D-S403C-C404L-P406A-G443D-P444H-L448W-L449I-A459N | +++ |
| A241D-S403C-C404L-P406A-G443D-P444H-L448W-L449I-A460N | +++ |
| A241D-S403C-C404L-P406A-G443D-P444H-L448W-L449I-A460L | +++ |
| A241D-S403C-C404L-P406A-G443D-P444H-L448W-L449I-A460M | +++ |
| A241D-S403C-C404L-P406A-G443D-P444H-L448W-L449I-A460R | +++ |
| A241D-S403C-C404L-P406A-G443D-P444H-L448W-L449I-R461V | +++ |
| A241D-S403C-C404L-P406A-G443D-P444H-L448W-L449I-R461S | +++ |
| E154D-A241D-E339H-S403C-C404L-P406A-G443D-P444H-L448W-L449I | +++ |
| A241D-L302R-E339H-S403C-C404L-P406A-G443D-P444H-L448W-L449I | +++ |
| A241D-E339H-A363G-S403C-C404L-P406A-G443D-P444H-L448W-L449I | +++ |
| A241D-E339H-R390D-S403C-C404L-P406A-G443D-P444H-L448W-L449I | +++ |
| A241D-E339H-R390L-S403C-C404L-P406A-G443D-P444H-L448W-L449I | +++ |
| A241D-E339H-R390N-S403C-C404L-P406A-G443D-P444H-L448W-L449I | +++ |
| A241D-E339H-R390Q-S403C-C404L-P406A-G443D-P444H-L448W-L449I | +++ |
| A241D-E339H-R391D-S403C-C404L-P406A-G443D-P444H-L448W-L449I | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
|---|---|
| A241D-E339H-R391W-S403C-C404L-P406A-G443D-P444H-L448W-L449I | +++ |
| A241D-E339H-E394Q-S403C-C404L-P406A-G443D-P444H-L448W-L449I | +++ |
| V3M-A241D-E339H-E394T-S403C-C404L-P406A-G443D-P444H-L448W-L449I | +++ |
| A241D-E339H-G398R-S403C-C404L-P406A-G443D-P444H-L448W-L449I | +++ |
| A129V-A241D-E339H-G398C-S403C-C404L-P406A-G443D-P444H-L448W-L449I | +++ |
| A241D-E339H-S403C-C404L-P406A-V408L-G443D-P444H-L448W-L449I | +++ |
| A241D-E339H-S403C-C404L-P406A-V408M-G443D-P444H-L448W-L449I | +++ |
| A241D-E339H-S403C-C404L-P406A-E441S-G443D-P444H-L448W-L449I | +++ |
| A241D-E339H-S403C-C404L-P406A-D442H-G443D-P444H-L448W-L449I | +++ |
| A241D-E339H-S403C-C404L-P406A-D442R-G443D-P444H-L448W-L449I | +++ |
| I168V-A241D-E339H-S403C-C404L-P406A-G443D-P444H-V445L-L448W-L449I | +++ |
| A241D-E339H-S403C-C404L-P406A-G443D-P444H-L446M-L448W-L449I | +++ |
| A241D-E339H-S403C-C404L-P406A-G443D-P444H-L448W-L449I-Y452F | +++ |
| A241D-E339H-S403C-C404L-P406A-G443D-P444H-L448W-L449I-T453L | +++ |
| A241D-E339H-S403C-C404L-P406A-G443D-P444H-L448W-L449I-P454H | +++ |
| A241D-E339H-S403C-C404L-P406A-G443D-P444H-L448W-L449I-P454K | +++ |
| A241D-E339H-S403C-C404L-P406A-G443D-P444H-L448W-L449I-P454R | +++ |
| A241D-E339H-S403C-C404L-P406A-G443D-P444H-L448W-L449I-P454S | +++ |
| A241D-E339H-S403C-C404L-P406A-G443D-P444H-L448W-L449I-P454T | +++ |
| A241D-E339H-S403C-C404L-P406A-G443D-P444H-L448W-L449I-P454W | +++ |
| A241D-E339H-S403C-C404L-P406A-G443D-P444H-L448W-L449I-R461V-P479S | +++ |
| A241D-S403C-C404L-P406A-Q407A-G443N-L448W | +++ |
| A241D-S403C-C404L-P406A-D442A-G443N-L448W | +++ |
| A241D-S403C-C404L-P406A-G443N-L448W-T450H | +++ |
| A241D-S403C-C404L-P406A-G443N-L448W-T453R | +++ |
| A241D-S403C-C404L-P406A-G443N-L446M-L448W | +++ |
| A241D-E339H-S403C-C404L-P406A-E441K-G443D-P444H-L446M-L448W-L449I | +++ |
| M197V-G237A-A241D-S403C-C404L-P406A-G443F-L448W-T450M | +++ |
| M197V-G237D-A241D-S403C-C404L-P406A-G443F-L448W-T450M | +++ |
| M197V-G237N-A241D-S403C-C404L-P406A-G443F-L448W-T450M | +++ |
| M197V-G237P-A241D-S403C-C404L-P406A-G443F-L448W-T450M | +++ |
| M197V-D238H-A241D-S403C-C404L-P406A-G443F-L448W-T450M | +++ |
| M197V-D238R-A241D-S403C-C404L-P406A-G443F-L448W-T450M | +++ |
| M197V-D238S-A241D-S403C-C404L-P406A-G443F-L448W-T450M | +++ |
| M197V-D238W-A241D-S403C-C404L-P406A-G443F-L448W-T450M | +++ |
| M197V-A241D-L302A-S403C-C404L-P406A-G443F-L448W-T450M | +++ |
| M197V-A241D-L302K-S403C-C404L-P406A-G443F-L448W-T450M | +++ |
| M197V-A241D-L302M-S403C-C404L-P406A-G443F-L448W-T450M | +++ |
| M197V-A241D-L302R-S403C-C404L-P406A-G443F-L448W-T450M | +++ |
| M197V-A241D-A359V-S403C-C404L-P406A-G443F-L448W-T450M | +++ |
| M197V-A241D-G398R-S403C-C404L-P406A-G443F-L448W-T450M | +++ |
| M197V-A241D-E394C-S403C-C404L-P406A-G443F-L448W-T450M | +++ |
| M197V-A241D-E394D-S403C-C404L-P406A-G443F-L448W-T450M | +++ |
| M197V-A241D-V396I-S403C-C404L-P406A-G443F-L448W-T450M | +++ |
| V35I-M197V-A241D-S403C-C404L-P406A-Q407I-G443F-L448W-T450M | +++ |
| M197V-A241D-S403C-C404L-P406A-V408A-G443F-L448W-T450M | +++ |
| Y2N-M197V-A241D-S403C-C404L-P406A-G443F-L448W-T450M | +++ |
| M197V-A241D-S403C-C404L-P406A-R439G-G443F-L448W-T450M | +++ |
| M197V-A241D-S403C-C404L-P406A-F440L-G443F-L448W-T450M | +++ |
| M197V-A241D-S403C-C404L-P406A-G443F-L448W-T450M-A460F | +++ |
| M197V-A241D-S403C-C404L-P406A-G443F-L448W-T450M-A460L | +++ |
| M197V-A241D-S403C-C404L-P406A-G443F-L448W-T450M-A460R | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
|---|---|
| M197V-A241D-S403C-C404L-P406A-G443F-L448W-T450M-P454T | +++ |
| M197V-A241D-S403C-C404L-P406A-G443F-L448W-T450M-A462V | +++ |
| S403C-C404M-P406G-Q407T-G443Y-L446I-L448W-T450H | +++ |
| M5I-M197V-S403C-C404M-P406G-D442N-G443Y-L446I-L448W-T450H | +++ |
| M197V-A241D-S403C-C404L-P406A-G443D-P444H-L448W-L449V-A459D | +++ |
| A241D-S403C-C404L-P406A-G443D-L448W-L449I-A459G | +++ |
| S403C-C404M-P406A-Q407T-G443Y-L446I-L448W-T450H-A459G | +++ |
| S403C-C404M-P406A-G443Y-L446I-L448W-T450H-A459G | +++ |
| A241D-S403C-C404L-P406A-G443D-L448W-L449I-A459R | +++ |
| A241D-S403C-C404L-P406A-G443Y-L448W-T450M-A460E | +++ |
| A241D-S403C-C404L-P406A-V408I-P444H-L446M-L448W-T450M-A460G | +++ |
| M197V-A241D-S403C-C404L-P406A-G443D-P444H-L448W-L449V-A460G-A462V | +++ |
| A241D-S403C-C404L-P406A-G443Y-L448W-T450M-A460L | +++ |
| S403C-C404M-P406A-Q407T-G443Y-L446I-L448W-T450H-A460L | +++ |
| A241D-S403C-C404L-P406A-V408I-P444H-L446M-L448W-T450M-A460Q | +++ |
| A241D-S403C-C404L-P406A-G443Y-L448W-T450M-A462C | +++ |
| M197V-S403C-C404M-P406A-D442N-G443Y-L446I-L448W-T450H-A462C | +++ |
| A241D-S403C-C404L-P406A-G443Y-L448W-T450M-A462V | +++ |
| S403C-C404M-P406A-Q407T-G443Y-L446I-L448W-T450H-A462V | +++ |
| S403C-C404M-P406A-Q407T-G443Y-L446I-L448W-T450H-P454Q-A462V | +++ |
| H198W-S403V-C404M-P406A-Q407T-G443Y-L446I-L448W-T450H | +++ |
| L74V-H198W-S403V-C404M-P406A-Q407T-G443Y-L446I-L448W-T450H | +++ |
| H198W-S403C-C404M-P406A-D442Q-G443Y-L446I-L448W-T450H | +++ |
| A241D-S403C-C404L-P406A-E441G-G443D-L448W-L449I | +++ |
| Q208L-A241D-S403C-C404L-P406A-V408I-G443R-P444H-L446M-L448W-T450M | +++ |
| A241D-S403C-C404L-P406A-V408I-G443W-P444H-L446M-L448W-T450M | +++ |
| A241D-S403C-C404L-P406A-G443D-L448W-L449I-H458G | +++ |
| L195V-S403C-C404M-P406A-Q407T-G443Y-L446I-L448W-T450H | +++ |
| L195V-S403C-C404M-P406A-G443Y-L446I-L448W-T450H | +++ |
| M197V-A241D-S403C-C404L-P406A-G443Y-L448W-T450M | +++ |
| M197V-S403C-C404M-P406A-Q407T-G443Y-L446I-L448W-T450H | +++ |
| M197V-S403C-C404M-P406A-D442N-G443Y-L446I-L448W-T450H-E456Q | +++ |
| S403C-C404F-P406A-Q407T-G443Y-L446I-L448W-T450H | +++ |
| S403C-C404M-P406A-Q407T-G443Y-P444F-L446I-L448W-T450H | +++ |
| A241D-S403C-C404L-P406A-G443D-L448W-L449I-P454K | +++ |
| M197V-A241D-S403C-C404L-P406A-G443D-P444H-L448W-L449V-P454K | +++ |
| A241D-S403C-C404L-P406A-G443D-L448W-L449I-P454R | +++ |
| M197V-A241D-S403C-C404L-P406A-G443D-P444H-L448W-L449V-P454R | +++ |
| A241D-S403C-C404L-P406A-G443D-L448W-L449I-Q455S | +++ |
| M197V-S403C-C404M-P406A-D442N-G443Y-L446I-L448W-T450H-Q455V | +++ |
| S403C-C404M-P406A-Q407T-G443Y-L446I-L448W-T450H-R457K | +++ |
| M197V-S403C-C404M-P406A-D442N-G443Y-L446I-L448W-T450H-R461G | +++ |
| A241D-S403C-C404L-P406A-V408I-P444H-L446M-L448W-T450M-R461S | +++ |
| M197V-A241D-S403C-C404L-P406A-G443D-P444H-L448W-L449V-T450H | +++ |
| A241D-S403C-C404L-P406A-G443D-L448W-L449I-T450V | +++ |
| M197V-A241D-S403C-C404L-P406A-G443D-P444H-L448W-L449V-T450V | +++ |
| H36Y-M197V-S403C-C404M-P406A-D442N-G443Y-L446I-L448W-T450H-T453G | +++ |
| S403C-C404M-P406A-Q407T-G443Y-L446I-L448W-T450H-T453N | +++ |
| H198W-S403C-C404M-P406A-G443Y-L446I-L448W-T450H-T453P | +++ |
| A241D-S403C-C404L-P406A-V408I-P444H-L446M-L448W-T450M-T453R | +++ |
| A241D-S403C-C404L-P406A-V408I-P444H-L446M-L448W-T450M-T453S | +++ |
| S403C-C404M-P406A-Q407T-G443Y-V445L-L446I-L448W-T450H | +++ |
| S403C-C404M-P406A-Q407T-G443Y-V445S-L446I-L448W-T450H | +++ |
| M197V-A241D-S403C-C404L-P406A-G443D-P444H-L448W | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
|---|---|
| A241D-S403C-C404L-P406A-V408I-P444H-L446M-L448W-T450M-Y452F | +++ |
| M5I-A241D-S403C-C404L-P406A-G443Y-L448W-T450M | +++ |
| M197V-A241D-S403C-C404L-P406A-G443F-L446M-L448W-T450M | +++ |
| M197V-S403C-C404L-P406A-D442N-G443Y-L446M-L448W-T450H | +++ |
| M197V-S403C-C404L-P406A-D442N-G443Y-L448W-T450M | +++ |
| M197V-S403C-C404L-P406A-D442N-G443Y-L448W-T450H | +++ |
| S403C-C404L-P406A-Q407T-G443Y-L446M-L448W-T450H | +++ |
| S403C-C404L-P406A-Q407T-G443Y-L446F-L448W-T450H | +++ |
| S403C-C404L-P406A-Q407T-G443Y-L448W-T450H | +++ |
| A241D-E339H-A343S-S403C-C404L-P406A-G443D-P444H-L448W-L449I-P454R | +++ |
| A241D-E339H-A350S-S403C-C404L-P406A-G443D-P444H-L446M-L448W-L449I | +++ |
| A241D-E339H-A395E-S403C-C404L-P406A-A426V-G443D-P444H-L446M-L448W-L449I | +++ |
| A241D-E339H-S403C-C404L-P406A-D442N-G443D-P444H-L448W-L449I-P454R | +++ |
| A241D-E339H-S403C-C404L-P406A-D442S-G443D-P444H-L448W-L449I-P454R | +++ |
| A241D-E339H-S403C-C404L-P406A-D442T-G443D-P444H-L446M-L448W-L449I | +++ |
| A241D-E339H-S403C-C404L-P406A-G443H-P444H-L448W-L449I-P454R | +++ |
| A241D-E339H-S403C-C404L-P406A-E441R-G443D-P444H-L448W-L449I-P454R | +++ |
| A241D-E339H-I347C-S403C-C404L-P406A-G443D-P444H-L448W-L449I-P454R | +++ |
| V3L-A241D-L302Q-E339H-S403C-C404L-P406A-G443D-P444H-L446M-L448W-L449I | +++ |
| A241D-E339H-S403C-C404L-L405T-P406A-G443D-P444H-L446M-L448W-L449I | +++ |
| M5I-A241D-E339H-S403C-C404L-P406A-G443D-P444H-L446M-L448W-L449I | +++ |
| A241D-E339H-S403C-C404L-P406A-G443D-P444H-L448W-L449I-P454R-Q455A | +++ |
| A241D-E339H-S403C-C404L-P406A-G443D-P444H-L448W-L449I-P454R-Q455N | +++ |
| A241D-S403C-C404L-P406A-G443D-P444H-L448W-L449I-P454R-A459E | +++ |
| A241D-S403C-C404L-P406A-G443D-P444H-L448W-L449I-P454R-A459M | +++ |
| A241D-S403C-C404L-P406A-G443D-P444H-L448W-L449I-P454R-A459Q | +++ |
| A241D-S403C-C404L-P406A-G443D-P444H-L448W-L449I-P454R-A459T | +++ |
| A241D-S403C-C404L-P406A-G443N-P444H-L448W-L449I-P454R | +++ |
| A241D-S403C-C404L-P406A-E441G-G443D-P444H-L448W-L449I-P454R | +++ |
| A241D-S403C-C404L-P406A-G443D-P444F-L448W-L449I-P454R | +++ |
| A241D-S403C-C404L-P406A-G443D-P444H-L448W-L449I-P454R-H458F | +++ |
| A241D-S403C-C404L-P406A-G443D-P444H-L448W-L449I-P454R-H458N | +++ |
| A241D-I296Q-S403C-C404L-P406A-G443D-P444H-L448W-L449I-P454R | +++ |
| A241D-L302A-S403C-C404L-P406A-G443D-P444H-L448W-L449I-P454R | +++ |
| A241D-S403C-C404L-P406A-G443D-P444H-L448W-L449I-T453S-P454R | +++ |
| V196I-A241D-S403C-C404L-P406A-G443D-P444H-L448W-L449I-P454R | +++ |
| A241D-V305I-S403C-C404L-P406A-G443D-P444H-L448W-L449I-P454R | +++ |
| A241D-V305T-S403C-C404L-P406A-G443D-P444H-L448W-L449I-P454R | +++ |
| M197V-G237A-A241D-S403C-C404L-P406A-E441G-G443F-L448W-T450M | +++ |
| M197V-G237A-A241D-S403C-C404L-P406A-E441H-G443F-L448W-T450M | +++ |
| M197V-G237A-A241D-S403C-C404L-P406A-E441T-G443F-L448W-T450M | +++ |
| M197V-A241D-S403C-C404L-P406A-F440L-G443F-L446M-L448W-T450M | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
| --- | --- |
| M197V-A241D-H277Y-S403C-C404L-P406A-F440L-G443F-L448W-L449I-T450M | +++ |
| M197V-G237A-A241D-S403C-C404L-P406A-G443F-P444H-L448W-T450M | +++ |
| M197V-G237A-A241D-S403C-C404L-P406A-G443F-P444I-L448W-T450M | +++ |
| M197V-A241D-S403C-C404L-P406A-Q407R-F440L-G443F-L448W-T450M | +++ |
| V6M-M197V-D238H-A241D-S403C-C404L-P406A-G443F-L448W-T450M-T453C | +++ |
| M197V-D238H-A241D-S403C-C404L-P406A-G443F-L448W-T450M-T453R | +++ |
| M197V-D238H-A241D-S403C-C404L-P406A-G443F-L448W-T450M-Y452F | +++ |
| A241D-S403C-C404L-P406A-P444H-L446M-L448W-T450M-Y452F | +++ |
| A241D-S403C-C404L-P406A-V408I-P444H-L446M-L448W-T450M-Y452F-Q455H | +++ |
| A241D-S403C-C404L-P406A-V408I-P444H-L446M-P447Q-L448W-T450M-A460G | +++ |
| A241D-S403C-C404L-P406A-V408I-P444H-L446M-L448W-T450M-Q455K-R461S | +++ |
| A241D-S403C-C404L-P406A-V408I-P444H-L446M-L448W-T450M-Q455V-R461S | +++ |
| Q204R-S403C-C404L-P406A-Q407T-G443Y-L446F-L448W-T450H | +++ |
| Q204S-S403C-C404L-P406A-Q407T-G443Y-L446F-L448W-T450H | +++ |
| L302F-S403C-C404L-P406A-Q407T-G443Y-L446F-L448W-T450H | +++ |
| L302S-S403C-C404L-P406A-Q407T-G443Y-L446F-L448W-T450H | +++ |
| E349S-S403C-C404L-P406A-Q407T-G443Y-L446F-L448W-T450H | +++ |
| A395C-S403C-C404L-P406A-Q407T-G443Y-L446F-L448W-T450H | +++ |
| S403C-C404L-P406A-Q407T-E441P-G443Y-L446F-L448W-T450H | +++ |
| S403C-C404L-P406A-Q407T-G443A-L446F-L448W-T450H | +++ |
| S403C-C404L-P406A-Q407T-G443Y-P444Q-L446F-L448W-T450H | +++ |
| S403C-C404L-P406A-Q407T-G443Y-L446F-L448W-T450H-H458L | +++ |
| S403C-C404L-P406A-Q407T-G443Y-L446F-L448W-T450H-H458M | +++ |
| A241D-E339H-H366F-S403C-C404L-P406A-G443D-P444H-L446M-L448W-L449I | +++ |
| A241D-E339H-H366F-S403C-C404L-P406A-G443D-P444H-L446M-L448W | +++ |
| A241D-E339H-H366I-S403C-C404L-P406A-G443D-P444H-L446M-L448W-L449I | +++ |
| A241D-E339H-L368I-S403C-C404L-P406A-G443D-P444H-L446M-L448W-L449I | +++ |
| A241D-E339H-L368M-S403C-C404L-P406A-G443D-P444H-L446M-L448W-L449I | +++ |
| A241D-E339H-L368M-S403C-C404L-L405M-P406A-G443D-P444H-L446M-L448W-L449I | +++ |
| A241D-E339H-A395V-S403C-C404L-P406A-D442N-G443D-P444H-L448W-L449I-P454R | +++ |
| A241D-E339H-S403C-C404L-P406A-D442N-G443D-P444H-L448W-L449I-P454R-A460F | +++ |
| A241D-E339H-E349M-S403C-C404L-P406A-D442N-G443D-P444H-L448W-L449I-P454R | +++ |
| A241D-E339H-S403C-C404L-P406A-E441H-D442N-G443D-P444H-L448W-L449I-P454R | +++ |
| A241D-E339H-S403C-C404L-P406A-E441N-D442N-G443D-P444H-L448W-L449I-P454R | +++ |
| A241D-E339H-S403C-C404L-P406A-E441R-D442N-G443D-P444H-L448W-L449I-P454R | +++ |
| A126V-A241D-E339H-S403C-C404L-P406A-D442N-G443D-P444H-L448W-L449I-P454R | +++ |
| A241D-E339H-S403C-C404L-P406A-D442N-G443D-P444H-L448W-L449I-P454R-H458E | +++ |
| A241D-E339H-S403C-C404L-P406A-D442N-G443D-P444H-L448W-L449I-P454R-H458G | +++ |
| A241D-E339H-S403C-C404L-P406A-D442N-G443D-P444H-L448W-L449I-P454R-H458L | +++ |
| A241D-E339H-S403C-C404L-P406A-D442N-G443D-P444H-L448W-L449I-P454R-H458Q | +++ |
| A241D-E339H-S403C-C404L-P406A-D442N-G443D-P444H-L448W-L449I-P454R-H458R | +++ |
| A241D-E339H-S403C-C404L-P406A-D442N-G443D-P444H-L448W-L449I-P454R-H458S | +++ |
| A241D-E339H-S403C-C404L-P406A-D442N-G443D-P444H-L448W-L449I-P454R-H458Y | +++ |

TABLE 13-continued

List of *Streptomyces* sp. 769 3-MethylCrotonate Decarboxylase variants presenting an increase in isobutene production from 3-methylcrotonic acid.

| Mutants | Activity relative to WT |
|---|---|
| A241D-E339H-S403C-C404L-P406A-D442N-G443D-P444H-L448W-L449V-P454R | +++ |
| A241D-L302C-E339H-S403C-C404L-P406A-D442N-G443D-P444H-L448W-L449I-P454R | +++ |
| A241D-E339H-S403C-C404L-L405V-P406A-D442N-G443D-P444H-L448W-L449I-P454R | +++ |
| A241D-E339H-S403C-C404L-P406A-Q407R-D442N-G443D-P444H-L448W-L449I-P454R | +++ |
| A241D-E339H-S403C-C404L-P406A-Q407S-D442N-G443D-P444H-L448W-L449I-P454R | +++ |
| A241D-E339H-S403C-C404L-P406A-D442N-G443D-P444H-L448W-L449I-P454R-Q455E | +++ |
| H36Y-A241D-R298S-E339H-S403C-C404L-P406A-D442N-G443D-P444H-L448W-L449I-P454R | +++ |
| A241D-E339H-S403C-C404L-P406A-D442N-G443D-P444H-L448W-L449I-P454A | +++ |
| A241D-E339H-S403C-C404L-P406A-D442N-G443D-P444H-L448W-L449I-P454D | +++ |
| A241D-E339H-S403C-C404L-P406A-D442N-G443D-P444H-L448W-L449I-P454L | +++ |
| A241D-E339H-S403C-C404L-P406A-D442N-G443D-P444H-L448W-L449I | +++ |
| A241D-E339H-S403C-C404L-P406A-D442N-G443D-P444H-L448W-L449I-P454S | +++ |
| A241D-E339H-S403C-C404L-P406A-D442N-G443D-P444H-L448W-L449I-P454R-R461A | +++ |
| A241D-E339H-S403C-C404L-P406A-D442N-G443D-P444H-L448W-L449I-P454R-R461L | +++ |
| A241D-E339H-S403C-C404L-P406A-D442N-G443D-P444H-L448W-L449I-P454R-R461M | +++ |
| A241D-E339H-S403C-C404L-P406A-D442N-G443D-P444H-L448W-L449I-P454R-R461Q | +++ |
| A241D-E339H-S403C-C404L-P406A-D442N-G443D-P444H-L448W-L449I-P454R-R461S | +++ |
| A241D-E339H-S403C-C404L-P406A-D442N-G443D-P444H-L448W-L449I-P454R-R461V | +++ |
| A241D-E339H-S403C-C404L-P406A-D442N-G443D-P444H-L448W-L449I-T450S-P454R | +++ |
| A241D-S403C-C404L-P406S-G443D-P444H-L448W-L449I | +++ |
| M5I-A241D-S403C-C404L-P406A-G443D-P444H-L448W-L449I | +++ |
| V166D-A241D-S403C-C404L-P406A-G443D-P444H-L448W-L449I-Y452F | +++ |

TABLE 14

List of the positions modified in the variants of *Streptomyces* sp. 769 3-MethylCrotonate Decarboxylase with increased activity

| Position | Wild-Type amino Acid | Mutations |
|---|---|---|
| 2 | Y | N |
| 3 | V | L, M |
| 5 | M | I |
| 6 | V | M |
| 24 | E | A, D, L, V |
| 25 | A | E |
| 35 | V | I |
| 36 | H | Y |
| 64 | N | H |
| 66 | A | H |
| 74 | L | V |
| 80 | A | S |
| 85 | P | L |
| 86 | S | N, Y |
| 126 | A | V |
| 129 | A | V |
| 154 | E | D |
| 166 | V | D |
| 168 | I | V |
| 175 | S | E |
| 195 | L | I, V |
| 196 | V | I |
| 197 | M | V |
| 198 | H | Q, W |
| 204 | Q | R, S |
| 208 | Q | L |
| 214 | K | T |
| 236 | I | L, V |
| 237 | G | A, D, N, P |
| 238 | D | H, R, S, W |
| 240 | V | I, N |
| 241 | A | D, N, V |
| 277 | H | Y |
| 296 | I | Q |
| 298 | R | S |
| 302 | L | A, C, F, K, M, Q, R, S |
| 305 | V | I, T |
| 339 | E | H |
| 343 | A | S |
| 347 | I | C |
| 349 | E | M, S |
| 350 | A | S |

TABLE 14-continued

List of the positions modified in the variants of *Streptomyces* sp. 769 3-MethylCrotonate Decarboxylase with increased activity

| Position | Wild-Type amino Acid | Mutations |
|---|---|---|
| 359 | A | C, V |
| 363 | A | G |
| 366 | H | F, I |
| 368 | L | I, M |
| 390 | R | D, L, N, Q, S |
| 391 | R | D, W |
| 394 | E | C, D, Q, T |
| 395 | A | C, E, V |
| 396 | V | I |
| 398 | G | C, R |
| 401 | F | Y |
| 402 | G | A |
| 403 | S | A, C, G, H, I, N, P, Q, R, V |
| 404 | C | F, L, M |
| 405 | L | H, I, M, T, V |
| 406 | P | A, G, S |
| 407 | Q | A, C, I K, R, S, T |
| 408 | V | A, C, I, L, M |
| 426 | A | V |
| 439 | R | C |
| 440 | F | L |
| 441 | E | G, H, K, N, P, R, S, T |
| 442 | D | A, C, E, G, H, L, M, N, Q, R, S, T |
| 443 | G | A, D, F, H, L, N, R, S, W, Y |
| 444 | P | A, E, F, H, I, L, Q, T |
| 445 | V | A, C, L, S, T |
| 446 | L | A, C, F, I, M, N, S, V |
| 447 | P | Q |
| 448 | L | F, W, Y |
| 449 | L | I, M, V |
| 450 | T | A, H, M, N, Q, S, V |
| 451 | C | N, S |
| 452 | Y | F |
| 453 | T | C, G, L, N, P, R, S |
| 454 | P | A, D, G, H, K, L, M, Q, R, S, T, V, W |
| 455 | Q | A, E, H, K, N, S, V |
| 456 | E | Q |
| 457 | R | K |
| 458 | H | E, F, G, L, M, N, Q, R, S, Y |
| 459 | A | D, E, G, M, N, Q, R, T, Y |
| 460 | A | E, F, G, L, M, N, Q, R |
| 461 | R | A, G, L, M, Q, S, V |
| 462 | A | C, V |
| 473 | A | S |
| 479 | P | C, I, L, M, S, T, V |
| 496 | R | L |

The invention claimed is:

1. A variant of a 3-methylcrotonic acid decarboxylase (MDC) showing an improved activity in converting 3-methylcrotonic acid into isobutene relative to a parent MDC having the amino acid sequence as set forth in SEQ ID NO: 14, wherein said variant comprises an amino acid sequence having at least 63% sequence identity to SEQ ID NO: 14 with a substitution, a deletion or an insertion at a position corresponding to amino acid residue 404 of SEQ ID NO: 14, and wherein said variant optionally further comprises a substitution, a deletion or an insertion at one or more amino acid residues corresponding to position(s) 2, 3, 5, 6, 24, 25, 35, 36, 64, 74, 80, 85, 86, 126, 129, 154, 166, 175, 195, 196, 197, 198, 204, 208, 214, 236, 237, 238, 240, 277, 298, 302, 339, 343, 347, 350, 359, 366, 368, 390, 391, 394, 395, 396, 398, 401, 402, 403, 405, 406, 407, 408, 426, 439, 440, 441, 442, 444, 446, 447, 448, 449, 450, 451, 452, 453, 454, 455, 456, 457, 458, 459, 460, 461, 462 and 473 of SEQ ID NO: 14.

2. The MDC variant of claim 1, wherein
(1) the amino acid residue at position 2 in the amino acid sequence shown in SEQ ID NO:14 or at a position corresponding to this position, is deleted or substituted with asparagine; and/or
(2) the amino acid residue at position 3 in the amino acid sequence shown in SEQ ID NO:14 or at a position corresponding to this position, is deleted or substituted with leucine or methionine; and/or
(3) the amino acid residue at position 5 in the amino acid sequence shown in SEQ ID NO:14 or at a position corresponding to this position, is deleted or substituted with isoleucine; and/or
(4) the amino acid residue at position 6 in the amino acid sequence shown in SEQ ID NO:14 or at a position corresponding to this position, is deleted or substituted with methionine; and/or
(5) the amino acid residue at position 24 in the amino acid sequence shown in SEQ ID NO:14 or at a position corresponding to this position, is deleted or substituted with alanine, aspartic acid, leucine or valine; and/or
(6) the amino acid residue at position 25 in the amino acid sequence shown in SEQ ID NO:14 or at a position corresponding to this position, is deleted or substituted with glutamic acid; and/or
(7) the amino acid residue at position 35 in the amino acid sequence shown in SEQ ID NO:14 or at a position corresponding to this position, is deleted or substituted with isoleucine; and/or
(8) the amino acid residue at position 36 in the amino acid sequence shown in SEQ ID NO:14 or at a position corresponding to this position, is deleted or substituted with tyrosine; and/or
(9) the amino acid residue at position 64 in the amino acid sequence shown in SEQ ID NO:14 or at a position corresponding to this position, is deleted or substituted with histidine; and/or
(10) the amino acid residue at position 74 in the amino acid sequence shown in SEQ ID NO:14 or at a position corresponding to this position, is deleted or substituted with valine; and/or
(11) the amino acid residue at position 80 in the amino acid sequence shown in SEQ ID NO:14 or at a position corresponding to this position, is deleted or substituted with serine; and/or
(12) the amino acid residue at position 85 in the amino acid sequence shown in SEQ ID NO:14 or at a position corresponding to this position, is deleted or substituted with leucine; and/or
(13) the amino acid residue at position 86 in the amino acid sequence shown in SEQ ID NO:14 or at a position corresponding to this position, is deleted or substituted with asparagine or tyrosine; and/or
(14) the amino acid residue at position 126 in the amino acid sequence shown in SEQ ID NO:14 or at a position corresponding to this position, is deleted or substituted with valine; and/or
(15) the amino acid residue at position 129 in the amino acid sequence shown in SEQ ID NO:14 or at a position corresponding to this position, is deleted or substituted with valine; and/or
(16) the amino acid residue at position 154 in the amino acid sequence shown in SEQ ID NO:14 or at a position corresponding to this position, is deleted or substituted with aspartic acid; and/or
(17) the amino acid residue at position 166 in the amino acid sequence shown in SEQ ID NO:14 or at a position corresponding to this position, is deleted or substituted with aspartic acid; and/or
(18) the amino acid residue at position 175 in the amino acid sequence shown in SEQ ID NO:14 or at a position corresponding to this position, is deleted or substituted with glutamic acid; and/or
(19) the amino acid residue at position 195 in the amino acid sequence shown in SEQ ID NO:14 or at a position corresponding to this position, is deleted or substituted with isoleucine or valine; and/or
(20) the amino acid residue at position 196 in the amino acid sequence shown in SEQ ID NO:14 or at a position corresponding to this position, is deleted or substituted with isoleucine; and/or
(21) the amino acid residue at position 197 in the amino acid sequence shown in SEQ ID NO:14 or at a position corresponding to this position, is deleted or substituted with valine; and/or
(22) the amino acid residue at position 198 in the amino acid sequence shown in SEQ ID NO:14 or at a position corresponding to this position, is deleted or substituted with glutamine or tryptophan; and/or
(23) the amino acid residue at position 204 in the amino acid sequence shown in SEQ ID NO:14 or at a position corresponding to this position, is deleted or substituted with arginine or serine; and/or
(24) the amino acid residue at position 208 in the amino acid sequence shown in SEQ ID NO:14 or at a position corresponding to this position, is deleted or substituted with leucine; and/or
(25) the amino acid residue at position 214 in the amino acid sequence shown in SEQ ID NO:14 or at a position corresponding to this position, is deleted or substituted with threonine; and/or
(26) the amino acid residue at position 236 in the amino acid sequence shown in SEQ ID NO:14 or at a position corresponding to this position, is deleted or substituted with leucine or valine; and/or
(27) the amino acid residue at position 237 in the amino acid sequence shown in SEQ ID NO:14 or at a position corresponding to this position, is deleted or substituted with alanine, aspartic acid, asparagine or proline; and/or
(28) the amino acid residue at position 238 in the amino acid sequence shown in SEQ ID NO:14 or at a position corresponding to this position, is deleted or substituted with histidine, arginine, serine or tryptophan; and/or
(29) the amino acid residue at position 240 in the amino acid sequence shown in SEQ ID NO:14 or at a position corresponding to this position, is deleted or substituted with isoleucine or asparagine; and/or
(30) the amino acid residue at position 277 in the amino acid sequence shown in SEQ ID NO:14 or at a position corresponding to this position, is deleted or substituted with tyrosine; and/or
(31) the amino acid residue at position 298 in the amino acid sequence shown in SEQ ID NO:14 or at a position corresponding to this position, is deleted or substituted with serine; and/or
(32) the amino acid residue at position 302 in the amino acid sequence shown in SEQ ID NO:14 or at a position corresponding to this position, is deleted or substituted with alanine, cysteine, phenylalanine, lysine, methionine, glutamine, arginine or serine; and/or
(33) the amino acid residue at position 339 in the amino acid sequence shown in SEQ ID NO:14 or at a position corresponding to this position, is deleted or substituted with histidine; and/or
(34) the amino acid residue at position 343 in the amino acid sequence shown in SEQ ID NO:14 or at a position corresponding to this position, is deleted or substituted with serine; and/or
(35) the amino acid residue at position 347 in the amino acid sequence shown in SEQ ID NO:14 or at a position corresponding to this position, is deleted or substituted with cysteine; and/or
(36) the amino acid residue at position 350 in the amino acid sequence shown in SEQ ID NO:14 or at a position corresponding to this position, is deleted or substituted with serine; and/or
(37) the amino acid residue at position 359 in the amino acid sequence shown in SEQ ID NO:14 or at a position corresponding to this position, is deleted or substituted with cysteine or valine; and/or

(38) the amino acid residue at position 366 in the amino acid sequence shown in SEQ ID NO:14 or at a position corresponding to this position, is deleted or substituted with isoleucine or phenylalanine; and/or
(39) the amino acid residue at position 368 in the amino acid sequence shown in SEQ ID NO:14 or at a position corresponding to this position, is deleted or substituted with isoleucine or methionine; and/or
(40) the amino acid residue at position 390 in the amino acid sequence shown in SEQ ID NO:14 or at a position corresponding to this position, is deleted or substituted with serine, aspartic acid, leucine, asparagine or glutamine; and/or
(41) the amino acid residue at position 391 in the amino acid sequence shown in SEQ ID NO:14 or at a position corresponding to this position, is deleted or substituted with aspartic acid or tryptophan; and/or
(42) the amino acid residue at position 394 in the amino acid sequence shown in SEQ ID NO:14 or at a position corresponding to this position, is deleted or substituted with cysteine, aspartic acid, glutamine or threonine; and/or
(43) the amino acid residue at position 395 in the amino acid sequence shown in SEQ ID NO:14 or at a position corresponding to this position, is deleted or substituted with cysteine, glutamic acid or valine; and/or
(44) the amino acid residue at position 396 in the amino acid sequence shown in SEQ ID NO:14 or at a position corresponding to this position, is deleted or substituted with isoleucine; and/or
(45) the amino acid residue at position 398 in the amino acid sequence shown in SEQ ID NO:14 or at a position corresponding to this position, is deleted or substituted with cysteine or arginine; and/or
(46) the amino acid residue at position 401 in the amino acid sequence shown in SEQ ID NO:14 or at a position corresponding to this position, is deleted or substituted with tyrosine; and/or
(47) the amino acid residue at position 402 in the amino acid sequence shown in SEQ ID NO:14 or at a position corresponding to this position, is deleted or substituted with alanine; and/or
(48) the amino acid residue at position 403 in the amino acid sequence shown in SEQ ID NO:14 or at a position corresponding to this position, is deleted or substituted with alanine, cysteine, glycine, histidine, isoleucine, asparagine, proline, glutamine, arginine or valine; and/or
(49) the amino acid residue at position 404 in the amino acid sequence shown in SEQ ID NO:14 or at a position corresponding to this position, is deleted or substituted with phenylalanine, leucine or methionine; and/or
(50) the amino acid residue at position 405 in the amino acid sequence shown in SEQ ID NO:14 or at a position corresponding to this position, is deleted or substituted with histidine, isoleucine, methionine, threonine or valine; and/or
(51) the amino acid residue at position 406 in the amino acid sequence shown in SEQ ID NO:14 or at a position corresponding to this position, is deleted or substituted with glycine, alanine or serine; and/or
(52) the amino acid residue at position 407 in the amino acid sequence shown in SEQ ID NO:14 or at a position corresponding to this position, is deleted or substituted with alanine, cysteine, isoleucine, lysine, arginine, serine or threonine; and/or
(53) the amino acid residue at position 408 in the amino acid sequence shown in SEQ ID NO:14 or at a position corresponding to this position, is deleted or substituted with isoleucine, alanine, cysteine, leucine, or methionine; and/or
(54) the amino acid residue at position 426 in the amino acid sequence shown in SEQ ID NO:14 or at a position corresponding to this position, is deleted or substituted with valine; and/or
(55) the amino acid residue at position 439 in the amino acid sequence shown in SEQ ID NO:14 or at a position corresponding to this position, is deleted or substituted with cysteine; and/or
(56) the amino acid residue at position 440 in the amino acid sequence shown in SEQ ID NO:14 or at a position corresponding to this position, is deleted or substituted with leucine; and/or
(57) the amino acid residue at position 441 in the amino acid sequence shown in SEQ ID NO:14 or at a position corresponding to this position, is deleted or substituted with glycine, histidine, lysine, asparagine, proline, arginine, serine or threonine; and/or
(58) the amino acid residue at position 442 in the amino acid sequence shown in SEQ ID NO:14 or at a position corresponding to this position, is deleted or substituted with alanine, cysteine, glutamic acid, glycine, histidine, leucine, methionine, asparagine, glutamine, arginine, serine or threonine; and/or
(59) the amino acid residue at position 444 in the amino acid sequence shown in SEQ ID NO:14 or at a position corresponding to this position, is deleted or substituted with alanine, glutamic acid, phenylalanine, histidine, isoleucine, leucine, glutamine or threonine; and/or
(60) the amino acid residue at position 446 in the amino acid sequence shown in SEQ ID NO:14 or at a position corresponding to this position, is deleted or substituted with alanine, cysteine, phenylalanine, isoleucine, methionine, asparagine, serine or valine; and/or
(61) the amino acid residue at position 447 in the amino acid sequence shown in SEQ ID NO:14 or at a position corresponding to this position, is deleted or substituted with glutamine; and/or
(62) the amino acid residue at position 448 in the amino acid sequence shown in SEQ ID NO:14 or at a position corresponding to this position, is deleted or substituted with phenylalanine, tryptophan or tyrosine; and/or
(63) the amino acid residue at position 449 in the amino acid sequence shown in SEQ ID NO:14 or at a position corresponding to this position, is deleted or substituted with isoleucine, methionine or valine; and/or
(64) the amino acid residue at position 450 in the amino acid sequence shown in SEQ ID NO:14 or at a position corresponding to this position, is deleted or substituted with alanine, histidine, methionine, asparagine, glutamine, serine or valine; and/or
(65) the amino acid residue at position 451 in the amino acid sequence shown in SEQ ID NO:14 or at a position corresponding to this position, is deleted or substituted with asparagine or serine; and/or
(66) the amino acid residue at position 452 in the amino acid sequence shown in SEQ ID NO:14 or at a position corresponding to this position, is deleted or substituted with phenylalanine; and/or
(67) the amino acid residue at position 453 in the amino acid sequence shown in SEQ ID NO:14 or at a position corresponding to this position, is deleted or substituted with cysteine, glycine, leucine, asparagine, proline, arginine or serine; and/or

(68) the amino acid residue at position 454 in the amino acid sequence shown in SEQ ID NO:14 or at a position corresponding to this position, is deleted or substituted with alanine, aspartic acid, glycine, histidine, lysine, leucine, methionine, glutamine, arginine, serine, threonine, valine or tryptophan; and/or

(69) the amino acid residue at position 455 in the amino acid sequence shown in SEQ ID NO:14 or at a position corresponding to this position, is deleted or substituted with alanine, glutamic acid, histidine, lysine, asparagine, serine or valine; and/or

(70) the amino acid residue at position 456 in the amino acid sequence shown in SEQ ID NO:14 or at a position corresponding to this position, is deleted or substituted with glutamine; and/or

(71) the amino acid residue at position 457 in the amino acid sequence shown in SEQ ID NO:14 or at a position corresponding to this position, is deleted or substituted with lysine; and/or

(72) the amino acid residue at position 458 in the amino acid sequence shown in SEQ ID NO:14 or at a position corresponding to this position, is deleted or substituted with glutamic acid, phenylalanine, glycine, leucine, methionine, asparagine, glutamine, arginine, serine or tyrosine; and/or

(73) the amino acid residue at position 459 in the amino acid sequence shown in SEQ ID NO:14 or at a position corresponding to this position, is deleted or substituted with aspartic acid, glutamic acid, glycine, methionine, asparagine, glutamine, arginine, threonine or tyrosine; and/or

(74) the amino acid residue at position 460 in the amino acid sequence shown in SEQ ID NO:14 or at a position corresponding to this position, is deleted or substituted with glutamic acid, phenylalanine, glycine, leucine, methionine, asparagine, glutamine or arginine; and/or

(75) the amino acid residue at position 461 in the amino acid sequence shown in SEQ ID NO:14 or at a position corresponding to this position, is deleted or substituted with alanine, glycine, leucine, methionine, glutamine, serine or valine; and/or

(76) the amino acid residue at position 462 in the amino acid sequence shown in SEQ ID NO:14 or at a position corresponding to this position, is deleted or substituted with cysteine or valine; and/or

(77) the amino acid residue at position 473 in the amino acid sequence shown in SEQ ID NO:14 or at a position corresponding to this position, is deleted or substituted with serine.

3. The MDC variant of claim 1, wherein said variant further comprises a substitution, a deletion or an insertion at one or more amino acid residues corresponding to position(s) 66, 168, 241, 296, 305, 349, 363, 443, 445, 479, and 496 of SEQ ID NO: 14.

4. The MDC variant of claim 3, wherein

(78) the amino acid residue at position 66 in the amino acid sequence shown in SEQ ID NO:14 or at a position corresponding to this position, is deleted or substituted with histidine; and/or

(79) the amino acid residue at position 168 in the amino acid sequence shown in SEQ ID NO:14 or at a position corresponding to this position, is deleted or substituted with valine; and/or

(80) the amino acid residue at position 241 in the amino acid sequence shown in SEQ ID NO:14 or at a position corresponding to this position, is deleted or substituted with aspartic acid, asparagine or valine; and/or

(81) the amino acid residue at position 296 in the amino acid sequence shown in SEQ ID NO:14 or at a position corresponding to this position, is deleted or substituted with glutamine; and/or

(82) the amino acid residue at position 305 in the amino acid sequence shown in SEQ ID NO:14 or at a position corresponding to this position, is deleted or substituted with isoleucine or threonine; and/or

(83) the amino acid residue at position 349 in the amino acid sequence shown in SEQ ID NO:14 or at a position corresponding to this position, is deleted or substituted with methionine or serine; and/or

(84) the amino acid residue at position 363 in the amino acid sequence shown in SEQ ID NO:14 or at a position corresponding to this position, is deleted or substituted with glycine; and/or

(85) the amino acid residue at position 443 in the amino acid sequence shown in SEQ ID NO:14 or at a position corresponding to this position, is deleted or substituted with alanine, aspartic acid, phenylalanine, histidine, leucine, asparagine, arginine, serine, tryptophan or tyrosine; and/or

(86) the amino acid residue at position 445 in the amino acid sequence shown in SEQ ID NO:14 or at a position corresponding to this position, is deleted or substituted with leucine, alanine, cysteine, serine or threonine; and/or

(87) the amino acid residue at position 479 in the amino acid sequence shown in SEQ ID NO:14 or at a position corresponding to this position, is deleted or substituted with cysteine, isoleucine, leucine, methionine, serine, threonine or valine; and/or

(88) the amino acid residue at position 496 in the amino acid sequence shown in SEQ ID NO:14 or at a position corresponding to this position, is deleted or substituted with leucine.

5. A method for producing isobutene from 3-methylcrotonic acid by incubating 3-methylcrotonic acid with the MDC variant of claim 1.

6. The method of claim 5, wherein the enzymatic conversion is carried out in vitro or by a host cell expressing the MDC variant of claim 1.

7. A composition comprising the MDC variant of claim 1.

8. A method for producing isobutene from 3-methylcrotonic acid by incubating 3-methylcrotonic acid with the MDC variant of claim 2.

9. The method of claim 8, wherein the enzymatic conversion is carried out in vitro or by a host cell expressing the MDC variant of claim 8.

10. A composition comprising the MDC variant of claim 2.

11. A method for producing isobutene from 3-methylcrotonic acid by incubating 3-methylcrotonic acid with the MDC variant of claim 2.

12. The method of claim 11, wherein the enzymatic conversion is carried out in vitro or by a host cell expressing the MCD variant of claim 2.

13. A composition comprising the MDC variant of claim 3.

14. A method for producing isobutene from 3-methylcrotonic acid by incubating 3-methylcrotonic acid with the MDC variant of claim 4.

15. The method of claim 14, wherein the enzymatic conversion is carried out in vitro or by a host cell expressing the MDC variant of claim 4.

16. A composition comprising the MDC variant of claim 4.

* * * * *

UNITED STATES PATENT AND TRADEMARK OFFICE
CERTIFICATE OF CORRECTION

PATENT NO.         : 10,988,752 B2
APPLICATION NO.    : 16/502472
DATED              : April 27, 2021
INVENTOR(S)        : François Stricher and Benoît Villiers It is certified that error appears in the above-identified patent and that said Letters Patent is hereby corrected as shown below:

In the Claims

In Claim 11, Column 344, Line 57, the claim should state:
--A method for producing isobutene from 3-methylcrotonic acid by incubating 3-methylcrotonic acid with the MDC variant of claim 3.--

In Claim 12, Column 344, Line 60, the claim should state:
--The method of claim 11, wherein the enzymatic conversion is carried out in vitro or by a host cell expressing the MCD variant of claim 3.--

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 16

<210> SEQ ID NO 1
<211> LENGTH: 512
<212> TYPE: PRT
<213> ORGANISM: Hypocrea atroviridis
<220> FEATURE:
<221> NAME/KEY: MISC_FEATURE
<222> LOCATION: (1)..(512)
<223> OTHER INFORMATION: Hypocrea atroviridis (strain ATCC 20476)

<400> SEQUENCE: 1

Met Ser Ser Thr Thr Tyr Lys Ser Glu Ala Phe Asp Pro Glu Pro Pro
1               5                   10                  15

His Leu Ser Phe Arg Ser Phe Val Glu Ala Leu Arg Gln Asp Asn Asp
            20                  25                  30

Leu Val Asp Ile Asn Glu Pro Val Asp Pro Asp Leu Glu Ala Ala Ala
        35                  40                  45

Ile Thr Arg Leu Val Cys Glu Thr Asp Asp Lys Ala Pro Leu Phe Asn
    50                  55                  60

Asn Val Ile Gly Ala Lys Asp Gly Leu Trp Arg Ile Leu Gly Ala Pro
65                  70                  75                  80

Ala Ser Leu Arg Ser Ser Pro Lys Glu Arg Phe Gly Arg Leu Ala Arg
                85                  90                  95

His Leu Ala Leu Pro Pro Thr Ala Ser Ala Lys Asp Ile Leu Asp Lys
            100                 105                 110

Met Leu Ser Ala Asn Ser Ile Pro Pro Ile Glu Pro Val Ile Val Pro
        115                 120                 125

Thr Gly Pro Val Lys Glu Asn Ser Ile Glu Gly Glu Asn Ile Asp Leu
    130                 135                 140

Glu Ala Leu Pro Ala Pro Met Val His Gln Ser Asp Gly Gly Lys Tyr
145                 150                 155                 160

Ile Gln Thr Tyr Gly Met His Val Ile Gln Ser Pro Asp Gly Cys Trp
            165                 170                 175

Thr Asn Trp Ser Ile Ala Arg Ala Met Val Ser Gly Lys Arg Thr Leu
        180                 185                 190

Ala Gly Leu Val Ile Ser Pro Gln His Ile Arg Lys Ile Gln Asp Gln
    195                 200                 205

Trp Arg Ala Ile Gly Gln Glu Ile Pro Trp Ala Leu Ala Phe Gly
210                 215                 220

Val Pro Pro Thr Ala Ile Met Ala Ser Ser Met Pro Ile Pro Asp Gly
225                 230                 235                 240

Val Ser Glu Ala Gly Tyr Val Gly Ala Ile Ala Gly Glu Pro Ile Lys
                245                 250                 255

Leu Val Lys Cys Asp Thr Asn Asn Leu Tyr Val Pro Ala Asn Ser Glu
            260                 265                 270

Ile Val Leu Glu Gly Thr Leu Ser Thr Thr Lys Met Ala Pro Glu Gly
        275                 280                 285

Pro Phe Gly Glu Met His Gly Tyr Val Tyr Pro Gly Glu Ser His Pro
    290                 295                 300

Gly Pro Val Tyr Thr Val Asn Lys Ile Thr Tyr Arg Asn Asn Ala Ile
305                 310                 315                 320

Leu Pro Met Ser Ala Cys Gly Arg Leu Thr Asp Glu Thr Gln Thr Met
                325                 330                 335

Ile Gly Thr Leu Ala Ala Ala Glu Ile Arg Gln Leu Cys Gln Asp Ala
            340                 345                 350

Gly Leu Pro Ile Thr Asp Ala Phe Ala Pro Phe Val Gly Gln Ala Thr
        355                 360                 365

Trp Val Ala Leu Lys Val Asp Thr Lys Arg Leu Arg Ala Met Lys Thr
    370                 375                 380

Asn Gly Lys Ala Phe Ala Lys Arg Val Gly Asp Val Val Phe Thr Gln
385                 390                 395                 400

Lys Pro Gly Phe Thr Ile His Arg Leu Ile Leu Val Gly Asp Asp Ile
                405                 410                 415

Asp Val Tyr Asp Asp Lys Asp Val Met Trp Ala Phe Thr Thr Arg Cys
            420                 425                 430

Arg Pro Gly Thr Asp Glu Val Phe Phe Asp Asp Val Val Gly Phe Gln
        435                 440                 445

Leu Ile Pro Tyr Met Ser His Gly Asn Ala Glu Ala Ile Lys Gly Gly
    450                 455                 460

Lys Val Val Ser Asp Ala Leu Leu Thr Ala Glu Tyr Thr Thr Gly Lys
465                 470                 475                 480

Asp Trp Glu Ser Ala Asp Phe Lys Asn Ser Tyr Pro Lys Ser Ile Gln
                485                 490                 495

Asp Lys Val Leu Asn Ser Trp Glu Arg Leu Gly Phe Lys Lys Leu Asp
            500                 505                 510

<210> SEQ ID NO 2
<211> LENGTH: 189
<212> TYPE: PRT
<213> ORGANISM: Escherichia coli K-12

<400> SEQUENCE: 2

Met Lys Arg Leu Ile Val Gly Ile Ser Gly Ala Ser Gly Ala Ile Tyr
1               5                   10                  15

Gly Val Arg Leu Leu Gln Val Leu Arg Asp Val Thr Asp Ile Glu Thr
            20                  25                  30

His Leu Val Met Ser Gln Ala Ala Arg Gln Thr Leu Ser Leu Glu Thr
            35                  40                  45

Asp Phe Ser Leu Arg Glu Val Gln Ala Leu Ala Asp Val Thr His Asp
        50                  55                  60

Ala Arg Asp Ile Ala Ala Ser Ile Ser Ser Gly Ser Phe Gln Thr Leu
65                  70                  75                  80

Gly Met Val Ile Leu Pro Cys Ser Ile Lys Thr Leu Ser Gly Ile Val
                85                  90                  95

His Ser Tyr Thr Asp Gly Leu Leu Thr Arg Ala Ala Asp Val Val Leu
            100                 105                 110

Lys Glu Arg Arg Pro Leu Val Leu Cys Val Arg Glu Thr Pro Leu His
        115                 120                 125

Leu Gly His Leu Arg Leu Met Thr Gln Ala Ala Glu Ile Gly Ala Val
    130                 135                 140

Ile Met Pro Pro Val Pro Ala Phe Tyr His Arg Pro Gln Ser Leu Asp
145                 150                 155                 160

Asp Val Ile Asn Gln Thr Val Asn Arg Val Leu Asp Gln Phe Ala Ile
                165                 170                 175

Thr Leu Pro Glu Asp Leu Phe Ala Arg Trp Gln Gly Ala
            180                 185

<210> SEQ ID NO 3
<211> LENGTH: 229
<212> TYPE: PRT
<213> ORGANISM: Candida albicans
<220> FEATURE:
<221> NAME/KEY: MISC_FEATURE
<222> LOCATION: (1)..(229)
<223> OTHER INFORMATION: Candida albicans (strain SC5314 / ATCC
      MYA-2876)

<400> SEQUENCE: 3

Met Ile Ala Arg Val Cys Leu Arg Arg Ser Asn Val Leu Pro Ile Phe
1               5                   10                  15

Gln Ile Pro Ser Arg Lys Tyr Ser Ile Asn Tyr Glu Lys Val Asn Asn
            20                  25                  30

Ser Ile Tyr Asn Asn Val Ile Lys Pro Lys Arg Ile Val Leu Ala Ile
        35                  40                  45

Thr Gly Ala Thr Gly Thr Gln Ile Gly Val Arg Leu Leu Glu Ile Leu
    50                  55                  60

Lys Glu Leu Gly Val Glu Thr His Leu Val Met Ser Lys Trp Gly Ile
65                  70                  75                  80

Ala Thr Leu Lys Tyr Glu Thr Asp Tyr Gln Val Asp Tyr Val Thr Ser
                85                  90                  95

Leu Ala Thr Lys Thr Tyr Ser Ala Arg Asp Val Thr Ala Pro Ile Ser
            100                 105                 110

Ser Gly Ser Phe Val His Asp Gly Met Ile Val Ala Pro Cys Ser Met
        115                 120                 125

Lys Ser Leu Ser Ala Ile Arg Thr Gly Phe Thr Glu Asp Leu Ile Val
    130                 135                 140

Arg Ala Ala Asp Val Ser Leu Lys Glu Arg Arg Lys Leu Leu Leu Val
145                 150                 155                 160

Ala Arg Glu Thr Pro Leu Ser Asp Ile His Leu Asp Asn Met Leu Tyr
                165                 170                 175

Leu Ser Arg Met Gly Val Thr Ile Phe Pro Pro Val Pro Ala Phe Tyr
            180                 185                 190

```
Thr Lys Pro Lys Thr Ile Asp Asp Ile Val Glu Gln Thr Cys Gly Arg
        195                 200                 205

Ile Leu Asp Asn Phe Gly Ile Asn Ile Asp Thr Phe Glu Arg Trp Asp
210                 215                 220

Gly Ile Asn His Arg
225

<210> SEQ ID NO 4
<211> LENGTH: 227
<212> TYPE: PRT
<213> ORGANISM: Aspergillus niger

<400> SEQUENCE: 4

Met Phe Asn Ser Leu Leu Ser Gly Thr Thr Thr Pro Asn Ser Gly Arg
1               5                   10                  15

Ala Ser Pro Pro Ala Ser Glu Met Pro Ile Asp Asn Asp His Val Ala
            20                  25                  30

Val Ala Arg Pro Ala Pro Arg Arg Arg Ile Val Val Ala Met Thr
        35                  40                  45

Gly Ala Thr Gly Ala Met Leu Gly Ile Lys Val Leu Ile Ala Leu Arg
50                  55                  60

Arg Leu Asn Val Glu Thr His Leu Val Met Ser Lys Trp Ala Glu Ala
65                  70                  75                  80

Thr Ile Lys Tyr Glu Thr Asp Tyr His Pro Ser Asn Val Arg Ala Leu
                85                  90                  95

Ala Asp Tyr Val His Asn Ile Asn Asp Met Ala Ala Pro Val Ser Ser
            100                 105                 110

Gly Ser Phe Arg Ala Asp Gly Met Ile Val Val Pro Cys Ser Met Lys
        115                 120                 125

Thr Leu Ala Ala Ile His Ser Gly Phe Cys Asp Asp Leu Ile Ser Arg
130                 135                 140

Thr Ala Asp Val Met Leu Lys Glu Arg Arg Leu Val Leu Val Ala
145                 150                 155                 160

Arg Glu Thr Pro Leu Ser Glu Ile His Leu Arg Asn Met Leu Glu Val
                165                 170                 175

Thr Arg Ala Gly Ala Val Ile Phe Pro Pro Val Pro Ala Phe Tyr Ile
            180                 185                 190

Lys Ala Gly Ser Ile Glu Asp Leu Ile Asp Gln Ser Val Gly Arg Met
        195                 200                 205

Leu Asp Leu Phe Asp Leu Asp Thr Gly Asp Phe Glu Arg Trp Asn Gly
210                 215                 220

Trp Glu Lys
225

<210> SEQ ID NO 5
<211> LENGTH: 242
<212> TYPE: PRT
<213> ORGANISM: Saccharomyces cerevisiae S288c

<400> SEQUENCE: 5

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
            20                  25                  30

Pro Ser Phe Leu Thr His Lys Leu Ser Lys Glu Val Thr Arg Ala Ser
        35                  40                  45
```

```
Thr Ser Pro Pro Arg Pro Lys Arg Ile Val Ala Ile Thr Gly Ala
 50                  55                  60

Thr Gly Val Ala Leu Gly Ile Arg Leu Leu Gln Val Leu Lys Glu Leu
 65                  70                  75                  80

Ser Val Glu Thr His Leu Val Ile Ser Lys Trp Gly Ala Ala Thr Met
                 85                  90                  95

Lys Tyr Glu Thr Asp Trp Glu Pro His Asp Val Ala Ala Leu Ala Thr
            100                 105                 110

Lys Thr Tyr Ser Val Arg Asp Val Ser Ala Cys Ile Ser Ser Gly Ser
            115                 120                 125

Phe Gln His Asp Gly Met Ile Val Val Pro Cys Ser Met Lys Ser Leu
130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Val Thr Arg Glu
                165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
            195                 200                 205

Lys Ser Leu His Asp Leu Leu Glu Gln Ser Val Gly Arg Ile Leu Asp
210                 215                 220

Cys Phe Gly Ile His Ala Asp Thr Phe Pro Arg Trp Glu Gly Ile Lys
225                 230                 235                 240

Ser Lys

<210> SEQ ID NO 6
<211> LENGTH: 180
<212> TYPE: PRT
<213> ORGANISM: Cryptococcus gattii WM276
<220> FEATURE:
<221> NAME/KEY: MISC_FEATURE
<222> LOCATION: (1)..(180)
<223> OTHER INFORMATION: serotype B

<400> SEQUENCE: 6

Met Arg Arg Lys Arg Tyr Val Val Ala Val Thr Gly Ala Thr Gly Ala
 1               5                  10                  15

Thr Leu Ala Ile Arg Leu Leu Gln Ala Leu Arg Ala Leu Asp Ile Glu
                20                  25                  30

Thr His Leu Ile Ile Ser Lys Trp Ala Val Lys Thr Leu Lys Tyr Glu
            35                  40                  45

Thr Asp Met Ile Glu Arg Glu Leu Lys Asp Leu Ala Asp Tyr Ser Tyr
 50                  55                  60

Ser Asn Ser Asp Leu Ala Ala Pro Ser Ser Gly Ser Phe Ile His
 65                  70                  75                  80

Asp Gly Met Phe Ile Ile Pro Cys Ser Met Lys Thr Leu Ala Ala Val
                 85                  90                  95

Arg Ile Gly Leu Gly Asp Glu Leu Ile Ser Arg Ser Ala Asp Val Cys
            100                 105                 110

Leu Lys Glu Gly Arg Lys Leu Met Leu Val Val Arg Glu Thr Pro Leu
            115                 120                 125

Asn Asp Ile His Leu Glu Asn Met Leu Phe Leu Arg Arg Ala Gly Ala
130                 135                 140

Ile Ile Phe Pro Pro Val Pro Ala Tyr Tyr Ile Arg Pro Gln Thr Ile
```

```
                      145                 150                 155                 160
Asp Asp Leu Thr Asn Gln Thr Val Gly Arg Ile Leu Asp Ser Ser Lys
                    165                 170                 175

Cys Ser Gln Lys
            180

<210> SEQ ID NO 7
<211> LENGTH: 192
<212> TYPE: PRT
<213> ORGANISM: Bacillus subtilis

<400> SEQUENCE: 7

Met Lys Leu Val Ile Gly Met Thr Gly Ala Thr Gly Ala Ile Phe Gly
1               5                   10                  15

Ile Arg Leu Leu Glu Tyr Leu Lys Ala Ala Glu Ile Glu Thr His Leu
            20                  25                  30

Val Val Ser Pro Trp Ala Asn Val Thr Ile Thr His Glu Thr Asp Tyr
        35                  40                  45

Thr Leu Lys Asp Val Glu Lys Leu Ala Ser Tyr Thr Tyr Ser His Lys
    50                  55                  60

Asp Gln Ala Ala Ala Ile Ser Ser Gly Ser Phe Glu Thr Asp Gly Met
65                  70                  75                  80

Ile Ile Ala Pro Cys Ser Met Lys Ser Leu Ala Ser Ile Arg Thr Gly
                85                  90                  95

Met Ala Asp Asn Leu Leu Thr Arg Ala Ala Asp Val Ile Leu Lys Glu
            100                 105                 110

Arg Lys Lys Leu Val Leu Leu Thr Arg Glu Thr Pro Leu Ser Gln Ile
        115                 120                 125

His Leu Glu Asn Met Leu Ala Leu Thr Lys Met Gly Ser Val Ile Leu
    130                 135                 140

Pro Pro Met Pro Ala Phe Tyr Asn Lys Pro Ala Asp Met Asp Glu Leu
145                 150                 155                 160

Ile Asp His Ile Val Phe Arg Thr Leu Asp Gln Phe Gly Ile Arg Leu
                165                 170                 175

Pro Glu Ala Lys Arg Trp Tyr Gly Ile Glu Lys Gln Lys Gly Gly Ile
            180                 185                 190

<210> SEQ ID NO 8
<211> LENGTH: 209
<212> TYPE: PRT
<213> ORGANISM: Pseudomonas aeruginosa

<400> SEQUENCE: 8

Met Ser Gly Pro Glu Arg Ile Thr Leu Ala Met Thr Gly Ala Ser Gly
1               5                   10                  15

Ala Gln Tyr Gly Leu Arg Leu Leu Asp Cys Leu Val Gln Glu Glu Arg
            20                  25                  30

Glu Val His Phe Leu Ile Ser Lys Ala Ala Gln Leu Val Met Ala Thr
        35                  40                  45

Glu Thr Asp Val Ala Leu Pro Ala Lys Pro Gln Ala Met Gln Ala Phe
    50                  55                  60

Leu Thr Glu Tyr Cys Gly Ala Ala Gly Gln Ile Arg Val Phe Gly
65                  70                  75                  80

Gln Asn Asp Trp Met Ala Pro Pro Ala Ser Gly Ser Ser Ala Pro Asn
                85                  90                  95

Ala Met Val Ile Cys Pro Cys Ser Thr Gly Thr Leu Ser Ala Val Ala
```

```
                100              105              110
Thr Gly Ala Cys Asn Asn Leu Ile Glu Arg Ala Ala Asp Val Ala Leu
            115                  120                  125

Lys Glu Arg Arg Pro Leu Val Leu Val Pro Arg Glu Ala Pro Phe Ser
130                  135                  140

Ser Ile His Leu Glu Asn Met Leu Lys Leu Ser Asn Leu Gly Ala Val
145                  150                  155                  160

Ile Leu Pro Ala Ala Pro Gly Phe Tyr His Gln Pro Gln Ser Val Glu
                165                  170                  175

Asp Leu Val Asp Phe Val Val Ala Arg Ile Leu Asn Thr Leu Gly Ile
                180                  185                  190

Pro Gln Asp Met Leu Pro Arg Trp Gly Glu Gln His Leu Val Ser Asp
                195                  200                  205

Glu

<210> SEQ ID NO 9
<211> LENGTH: 219
<212> TYPE: PRT
<213> ORGANISM: Enterobacter sp.
<220> FEATURE:
<221> NAME/KEY: MISC_FEATURE
<222> LOCATION: (1)..(219)
<223> OTHER INFORMATION: Enterobacter sp. DC4

<400> SEQUENCE: 9

Met Leu Arg Gln Val Arg Ala Asn Ala Leu Thr Cys Asn Ser Pro Gln
1               5                   10                  15

Asn Pro Ala Gln Ser Ala Leu Lys Ser Val Arg Ala Lys Ile Met Lys
                20                  25                  30

Arg Leu Ile Val Gly Leu Ser Gly Ala Ser Gly Ala Ile Tyr Gly Val
            35                  40                  45

Arg Leu Leu Gln Val Leu Arg Asn Val Ala Glu Val Glu Thr His Leu
        50                  55                  60

Val Met Ser Gln Ala Ala Arg Gln Thr Leu Ser Leu Glu Thr Asp Leu
65                  70                  75                  80

Ser Leu Arg Asp Val Gln Ala Leu Ala Asp Val Val His Asp Ala Arg
                85                  90                  95

Asp Ile Ala Ala Ser Ile Ser Ser Gly Ser Phe Lys Thr Ala Gly Met
                100                 105                 110

Val Ile Leu Pro Cys Ser Ile Lys Thr Leu Ser Gly Ile Val Asn Ser
            115                 120                 125

Tyr Thr Asp Thr Leu Val Thr Arg Ala Ala Asp Val Val Leu Lys Glu
        130                 135                 140

Arg Arg Pro Leu Val Leu Cys Val Arg Glu Thr Pro Leu His Leu Gly
145                 150                 155                 160

His Leu Arg Leu Met Thr Gln Ala Ala Glu Leu Gly Ala Ile Ile Met
                165                 170                 175

Pro Pro Val Pro Ala Phe Tyr His Arg Pro Thr Ser Leu Asp Asp Val
                180                 185                 190

Ile Asn Gln Thr Val Asn Arg Val Leu Asp Gln Phe Asp Ile Asp Leu
                195                 200                 205

Pro Glu Asp Leu Phe Thr Arg Trp Gln Gly Ala
                210                 215

<210> SEQ ID NO 10
<211> LENGTH: 503
```

```
<212> TYPE: PRT
<213> ORGANISM: Cladophialophora psammophila CBS 110553

<400> SEQUENCE: 10
```

| | | | | | | | | | | | | | | |
|---|---|---|---|---|---|---|---|---|---|---|---|---|---|---|
| Met | Val | Ser | Ser | Thr | Phe | Thr | Gln | Pro | Pro | Asp | Gly | Pro | Ala | His | Leu |
| 1 | | | | 5 | | | | | 10 | | | | | 15 | |

Ser Phe Arg Ser Phe Val Ser Ala Leu Lys Glu Asp Gly Asp Leu Val
            20                  25                  30

Glu Ile Asn Asp Glu Ile Asp Pro Tyr Leu Glu Ala Ala Ala Ile Ile
        35                  40                  45

Arg Lys Val Cys Glu Thr Asp Gly Lys Ala Pro Leu Phe Asn Asn Leu
    50                  55                  60

Lys Gly Asn Val Asn Gly Phe Trp Arg Ile Leu Gly Ala Pro Ala Ser
65                  70                  75                  80

Leu Arg Arg Asp Pro Ser Arg Arg Tyr Ala Arg Leu Ala Arg His Leu
                85                  90                  95

Ala Leu Pro Pro Thr Ala Gly Met Lys Asp Ile Leu Asp Lys Met Leu
            100                 105                 110

Ser Ala Lys Ser Ser Ala Pro Ile Pro Pro Lys Val Val Ser Thr Gly
        115                 120                 125

Pro Cys Lys Ala His Ile Leu Asp Glu Phe Asp Leu Glu Lys Leu Pro
    130                 135                 140

Ala Pro Phe Leu His Gln Ser Asp Gly Lys Tyr Ile Gln Thr Tyr
145                 150                 155                 160

Gly Met His Val Ile Gln Ser Pro Asp Gly Thr Trp Thr Asn Trp Ser
                165                 170                 175

Ile Ala Arg Ala Met Val Lys Asp Lys Asn His Leu Val Gly Leu Val
            180                 185                 190

Ile Glu Pro Gln His Ile Trp Gln Ile Arg Glu Gln Trp Lys Ala Ile
        195                 200                 205

Gly Lys Asp Val Pro Trp Ala Leu Cys Phe Gly Val Pro Pro Ala Ala
    210                 215                 220

Ile Met Ala Ala Ser Met Pro Leu Pro Ser Gly Leu Ser Glu Ala Asp
225                 230                 235                 240

Tyr Ile Gly Ala Met Thr Gly Thr Ala Leu Asp Val Val Lys Cys Glu
                245                 250                 255

Thr Asn Asp Leu Tyr Val Pro Ala Thr Ser Glu Ile Val Phe Glu Gly
            260                 265                 270

Thr Leu Ser Val Ser Glu Leu Ala Pro Glu Gly Pro Phe Gly Glu Met
        275                 280                 285

His Gly Tyr Val Phe Pro Gly Asp Ser His Leu Gln Pro Val Tyr Thr
    290                 295                 300

Val Asn Lys Ile Thr His Arg Thr Asp Ala Ile Leu Pro Val Ser Asn
305                 310                 315                 320

Cys Gly Arg Ile Thr Asp Glu Thr Gln Thr Met Ile Gly Pro Leu Ala
                325                 330                 335

Ala Ala Glu Ile Arg Gln Leu Cys Gln Asp His Gly Leu Pro Ile Lys
            340                 345                 350

Glu Ala Met Gly Leu Phe Glu Thr Gln Val Thr Trp Val Ala Leu Gln
        355                 360                 365

Val Asp Thr Lys Lys Leu Ala Asp Met Asn Leu Thr Pro Glu Ala Phe
    370                 375                 380

Arg Lys Leu Val Gly Asp Leu Val Tyr Gly His Lys Ala Gly Tyr Thr
385                 390                 395                 400

```
Ile His Arg Leu Val Leu Val Gly Glu Asp Ile Asp Val Tyr Asp Phe
                405                 410                 415

Lys Asp Val Leu Phe Ala Phe Ser Thr Arg Cys Arg Pro Gln Thr Asp
            420                 425                 430

Glu Leu Phe Tyr Gln Asp Cys Arg Gly Phe Ala Leu Ile Pro Tyr Met
        435                 440                 445

Gly His Gly Thr Ala Ala Pro His Lys Gly Lys Val Val Ser Asp
    450                 455                 460

Ala Leu Leu Pro Ala Glu Tyr Thr Gly Gly Gln Asp Trp Glu Leu Ala
465                 470                 475                 480

Asp Phe Lys His Ser Tyr Pro Glu Asn Leu Gln Lys Ser Val Asp Glu
                485                 490                 495

Arg Trp Ser Ala Trp Gly Phe
                500

<210> SEQ ID NO 11
<211> LENGTH: 505
<212> TYPE: PRT
<213> ORGANISM: Cladophialophora immunda

<400> SEQUENCE: 11

Met Val Ser Asn Thr Phe Thr Gln Ser Ser Glu Gly Pro Ala His Leu
1               5                   10                  15

Ser Phe Arg Ser Phe Val Ala Ala Leu Lys Glu Asp Gly Asp Val Val
            20                  25                  30

Glu Ile Asn Asp Glu Val Asp Pro His Leu Glu Ala Ala Ala Ile Ile
        35                  40                  45

Arg Lys Ala Cys Glu Thr Asp Asp Lys Ala Pro Leu Leu Asn Asn Leu
    50                  55                  60

Lys Gly Asn Val Asn Gly Phe Trp Arg Ile Leu Gly Ala Pro Ala Ser
65                  70                  75                  80

Leu Arg Arg Asp Pro Ser Glu Arg Tyr Ala Arg Leu Ala Arg His Leu
                85                  90                  95

Ala Leu Pro Pro Thr Ala Gly Met Lys Asp Ile Leu Asp Lys Met Leu
            100                 105                 110

Ser Ala Lys Thr Ser Ala Pro Val Pro Pro Arg Val Val Ser Thr Gly
        115                 120                 125

Pro Cys Lys Glu His Ile Leu Asp Gln Phe Asp Leu Glu Lys Leu Pro
    130                 135                 140

Ser Pro Phe Leu His Gln Ser Asp Gly Gly Lys Tyr Ile Gln Thr Tyr
145                 150                 155                 160

Gly Met His Val Val Gln Ser Pro Asp Gly Lys Trp Thr Asn Trp Ser
                165                 170                 175

Ile Ala Arg Ala Met Val Lys Asp Lys Asn His Leu Val Gly Leu Val
            180                 185                 190

Ile Glu Pro Gln His Ile Trp Gln Ile Arg Gln Gln Trp Lys Ala Ile
        195                 200                 205

Gly Lys Asp Val Pro Trp Ala Leu Cys Phe Gly Val Pro Pro Ala Ala
    210                 215                 220

Ile Met Ala Ala Ser Met Pro Leu Pro Glu Gly Val Thr Glu Ala Asp
225                 230                 235                 240

Tyr Ile Gly Ala Met Thr Gly Asn Pro Leu Asp Val Val Lys Cys Glu
                245                 250                 255

Thr Asn Asp Met Tyr Val Pro Ala Asn Ser Glu Ile Val Phe Glu Gly
```

```
                260                 265                 270
Thr Leu Ser Val Ser Glu Leu Ala Pro Glu Gly Pro Phe Gly Glu Met
            275                 280                 285

His Gly Tyr Val Phe Pro Gly Asp Ser His Pro Gln Pro Val Tyr Thr
        290                 295                 300

Val Asn Lys Ile Thr His Arg Thr Asp Ala Ile Leu Pro Val Ser Asn
305                 310                 315                 320

Cys Gly Arg Ile Thr Asp Glu Thr Gln Thr Met Ile Gly Pro Leu Ala
                325                 330                 335

Ala Ala Glu Ile Arg Gln Leu Cys Gln Asp His Ser Leu Pro Val Lys
            340                 345                 350

Glu Ala Met Ala Leu Phe Glu Thr Gln Val Thr Trp Val Ala Leu Gln
        355                 360                 365

Ile Asp Thr Lys Lys Leu Arg Asp Met Lys Leu Ala Pro Glu Ala Phe
    370                 375                 380

Arg Lys Leu Val Gly Asp Leu Val Phe Gly His Lys Ala Gly Tyr Thr
385                 390                 395                 400

Ile His Arg Leu Val Leu Val Gly Glu Asp Ile Asp Val Tyr Asp Phe
                405                 410                 415

Lys Asp Val Leu Phe Ala Phe Ser Thr Arg Cys Arg Pro Gln Thr Asp
            420                 425                 430

Glu Leu Phe Tyr Gln Asp Cys Arg Gly Phe Ala Leu Ile Pro Tyr Met
        435                 440                 445

Gly His Gly Thr Ala Glu Pro Asn Lys Gly Gly Lys Val Val Ser Asp
    450                 455                 460

Ala Leu Leu Pro Ala Glu Tyr Ala Gly Gly Gln Asn Trp Glu Leu Ala
465                 470                 475                 480

Asp Phe Lys His Ser Tyr Pro Glu His Leu Gln Lys Ser Val Asn Glu
                485                 490                 495

Arg Trp Met Ala Trp Gly Phe Gly Lys
            500                 505

<210> SEQ ID NO 12
<211> LENGTH: 508
<212> TYPE: PRT
<213> ORGANISM: Sphaerulina musiva SO2202

<400> SEQUENCE: 12

Met Ser Ser Ser Lys Gln Gln His Leu Ser His Ala Asn Gln Glu Leu
1               5                   10                  15

Pro His Leu Asn Phe Arg Ser Phe Val Gln Ala Leu Lys Asp Asp Gly
            20                  25                  30

Asp Leu Ile Glu Ile Asp Asp Glu Ile Asp Pro His Leu Glu Ala Gly
        35                  40                  45

Ala Ile Ile Arg Arg Ala Cys Glu Thr Asp Gly Lys Ala Pro Leu Leu
    50                  55                  60

Asn Asn Leu Lys Gly Ala Lys Asp Gly Leu Trp Arg Ile Leu Gly Ala
65                  70                  75                  80

Pro Ala Ser Leu Arg Ser Asp Pro Ser Gln Lys Tyr Gly Arg Val Ala
                85                  90                  95

Arg His Leu Ala Leu Pro Pro Thr Ala Thr Met Lys Asp Ile Leu Asp
            100                 105                 110

Lys Met Leu Ser Ala Ala His Ala Glu Pro Ile Pro Pro Asn Ile Val
        115                 120                 125
```

```
Glu Ser Gly Pro Val Lys Glu Asn Lys Leu Val Asp Gly Glu Phe Asp
        130                 135                 140

Leu Ser Thr Leu Pro Ala Pro Trp Leu His Gln Ala Asp Gly Gly Lys
145                 150                 155                 160

Tyr Ile Gln Thr Tyr Gly Met His Ile Val Gln Ser Pro Asp Gly Lys
                165                 170                 175

Trp Thr Asn Trp Ser Ile Ala Arg Ala Met Val His Asp Lys Asn His
            180                 185                 190

Leu Thr Gly Leu Val Ile Glu Pro Gln His Ile Trp Gln Ile His Gln
        195                 200                 205

Gln Trp Lys Lys Val Gly Lys Asp Val Pro Trp Ala Leu Ala Phe Gly
210                 215                 220

Val Pro Pro Ala Ala Ile Met Ala Ala Ser Met Pro Ile Pro Asp Gly
225                 230                 235                 240

Val Thr Glu Ala Gly Tyr Ile Gly Ala Met Thr Gly Ser Ala Leu Asp
                245                 250                 255

Val Val Lys Cys Glu Thr Asn Gly Met Tyr Val Pro Ala Asn Ala Glu
                260                 265                 270

Ile Val Leu Glu Gly Thr Leu Ser Ile Thr Glu Thr Ala Pro Glu Gly
            275                 280                 285

Pro Phe Gly Glu Met His Gly Tyr Val Phe Pro Gly Asp Thr His Pro
        290                 295                 300

Trp Pro Lys Tyr Lys Val Asp Ala Ile Thr Tyr Arg Asn Gly Ala Ile
305                 310                 315                 320

Leu Pro Val Ser Asn Cys Gly Arg Ile Thr Asp Glu Thr His Thr Leu
                325                 330                 335

Ile Gly Pro Leu Ala Ala Ala Gln Ile Arg Gln Leu Cys Gln Asp Ala
            340                 345                 350

Gly Leu Pro Ile Thr Asp Ala Phe Ala Pro Phe His Thr Gln Val Thr
        355                 360                 365

Trp Val Ala Leu Lys Val Asp Ile Glu Lys Leu Gly Lys Met Asn Thr
370                 375                 380

Thr Pro Glu Ala Phe Arg Lys Gln Val Gly Asp Leu Val Phe Asn His
385                 390                 395                 400

Lys Ala Gly Tyr Thr Ile His Arg Leu Val Leu Cys Gly Ser Asp Ile
                405                 410                 415

Asp Val Tyr Glu Trp Asp Ile Ala Phe Ala Phe Ser Thr Arg Cys
            420                 425                 430

Arg Pro Asn Lys Asp Glu Thr Phe Tyr Glu Asp Cys Gln Gly Phe Pro
        435                 440                 445

Leu Ile Pro Tyr Met Ser His Gly Thr Gly Ser Pro Ile Lys Gly Gly
450                 455                 460

Lys Val Ile Ser Asp Ala Leu Met Pro Ser Glu Tyr Arg Gly Gln Gln
465                 470                 475                 480

Asp Trp Gln Gln Ala Ser Phe Lys His Ser Tyr Pro Glu Ser Leu Gln
                485                 490                 495

Lys Ser Val Ile Glu Arg Trp Ala Ser Trp Gly Phe
            500                 505

<210> SEQ ID NO 13
<211> LENGTH: 503
<212> TYPE: PRT
<213> ORGANISM: Cladophialophora bantiana CBS 173.52

<400> SEQUENCE: 13
```

```
Met Ala Ser Arg Thr Phe Thr Gln Pro Ser Asp Gly Pro Ala His Leu
1               5                   10                  15

Ser Phe Arg Ser Phe Val Ser Ala Leu Lys Glu Asp Gly Asp Leu Val
            20                  25                  30

Glu Ile Asn Asp Glu Ile Asp Pro Tyr Leu Glu Ala Ala Ala Ile Ile
            35                  40                  45

Arg Lys Ala Cys Glu Thr Asp Gly Lys Ala Pro Leu Phe Asn Asn Leu
            50                  55                  60

Lys Gly Asn Val Asn Gly Phe Trp Arg Ile Leu Gly Ala Pro Ala Ser
65                  70                  75                  80

Leu Arg Arg Asp Pro Ser Arg Arg Tyr Ala Arg Leu Ala Arg His Leu
                85                  90                  95

Ala Leu Pro Pro Thr Ala Gly Met Lys Asp Ile Leu Asp Lys Val Leu
            100                 105                 110

Ser Ala Lys Thr Ser Ala Pro Ile Pro Pro Lys Val Val Ser Thr Gly
            115                 120                 125

Pro Cys Lys Ala His Ile Leu Asp Glu Phe Asp Leu Glu Lys Leu Pro
    130                 135                 140

Ala Pro Phe Leu His Gln Cys Asp Gly Lys Tyr Ile Gln Thr Tyr
145                 150                 155                 160

Gly Met His Val Val Gln Ser Pro Asp Gly Thr Trp Thr Asn Trp Ser
                165                 170                 175

Ile Ala Arg Ala Met Val Lys Asp Lys Asn His Leu Val Gly Leu Val
            180                 185                 190

Ile Glu Pro Gln His Ile Trp Gln Ile Arg Glu Gln Trp Lys Ala Ile
            195                 200                 205

Gly Lys Asp Val Pro Trp Ala Leu Cys Phe Gly Val Pro Pro Ala Ala
    210                 215                 220

Ile Met Ala Ala Ser Met Pro Leu Pro Asp Gly Ile Ser Glu Ala Asp
225                 230                 235                 240

Tyr Ile Gly Ala Met Thr Gly Thr Ala Leu Asp Val Val Lys Cys Glu
            245                 250                 255

Thr Asn Asp Leu Tyr Val Pro Ala Thr Ser Glu Ile Val Phe Glu Gly
            260                 265                 270

Thr Leu Ser Val Ser Glu Leu Ala Pro Glu Gly Pro Phe Gly Glu Met
            275                 280                 285

His Gly Tyr Val Phe Pro Gly Asp Ser His Leu Gln Pro Val Tyr Thr
            290                 295                 300

Val Asn Lys Ile Thr His Arg Thr Asp Ala Ile Leu Pro Val Ser Asn
305                 310                 315                 320

Cys Gly Arg Ile Thr Asp Glu Thr Gln Thr Met Ile Gly Pro Leu Ala
            325                 330                 335

Ala Ala Glu Ile Arg Gln Leu Cys Gln Asp His Gly Leu Pro Ile Lys
            340                 345                 350

Glu Ala Met Gly Leu Phe Glu Thr Gln Val Thr Trp Val Ala Leu Gln
            355                 360                 365

Val Asp Thr Lys Lys Leu Ala Asp Met Asn Leu Ala Pro Glu Ala Phe
    370                 375                 380

Arg Lys Val Val Gly Asp Leu Val Tyr Gly His Lys Ala Gly Tyr Thr
385                 390                 395                 400

Ile His Arg Leu Val Leu Val Gly Glu Asp Ile Asp Val Tyr Asp Phe
            405                 410                 415
```

Lys Asp Val Leu Phe Ala Phe Ser Thr Arg Cys Arg Pro Gln Thr Asp
                420                 425                 430

Glu Leu Phe Tyr Gln Asp Cys Arg Gly Phe Ala Leu Ile Pro Tyr Met
            435                 440                 445

Gly His Gly Thr Ala Ala Pro Asn Lys Gly Lys Val Val Ser Asp
        450                 455                 460

Ala Leu Leu Pro Ala Glu Tyr Thr Gly Gly Gln Asp Trp Glu Leu Ala
465                 470                 475                 480

Asp Phe Lys His Ser Tyr Pro Glu Asn Leu Gln Lys Ser Val Asp Glu
                485                 490                 495

Arg Trp Ser Ala Trp Gly Phe
                500

<210> SEQ ID NO 14
<211> LENGTH: 501
<212> TYPE: PRT
<213> ORGANISM: Streptomyces sp. 769

<400> SEQUENCE: 14

Met Tyr Val Gln Met Val Phe Val Lys Glu Val Pro Val Gln His Pro
1               5                   10                  15

Ser Asp Leu Arg Glu His Ile Glu Ala Leu Glu Lys Leu Gly Asp Leu
                20                  25                  30

Asp Arg Val His Asp Glu Val Asp Trp Asn Leu Glu Ala Ala Ala Gln
            35                  40                  45

Thr Arg Tyr Ser Thr Glu His His Leu Pro Ala Pro Leu Phe Glu Asn
        50                  55                  60

Val Ala Gly Val Ala Glu Gly Phe Arg Leu Leu Gly Ala Pro Ala Ala
65                  70                  75                  80

Leu Ser Ser Asp Pro Ser Arg Pro Tyr Ala Arg Val Ala Leu Ser Val
                85                  90                  95

Gly Leu Arg Pro Glu Ala Thr Gly Arg Glu Val Val Glu His Leu Val
                100                 105                 110

Ala Ala Arg His Arg Pro Gly Val Pro Pro Val Ala Val Ala Ala Glu
            115                 120                 125

Ala Ala Pro Val Lys Ala Asn Val Leu Leu Gly Asp Glu Ala Asp Leu
130                 135                 140

Asn Arg Phe Pro Val Pro Phe Val His Glu Gly Asp Gly Asn Arg Tyr
145                 150                 155                 160

Ala Asn Thr Tyr Gly Val Ile Ile Ala Gln Thr Pro Asp Gly Ser Trp
                165                 170                 175

Thr Asn Trp Ser Ile Ala Arg Ile Met Met Ile Asp Gly Lys His Met
                180                 185                 190

Thr Gly Leu Val Met His Pro Gln His Ile Ala Gln Val Trp Gln Gln
            195                 200                 205

Trp Ala Asp Leu Gly Lys Pro Met Pro Tyr Ala Leu Val Gln Gly Gly
        210                 215                 220

Asp Pro Ala Ile Pro Tyr Val Gly Gly Ile Pro Ile Gly Asp Gly Val
225                 230                 235                 240

Ala Glu Ser Ala Tyr Ile Gly Ala Leu Ile Gly Arg Pro Leu Glu Val
                245                 250                 255

Val Lys Ala Glu Leu Ser Asp Leu Met Val Pro Ala Gly Ala Glu Ile
                260                 265                 270

Val Ile Glu Gly His Leu Ser Val Gln Arg Asp Gly Val Glu Gly Pro
            275                 280                 285

```
Phe Gly Glu Phe Ala Gly Tyr Ile Pro Arg Glu Thr Ser Leu Gln Pro
    290                 295                 300

Val Tyr Thr Val Glu Ala Ile Thr His Arg Asp Ala Pro Ile Trp Pro
305                 310                 315                 320

Leu Val Ala Glu Gly Lys Pro Thr Asp Asp Phe His Thr Val Thr Gly
                325                 330                 335

Ile Gly Glu Ala Ala Gly Ala Leu Asp Ala Ile Arg Glu Ala Gly Leu
            340                 345                 350

Pro Ala Ala Ser Ala Trp Ala Pro Leu Ser Ala Ala Ser His Trp Leu
        355                 360                 365

Val Val Thr Ala Pro Gly Asn Trp Arg Glu Leu Leu Pro Gly Val Ser
370                 375                 380

Glu Glu Gln Tyr Ala Arg Arg Val Gly Glu Ala Val Phe Gly Thr Lys
385                 390                 395                 400

Phe Gly Ser Cys Leu Pro Gln Val Phe Leu Leu Asp Asp Phe Asp
                405                 410                 415

Pro Thr Asp Asp Ala Asp Leu Leu Trp Ala Leu Ala Thr Arg Val His
            420                 425                 430

Pro Asp Gly Arg Val Val Arg Phe Glu Asp Gly Pro Val Leu Pro Leu
        435                 440                 445

Leu Thr Cys Tyr Thr Pro Gln Glu Arg His Ala Ala Arg Ala Thr Lys
    450                 455                 460

Val Val His Glu Ala Leu Leu Ser Ala Pro Gly Glu Arg Glu Pro Gln
465                 470                 475                 480

Ser Thr Phe Ala Asp Ala Tyr Pro Ala Glu Val Arg Ala Lys Val Arg
                485                 490                 495

Ala Arg Tyr Pro Asn
            500

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (10)..(10)
<223> OTHER INFORMATION: Xaa can be any amino acid
<220> FEATURE:
<221> NAME/KEY: MISC_FEATURE
<222> LOCATION: (11)..(11)
<223> OTHER INFORMATION: Xaa can be any amino acid
<220> FEATURE:
```

```
<221> NAME/KEY: MISC_FEATURE
<222> LOCATION: (12)..(12)
<223> OTHER INFORMATION: Xaa can be any amino acid

<400> SEQUENCE: 15

Lys Xaa Gly Xaa Xaa Xaa His Arg Xaa Xaa Xaa Xaa Gly
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be alanine, proline, valine
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be alanine, proline, threonine
<220> FEATURE:
<221> NAME/KEY: MISC_FEATURE
<222> LOCATION: (6)..(6)
<223> OTHER INFORMATION: Xaa can be phenylalanine, isoleucine,
      methionine
<220> FEATURE:
<221> NAME/KEY: MISC_FEATURE
<222> LOCATION: (9)..(9)
<223> OTHER INFORMATION: Xaa can be isoleucine, leucine
<220> FEATURE:
<221> NAME/KEY: MISC_FEATURE
<222> LOCATION: (10)..(10)
<223> OTHER INFORMATION: Xaa can be alanine, isoleucine, leucine, valine
<220> FEATURE:
<221> NAME/KEY: MISC_FEATURE
<222> LOCATION: (11)..(11)
<223> OTHER INFORMATION: Xaa can be isoleucine, leucine, valine
<220> FEATURE:
<221> NAME/KEY: MISC_FEATURE
<222> LOCATION: (12)..(12)
<223> OTHER INFORMATION: Xaa can be any amino acid

<400> SEQUENCE: 16

Lys Xaa Gly Xaa Xaa Xaa His Arg Xaa Xaa Xaa Xaa Gly
1               5                   10
```